US010823737B2

(12) United States Patent
Mikulits et al.

(10) Patent No.: US 10,823,737 B2
(45) Date of Patent: Nov. 3, 2020

(54) SOLUBLE AXL RECEPTOR TYROSINE KINASE IN THE DIAGNOSIS OF CANCER

(71) Applicant: Medizinische Universität Wien, Vienna (AT)

(72) Inventors: Wolfgang Mikulits, Vienna (AT); Patrick Reichl, Vienna (AT)

(73) Assignee: Medizinische Universität Wien, Vienna (AT)

( * ) Notice: Subject to any disclaimer, the term of this patent is extended or adjusted under 35 U.S.C. 154(b) by 1 day.

(21) Appl. No.: 15/126,661

(22) PCT Filed: Mar. 18, 2015

(86) PCT No.: PCT/EP2015/055724
§ 371 (c)(1),
(2) Date: Sep. 16, 2016

(87) PCT Pub. No.: WO2015/140231
PCT Pub. Date: Sep. 24, 2015

(65) Prior Publication Data
US 2017/0146540 A1 May 25, 2017

(30) Foreign Application Priority Data
Mar. 18, 2014 (EP) .................................... 14160589

(51) Int. Cl.
G01N 33/574 (2006.01)
(52) U.S. Cl.
CPC . G01N 33/57438 (2013.01); G01N 33/57488 (2013.01); G01N 33/57492 (2013.01); *G01N 2333/47* (2013.01); *G01N 2333/71* (2013.01); *G01N 2333/912* (2013.01)
(58) Field of Classification Search
None
See application file for complete search history.

(56) References Cited

U.S. PATENT DOCUMENTS

| 2008/0194043 A1* | 8/2008 | Astle | .................. | C12Q 1/6886 436/501 |
| 2009/0317844 A1 | 12/2009 | Riady | | |
| 2014/0121126 A1* | 5/2014 | Bivona | ............ | G01N 33/57423 506/9 |

FOREIGN PATENT DOCUMENTS

WO    WO 2011/091305    7/2011

OTHER PUBLICATIONS

Costa et al. (Journal of Cellular Physiology 168: 737-744, 1996).*
He et al., "Differential expression of Axl in hepatocellular carcinoma and correlation with tumor lymphatic metastasis," *Molecular Carcinogenesis*, 49:882-891, 2010.
Lee et al., "Gas6/axl pathway promotes tumor invasion through the transcriptional activation of slug in hepatocellular carcinoma," *Carcinogenesis*, 35(4):769-775, 2014.
Li et al., "Axl glycosylation mediates tumor cell proliferation, invasion and lymphatic metastasis in murine hepatocellular carcinoma," *World Journal of Gastroenterology*, 18(38):5369-5376, 2012.
PCT International Preliminary Report on Patentability issued in International Application No. PCT/EP2015/055724, dated Sep. 29, 2016.
PCT International Search Report and Written Opinion issued in International Application No. PCT/EP2015/055724, dated May 20, 2015.

* cited by examiner

*Primary Examiner* — Alana Harris Dent
(74) *Attorney, Agent, or Firm* — Parker Highlander PLLC

(57) ABSTRACT

The present invention relates to a method for assessing whether a patient suffers from cancer, such as hepatocellular carcinoma, or is prone to suffering from cancer, such as hepatocellular carcinoma, wherein said method comprises determining the amount of soluble AXL in a sample from the patient. The patient is assessed to suffer from cancer or to be prone to suffering from cancer when the amount of soluble AXL is increased in comparison to a control. The present invention relates to the use of soluble AXL for assessing whether a patient suffers from cancer, such as hepatocellular carcinoma, or is prone to suffering from cancer, such as hepatocellular carcinoma. Also a kit for use in the methods of the present invention is provided.

16 Claims, 28 Drawing Sheets

Specification includes a Sequence Listing.

FIGS. 4A-B
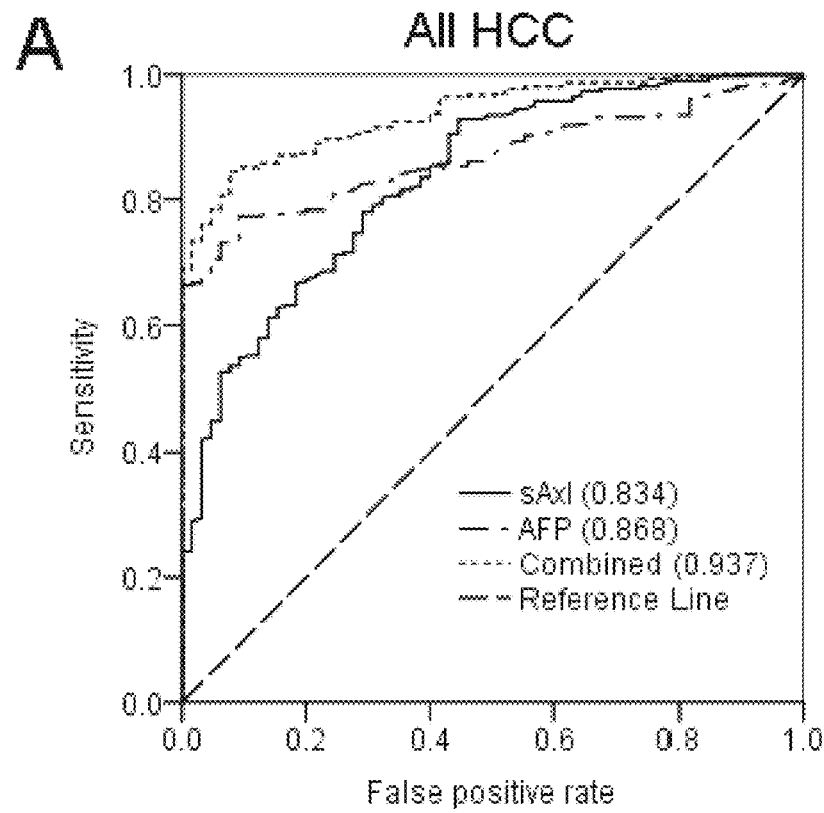
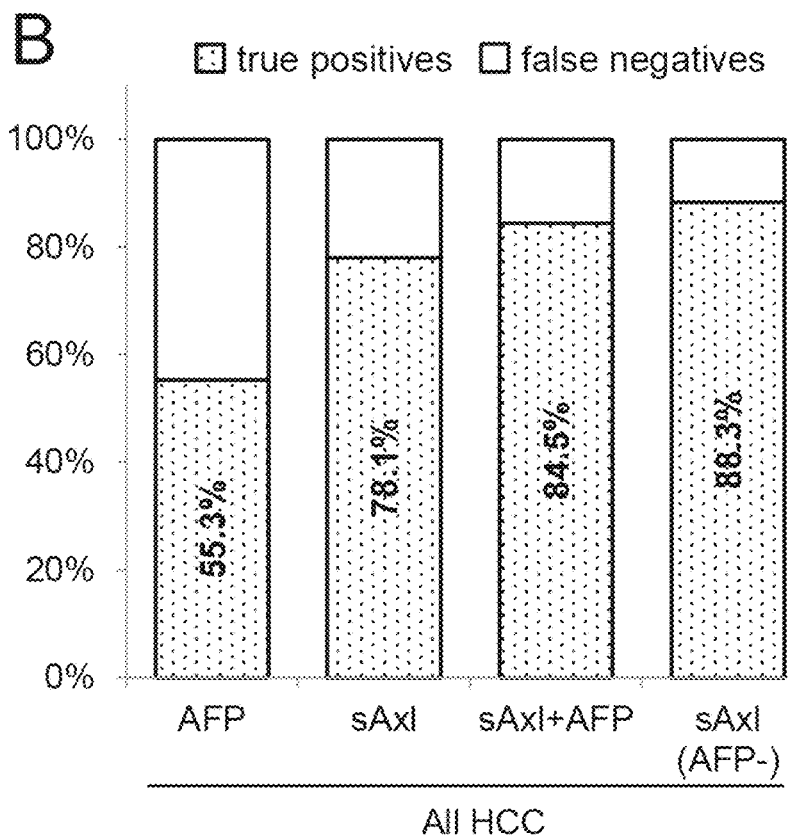

FIGS. 4C-D
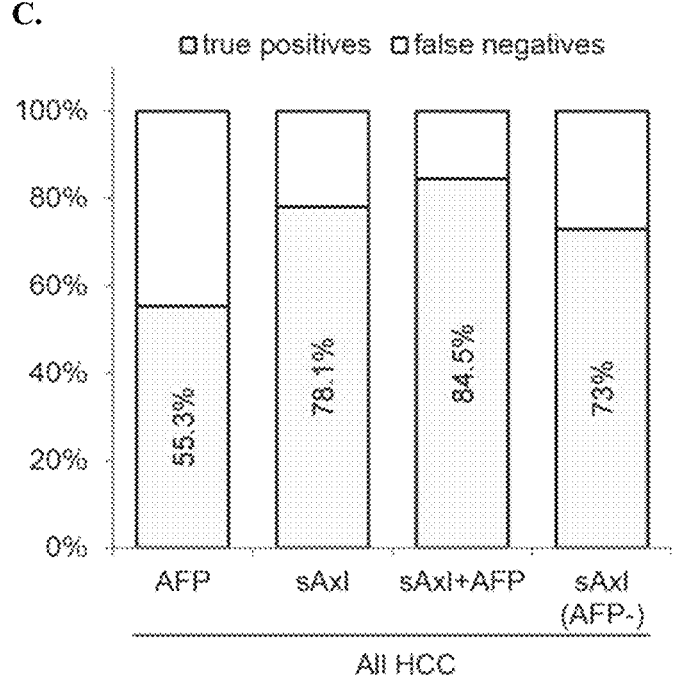
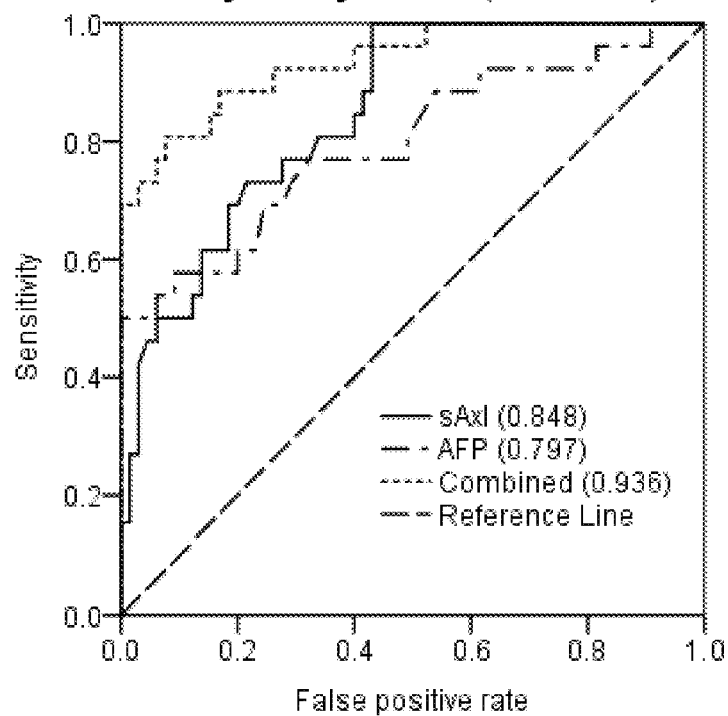

FIGS. 4E-F
E.
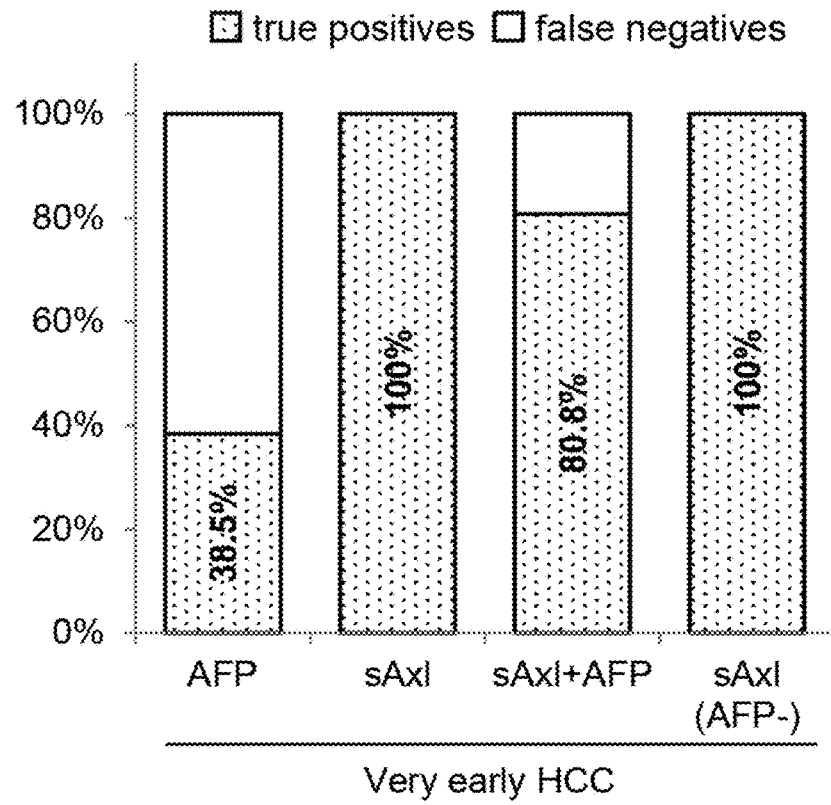
F.
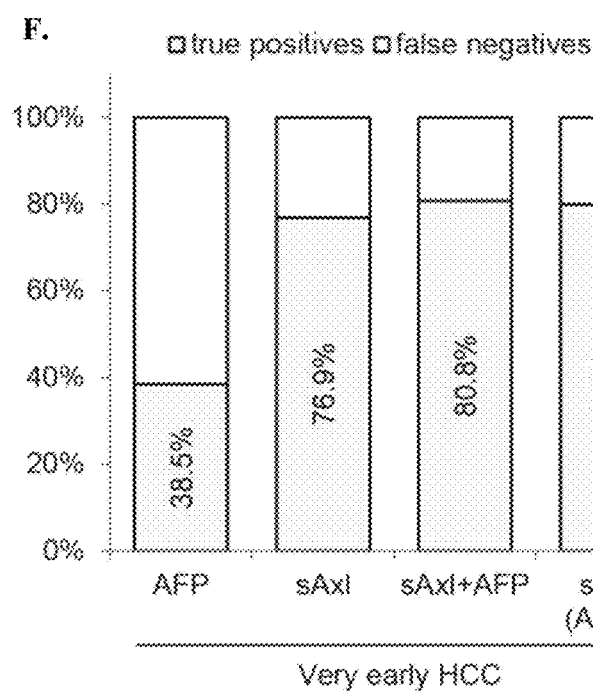

FIGS. 4G-H
G.
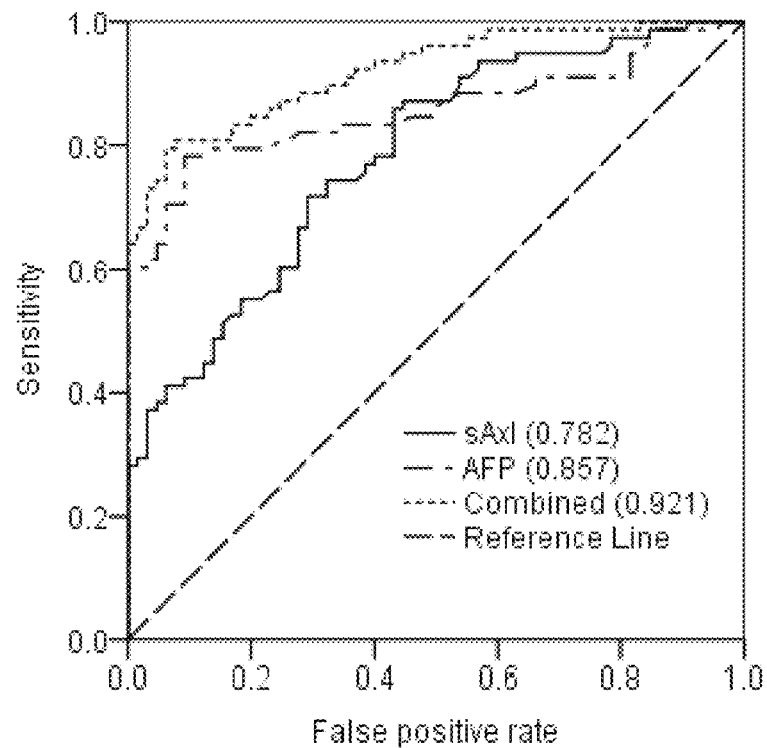
H.
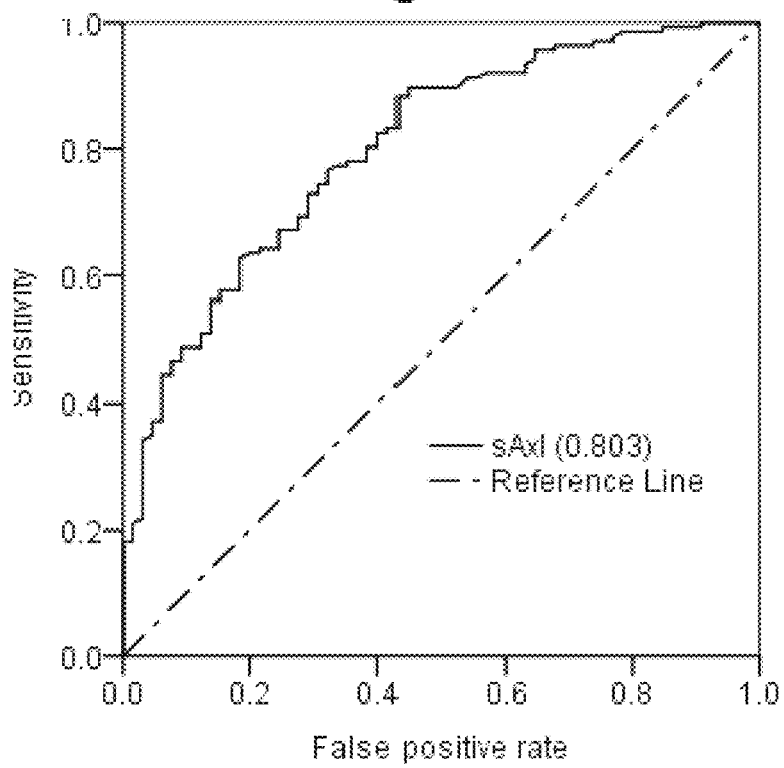

FIGS. 5A-B
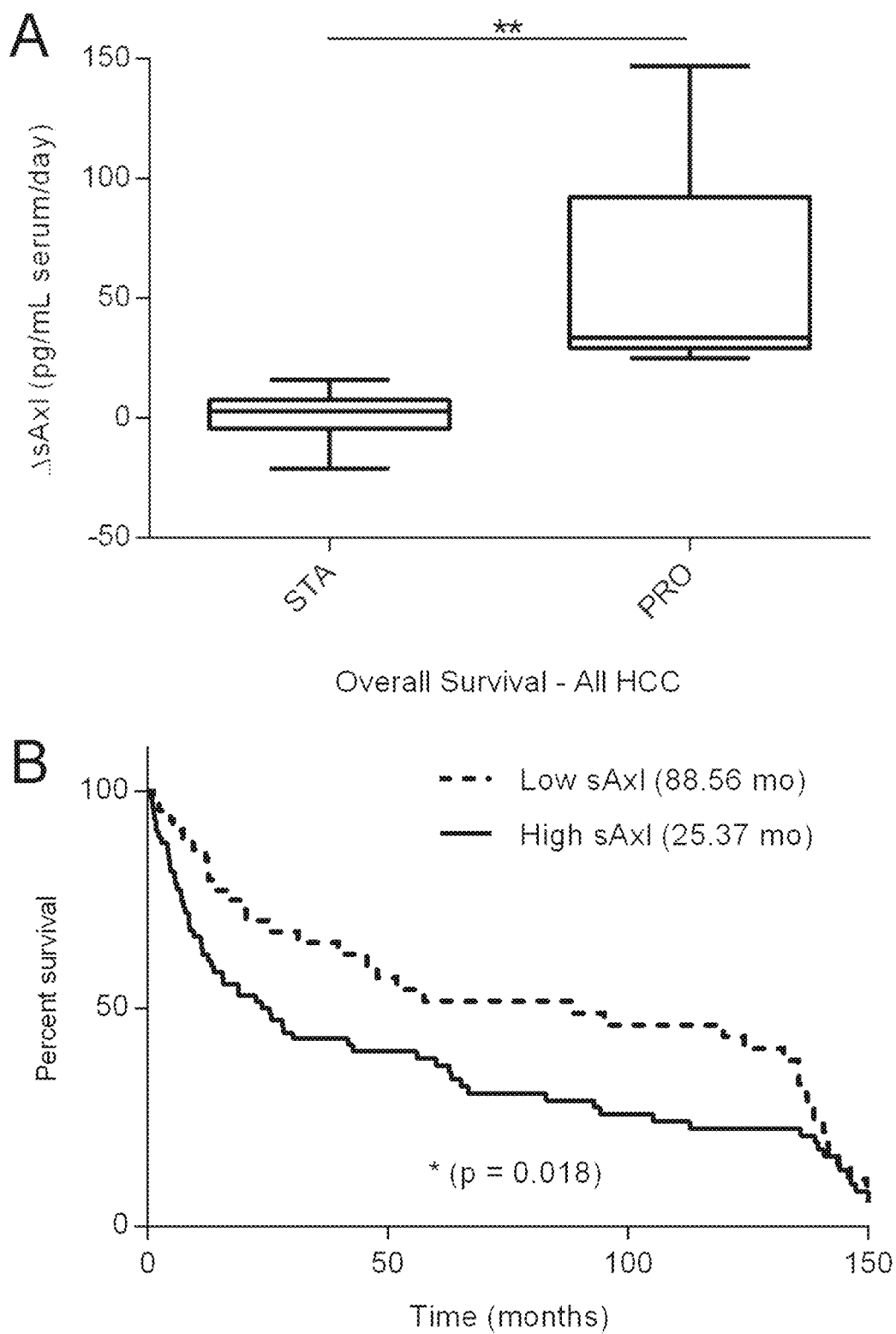

Figure 8A:
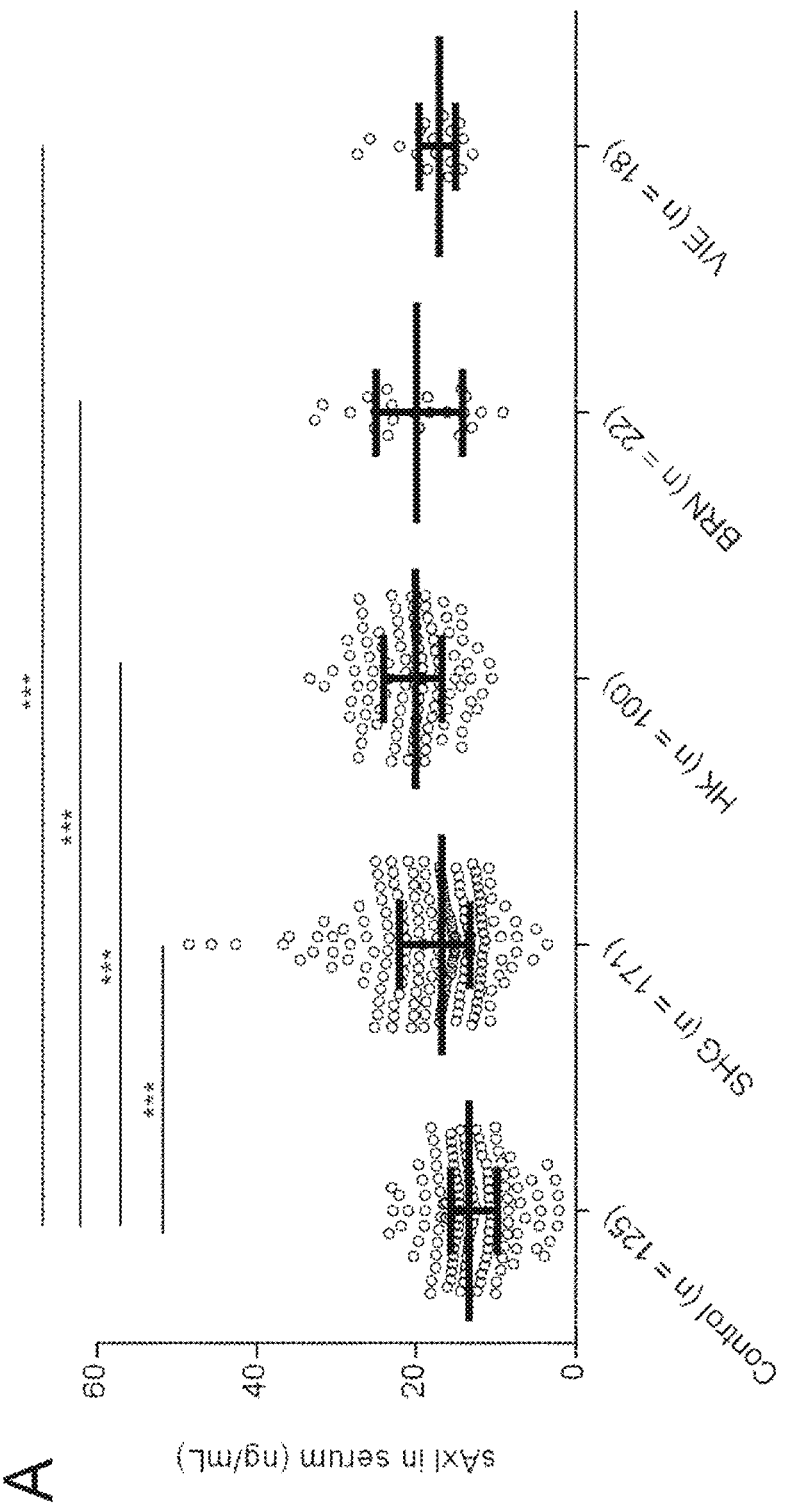

FIGS. 8B-C
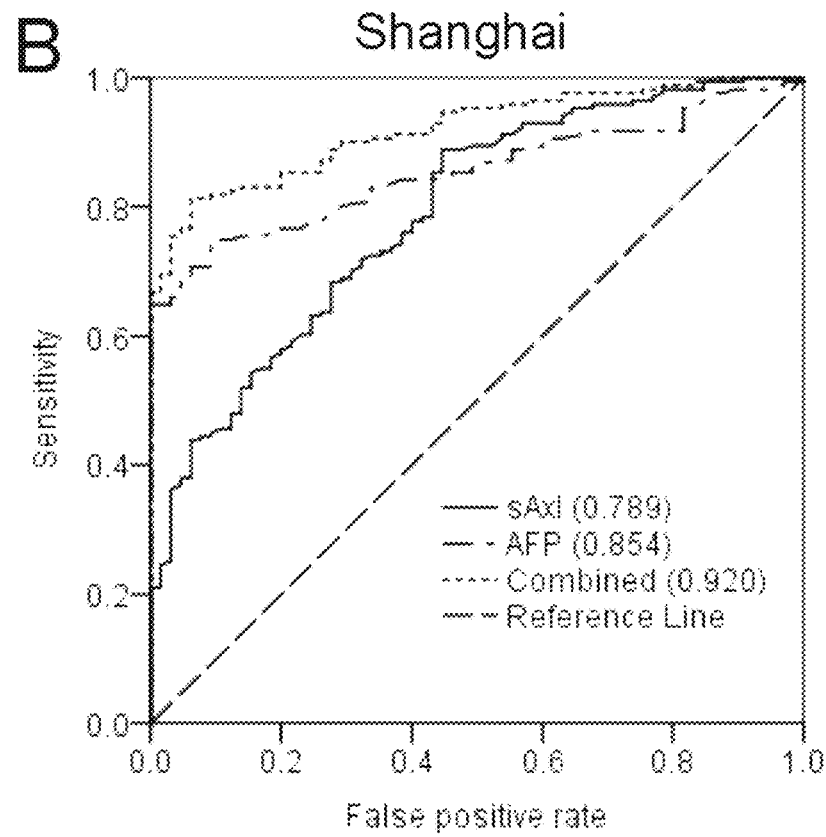
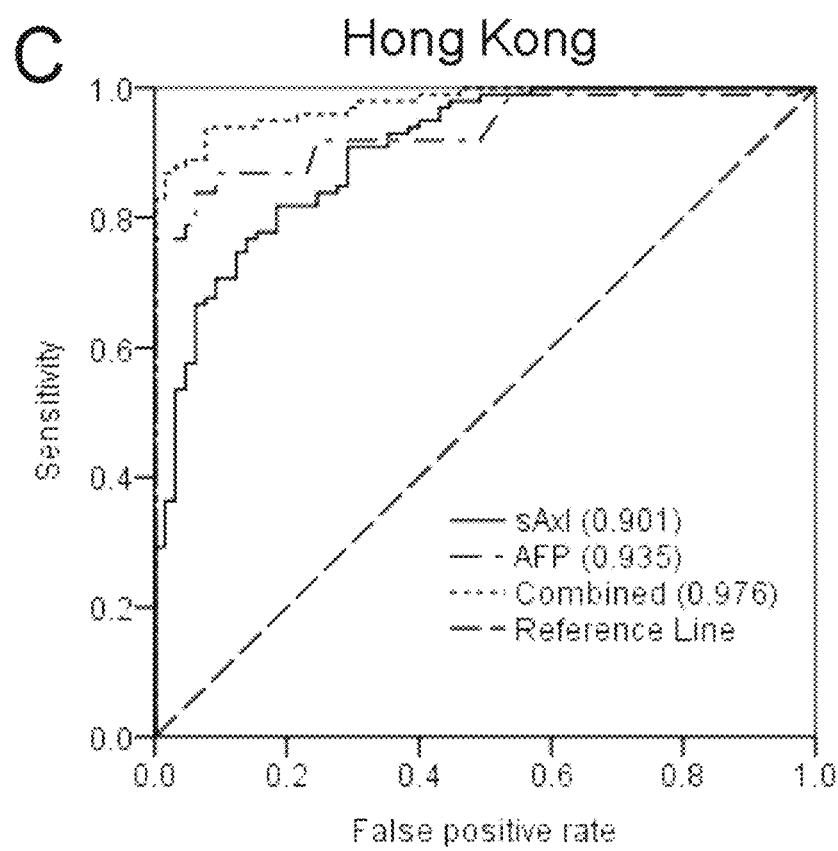

FIGS. 8D-E
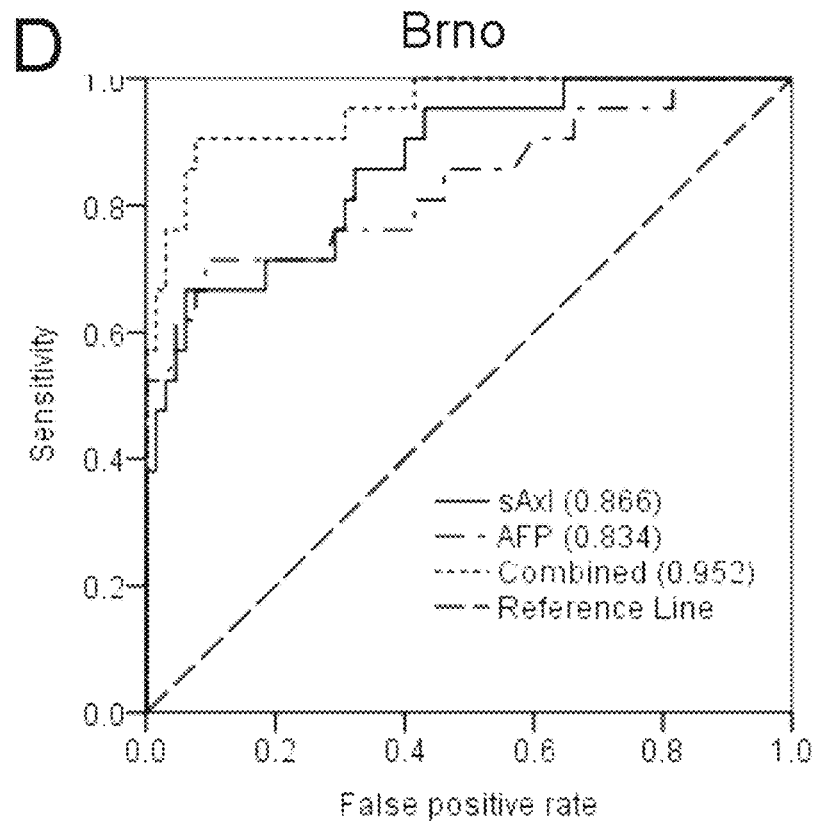
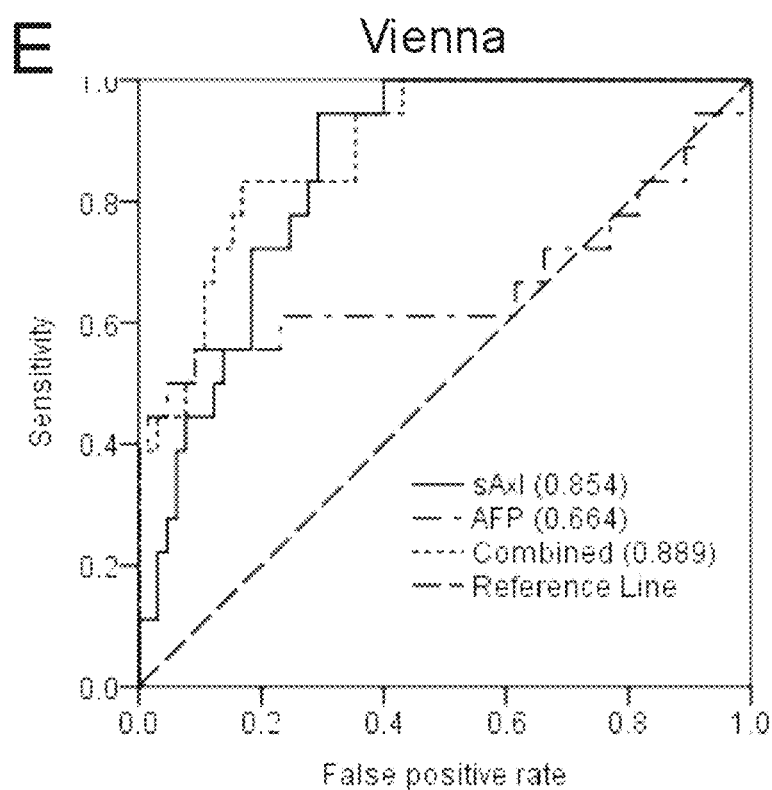

FIGS. 10A-D
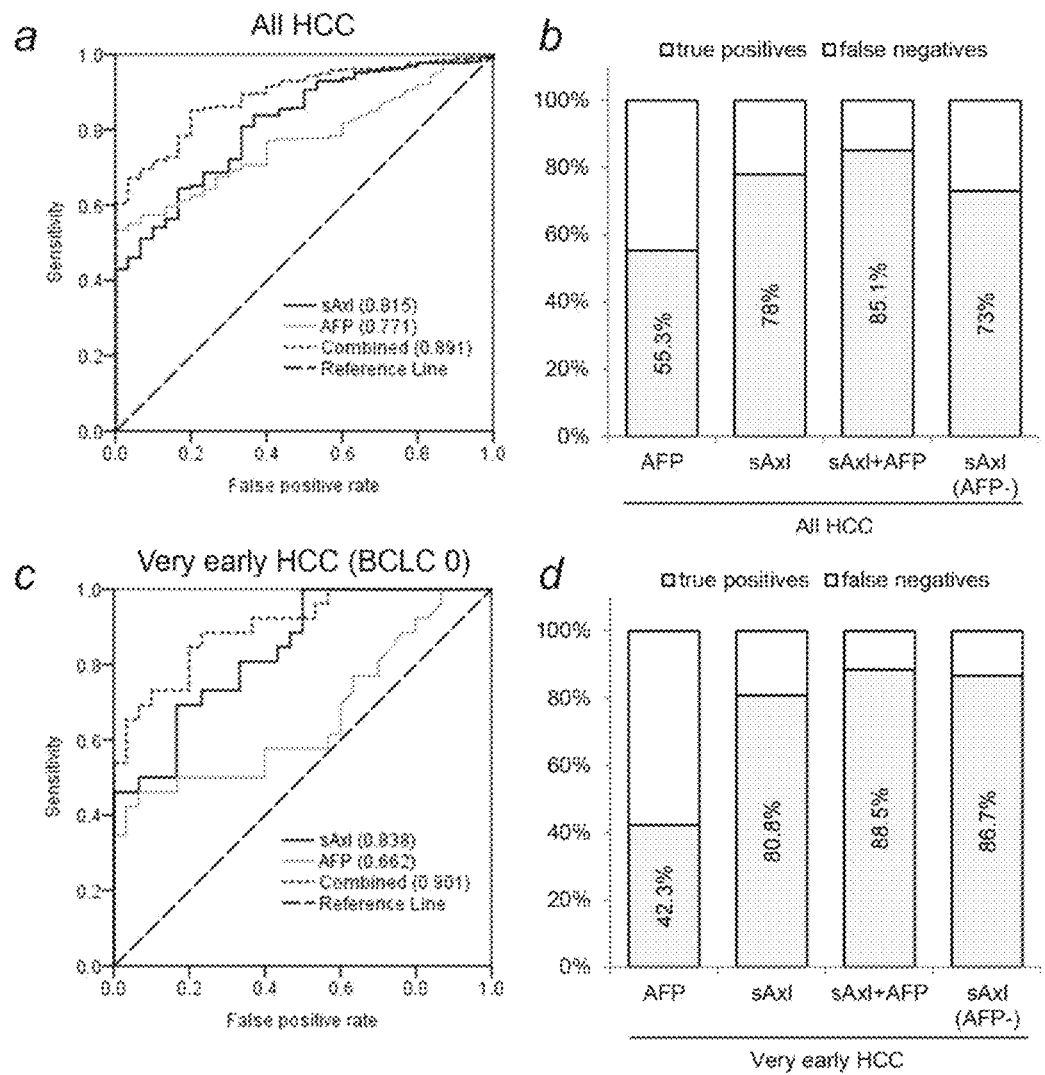

FIGS. 11A-B
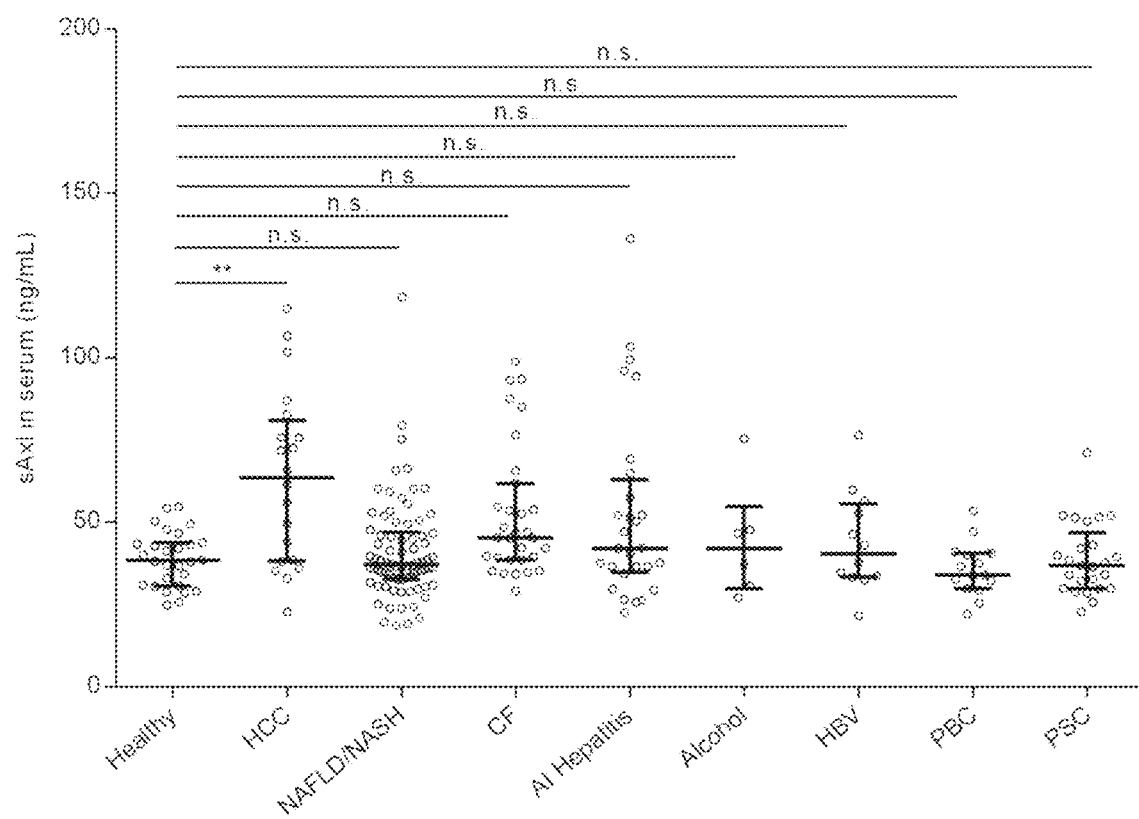
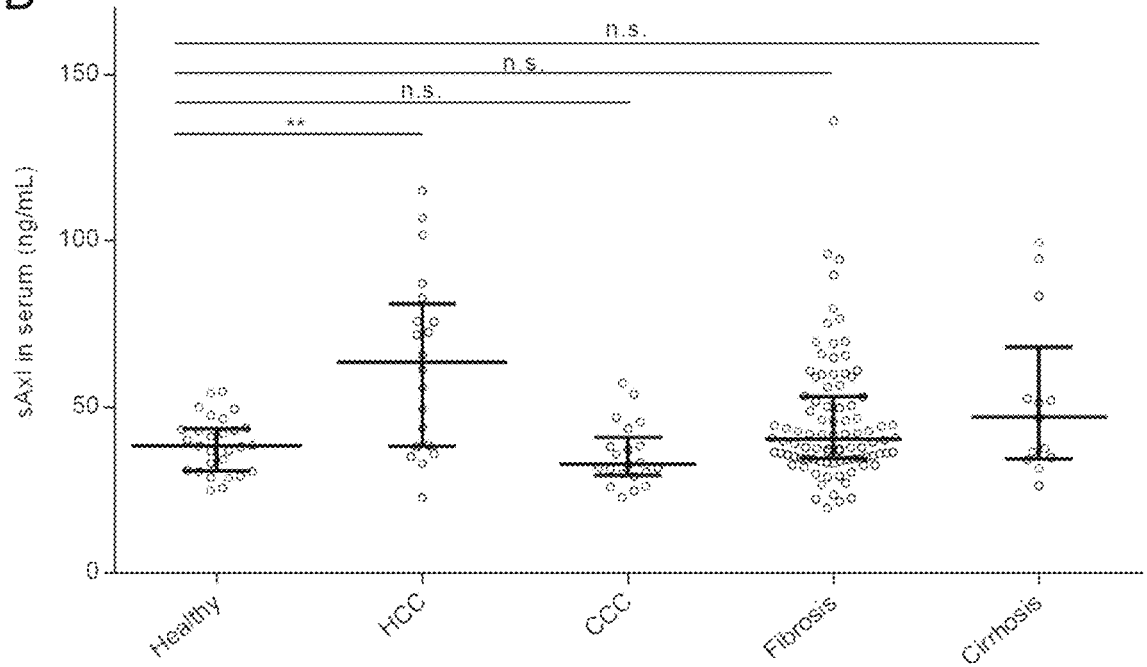

FIGS. 12A-B
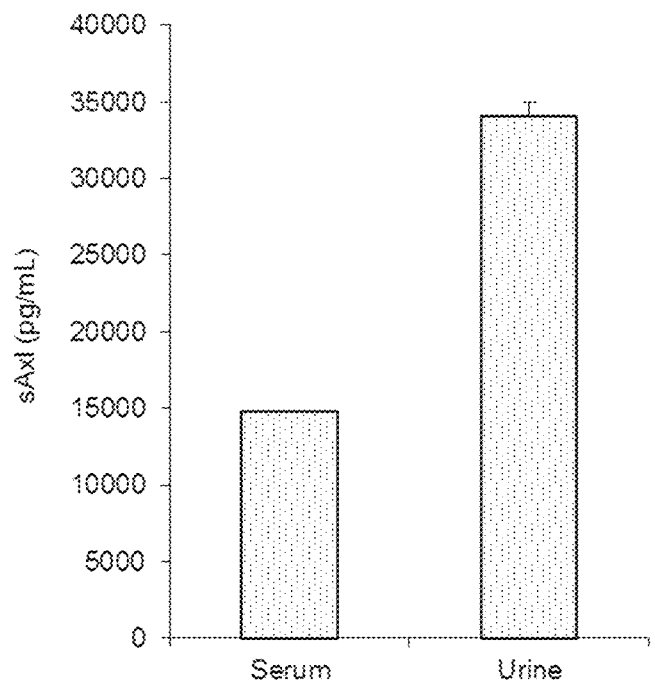
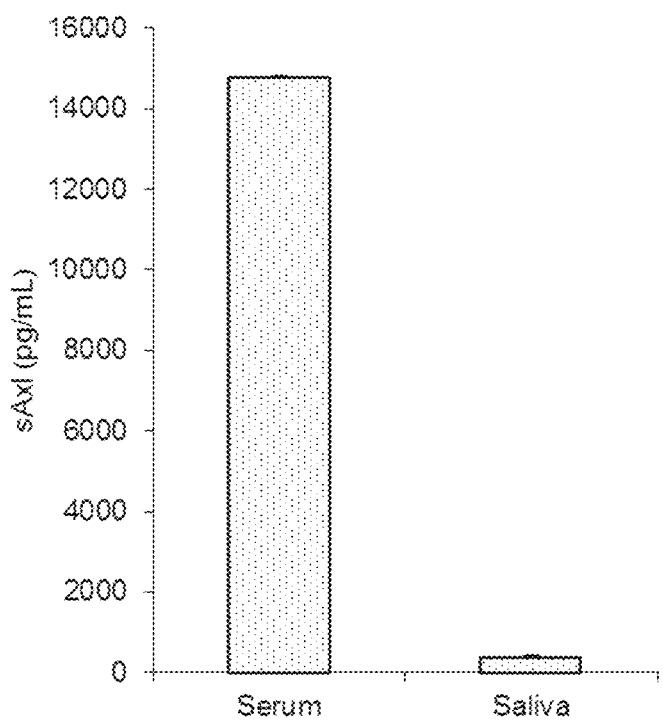

FIGS. 13A-C
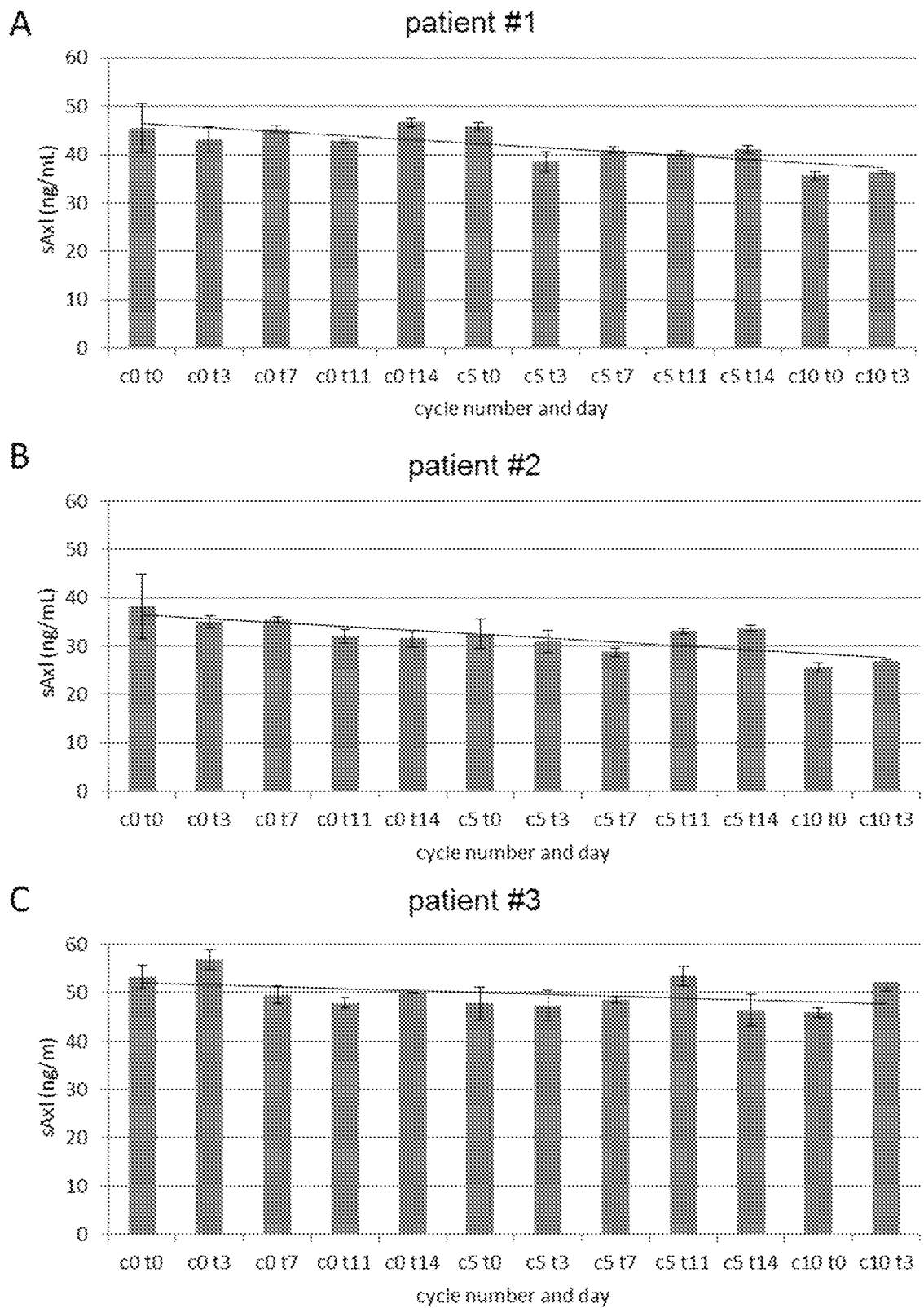

SOLUBLE AXL RECEPTOR TYROSINE KINASE IN THE DIAGNOSIS OF CANCER

This application is a national phase application under 35 U.S.C. § 371 of International Application No. PCT/EP2015/055724, filed Mar. 18, 2015, which claims priority to European Application No. 14160589.9, filed Mar. 18, 2014, the entire contents of each of which are incorporated herein by reference.

The present invention relates to a method for assessing whether a patient suffers from cancer, such as hepatocellular carcinoma, or is prone to suffering from cancer, such as hepatocellular carcinoma, wherein said method comprises determining the amount of soluble AXL receptor tyrosine kinase (soluble AXL, sAXL) in a sample from the patient. The patient is assessed to suffer from cancer or to be prone to suffering from cancer when the amount of soluble AXL is increased in comparison to a control. The present invention relates to the use of soluble AXL for assessing whether a patient suffers from cancer, such as hepatocellular carcinoma, or is prone to suffering from cancer, such as hepatocellular carcinoma. Also a kit for use in the methods of the present invention is provided.

Hepatocellular carcinoma (HCC) is the most frequently diagnosed liver malignancy and the third most common cause of cancer-related mortality worldwide (Ferlay J. (2008) Int J Cancer, 127:2893-2917). Even though patients with early HCC achieve a 5-year survival rate of 70% after liver resection or transplantation, the majority of tumors are diagnosed at advanced stages, leading to a median survival of less than 1 year (Llovet J M (1999) Hepatology 29:62-7; Singal A. G. (2010) Current Opinion in Gastroenterology 26:189-95; Altekruse S. F. (2009) Journal of Clinical Oncology 27:1485-91) If diagnosed at early stages, patients with hepatocellular carcinoma (HCC) can be subjected to favorable therapies, whereas therapeutic options at later stages are very limited. Hence, the detection of HCC in particular at an early stage by blood analysis is an urgent need.

Due to the lack of suitable biomarkers, most HCCs are undetected until they reach advanced stages, greatly reducing treatment options as compared to early stage HCC. According to the European Association for the Study of the Liver and the American Association for the Study of Liver Diseases (EASL-AASLD), liver resection and percutaneous ablation are the therapies of choice in early stage HCC these cases, avoiding the waiting period for a donor liver and leading to a high 5-year survival of 70%.[27]

Various screening procedures such as abdominal ultrasonography or measurement of serum α-fetoprotein (AFP) have been implemented for high-risk patients to detect HCC at an early stage. However, ultrasound exhibits only moderate sensitivity of 60%, which is highly dependent on operator experience. With respect to AFP, sensitivity ranges from only 25% to 65% with limited specificity (Singal A. (2009) Aliment Pharmacol Ther 30:37-47; Paul S. B. (2007) Oncology; 72 Suppl 1:117-23). Consequently, several further biomarkers have been suggested to increase the accuracy of early HCC detection, such as des-gamma carboxyprothrombin (DCP), lectin-bound AFP (AFP-L3%) and Dickkopf-1 (DKK1). Reports about the performance of these markers are conflicting and a recent study has identified DKK1 to be more sensitive as compared to AFP, DCP and AFP-L3% in detecting early HCC (Marrero J. A. (2009) Gastroenterology 137:110-8; Durazo F. A. (2008) Journal of Gastroenterology and Hepatology 23:1541-8; Shen Q. (2012) The Lancet Oncology 13:817-26). In addition, combination of AFP, DCP and AFP-L3% only modestly increases sensitivity as compared to AFP alone, with specificity being reduced. These prototypic examples highlight the need for more reliable biomarkers (Carr B. I. (2007) Digestive Diseases and Sciences 52:776-82; El-Serag H. B. (2011) Therapeutic Advances in Gastroenterology 4:5-10).

Thus, the technical problem underlying the present invention is the provision of reliable means and methods for diagnosing cancer.

The technical problem is solved by provision of the embodiments characterized in the claims.

Accordingly, the present invention relates to a method for assessing whether a patient suffers from liver cancer or is prone to suffering from liver cancer, said method comprising
  determining the amount of soluble AXL in a sample from said patient; and
  assessing that said patient suffers from liver cancer or is prone to suffering from liver cancer when the amount of soluble AXL is increased in comparison to a control.

The present invention relates to the following items:
1. A method for assessing whether a patient suffers from liver cancer or is prone to suffering from liver cancer, said method comprising
  determining the amount of soluble AXL in a sample from said patient; and
  assessing that said patient suffers from liver cancer or is prone to suffering from liver cancer when the amount of soluble AXL is increased in comparison to a control.
2. The method of item 1, wherein said liver cancer is hepatocellular carcinoma.
3. The method of item 2, wherein said hepatocellular carcinoma is very early hepatocellular carcinoma.
4. The method of item 3, wherein said very early hepatocellular carcinoma is stage 0 hepatocellular carcinoma.
5. The method of item 2, wherein said hepatocellular carcinoma is early hepatocellular carcinoma.
6. The method of item 5, wherein said early hepatocellular carcinoma is stage A hepatocellular carcinoma.
7. The method of any one of items 2 to 6, wherein said amount of soluble AXL is at least 1.05-fold, preferably at least 1.2-fold increased in comparison to a control.
8. The method of any one of items 2 to 7, wherein said amount of soluble AXL in a sample from said patient is at least about 14 ng/ml, preferably at least about 15 ng/ml.
9. The method of any one of items 3, 4, and 7, wherein said amount of soluble AXL in a sample from said patient is about 18 ng/ml.
10. The method of any one of items 5 to 7, wherein said amount of soluble AXL in a sample from said patient is about 16 ng/ml.
11. The method of any one of items 2 to 10, wherein said amount of soluble AXL in a control is about 13 ng/ml.
12. The method of item 2, wherein said hepatocellular carcinoma is advanced hepatocellular carcinoma.
13. The method of item 12, wherein said advanced hepatocellular carcinoma is stage B, C or D hepatocellular carcinoma.
14. The method of item 12 or 13, wherein said amount of soluble AXL is at least 1.2-fold increased in comparison to a control.
15. The method of any one of items 12 to 14, wherein said amount of soluble AXL in a sample from said patient is higher than about 18 ng/ml.
16. The method of any one of items 12 to 15, wherein said amount of soluble AXL in a control is about 13 ng/ml.
17. The method of any one of items 1 to 16, wherein said patient has one or more risk factors.

18. The method of item 17, wherein said one or more risk factor is one or more of hepatitis B, hepatitis C, cirrhosis of the liver, alcoholism and/or smoking.
19. The method of item 17 or item 18, wherein said one or more risk factor is one or more of overweight, obesity, type 2 diabetes, metabolic syndrome, aflatoxin, hemochromatosis and/or Wilson's disease.
20. The method of any one of items 1 to 19, wherein said method further comprises assessing the amount of alpha-fetoprotein (AFP) in a sample from said patient.
21. The method of item 20, wherein said patient is assessed to suffer from liver cancer or is prone to suffering from liver cancer when the amount of alpha-fetoprotein (AFP) is above a threshold value.
22. The method of item 20 or 21, wherein said amount of alpha-fetoprotein (AFP) in a sample from said patient is higher than about 20 ng/ml.
23. The method of item 20, wherein the amount of alpha-fetoprotein (AFP) is below a threshold value.
24. The method of item 20 or 23, wherein said amount of alpha-fetoprotein (AFP) in a sample from said patient is lower than about 20 ng/ml.
25. The method of any one of items 1 to 24, wherein soluble AXL is selected from the group consisting of
    (a) a polypeptide comprising an amino acid encoded by a nucleic acid molecule having the nucleic acid sequence as depicted in SEQ ID NO: 3;
    (b) a polypeptide having an amino acid sequence as depicted in SEQ ID NO:4;
    (c) a polypeptide encoded by a nucleic acid molecule encoding a peptide having an amino acid sequence as depicted in SEQ ID NO:4;
    (d) a polypeptide comprising an amino acid encoded by a nucleic acid molecule hybridizing under stringent conditions to the complementary strand of nucleic acid molecules as defined in (a) or (c);
    (e) a polypeptide having at least 70% identity to the polypeptide of any one of (a) to (d); and
    (f) a polypeptide comprising an amino acid encoded by a nucleic acid molecule being degenerate as a result of the genetic code to the nucleotide sequence of a nucleic acid molecule as defined in (a), (c) and (d).
26. The method of any one of items 20 to 25, wherein AFP is selected from the group consisting of
    (a) a polypeptide comprising an amino acid encoded by a nucleic acid molecule having the nucleic acid sequence as depicted in SEQ ID NO: 5;
    (b) a polypeptide having an amino acid sequence as depicted in SEQ ID NO:6;
    (c) a polypeptide encoded by a nucleic acid molecule encoding a peptide having an amino acid sequence as depicted in SEQ ID NO:6;
    (d) a polypeptide comprising an amino acid encoded by a nucleic acid molecule hybridizing under stringent conditions to the complementary strand of nucleic acid molecules as defined in (a) or (c);
    (e) a polypeptide having at least 70% identity to the polypeptide of any one of (a) to (d); and
    (f) a polypeptide comprising an amino acid encoded by a nucleic acid molecule being degenerate as a result of the genetic code to the nucleotide sequence of a nucleic acid molecule as defined in (a), (c) and (d).
27. The method of any one of items 1 to 26, wherein said method further comprises assessing the amount of Dickkopf-1 (DKK-1) in a sample from said patient.
28. The method of item 27, wherein said patient is assessed to suffer from liver cancer or is prone to suffering from liver cancer when the amount of Dickkopf-1 (DKK-1) is above a threshold value.
29. The method of item 27 or 28, wherein DKK-1 is selected from the group consisting of (a) a polypeptide comprising an amino acid encoded by a nucleic acid molecule having the nucleic acid sequence as depicted in SEQ ID NO: 7;
    (b) a polypeptide having an amino acid sequence as depicted in SEQ ID NO:8;
    (c) a polypeptide encoded by a nucleic acid molecule encoding a peptide having an amino acid sequence as depicted in SEQ ID NO:8;
    (d) a polypeptide comprising an amino acid encoded by a nucleic acid molecule hybridizing under stringent conditions to the complementary strand of nucleic acid molecules as defined in (a) or (c);
    (e) a polypeptide having at least 70% identity to the polypeptide of any one of (a) to (d); and
    (f) a polypeptide comprising an amino acid encoded by a nucleic acid molecule being degenerate as a result of the genetic code to the nucleotide sequence of a nucleic acid molecule as defined in (a), (c) and (d).
30. The method of any one of items 1 to 29, wherein said sample is a blood sample.
31. The method of item 30, wherein said blood sample is a serum sample, a plasma sample or a peripheral blood sample.
32. The method of item 30, wherein said blood sample is serum.
33. The method of any one of items 1 to 32, wherein the amount of said one or more of soluble AXL, AFP and/or DKK-1 is determined by protein detection/quantifying techniques like Enzyme-linked immunosorbent assay (ELISA), immunohistochemistry (IHC), by immunoassay, gel- or blot-based methods, IHC, mass spectrometry, flow cytometry, or FACS.
34. The method of any one of items 1 to 32, wherein the amount of said one or more of soluble AXL, AFP and/or DKK-1 is determined by ELISA.
35. The method of any one of items 1 to 34, wherein the control is a control sample.
36. The method of item 35, wherein the control sample is a sample from a healthy person or from a hepatic fibrosis or from a liver cirrhosis patient.
37. The method of any one of items 1 to 36, wherein the sample to be assessed is diluted 1:10.
38. The method of item 37, wherein the sample to be assessed is diluted in phosphate buffered saline buffer.
39. The method of item 36 or 37, wherein the sample to be assessed is diluted in phosphate buffered saline buffer supplemented with 1% bovine serum albumin.
40. The method of any one of items 1, 2 and 17 to 36, wherein the sample to be assessed is diluted 1:50.
41. The method of item 40, wherein the sample to be assessed is diluted in phosphate buffered saline buffer.
42. The method of item 40 or 41, wherein the sample to be assessed is diluted in phosphate buffered saline buffer supplemented with 1% bovine serum albumin.
43. The method of any one of items 1, 2 and 17 to 42, wherein said amount of soluble AXL is at least 1.05-fold, preferably at least 1.2-fold, at least 1.3-fold, at least 1.4-fold, at least 1.5-fold, more preferably at least 1.6-fold increased in comparison to a control.

44. The method of any one of items 1, 2 and 17 to 43, wherein said amount of soluble AXL in a sample from said patient is at least about 63 ng/ml, particularly about 63.44 ng/ml.
45. The method of any one of items 1, 2 and 17 to 44, wherein said amount of soluble AXL in a control is about 38 ng/ml, particularly about 38.33 ng/ml.
46. The method of any one of items 1 to 45, wherein said patient is a human patient.
47. Kit for use in the method according to any one of items 1 to 46.
48. Kit of item 47, comprising a binding molecule specifically binding to soluble AXL, a binding molecule specifically binding to AFP and/or a binding molecule specifically binding to DKK-1.
49. The kit of item 48, wherein said binding molecule is an antibody.
50. A binding molecule, such as antibody, for use in the method according to any one of items 1 to 46.
51. A method of assessing a prognosis of a patient, said method comprising
    determining in a sample from said patient the amount of sAXL; and
    assessing that the patient has an increased predisposition to an adverse outcome, when the amount of sAXL is increased in comparison to a control, wherein the patient suffers from liver cancer, is prone to suffering from liver cancer or is suspected of suffering from liver cancer.
52. The method of item 51, wherein said liver cancer is hepatocellular carcinoma.
53. The method of item 52, wherein said hepatocellular carcinoma is advanced hepatocellular carcinoma.
54. The method of item 53, wherein said advanced hepatocellular carcinoma is stage B, C or D hepatocellular carcinoma.
55. The method of any one of items 51 to 54, wherein said amount of soluble AXL in a sample from said patient is higher than about 18 ng/ml.
56. The method of any one of items 51 to 55, wherein said patient has one or more risk factors.
57. The method of item 56, wherein said one or more risk factor is one or more of hepatitis B, hepatitis C, cirrhosis of the liver, alcoholism and/or smoking.
58. The method of item 56 or 57, wherein said one or more risk factor is one or more of overweight, obesity, type 2 diabetes, metabolic syndrome, aflatoxin, hemochromatosis and/or Wilson's disease.
59. The method of any one of items 51 to 58, wherein soluble AXL is selected from the group consisting of
    (a) a polypeptide comprising an amino acid encoded by a nucleic acid molecule having the nucleic acid sequence as depicted in SEQ ID NO: 3;
    (b) a polypeptide having an amino acid sequence as depicted in SEQ ID NO:4;
    (c) a polypeptide encoded by a nucleic acid molecule encoding a peptide having an amino acid sequence as depicted in SEQ ID NO:4;
    (d) a polypeptide comprising an amino acid encoded by a nucleic acid molecule hybridizing under stringent conditions to the complementary strand of nucleic acid molecules as defined in (a) or (c);
    (e) a polypeptide having at least 70% identity to the polypeptide of any one of (a) to (d); and
    (f) a polypeptide comprising an amino acid encoded by a nucleic acid molecule being degenerate as a result of the genetic code to the nucleotide sequence of a nucleic acid molecule as defined in (a), (c) and (d).
60. The method of any one of items 51 to 59, wherein the amount of soluble AXL is determined by protein detection/quantifiying techniques like ELISA (such as Sandwich ELISA), immunohistochemistry (IHC), by immunoassay, gel- or blot-based methods, IHC, mass spectrometry, flow cytometry, or FACS.
61. The method of any one of items 51 to 60, wherein said sample is a blood sample.
62. The method of item 61, wherein said blood sample is a serum sample, a plasma sample or a peripheral blood sample.
63. The method of item 61, wherein said blood sample is serum.
64. The method of any one of items 51 to 63, wherein said patient is a human patient.
65. Kit for use in the method according to any one of items 51 to 64.
66. Kit of item 65, comprising a binding molecule specifically binding to soluble AXL.
67. The kit of item 66, wherein said binding molecule is an antibody.
68. A binding molecule, such as antibody, for use in the in the method according to any one of items 51 to 64.
69. Use of sAXL or of an antibody specifically binding thereto in the diagnosis of liver cancer.
70. Use of sAXL or of an antibody specifically binding thereto for the preparation of a diagnostic kit for use in the diagnosis of liver cancer.
71. The use of sAXL or of an antibody specifically binding thereto according to item 69 or 70, wherein said liver cancer is hepatocellular carcinoma (HCC).

The present invention relates to a method for assessing whether a patient suffers from liver cancer or is prone to suffering from liver cancer, said method comprising
    determining the amount of soluble AXL in a sample from said patient; and
    assessing that said patient suffers from liver cancer or is prone to suffering from liver cancer when the amount of soluble AXL is increased in comparison to a control.

The herein provided method may, optionally, comprise a step of obtaining a sample from the patient.

Thus, the present invention relates to a method for assessing whether a patient suffers from liver cancer or is prone to suffering from liver cancer, said method comprising
    obtaining a sample from said patient;
    determining the amount of soluble AXL in said sample from said patient; and
    assessing that said patient suffers from liver cancer or is prone to suffering from liver cancer when the amount of soluble AXL is increased in comparison to a control.

In accordance with the above, the present invention relates to the use of soluble AXL (optionally in combination with AFP and/or DKK-1) for assessing whether a patient suffers from liver or is prone to suffering from liver cancer. All explanations and definitions provided herein in relation to "diagnosing liver cancer" (assessing whether a patient suffers from liver or is prone to suffering from liver cancer) apply mutatis mutandis in this context. In other words, the present invention relates to the use of sAXL or of an antibody specifically binding thereto in the diagnosis of liver cancer. The present invention relates to the use of sAXL or of an antibody specifically binding thereto for the preparation of a diagnostic kit for use in the diagnosis of liver cancer.

Preferably, the liver cancer is hepatocellular carcinoma (HCC). The term "hepatocellular carcinoma" and "HCC" are used interchangeably herein.

In a preferred embodiment, the present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL is increased in comparison to a control.

The present invention solves the above identified technical problem; see Example 1. As documented herein below and in the appended example, it was surprisingly found that soluble AXL receptor tyrosine kinase (sAXL) is an excellent biomarker of cancer, in particular hepatocellular carcinoma, such as early HCC. The terms "soluble AXL", "sAXL", "soluble AXL receptor tyrosine kinase" and the like are used interchangeably herein.

An increase in soluble AXL indicates that a patient suffers from liver cancer or is prone to suffering from liver cancer, as shown in the appended example.

Figure 1A:
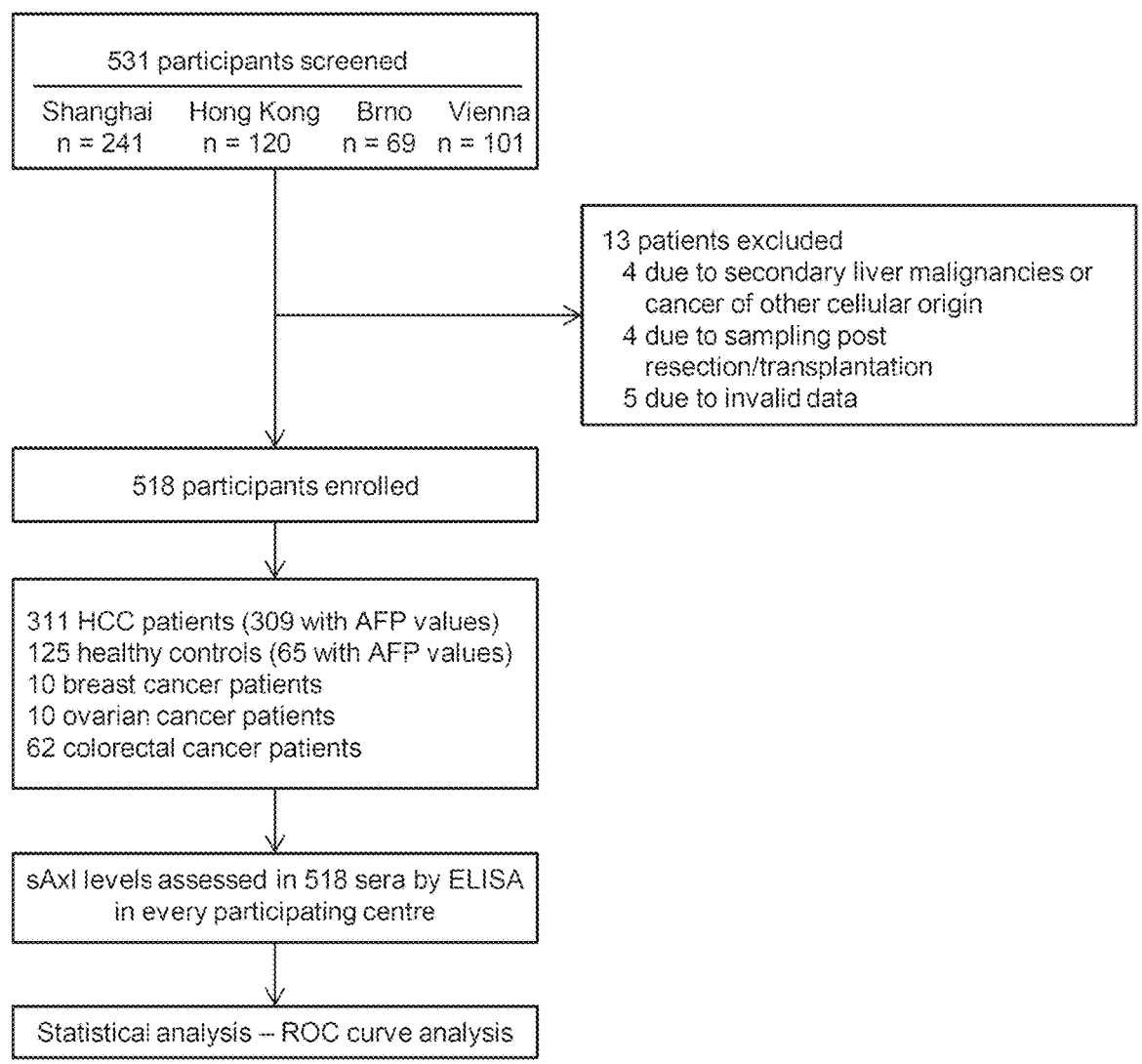
Figure 1B:
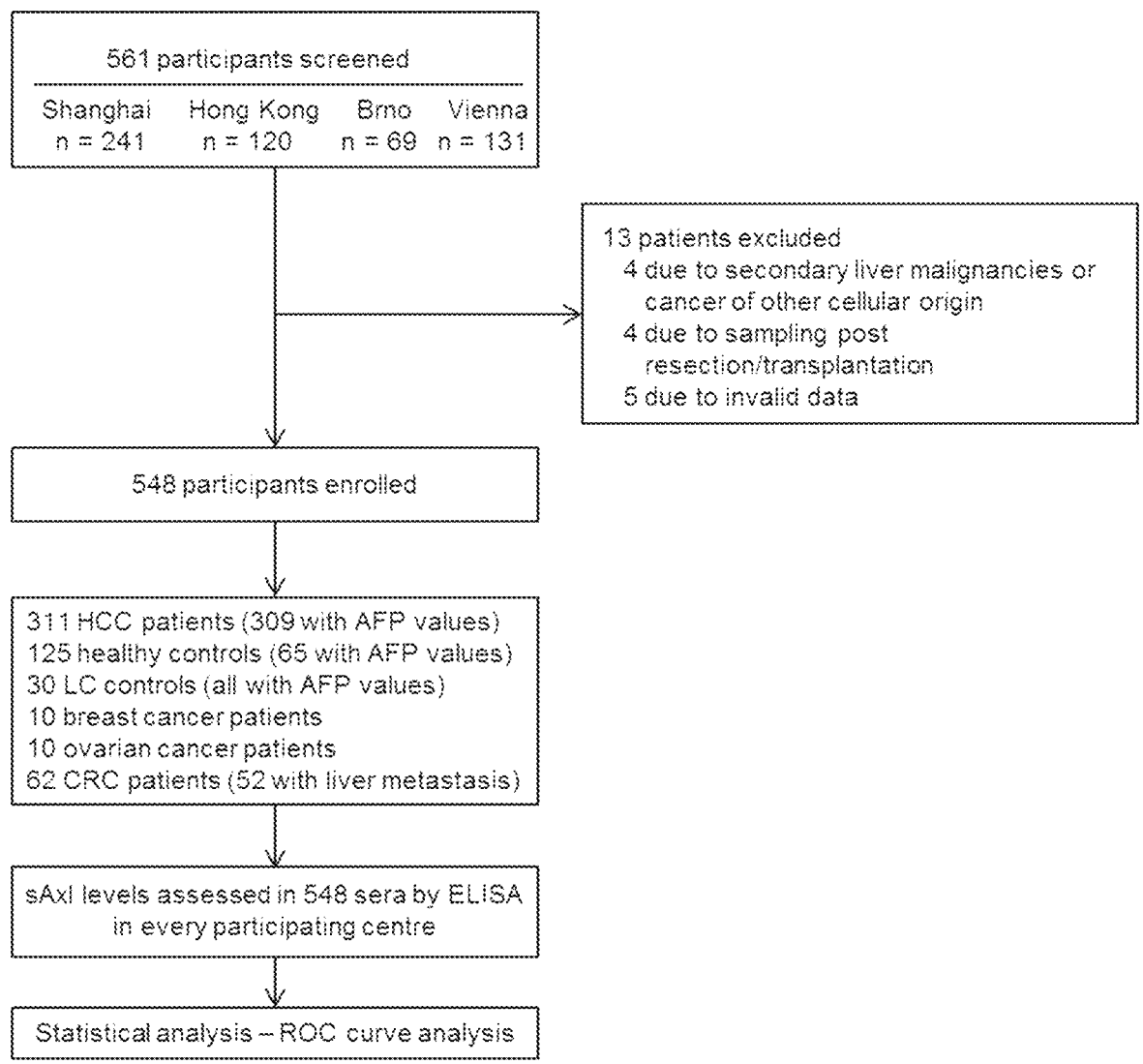

Example 1 shows the results of extensive clinical studies with participants from centers in Austria, the Czech Republic and China. Thus, the diagnostic accuracy of sAXL in a large-scale study, including patients from four different cancer centers located in Europe and Asia was assessed. 518 participants were enrolled in the study presented herein (FIG. 1A). Additionally, 30 liver cirrhosis patients were included, so that in total 548 participants were enrolled in the study (FIG. 1B). Serum levels of sAXL were assessed in 311 HCC, 10 breast cancer, 10 ovarian cancer and 62 colorectal cancer patients as well as 125 healthy donors 30 liver cirrhosis patients by enzyme-linked immunosorbent assay (ELISA). Diagnostic accuracy of sAXL was assessed by receiver operating characteristics (ROC) curve analysis and compared to the known marker α-fetoprotein (AFP).

It was surprisingly found that soluble AXL receptor tyrosine kinase (sAXL) provides a reliable diagnosis of hepatocellular carcinoma (HCC). sAXL was able to detect HCC with high sensitivity and specificity, especially among very early HCC (BCLC 0) as well as AFP-negative patients. Increased sAXL was not found in other cancers or secondary hepatic malignancies, indicating that sAXL is a valuable and specific diagnostic protein biomarker, which can be included in screening procedures for HCC.

The gist of the present invention lies in the surprising finding that the amount of soluble AXL is increased in a sample from a liver cancer patient (like a HCC patient) compared to a control.

Median serum concentrations of sAXL were significantly increased in HCC (18.575 ng/mL) as compared to healthy controls (13.388 ng/mL) or liver cirrhosis controls, but not in other cancers investigated; see FIG. 2. High sAXL levels (>18.575 ng/mL) were associated with vessel invasion (p=0.045) and lymph node metastasis (p<0.001); see FIG. 3.

The diagnostic value of sAXL in HCC was assessed by comparison with the established serum marker AFP. ROC curve analysis revealed a diagnostic performance of sAXL (AUC 0.834 [0.792-0.870]) and of AFP (AUC 0.868 [0.829-0.900]) in all HCC patients. Sensitivity was higher for sAXL (78.1%) at the optimal cut-off of 14.053 ng/mL as compared to AFP (55.3%) at the clinically used cut-off of 20 ng/mL (FIG. 4A; 4B; 4C; Table 2). Again, diagnostic performance of sAXL was high across all centers included in this study (FIG. 8B-E; Shanghai, AUC 0.789 [0.727-0.852]; Hong Kong, AUC, 0.901 [0.855-0.947]; Brno, AUC 0.866 [0.777-0.955]; Vienna AUC 0.854 [0.773-0.935]).

sAXL even outperformed AFP in particular in detecting very early HCC (sAXL, AUC 0.848 [0.757-0.914]; AFP, AUC 0.797 [0.699-0.874]). Again, sensitivity of sAXL was much higher (100%) at a cut-off of 11.841 ng/mL than of AFP (38.5%; FIG. 4D; 4E; 4F; Table 2).

Almost half (45%) of all patients included in the study presented herein exhibited AFP levels below the clinically used cut-off and thus would not have been identified. In these AFP-negative patients, sAXL also shows a high performance in detecting HCC. Therefore, in AFP-negative HCC, sAXL was surprisingly also demonstrated as a valid marker for HCC detection (AUC 0.803 [0.741-0.855]; FIG. 4H) with a sensitivity of 88.3% and a specificity of 56.9% at a cut-off level of 11.841 ng/mL (FIG. 4B; Table 2), allowing to overcome the absence of the diagnostic marker AFP. Thus, sAXL allows the reliable identification of HCC patients which are diagnosed negative using AFP as marker. Among very early, AFP-negative patients, sAXL showed even higher sensitivity of 100% and specificity of 56.9% at a cut-off of 11.841 ng/mL (FIG. 4E; Table 2).

It is demonstrated herein that most cultured HCC cell lines produce sAXL and that sAXL serum levels of HCC patients are significantly higher (median 18.575 ng/mL) as compared to healthy controls (median 13.388 ng/mL; p<0.0001), indicating that HCC-derived sAXL is a major contributor to total sAXL serum concentrations (FIG. 2A, B). sAXL does not correlate with clinical parameters of HCC patients such as age, gender or HBV/HCV status (Table 1). Importantly, cirrhotic HCC do not exhibit higher sAXL concentrations as compared to non-cirrhotic patients, ruling out a possible contribution of myofibroblast-derived sAXL (Table 1). Similarly, patients suffering from breast, ovarian or colorectal cancer do not show increased sAXL levels either, further underlining a specific role of sAXL as a biomarker of HCC (FIG. 2C). Remarkably, in the case of colon cancer, where the liver is the dominant metastatic site, hepatic dissemination did not alter sAXL serum levels, allowing a clear discrimination between HCC and secondary hepatic malignancy (FIG. 2C). Tzeng (2013) Journal of gastrointestinal surgery: official journal of the Society for Surgery of the Alimentary Tract; 17:195-201; quiz p −2.

These data show that sAXL is a highly accurate and reliable diagnostic marker for HCC, in particular for very early and/or AFP-negative HCC.

Figure 9:
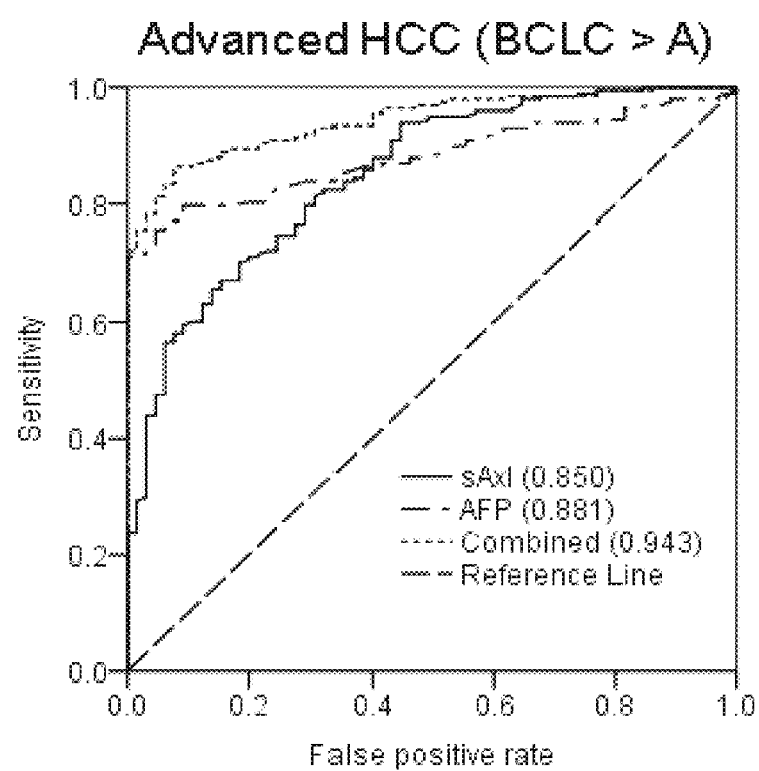

Furthermore, the data show that even better results can be obtained if the diagnostic test is performed with sAXL and one or more further markers, like AFP and or Dickkopf-1 (DKK1). Combined analysis of sAXL and AFP revealed an exceptional accuracy of 0.937 [0.907-0.959] with a sensitivity of 84.5% and a specificity of 92.3% in detecting HCC (FIG. 4A; 4B; 4C; Table 2). This was shown to be valid throughout all stages, with AUC 0.936 [0.864-0.976] in very early HCC, AUC 0.921 [0.864-0.952] in early HCC and AUC 0.943 [0.908-0.968] in advanced stage HCC (FIG. 4D, 4G and FIG. 9). Thus, the combination of both biomarkers shows exceptional accuracy (AUC 0.936; FIG. 4D, Table 2). Therefore, it is demonstrated herein that a combination of sAXL and AFP outperforms other recently proposed candidate biomarkers, most notably DKK1, in particular in detecting very early stages of HCC; see Shen (2012) The lancet oncology; 13:817-26.

Such excellent results as provided herein are surprising; as mentioned above, a combination of AFP with other markers (like DCP and AFP-L3%) only modestly increased sensitivity as compared to AFP alone, with specificity being reduced; see Carr (2007) Digestive diseases and sciences; 52:776-82; El-Serag (2011) Therapeutic advances in gastroenterology; 4:5-10.

Terms like "sensitivity", "specificity", "accuracy", "ROC", "PPV", "NPV" and the like are known in the art and used accordingly herein.

For example, "(diagnostic) sensitivity" refers generally to the percentage of persons identified by the assay as positive for the disorder among all subjects with the disorder.

"(Diagnostic) specificity" is the percentage of persons identified by the assay as negative for the disorder among all subjects without the disorder.

"Sensitivity" and "specificity" indicate the validity of a diagnostic test. "Sensitivity" indicates the probability that an individual with cancer obtains a positive test result when applying a diagnostic test. "Specificity" indicates the probability that a healthy individual obtains a negative test result when applying a diagnostic test. Thus, high "sensitivity" and "specificity" values indicate that cancer patients and healthy patients are classified correctly as "sick" and "healthy", respectively.

The diagnostic accuracy of a test represents the rate of correct classification or discrimination (no. of correct decisions/no. of cases). It is inversely correlated to the extent overlapping between the normal and diseased population, corresponding to sensitivity and specificity of a diagnostic test. In the case of ROC curves, the area under the curve expresses this overlap, without being limited to a single diagnostic threshold and is therefore are a well-established summary measure of accuracy.

The AUROC (short for "area under the ROC curve", also sometimes abbreviated as "ROC") is a parameter for the accuracy of a diagnostic test. The accuracy of the test depends on how well the test separates the group being tested into those with and without the disease. An AUROC value of 1 represents a perfect test; an AUROC value of 0.5 represents a worthless test. Thus, AUROC value that is closer to 1 indicates a better test.

Furthermore, it was found unexpectedly herein that sAXL is not only an excellent diagnostic marker, but also a prognostic marker.

Figure 3A:
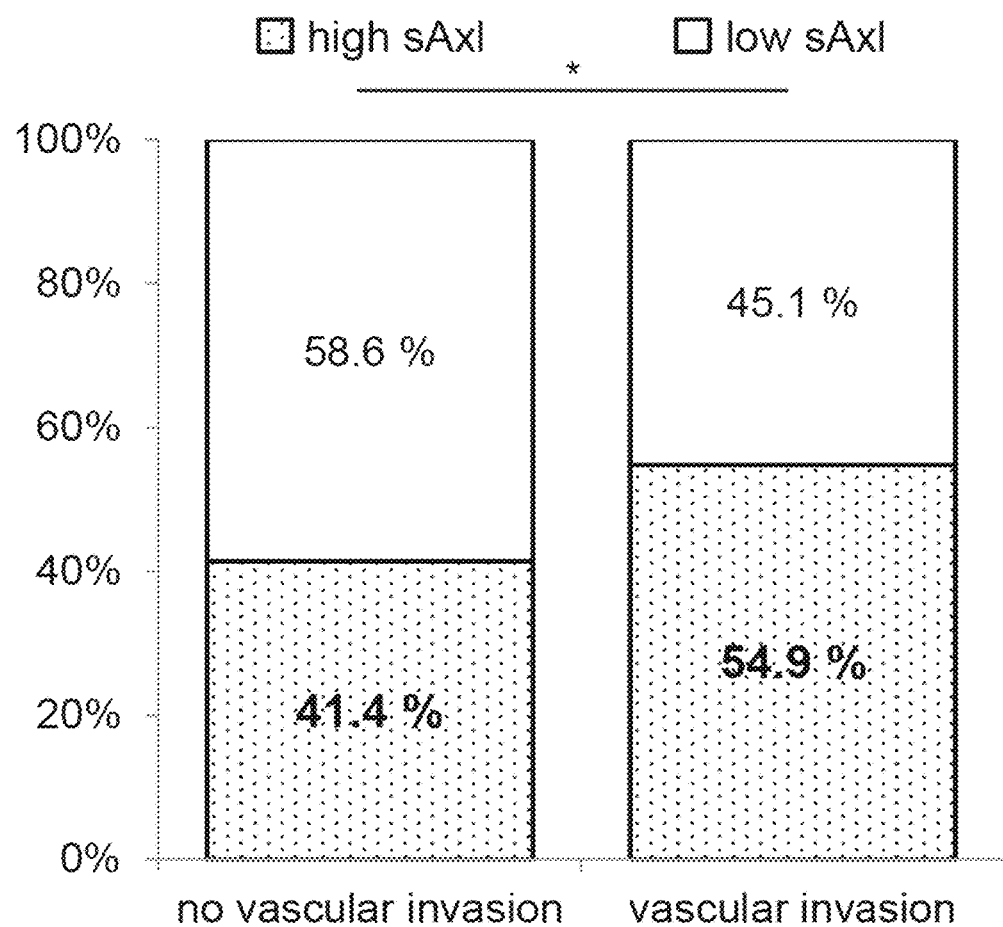
Figure 3B:
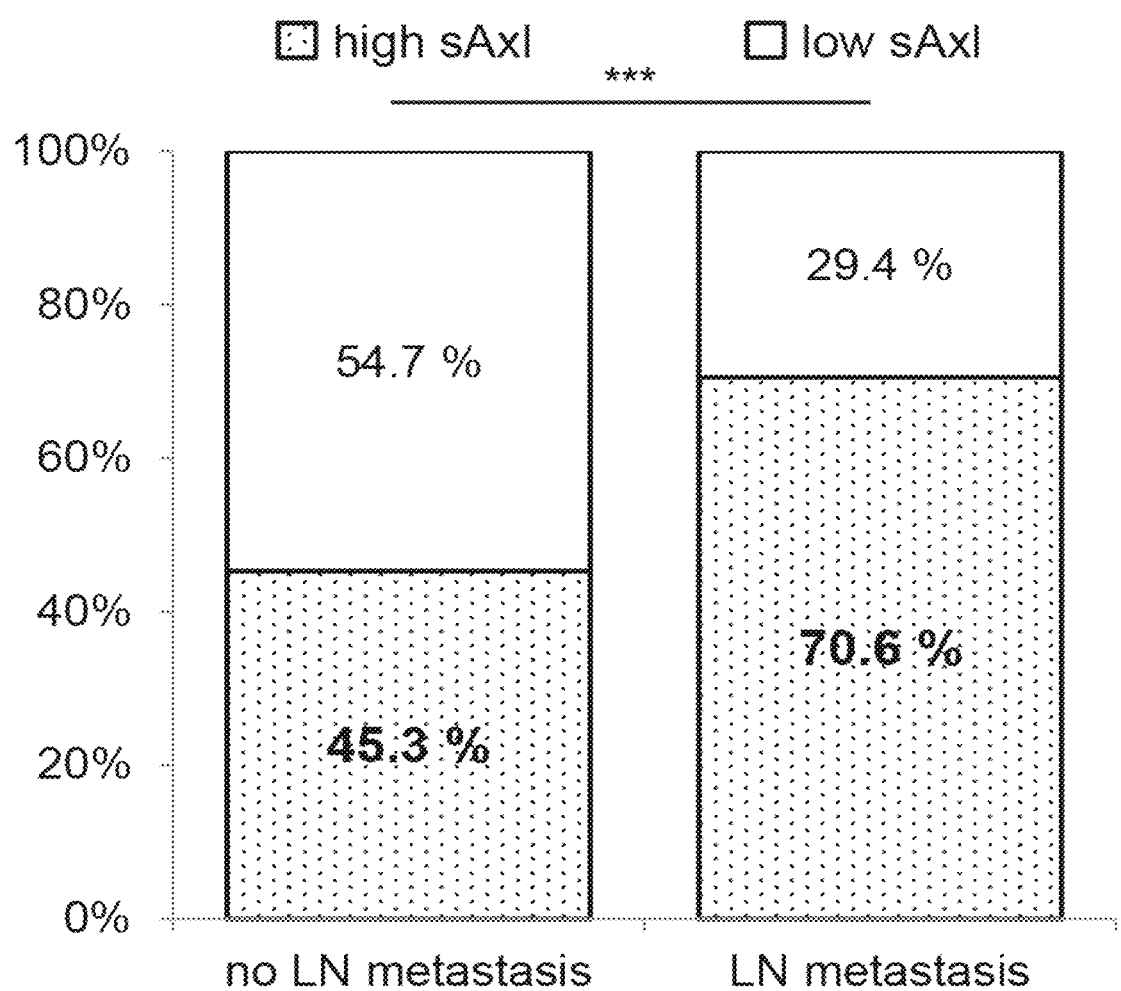
Figure 5C:
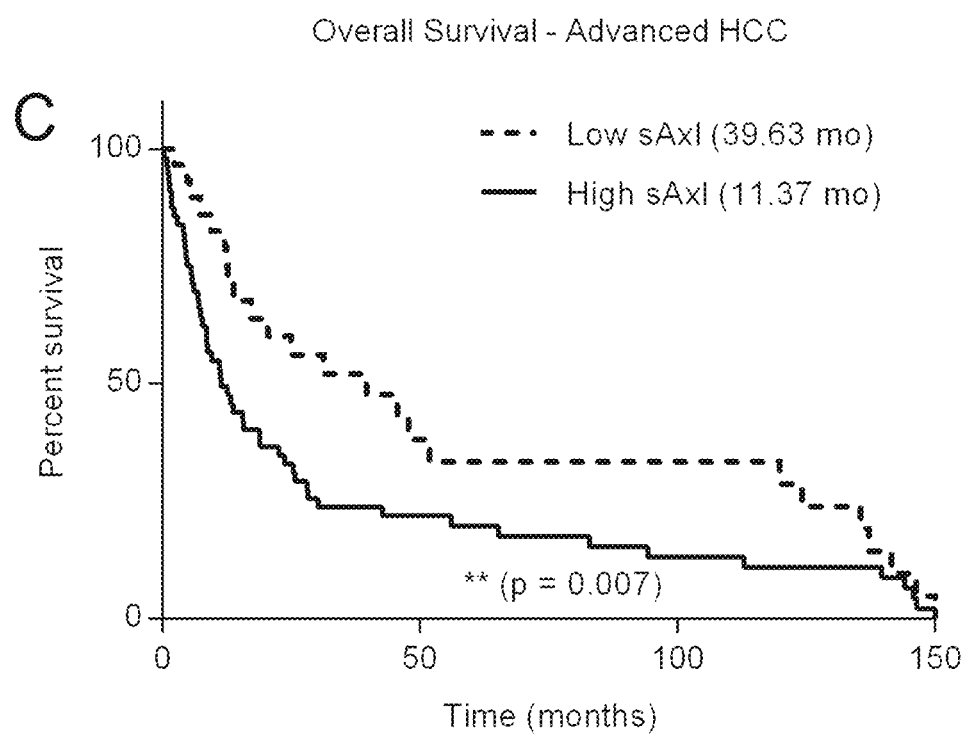

It was demonstrated herein that sAXL concentrations are slightly higher in advanced HCC cases (median 18.880 ng/mL) as compared to early HCCs (median 16.438 ng/mL), although not statistically significant. In addition, high sAXL serum concentrations (>18.575 ng/mL) are associated with vascular invasion (p=0.045; FIG. 3A; Table 1) and lymph node metastasis (p<0.001; FIG. 3B; Table 1), indicating that AXL may play an increasingly prominent role in late HCC progression and possibly in epithelial to mesenchymal transition (EMT) as well (van Zijl F. (2009). Future Oncol 5:1169-1179. Accordingly, patients exhibiting high sAXL have a decreased overall survival as compared to those showing low levels (FIGS. 5B and 5C).

A prognostic role of sAXL was addressed by analyzing samples from different time points post diagnosis of patients undergoing treatment, ranging from two months to two years. The data revealed a significantly higher rate of change of sAXL levels in patients exhibiting tumor progression (median 33.518 pg/mL/day, n=5) as compared to those showing stable disease (median 3.06 pg/mL/day, n=6, p=0.0043; FIG. 5A). Among all HCC stages, patients exhibiting high sAXL show a significantly decreased overall survival (median 25.37 mo, p=0.018) as compared to those with low sAXL serum levels (median 88.56 mo; FIG. 5B).

This decrease was even more pronounced among advanced HCC patients (high sAXL median 11.37 mo, low sAXL median 39.63 mo, p=0.007; FIG. 5C). These data suggest that sAXL levels reflect disease progression.

Summarizing the above, sAXL shows a high specificity, especially in detecting early stages of HCC, as compared to AFP alone, and a combination of sAXL and AFP further increases accuracy. Furthermore, sAXL performs well in AFP-negative HCC patients. Therefore, sAXL represents a valuable biomarker and is useful in screening procedures in particular for early HCC. In this respect, two cut-offs for sAXL in HCC screening can be used, one offering exceptional sensitivity in the detection of very early and AFP-negative HCC (about 11.841 ng/mL) and a second one—exhibiting both high sensitivity and specificity (about 14.053 ng/mL)—that is suitable for diagnostic confirmation. As sAXL levels are elevated in early as well as in advanced HCC, various AXL-mediated functions might be essential throughout different stages of liver cancer. Accordingly, increased sAXL levels in HCC patients correlate with vascular invasion, lymph node metastasis and decreased survival.

The prior art provided no pointer to the present invention.

Receptor tyrosine kinase AXL signaling promotes tumorigenesis through alteration of several cellular processes, in particular tumor cell survival, migration and proliferation (Korshunov V. A. (2012) Clin Sci 122:361-8). Abnormal expression of AXL can provide a survival advantage for certain cancer cells; therefore, AXL has been proposed as drug target; Verma (2011) Mol Cancer Ther 10, 1763-1773 and Linger (2010) Expert Opin Ther Targets 14(10, 1073-1090. Ishikawa (2012) reports that higher expression of AXL predicts poor outcome in lung adenocarcinoma patients; Ishikawa (2012) Ann Surg Oncol DOI 10.1245/s10434-012-2795-3.

AXL is activated by the binding of its ligand growth-arrest specific protein 6 to the extracellular domain (ECD) leading to subsequent phosphorylation of downstream targets. The ECD can be proteolytically processed, possibly by matrix metalloproteinases (MMPs), resulting in the release of an 80 kDa soluble protein (sAXL) that can be detected in serum (O'Bryan J. P. (1995) The Journal of Biological Chemistry 270:551-7; Weinger J. G. (2009) The American Journal of Pathology 175:283-93; Ekman C. (2010) Journal of Thrombosis and Haemostasis 8:838-44).

sAXL has been disclosed in O'Bryan (1995) J Biol Chem 270(2), 551-557. sAXL is released after proteolytic cleavage of human AXL in the ECD. Albeit MMPs are considered to play a role in shedding of sAXL, the specific protease involved in this process is still unknown (Weinger J. G. (2009) The American Journal of Pathology 175:283-93). Several MMPs are known to be differentially expressed in HCC cell lines and no data are available, which show a molecular link between MMP expression and its impact on sAXL release in relation to its expression (Giannelli G. (2001) Laboratory Investigation 81:613-27; Kim J. R. (2004) The International Journal of Biochemistry & Cell Biology 36:2293-306).

Receptor tyrosine kinase AXL has been implicated in several pathological conditions, including cancer. Alterations of sAXL levels in human sera have been documented with different outcomes in a number of pathological conditions including cancer (Gustafsson A. (2009) Clinical Cancer Research 15:4742-9; Ekman C. (2010) Clinical Biochemistry 43:110-4). Yet, the art has not proposed, let alone used, sAXL as diagnostic marker.

AXL expression is upregulated in many tumor types, such as breast, lung, brain and liver cancer and correlates with poor prognosis and metastasis in lung and breast cancer as well as in mesothelioma (Gjerdrum C. (2010) Proceedings of the National Academy of Sciences of the United States of America 107:1124-9; Ishikawa M. (2013) Ann Surg Oncol. Suppl 3:S467-76; Linger R. M. (2010) Expert Opinion on Therapeutic Targets 14:1073-90) WO 2013/090776 discloses upregulation of AXL in endometriosis and kidney disease. Elevated AXL expression has been reported in primary HCC (Tsou A. P. (1998) Genomics 50:331-40). The role of AXL in cancer development has been extensively studied in recent years. AXL signaling regulates cellular processes relevant for tumorigenesis such as proliferation, survival and chemoresistance as well as those required in tumor progression and metastatic dissemination including migration and invasion (Korshunov V. A. (2012) Clin Sci 122:361-8). Therefore, multiple AXL-specific functions might be involved in all stages of HCC. It has recently been shown that AXL is an essential regulator of epithelial to mesenchymal transition (EMT) and invasiveness of breast cancer cells (Gjerdrum C. (2010) Proceedings of the National Academy of Sciences of the United States of America 107:1124-9; Asiedu M. K. (2013) Oncogene; doi: 10.1038/onc.2013.57, Epub ahead of print).

Prior to the present invention, only few research articles concerning sAXL in general and even less regarding its role in cancer were available. A single study evaluated a possible role of sAXL in renal cell carcinoma but did not show any correlation between sAXL and cancer status (Gustafsson A. (2009) Clinical Cancer Research 15:4742-9). Though several studies have investigated the role of intracellular AXL expression in different cancers the question whether HCC-derived sAXL could have a diagnostic value in this context was not raised (Gjerdrum C. (2010) Proceedings of the National Academy of Sciences of the United States of America 107:1124-9; Ishikawa M. (2013) Ann Surg Oncol. Suppl 3:S467-76; Linger R. M. (2010) Expert Opinion on Therapeutic Targets 14:1073-90).

Four studies described that AXL might play a role in HCC.

Tsou (1998) found AXL upregulated in primary HCC as compared to adjacent tissue (Tsou (1998) Genomics 50: 331-340). He (2010) showed a role of AXL in lymph node metastasis of murine HCC cells (He (2010) Mol Carcinog 49: 882-891). Xu (2011) et al found that AXL acts downstream of the Hippo pathway to trigger HCC invasion and metastasis (Xu (2011) Oncogene 30: 1229-1240). Lee et al showed activation of AXL and downstream Slug in HCC cell lines (without correlation with primary HCC) which caused enhanced migration (Lee (2013) Carcinogenesis 35:769-75).

However, soluble AXL (sAXL) was neither used nor proposed in these studies as potential biomarker.

Gustafsson found a reduction of sAXL in the serum of renal cell carcinoma patients as compared to healthy controls (282 patients, 65 controls); see Gustafsson (2009) Clinical Cancer Research 15(14): 4742-9. These data did not indicate that increased sAXL levels might be suitable as diagnostic marker of cancer.

The data presented herein document that sAXL is not useful in the diagnosis of certain cancers, like breast cancer, ovarian cancer, colorectal cancer and liver metastatic cancer; see FIG. 2C.

By contrast, it is surprisingly demonstrated herein that sAXL levels are elevated in supernatants of HCC cell lines and in sera of HCC patients. Therefore, sAXL is a highly useful marker in the diagnosis of liver cancer, such as HCC.

It is shown herein that AXL is expressed in a majority (64%) of HCC cell lines, and that sAXL production strongly correlates with intracellular expression in vitro (FIG. 6). Thus, sAXL levels reflect intracellular AXL expression and it is believed that differences in MMP expression might have a limited impact on sAXL shedding. In view of the prior art discussed above, these results are surprising.

A potential role of sAXL in non-cancerous disorders has also been disclosed; see below. Yet, these conflicting prior art disclosures do not provide for a rationale to use sAXL as diagnostic marker in cancer.

Increased sAXL has been associated with severe preeclampsia (58 patients, 31 healthy pregnant controls) (Liu X. (2013) Clinical Biochemistry doi: 10.1016/j.clinbiochem.2013.11.001. [Epub ahead of print]). sAXL is also increased in systemic lupus erythematosus and Behcets disease (89 female SLE and 49 male BD patients, 27 healthy controls). sAXL is further increased in patients exhibiting sepsis (231 septic or infected patients, 100 blood donor controls) (Ekman C. (2010) Crit Care 14: R158). sAXL is decreased in patients with abdominal aortic aneurysm (145 patients, 141 controls) (Ekman C. (2010) Clinical Biochemistry 43: 110-4).

The present invention relates to a method for assessing whether a patient suffers from liver cancer or is prone to suffering from liver cancer, said method comprising
    determining the amount of soluble AXL in a sample from said patient; and
    assessing that said patient suffers from liver cancer or is prone to suffering from liver cancer when the amount of soluble AXL is increased in comparison to a control.

Preferably, the methods or uses provided herein are in vitro methods or in vitro uses. The term "assessing whether a patient suffers from liver cancer or is prone to suffering from liver cancer" is used interchangeably herein with the term "diagnosing liver cancer". Preferably, the patient is a human patient.

It is believed that the herein provided method is primarily useful in the diagnosis of cancer or carcinoma of hepatocyte origin, i.e. wherein the cells of origin of a cancer or carcinoma is(are) (a) liver cell(s). The diagnosis of a liver cancer/malignant neoplasm of liver, particularly primary liver cancer, is therefore envisaged herein. The terms liver cancer, malignant neoplasm of liver, liver cell carcinoma, liver cell cancer can be used interchangeably herein.

The present invention relates to a method for assessing whether a patient suffers from a primary liver cancer or is prone to suffering from a primary liver cancer, said method comprising
    determining the amount of soluble AXL in a sample from said patient; and
    assessing that said patient suffers from primary liver cancer or is prone to suffering from primary liver cancer when the amount of soluble AXL is increased in comparison to a control.

For example, the following exemplary (primary) liver cancer can be diagnosed in accordance with the present invention: liver cell carcinoma (such as hepatocellular carcinoma or hepatoma), hepatoblastoma; angiosarcoma of liver (such as Kupffer cell sarcoma), other sarcomas of liver, other specified carcinomas of liver or liver, unspecified (i.e. unspecified carcinomas of liver, including mixed liver cancers).

Malignant neoplasms of liver and malignant neoplasm of intrahepatic bile ducts, particularly primary liver cancers, can be classified in accordance with the ICD-10 version: 2010 of the World Health Organization (WHO) as follows:
C22 Malignant neoplasm of liver and intrahepatic bile ducts
Excl.:
biliary tract NOS (C24.9)
secondary malignant neoplasm of liver (C78.7)
C22.0 Liver cell carcinoma
Incl.:
Hepatocellular carcinoma
Hepatoma
C22.1 Intrahepatic bile duct carcinoma
Incl.:
Cholangiocarcinoma
C22.2 Hepatoblastoma
C22.3 Angiosarcoma of liver
Incl.:
Kupffer cell sarcoma
C22.4 Other sarcomas of liver
C22.7 Other specified carcinomas of liver
C22.9 Liver, unspecified As shown in the appended example and FIG. 2, the method can particularly be used for assessing whether a patient suffers from hepatocellular carcinoma (HCC) or is prone to suffering from hepatocellular carcinoma (HCC). Preferably, the cancer is therefore hepatocellular carcinoma (HCC). By contrast, the method is not useful for assessing whether a patient suffers from breast cancer, ovarian cancer, colorectal cancer, or liver metastatic colorectal cancer (liver metastatic CRC) or is prone to suffering from breast cancer, ovarian cancer, colorectal cancer, or liver metastatic colorectal cancer (liver metastatic CRC).

In a preferred embodiment, the present invention relates to a method for assessing whether a patient suffers from hepatocellular carcinoma or is prone to suffering from hepatocellular carcinoma, said method comprising
  determining the amount of soluble AXL in a sample from said patient; and
  assessing that said patient suffers from hepatocellular carcinoma or is prone to suffering from hepatocellular carcinoma when the amount of soluble AXL is increased in comparison to a control.

In a very preferred embodiment, the present invention relates to a method for assessing whether a patient suffers from primary hepatocellular carcinoma or is prone to suffering from primary hepatocellular carcinoma, said method comprising
  determining the amount of soluble AXL in a sample from said patient; and
  assessing that said patient suffers from primary hepatocellular carcinoma or is prone to suffering from primary hepatocellular carcinoma when the amount of soluble AXL is increased in comparison to a control.

Hepatocellular carcinoma is the most common type of liver cancer. HCC is often secondary to either a viral hepatitis infection (hepatitis B or C) or cirrhosis. Alcoholism is the most common cause of hepatic cirrhosis. As explained above, survival of patients is low, if HCC is diagnosed (and treated) at an advanced stage. It is therefore particularly preferred herein that the malignant neoplasms as defined herein, such as HCC, is diagnosed (and treated) at an early stage.

For example, hepatocellular carcinoma can be very early hepatocellular carcinoma. Very early hepatocellular carcinoma can, for example, be classified as stage 0 hepatocellular carcinoma.

Hepatocellular carcinoma can be early hepatocellular carcinoma. Early hepatocellular carcinoma can, for example, be classified as stage A hepatocellular carcinoma.

The present invention relates to a method for assessing whether a patient suffers from very early hepatocellular carcinoma or is prone to suffering from very early hepatocellular carcinoma, said method comprising
  determining the amount of soluble AXL in a sample from said patient; and
  assessing that said patient suffers from very early hepatocellular carcinoma or is prone to suffering from very early hepatocellular carcinoma when the amount of soluble AXL is increased in comparison to a control.

The present invention relates to a method for assessing whether a patient suffers from stage 0 hepatocellular carcinoma or is prone to suffering from stage 0 hepatocellular carcinoma, said method comprising
  determining the amount of soluble AXL in a sample from said patient; and
  assessing that said patient suffers from stage 0 hepatocellular carcinoma or is prone to suffering from stage 0 hepatocellular carcinoma when the amount of soluble AXL is increased in comparison to a control.

The present invention relates to a method for assessing whether a patient suffers from early hepatocellular carcinoma or is prone to suffering from early hepatocellular carcinoma, said method comprising
  determining the amount of soluble AXL in a sample from said patient; and
  assessing that said patient suffers from early hepatocellular carcinoma or is prone to suffering from early hepatocellular carcinoma when the amount of soluble AXL is increased in comparison to a control.

The present invention relates to a method for assessing whether a patient suffers from stage A hepatocellular carcinoma or is prone to suffering from stage A hepatocellular carcinoma, said method comprising
  determining the amount of soluble AXL in a sample from said patient; and
  assessing that said patient suffers from stage A hepatocellular carcinoma or is prone to suffering from stage A hepatocellular carcinoma when the amount of soluble AXL is increased in comparison to a control.

Since primary cancers of the liver most frequently show either evidence of hepatocellular or cholangiocellular differentiation, it was long accepted that hepatocellular and cholangiocellular carcinomas arise from their healthy, fully differentiated epithelial cell types (El-Serag, H. B. (2007) Gastroenterology 132, 2557-76; Parkin, D. M. (1993) Cancer Epidemiol Biomarkers Prev, 2, 537-44. This view has recently been thrown into doubt, as it has become clear that precursor-lesions of HCC exhibit cholangiocellular as well as hepatocellular characteristics (Alison M. R. (2005) Stem Cell Reviews 1: 253-60). Furthermore, the discovery of hepatic progenitor cells (oval cells) residing in the canals of Hering and with the ability to differentiate into either hepatocytes or cholangiocytes has led to a new model of hepatocellular carcinogenesis, implicating a multi-step process (Roskams T. (2006) Oncogene; 25: 3818-22). In this respect, an undifferentiated oval cell expressing HC as well as CC markers, subjected to repeated injuries such as alcohol or chronic viral infection, could itself be the origin of liver cancer, leading to a pre-malignant lesion initially exhibiting both phenotypes and ultimately progressing into HCC. HCCs are identified and staged according to the WHO classification, which has recently been reviewed and takes into account macroscopic (e.g. tumor size, growth pattern etc.) and microscopic (e.g. differentiaton, vascular invasion etc.) features (Flejou J. F. (2011) Annales de Pathologie 31: S27-31).

The following classifications are presently and recommended.

In accordance with the present invention, patients can be classified into very early, early and advanced HCC according to the established Barcelona Clinic Liver Cancer (BCLC) classification. Very early HCCs (n=26) are defined as BCLC stage 0 (single nodule<2 cm) and early HCCs (n=78) as BCLC stage A (single nodule<5 cm or 3 nodules<3 cm). BCLC stage B, C and D (large, multiple nodules, vascular invasion or extrahepatic secondary tumors) are classified as advanced HCCs (n=200) (Llovet J. M. (1999) Seminars in Liver Disease 19:329-38).

References for Tables: Greene F. L. (2002) AJCC cancer staging manual, 6th edn. Springer, 435p; Bruix J. (2011) American Association for the Study of Liver Diseases. http://www.aasld.org/practiceguidelines 2011; O'Neil B. H., (2007) Oncologist 12:1425-1432.

| Adapted classification | BCLC stage | PS | Tumor characteristcs | Liver function | Treatment options | Nature of treatment |
|---|---|---|---|---|---|---|
| Very early | 0 (very early) | 0 | Single <2 cm | Child-Pugh A | Resection, RFA | Curative |
| Early | A (early) | 0 | Single <5 cm or 3 tumors <3 cm | Child-Pugh A-B | Transplantation, RFA | |
| Advanced | B (intermediate) | 0 | Large, multinodular | Child-Pugh A-B | TACE | Palliative |
| | C (advanced) | 1-2 | Vascular invasion or metastases | Child-Pugh A-B | Sorafenib | |
| | D (terminal) | 3-4 | Any | Child-Pugh C | Supportive care | |

BCLC, Barcelona Clinic Liver Cancer.
PS, performance status.
RFA, radiofrequency ablation.
TACE, transarterial chemoembolization
BCLC stage classification criteria and clinical consequences.

Also the following classifications can be used in accordance with the present invention:

| TNM tumor characteristics | |
|---|---|
| | Tumor characteristics |
| T1 | Single tumor without vascular invasion |
| T2 | Single tumor with vascular invasion, or multiple tumors, none >5 cm |
| T3 | Multiple tumors, any >5 cm, or tumors involving major branch of portal or hepatic veins |
| T4 | Tumors with direct invasion of adjacent organs other than the gallbladder, Or perforation of visceral peritoneum |
| M1 | Regional lymph node metastasis |
| M1 | Distant metastasis |

| TNM stage classification criteria | | | |
|---|---|---|---|
| TNM stage (UICC VI) | Tumor | Node | Metastasis |
| I | T1 | N0 | M0 |
| II | T2 | N0 | M0 |
| IIIA | T3 | N0 | M0 |
| IIIB | T4 | N0 | M0 |
| IIIC | Any T | N1 | M0 |
| IV | Any T | Any N | M1 |

Since survival of patients is low, if liver cancer is diagnosed (and treated) at an advanced stage, the present invention is particularly useful in the diagnosis of very early or early liver cancer, like very early or early hepatoceullar carcinoma (HCC).

The patient as defined herein can be/is suspected of suffering from liver cancer (preferably HCC) and therefore a diagnosis/assessment of liver cancer is warranted. Patients suspected of suffering from liver cancer (preferably HCC) are, for example, patients having risk factors as described herein below.

The following treatment options are conceivable and currently recommended after diagnosis of HCC (see also tabe above re Barcelona classification):

Very early HCC: resection, Radio frequency ablation (RFA).

Early HCC: Transplantation, Radio frequency ablation (RFA) Advanced HCC:

Stage B: TACE,

Stage C: Sorafenib (including co-therapy with sorafenib, e.g. co-therapy with sorafenib and Mapk14 inhibitors, e.g. second-generation Mapk14 inhibitors such as skepinone-L and/or PH-797804)

Stage D: Supportive care

RFA is a medical procedure in which part of the electrical conduction system of the tumor is ablated using the heat generated from high frequency alternating current (usually in the range of 350-500 kHz).

The term TACE refers to transarterial chemoembolization. TACE is a minimally invasive procedure performed in interventional radiology to restrict a tumor's blood supply.

Of particular interest and preferred herein is the diagnosis in patients that are at risk of developing a liver cancer, like hepatoceullar carcinoma (HCC). In particular the term "patient prone to suffering from liver cancer" as used herein refers to a patient at risk of developing a liver cancer. Such patients have, for example, (inherited) risk factors. Here, the present invention can provide an early diagnosis that can help to initiate appropriate therapy so as to avoid or delay the development of a cancer/tumor.

Generally, the patients that have been assessed to suffer from liver cancer or to be prone to suffering from liver cancer (in other words diagnosed positive for liver cancer) can be subject to co-therapy with sorafenib, e.g. co-therapy with sorafenib and Mapk14 inhibitors, e.g. second-generation Mapk14 inhibitors such as skepinone-L and/or PH-797804.

Elevated Axl-expression has recently been associated with drug-resistance on several levels in a number of cancers. In this respect, pharmacological interference with Axl has been shown to restore chemosensitivity and a number of compounds are currently tested in Phase I and Phase II clinical trials [1]. In HCC, it has recently been shown that Axl has a tumor-promoting role by modulating TGF-beta signaling. Thus, pharmacological co-inhibition of Axl in TGF-beta-positive HCC patients could have a major impact on current HCC treatment strategies relying on Sorafenib. Another mechanism of Sorafenib resistance in HCC has recently been associated with Mapk14, a member of the MAP kinase family also known as p38alpha. Inhibition of Mapk14 was shown to sensitize HCC cells to Sorafenib therapy and to overcome Sorafenib resistance. Thus, pharmacological inhibition of Mapk14 in combination with Sorafenib could have strong beneficial therapeutic effects in current HCC therapies [2].

1. Wu, X., et al., *AXL kinase as a novel target for cancer therapy*. Oncotarget, 2014. 5(20): p. 9546-63.
2. Rudalska, R., et al., *In vivo RNAi screening identifies a mechanism of sorafenib resistance in liver cancer*. Nat Med, 2014. 20(10): p. 1138-46.

The present invention relates to a method for assessing whether a patient is prone to suffering from liver cancer, said method comprising
  determining the amount of soluble AXL in a sample from said patient; and
  assessing that said patient is prone to suffering from liver cancer when the amount of soluble AXL is increased in comparison to a control.

The present invention relates to a method for assessing whether a patient is prone to suffering from a primary liver cancer, said method comprising
  determining the amount of soluble AXL in a sample from said patient; and
  assessing that said patient is prone to suffering from primary liver cancer when the amount of soluble AXL is increased in comparison to a control.

In a preferred embodiment, the present invention relates to a method for assessing whether a patient is prone to suffering from hepatocellular carcinoma, said method comprising
  determining the amount of soluble AXL in a sample from said patient; and
  assessing that said patient is prone to suffering from hepatocellular carcinoma when the amount of soluble AXL is increased in comparison to a control.

In a very preferred embodiment, the present invention relates to a method for assessing whether a patient is prone to suffering from primary hepatocellular carcinoma, said method comprising
  determining the amount of soluble AXL in a sample from said patient; and
  assessing that said patient is prone to suffering from primary hepatocellular carcinoma when the amount of soluble AXL is increased in comparison to a control.

The main risk factors for liver cancer (like hepatocellular carcinoma) are hepatitis B, hepatitis C, cirrhosis of the liver, and/or alcoholism.

Risk factors for hepatocellular carcinoma are, in particular:
  Hepatitis B
  Hepatitis C
  Cirrhosis of the liver
  Aflatoxin
  Alcoholism
  Smoking In countries like China and sub-saharan Africa hepatitis (like hepatis B or hepatis C) is endemic and therefore the major cause of HCC. In many other countries, where hepatitis is rare, the major cause of HCC is alcohol abuse).

Also type 2 diabetes, obesity, fatty liver and/or metabolic syndrome (specifically, when evidence of non-alcoholic fatty liver disease (NAFLD) is present) are risk factors for hepatocellular carcinoma. It is believed that an increased circulating insulin concentration can increase the risk of hepatocellular carcinoma.

Accordingly, also the following factors are risk factors for hepatocellular carcinoma:
  Overweight
  Obesity
  Type 2 Diabetes
  Metabolic syndrome
  Fatty liver (disease)
  Hemochromatosis
  Wilson's disease The American Society of Addiction Medicine defines alcoholism as "a primary, chronic disease with genetic, psychosocial, and environmental factors influencing its development and manifestations. The disease is often progressive and fatal. It is characterized by continuous or periodic impaired control over drinking, preoccupation with the drug alcohol, use of alcohol despite adverse consequences, and distortions in thinking, most notably denial." (Morse R. M. (1992) JAMA 268:1012-1014.) Nevertheless, there still is no final agreement on the dose-effect relationship between alcohol intake and risk of developing liver cancer. However, it is widely accepted that a threshold alcohol intake of 75 g/day is associated with an increased risk of developing liver disease. (Sorensen T. I. (1989) Liver 9:189-197.)

Several studies have investigated the relation between smoking and liver cancer development. One study including 4050 male participants observed a 3-fold increased risk of primary liver cancer as compared to never-smokers. Another investigation including 283112 subjects found an increased risk of hepatocellular carcinoma in subjects who had smoked for >20 years as compared to those who had smoked for less than 10 years. The Japan Collaborative Cohort Study including 65528 subjects found an increased risk of death due to HCC among smokers and current ex-smokers. Blonski W. (2010) World J Gastroenterol 16:3603-3615.)

The following relates to patients to be assessed in accordance with the present invention, wherein these patients have one or more of the above mentioned risk-factors, like cirrhosis of the liver, alcoholism, smoking, obesity, overweight, type 2 diabetes, fatty liver disease and/or metabolic syndrome. The assessment of patients having one or more of these risk factors is preferred herein.

The present invention relates to method for assessing whether a patient suffers from liver cancer or is prone to suffering from liver cancer, said method comprising
  determining the amount of soluble AXL in a sample from said patient; and
  assessing that said patient suffers from liver cancer or is prone to suffering from liver cancer when the amount of soluble AXL is increased in comparison to a control, wherein said patient has one or more risk factors, like one or more of hepatitis B, hepatitis C, cirrhosis of the liver, alcoholism, smoking, overweight, obesity, type 2 diabetes, metabolic syndrome, aflatoxin, hemochromatosis and/or Wilson's disease.

The present invention relates to method for assessing whether a patient suffers from liver cancer or is prone to suffering from liver cancer, said method comprising
determining the amount of soluble AXL in a sample from said patient; and
assessing that said patient suffers from liver cancer or is prone to suffering from liver cancer when the amount of soluble AXL is increased in comparison to a control, wherein said patient has one or more risk factors, like one or more of cirrhosis of the liver, alcoholism, smoking, overweight, obesity, type 2 diabetes, fatty liver disease and/or metabolic syndrome.

The present invention relates to method for assessing whether a patient suffers from hepatocellular carcinoma or is prone to suffering from hepatocellular carcinoma, said method comprising
determining the amount of soluble AXL in a sample from said patient; and
assessing that said patient suffers from hepatocellular carcinoma or is prone to suffering from hepatocellular carcinoma when the amount of soluble AXL is increased in comparison to a control,
wherein said patient has one or more risk factors, like one or more of cirrhosis of the liver, alcoholism, smoking, overweight, obesity, type 2 diabetes, fatty liver disease and/or metabolic syndrome.

Cirrhosis is a result of advanced liver disease and is characterized by replacement of liver tissue by fibrosis (scar tissue) and regenerative nodules. Cirrhosis is associated with a partial or complete loss of liver function. Cirrhosis is often caused by alcoholism, hepatitis B, hepatitis C, and/or fatty liver disease.

Fatty liver, also known as fatty liver disease (FLD), is a reversible condition wherein large vacuoles of triglyceride fat accumulate in liver cells via the process of steatosis. Steatosis relates to the abnormal retention of lipids within a cell. Fatty liver can be considered a single disease that occurs worldwide in those with excessive alcohol intake and the obese. The condition is also associated with other diseases that influence fat metabolism. There are two main subtypes of fatty liver disease, namely alcoholic FLD and nonalcoholic FLD Both show microvesicular and macrovesicular fatty changes at different stages.

Non-alcoholic fatty liver disease (NAFLD) is one cause of a fatty liver, occurring when fat is deposited in the liver not due to excessive alcohol consume. It is related to insulin resistance and the metabolic syndrome. Non-alcoholic steatohepatitis (NASH) is the most extreme form of NAFLD, and is regarded as a major cause of cirrhosis of the liver of unknown cause.

Fatty liver disease can be classified in accordance with the ICD-10 version:2010 of the World Health Organization (WHO) as follows:
K70 Alcoholic liver disease
K70.0 Alcoholic fatty liver
K70.1 Alcoholic hepatitis
K70.2 Alcoholic fibrosis and sclerosis of liver
K70.3 Alcoholic cirrhosis of liver
Incl.:
Alcoholic cirrhosis NOS
K70.4 Alcoholic hepatic failure
Incl.:
Alcoholic hepatic failure:
  NOS
  acute
  chronic
  subacute
  with or without hepatic coma
K70.9 Alcoholic liver disease, unspecified
K76.0 Fatty (change of) liver, not elsewhere classified
Incl.:
Nonalcoholic fatty liver disease (NAFLD)
Excl.:
nonalcoholic steatohepatitis (K75.8)
K76.1 Chronic passive congestion of liver
Incl.:
Cardiac:
cirrhosis (so-called) of liver
sclerosis
K76.2 Central haemorrhagic necrosis of liver
Excl.:
liver necrosis with hepatic failure (K72.-)
K76.3 Infarction of liver
K76.4 Peliosis hepatis
Incl.:
Hepatic angiomatosis
K76.5 Hepatic veno-occlusive disease
Excl.:
Budd-Chiari syndrome (I82.0)
K76.6 Portal hypertension
K76.7 Hepatorenal syndrome
Excl.:
following labour and delivery (O90.4)
K76.8 Other specified diseases of liver
Incl.:
Simple cyst of liver
Focal nodular hyperplasia of liver
Hepatoptosis
K76.9 Liver disease, unspecified Obesity is a condition where excess body fat accumulates to such an extent that one's health may be affected; see Amer (2010) Biochem and Biophys Res Comm 396, 101-104. Especially in developed countries obesity is increasing and constitutes a major health problem, as obesity also enhances the risk for cardiovascular disease and metabolic disorders such as type 2 diabetes; see Spalding (2008) Nature 453, 783-787.

Overweight and obesity are defined as abnormal or excessive fat accumulation that may impair health. Body mass index (BMI) is a simple index of weight-for-height that is commonly used to classify overweight and obesity in adults. It is defined as a person's weight in kilograms divided by the square of his height in meters ($kg/m^2$).

An "overweight" patient is often defined as having a body mass index (BMI) above 25 $kg/m^2$. In context of the present invention, "overweight" is preferably defined as a body mass index (BMI) between 25 to 30 $kg/m^2$ and "obesity" is preferably defined as a body mass index (BM) of higher than 30 $kg/m^2$. "Severe obesity" is usually defined as a body mass index (BM) of 40 $kg//m^2$ and higher than 40 $kg/m^2$. These definitions are in line with the present definition of the WHO: according to the WHO, a BMI greater than or equal to 25 is overweight and a BMI greater than or equal to 30 is obesity.

According to WHO, raised BMI is a major risk factor for noncommunicable diseases such as cardiovascular diseases (mainly heart disease and stroke), diabetes, musculoskeletal disorders (especially osteoarthritis—a highly disabling degenerative disease of the joints) and some cancers (endometrial, breast, and colon). The risk for these noncommunicable diseases increases with the increase in BMI. Accordingly, patients prone to suffering from cancer to be assessed according to the present invention may have the above secondary disorders and diseases.

In one aspect, patients prone to suffering from cancer to be assessed according to the present are overweight or obese children. It is known in the art that childhood obesity is associated with a higher chance of obesity, premature death and disability in adulthood. In addition to increased future risks, obese children experience breathing difficulties, increased risk of fractures, hypertension, early markers of cardiovascular disease, insulin resistance and psychological effects. Accordingly, the diagnosis of these patients (having, for example, childhood obesity) is envisaged in the present invention.

BMI provides the most useful population-level measure of overweight and obesity as it is the same for both sexes and for all ages of adults. However, it should be considered a rough guide because it may not correspond to the same degree of fatness in different individuals. In certain medically indicated cases, it is therefore envisaged that also patients with a BMI below 25 kg/m$^2$ can be assessed in accordance with the present invention. In the same vein, not every subject/patient with a high BMI (e.g. between 25 to 30 kg/m$^2$ or higher than 30 kg/m$^2$) is an "obese" or "overweight" patient—it is well known that individuals with greater than average muscle mass (e.g. certain athletes (like bodybuilders)) will have a higher BMI without having abnormal or excessive fat accumulation.

Therefore, the patient that is to be assessed in accordance with the present invention may be characterized by the presence of 20% or more body fat in the subject/patient. For example, a body fat percentage of 25% or more may be characteristic for an overweight/obese man, and a body fat percentage of 32% or more may be characteristic for an overweight/obese woman. It is known in the art that a person's body fat percentage is the total weight of the person's fat divided by the person's weight.

The body's fat consists of essential body fat and storage body fat. Essential body fat is necessary to maintain life and reproductive functions. Essential fat is usually 3%-5% in men, and 8-12% in women. Storage body fat consists of fat accumulation in adipose tissue, part of which protects internal organs in the chest and abdomen.

The table below describes different percentages that are often used in the art to characterize the percentage of essential fat and the percentage of total fat in men and women:

| Description | Women | Men |
|---|---|---|
| Essential fat | 10-13% | 2-5% |
| Athletes | 14-20% | 6-13% |
| Fitness | 21-24% | 14-17% |
| Average | 25-31% | 18-24% |
| Obese | 32%+ | 25%+ |

The percentage of storage fat or extra fat as denoted herein may be calculated from the above given exemplary values. Yet, it is often difficult to exactly determine the percentage of essential fat and of storage fat. Therefore, the total fat percentage is routinely determined/estimated and used in the art in order to classify a subject/patient as overweight/obese. Appropriate measurement techniques are known in the art and include Near-infrared interactance or Dual energy X-ray absorptiometry (DXA). Also multicompartment models can be used; these models can include DXA measurement of bone, plus independent measures of body water and body volume. Various other components may be independently measured, such as total body potassium. Also in-vivo neutron activation can quantify all the elements of the body and use mathematical relations among the measured elements in the different components of the body (fat, water, protein, etc.) to develop simultaneous equations to estimate total body composition, including body fat. Also body average density measurement can be used to determine a subject/patients body fat percentage: this technique involves the measurement of a person's average density (total mass divided by total volume) and the application of a formula to convert that to body fat percentage. Bioelectrical impedance analysis is also a well known technique to estimate body fat percentage. Also anthropometric methods (measurements made of various parameters of the human body, such as circumferences of various body parts or thicknesses of skinfolds) may be used. Because most anthropometric formulas such as the Durnin-Womersley skinfold method, the Jackson-Pollock skinfold method, and the US Navy circumference method, estimate body density, the body fat percentage is obtained by applying a second formula, such as the Siri or Brozek formula. Further, Skinfold methods may applied and the body fat percentage may even be calculated from the BMI. These and other methods are well known and can be deduced from reviews like Lee (2008) Curr Opin Clin Nutr Metab Care 11(5), 566-572 and Gallagher (2008) Int J Body Compos Res 6(4): 141-148 which are incorporated in their entirety herein.

Preferably, the body fat percentage of a male patient/subject to be assessed herein is at least 18%, 19%, 20%, 21%, 22%, 23%, 24% and more preferably, at least 25%. The body fat percentage of a female patient/subject to be assessed herein is at least at least 25%, 26%, 27%, 28%, 29%, more preferably 30%, 31% and even more preferably at least 32%. The identification of obese patients according to the body fat percentage (for example determined according to the bioelectrical impedance criterion) may be especially advantageous in individuals having a BMI of below 30 kg/m$^2$; according to the bioelectrical impedance criterion a man may be considered obese in case of a body fat percentage of at least 25% and a woman may be considered obese in case of a body fat percentage of at least 30%; see Frankenfield (2001) Nutrition 17:26-30 which is incorporated in its entirety herein. Upper limits of body fat percentage will have to be calculated on an individual basis; yet, typically body fat percentage does not exceed about 60% even in severely obese subjects/patients.

Further, a patient to be assessed herein may have a disorder which involves higher levels of triglycerides in the blood of the patient. The recommended level of triglycerides (in a normal range) is in males 40-160 mg/dL and in females 35 to 135 mg/dL. However, in Germany also "higher levels" are tolerated on being normal; e.g. 250 mg/dL. Accordingly, higher levels of triglycerides are preferably above 150 mg/dL, more preferably above 200 mg/dL and most preferably above 250 mg/dL.

Accordingly, the patients to be assessed in accordance with the present invention can have overweight, obesity, and/or eating disorders leading to increased BMI/body fat percentage/body weight/body mass as defined herein above. Also envisaged is the assessment of patients with disorders related to higher or pathologically high BMI/body fat percentage/body weight due to the use of drugs (like corticosteroids, antipsychotic drugs, antidepressants, particularly tricyclic antidepressants, oral contraceptives, etc.).

According to the International Statistical Classification of Diseases and Related Health Problems (10th Revision, Version for 2007) issued by the World Health Organization, the following diseases and disorders relate to obesity:
E66 Obesity
    Excludes adiposogenital dystrophy (E23.6)
        lipomatosis:
            NOS (E88.2)
            dolorosa [Dercum] (E88.2)
        Prader-Willi syndrome (Q87.1)
E66.0 Obesity due to excess calories
E66.1 Drug-induced obesity
    Use additional external cause code (Chapter XX), if desired, to identify drug.
E66.2 Extreme obesity with alveolar hypoventilation
    Pickwickian syndrome
E66.8 Other obesity
    Morbid obesity
E66.9 Obesity, unspecified
    Simple obesity NOS In accordance with this invention it is also envisaged that patients are to be assessed with secondary disorders related to a (pathological) increase of body weight/BMI/body fat percentage (e.g. overweight/obesity). These "secondary disorders" may comprise, but are not limited to diabetes type 2, high blood pressure (hypertension), cardio-vascular diseases, problems with sexual function and disorder of the muscular or bone system, and lipid disorders (such as hypertriglyceridemia and hypercholesterolemia), growth hormone deficiency, partial growth hormone deficiency or neuro-secretory dysfunction of growth hormone secretion. Problems with sexual function may comprise libido problems, penile dysfunction as well as FSAD (Female Sexual Arousal Disorder). Also dyslipidaemia may be a "secondary disorder".

Secondary disorders of the metabolism linked to higher body weight/body mass/BMI/body fat percentage may also comprise, but are not limited to, glycogen storage diseases, lipid storage diseases (like Gaucher or Niemann Pick), endocrine disorders (like Cushings, hypothyroidism, insulinomas, lack of growth hormone, diabetes, adrenogenital syndrome, diseases of the adrenal cortex), tumors and metastases (such as craniopharyngeomas), Prader-Willi syndrome, Down syndrome and genetic diseases and syndromes (like, e.g., hyperlipoproteinemias, hypothalamic disorders, Fröhlich syndrome or empty sella syndrome).

Diabetes mellitus type 2 is a condition relating to non-insulin-dependent diabetes mellitus. Non-insulin-dependent diabetes mellitus is a risk factor/secondary disorder in context of the present invention. Diabetes mellitus type 2 results from insulin resistance, a condition in which cells fail to use insulin properly, sometimes combined with an absolute insulin deficiency. This form was previously referred to as non insulin-dependent diabetes mellitus (NIDDM) or "adult-onset diabetes".

Non-insulin-dependent diabetes mellitus can be classified in accordance with the ICD-10 version:2010 of the World Health Organization (WHO) as follows:
E11 Non-insulin-dependent diabetes mellitus
Incl.:
diabetes (mellitus)(nonobese)(obese):
    adult-onset
    maturity-onset
    nonketotic
    stable
    type II
non-insulin-dependent diabetes of the young Excl.:
diabetes mellitus (in):
    malnutrition-related (E12.-)
    neonatal (P70.2)
    pregnancy, childbirth and the puerperium (O24.-)
glycosuria:
    NOS (R81)
    renal (E74.8)
impaired glucose tolerance (R73.0)
postsurgical hypoinsulinaemia (E89.1)

Metabolic syndrome is a disorder of energy utilization and storage, diagnosed by a co-occurrence of 3 out of five of the following medical conditions: abdominal (central) obesity, elevated blood pressure, elevated fasting plasma glucose, high serum triglycerides, and low high-density cholesterol (HDL) levels. Metabolic syndrome increases the risk of developing cardiovascular disease, particularly heart failure, and diabetes. Some studies have shown the prevalence in the USA to be an estimated 34% of the adult population and the prevalence increases with age. Metabolic syndrome is also known as metabolic syndrome X, cardiometabolic syndrome, syndrome X, insulin resistance syndrome, Reaven's syndrome (named for Gerald Reaven), and CHAOS (in Australia).

A joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity published a guideline to harmonize the definition of the metabolic syndrome. This definition recognizes that the risk associated with a particular waist measurement will differ in different populations. Whether it is better at this time to set the level at which risk starts to increase or at which there is already substantially increased risk will be up to local decision-making groups. However, for international comparisons and to facilitate the etiology, it is critical that a commonly agreed-upon set of criteria be used worldwide, with agreed-upon cut points for different ethnic groups and sexes. Obviously, there are many people in the world of mixed ethnicity, and in these cases, pragmatic decisions will have to be made.

The previous definitions of the metabolic syndrome by the International Diabetes Federation and the revised National Cholesterol Education Program are very similar and they identify individuals with a given set of symptoms as having metabolic syndrome. There are two differences, however: the IDF definition states that if body mass index (BMI) is greater than 30 kg/m$^2$, central obesity can be assumed, and waist circumference does not need to be measured. However, this potentially excludes any subject without increased waist circumference if BMI is less than 30. Conversely, the NCEP definition indicates that metabolic syndrome can be diagnosed based on other criteria. Also, the IDF uses geography-specific cut points for waist circumference, while NCEP uses only one set of cut points for waist circumference regardless of geography. These two definitions are much more similar than the original NCEP and WHO definitions.

The International Diabetes Federation consensus worldwide definition of the metabolic syndrome (2006) is: Central obesity (defined as waist circumference with ethnicity-specific values) AND any two of the following:
    Raised triglycerides: >150 mg/dL (1.7 mmol/L), or specific treatment for this lipid abnormality Reduced HCL cholesterol: <40 mg/dL (1.03 mmol/L) in males, <50 mg/dL (1.29 mmol/L) in females, or specific treatment for this lipid abnormality Raised blood pressure (BP): systolic BP>130 or diastolic BP>85 mm Hg, or treatment of previously diagnosed hypertension Raised fasting plasma glucose (FPG): >100 mg/dL (5.6 mmol/L), or previously diagnosed type 2 diabetes If FPG is >5.6 mmol/L or 100 mg/dL, an oral glucose tolerance test is strongly recommended, but is not necessary to define presence of the syndrome.

If BMI is >30 kg/m$^2$, central obesity can be assumed and waist circumference does not need to be measured The World Health Organization 1999 criteria require the presence of any one of diabetes mellitus, impaired glucose tolerance, impaired fasting glucose or insulin resistance, AND two of the following:

Blood pressure: ≥140/90 mmHg

Dyslipidemia: triglycerides (TG): ≥1.695 mmol/L and high-density lipoprotein cholesterol (HDL-C)≤0.9 mmol/L (male), ≤1.0 mmol/L (female)

Central obesity: waist:hip ratio>0.90 (male); >0.85 (female), or body mass index>30 kg/m$^2$ Microalbuminuria: urinary albumin excretion ratio>20 μg/min or albumin:creatinine ratio≥30 mg/g The European Group for the Study of Insulin Resistance (1999) requires insulin resistance defined as the top 25% of the fasting insulin values among nondiabetic individuals AND two or more of the following:

Central obesity: waist circumference≥94 cm or 37 inches (male), ≥80 cm or 31.5 inches (female)

Dyslipidemia: TG≥2.0 mmol/L and/or HDL-C<1.0 mmol/L or treated for dyslipidemia

Hypertension: blood pressure≥140/90 mmHg or antihypertensive medication

Fasting plasma glucose≥6.1 mmol/L

The US National Cholesterol Education Program Adult Treatment Panel III (2001) requires at least three of the following:

Central obesity: waist circumference≥102 cm or 40 inches (male), ≥88 cm or 35 inches (female)

Dyslipidemia: TG≥1.7 mmol/L (150 mg/dl)

Dyslipidemia: HDL-C<40 mg/dL (male), <50 mg/dL (female)

Blood pressure≥130/85 mmHg (or treated for hypertension)

Fasting plasma glucose≥6.1 mmol/L (110 mg/dl)

There is confusion as to whether, in 2004, the AHA/NHLBI intended to create another set of guidelines or simply update the NCEP ATP III definition. According to Scott Grundy, University of Texas Southwestern Medical School, Dallas, Tex., the intent was just to update the NCEP ATP III definition and not create a new definition.

Elevated waist circumference:
Men—greater than 40 inches (102 cm)
Women—greater than 35 inches (88 cm)

Elevated triglycerides: Equal to or greater than 150 mg/dL (1.7 mmol/L)

Reduced HDL ("good") cholesterol:
Men—Less than 40 mg/dL (1.03 mmol/L)
Women—Less than 50 mg/dL (1.29 mmol/L)

Elevated blood pressure: Equal to or greater than 130/85 mm Hg or use of medication for hypertension Elevated fasting glucose: Equal to or greater than 100 mg/dL (5.6 mmol/L) or use of medication for hyperglycemia High-sensitivity C-reactive protein has been developed and used as a marker to predict coronary vascular diseases in metabolic syndrome, and it was recently used as a predictor for nonalcoholic fatty liver disease (steatohepatitis) in correlation with serum markers that indicated lipid and glucose metabolism Fatty liver disease and steatohepatitis can be considered as manifestations of metabolic syndrome, indicative of abnormal energy storage as fat in ectopic distribution. Reproductive disorders (such as polycystic ovary syndrome in women of reproductive age), and erectile dysfunction or decreased total testosterone (low testosterone-binding globulin) in men can be attributed to metabolic syndrome The following relates to the determination of the amount of sAXL in a sample from the patient.

It is demonstrated herein that median serum concentrations of sAXL are significantly increased in all HCC (18.575 ng/mL) as compared to healthy controls (13.388 ng/mL). This represents an about 1.38-fold increase of sAXL in a sample from a HCC patient as compared to a sample from a control (like a healthy person).

Moreover, it is shown herein that patients can be assessed positive for HCC, if the median serum concentrations of sAXL are about 14.053 ng/ml in a sample from a patient. Accordingly, the amount of soluble AXL in a sample from a patient assessed positive for HCC in accordance with the present invention is at least 1.05-fold, 1.1-fold, preferably at least 1.2-fold, more preferably at least 1.3 fold increased in comparison to a control.

The term "assessed positive for a liver cancer" as used herein means that a patient is assessed to suffer from liver cancer or to be prone to suffering from a liver cancer" in accordance with the present invention.

It is believed that the findings presented herein in relation to HCC can be generalized and apply, mutatis mutandis, to other liver cancers.

The present invention relates to a method for assessing whether a patient suffers from liver cancer or is prone to suffering from liver cancer, said method comprising determining the amount of soluble AXL in a sample from said patient; and assessing that said patient suffers from liver cancer or is prone to suffering from liver cancer when the amount of soluble AXL is increased in comparison to a control, wherein the amount of soluble AXL in a sample from the patient is at least 1.1-fold, preferably at least 1.2-fold, more preferably at least 1.3 fold increased in comparison to a control.

The present invention relates to a method for assessing whether a patient suffers from liver cancer or is prone to suffering from liver cancer, said method comprising determining the amount of soluble AXL in a sample from said patient; and assessing that said patient suffers from liver cancer or is prone to suffering from liver cancer when the amount of soluble AXL is increased in comparison to a control, wherein the amount of soluble AXL in a sample from the patient is at least 1.2-fold increased in comparison to a control.

The present invention relates to a method for assessing whether a patient suffers from liver cancer or is prone to suffering from liver cancer, said method comprising determining the amount of soluble AXL in a sample from said patient; and assessing that said patient suffers from liver cancer or is prone to suffering from liver cancer when the amount of soluble AXL is increased in comparison to a control, wherein the amount of soluble AXL in said sample from the patient is at least 1.3-fold increased in comparison to a control.

The present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL in said sample from the patient is at least 1.2-fold increased in comparison to a control.

A non-limiting example of a "control" may be a "healthy" control, for example a sample from a healthy individual. A healthy individual may, for example, be an individual that is not suffering from a liver cancer as defined herein, for example, from hepatocellular carcinoma. A healthy individual may, for example, be an individual that is not suffering from a disease or disorder associated with elevated amounts of sAXL. Preferably, the healthy individual is a human.

In accordance with the above, the reference or control relates to the amount of soluble AXL in (a sample of) the healthy control individual, i.e. it is the "normal" status of soluble AXL in (a sample of) the corresponding healthy control individual. The control may also relate to the amount of soluble AXL in (a sample of) the patient to be assessed herein, if, for example, the sample was obtained before the patient suffered from liver cancer or before the patient was prone to suffering from liver cancer. Thus, the control may relate to the amount of soluble AXL in (a sample of) the patient to be assessed herein, if, for example, the sample was obtained prior to the development liver cancer in the patient.

It was demonstrated herein that median serum concentrations of sAXL are significantly increased in very early HCC (18.064 ng/mL) and early HCC (16.430 ng/mL) as compared to healthy controls (13,388 ng/mL). Further, it was shown herein that median serum concentrations of sAXL are significantly increased in advanced HCC (18.880 ng/mL) as compared to healthy controls (13,388 ng/mL). This represents an about 1.35-fold increase of sAXL in a sample from a very early HCC patient as compared to a sample from a control (like a healthy person), an about 1.22-fold increase of sAXL in a sample from an early HCC patient as compared to a sample from a control (like a healthy person) and an about 1.41-fold increase of sAXL in a sample from a advanced HCC patient as compared to a sample from a control (like a healthy person).

Accordingly, the amount of soluble AXL in a sample from a patient assessed positive for very early HCC in accordance with the present invention is at least 1.1-fold, preferably at least 1.2-fold, more preferably at least 1.3 fold increased in comparison to a control. The amount of soluble AXL in a sample from a patient assessed positive for early HCC is at least 1.1-fold, preferably at least 1.2-fold increased in comparison to a control. The amount of soluble AXL in a sample from a patient assessed positive for advanced HCC is at least 1.1-fold, preferably at least 1.2-fold, more preferably at least 1.3 fold, and most preferably at least 1.4-fold increased in comparison to a control.

The present invention relates to a method for assessing whether a patient suffers from very early hepatocellular carcinoma or is prone to suffering from very early hepatocellular carcinoma, said method comprising
- determining the amount of soluble AXL in a sample from said patient; and
- assessing that said patient suffers from from very early hepatocellular carcinoma or is prone to suffering from very early hepatocellular carcinoma when the amount of soluble AXL in said sample from the patient is at least 1.1-fold, preferably at least 1.2-fold, more preferably at least 1.3 fold increased in comparison to a control.

The present invention relates to a method for assessing whether a patient suffers from stage 0 hepatocellular carcinoma or is prone to suffering from stage 0 hepatocellular carcinoma, said method comprising
- determining the amount of soluble AXL in a sample from said patient; and
- assessing that said patient suffers from stage 0 hepatocellular carcinoma or is prone to suffering from stage 0 hepatocellular carcinoma when the amount of soluble AXL in said sample from the patient is at least 1.1-fold, preferably at least 1.2-fold, more preferably at least 1.3 fold increased in comparison to a control.

The present invention relates to a method for assessing whether a patient suffers from early hepatocellular carcinoma or is prone to suffering from early hepatocellular carcinoma, said method comprising
- determining the amount of soluble AXL in a sample from said patient; and
- assessing that said patient suffers from from early hepatocellular carcinoma or is prone to suffering from early hepatocellular carcinoma when the amount of soluble AXL in said sample from the patient is at least 1.1-fold, preferably at least 1.2-fold increased in comparison to a control.

The present invention relates to a method for assessing whether a patient suffers from stage A hepatocellular carcinoma or is prone to suffering from stage A hepatocellular carcinoma, said method comprising
- determining the amount of soluble AXL in a sample from said patient; and
- assessing that said patient suffers from stage A hepatocellular carcinoma or is prone to suffering from stage A hepatocellular carcinoma when the amount of soluble AXL in said sample from the patient is at least 1.1-fold, preferably at least 1.2-fold increased in comparison to a control.

The present invention relates to a method for assessing whether a patient suffers from advanced hepatocellular carcinoma or is prone to suffering from advanced hepatocellular carcinoma, said method comprising
- determining the amount of soluble AXL in a sample from said patient; and
- assessing that said patient suffers from from advanced hepatocellular carcinoma or is prone to suffering from advanced hepatocellular carcinoma when the amount of soluble AXL in said sample from the patient is at least 1.1-fold, preferably at least 1.2-fold, more preferably at least 1.3 fold, and most preferably at least 1.4-fold increased in comparison to a control.

The present invention relates to a method for assessing whether a patient suffers from stage B, stage C, or stage D hepatocellular carcinoma or is prone to suffering from stage B, stage C, or stage D hepatocellular carcinoma, said method comprising
- determining the amount of soluble AXL in a sample from said patient; and
- assessing that said patient suffers from stage B, stage C, or stage D hepatocellular carcinoma or is prone to suffering from stage B, stage C, or stage D hepatocellular carcinoma when the amount of soluble AXL in said sample from the patient is at least 1.1-fold, preferably at least 1.2-fold, more preferably at least 1.3 fold, and most preferably at least 1.4-fold increased in comparison to a control.

Again, it is believed that the findings presented herein in relation to HCC can be generalized and apply, mutatis mutandis, to other liver cancers.

A patient can also be assessed positive for a liver cancer (i.e. a patient can be assessed to suffer from or to be prone to suffering from a liver cancer) if the amount of soluble AXL in a sample has a specific value or if the amount exceeds or falls below a specific (threshold) value.

In clinical practice (threshold) values of biomarkers (like proteins) are often indicated and used. Often, the values are indicated by a concentration of a biomarker (a protein) per a given volume of a sample. For example, the concentration can be indicated as "ng/ml". The term "ng/ml" as used herein refers to the quantity (in ng) of a protein in a volume (ml) of a sample (like serum). Likewise, a concentration might be indicated, for example, as "pg/µl" or "mg/l" and the like. A person skilled in the art is readily in the position to convert concentrations from "ng/ml" into e.g. "pg/µl" or "mg/l" (and vice versa). Concentrations converted into different units as exemplified above are encompassed in the present invention. Yet, a concentration of a biomarker is routinely indicated as "ng/ml".

For example, the (threshold) value of AFP in the diagnosis of HCC is (at least) 20 ng/ml.

As mentioned, the median serum concentration of sAXL in HCC was shown herein to be about 18.575 ng/mL. Corresponding serum concentrations of sAXL in very early HCC were shown herein to be about 18.064 ng/mL, in early HCC about 16.430 ng/mL and in advanced HCC about 18.880 ng/mL. By contrast, the median serum concentration of sAXL in healthy controls was shown to be about 13.388 ng/mL.

In accordance with the present invention, the term "amount of soluble AXL" as used herein can refer to a concentration as defined and described herein. It is comprehensible that the absolute amount of soluble AXL in a defined and specific volume (of a sample) can readily be calculated using a given or determined concentration (like the exemplary concentrations of soluble sAXL provided herein below).

For example, a kit to be used herein can be designed for use in ELISA, particularly Sandwich ELISA.

A kit to be used herein can accordingly comprise one capture antibody and one detection antibody, if one antigen is to be detected (e.g. one capture antibody specifically binding to sAXL and one detection antibody specifically binding to sAXL).

A kit to be used herein can comprise two capture and two detection antibodies, if two antigens are to be detected (e.g. one capture antibody specifically binding to sAXL, one capture antibody specifically binding to AFP, one detection antibody specifically binding to sAXL, and one detection antibody specifically binding to AFP; or one capture antibody specifically binding to sAXL, one capture antibody specifically binding to DKK-1, one detection antibody specifically binding to sAXL, and one detection antibody specifically binding to DKK-1).

Two capture and two detection antibodies can be used in a sandwich ELISA to measure levels of sAXL and AFP. The kit can further comprise recombinant sAXL and AFP (standards), microplates, washing buffer (Tween/phosphate buffered saline [PBS]), reagent diluent (bovine serum albumin/PBS), streptavidin-horseradish peroxidase, substrate solution (Hydrogen peroxide/tetramethylbenzidine) and stop solution (sulfuric acid).

Two capture and two detection antibodies can be used in a sandwich ELISA to measure levels of sAXL and Dickkopf-1 (DKK1). The kit can comprise recombinant sAXL and DKK1 (standards), microplates, wash buffer (Tween/phosphate buffered saline [PBS]), reagent diluent (bovine serum albumin/PBS), streptavidin-horseradish peroxidase, substrate solution (Hydrogen peroxide/tetramethylbenzidine) and stop solution (sulfuric acid).

The present invention relates to (a) binding molecule(s) for use in the herein provided methods. The present invention provides (a) binding molecule(s) useful for carrying out the methods of the invention. The present invention relates to the use of (a) binding molecule(s) in the herein provided methods.

Herein contemplated are antibodies that specifically bind to the above provided and defined soluble AXL, AFP and/or DKK-1 protein(s). Such antibodies can be used for diagnostic purposes in accordance with the present invention.

It is envisaged herein that the antibodies can specifically bind to (functional) fragments or (functional) derivatives of the soluble AXL, AFP and/or DKK-1 protein(s) as defined herein, for example also to polypeptides having at least 70% or more identity to herein soluble AXL, AFP and/or DKK-1 protein(s) protein(s).

Accordingly, the present invention relates to the use of these antibodies in the methods of the present invention.

Therefore, the present invention relates, inter alia, to the use of the herein above described binding molecule(s), such as antibody/antibodies, specifically binding to or specifically recognizing soluble AXL, AFP and/or DKK-1 protein(s) for assessing whether a patient suffers from liver cancer or is prone to suffering from a liver cancer. Primarily, the present invention relates to the use of the herein above described binding molecule(s), such as antibody/antibodies, specifically binding to or specifically recognizing soluble AXL, optionally in combination with binding molecule(s), such as antibody/antibodies, specifically binding to or specifically recognizing AFP protein(s) and/or binding molecule(s), such as antibody/antibodies, specifically binding to or specifically recognizing DKK-1 protein(s) for assessing whether a patient suffers from liver cancer or is prone to suffering from a liver cancer.

The present invention also relates to an antibody/antibodies as defined above or a composition comprising said antibody/antibodies for the preparation of a diagnostic kit (for use in the methods of the present invention).

The antibody may be a polyclonal antibody, a monoclonal antibody, a full antibody (immunoglobulin), a F(ab)-fragment, a F(ab)$_2$-fragment, a single-chain antibody, a chimeric antibody, a CDR-grafted antibody, a bivalent antibody-construct, a bispecific single chain antibody, a synthetic antibody or a cross-cloned antibody and the like.

Polyclonal or monoclonal antibodies or other antibodies (derived therefrom) can be routinely prepared using, inter alia, standard immunization protocols; see Ed Harlow, David Lane, (December 1988), Antibodies: A Laboratory Manual, Cold Spring Harbor Laboratory; or Ed Harlow, David Lane, (December 1998), Portable Protocols (Using Antibodies): A Laboratory Manual 2$^{nd}$ edition, Cold Spring Harbor Laboratory.

For example, immunization may involve the intraperitoneal or subcutaneous administration of the soluble AXL, AFP and/or DKK-1 protein(s)/polypeptide (and/or fragments, isoforms, homologues, derivatives thereof and so on) as defined herein to a mammal (e.g. rodents such as mice, rats, hamsters and the like). Preferably, fragments of soluble AXL, AFP and/or DKK-1 protein(s) are used.

Methods for the preparation and screening of antibodies specifically binding to an antigen are known in the art. Such methods can be used in accordance with the present invention. For example, antibodies recognizing the soluble AXL, AFP and/or DKK-1 protein(s) may be affinity purified. ELISA is commonly used for screening sera and/or assaying affinity column fractions. Western Blots can be used to demonstrate that the antibody can detect the actual protein of interest and to evaluate whether the antibody only recognizes the protein of interest, or if it cross-reacts with other proteins.

A person skilled in the art is in the position to apply and to adapt the teaching of these documents for the generation and validation of antibodies specifically binding to or specifically recognizing the polypeptides as defined herein in context of the present invention.

A general exemplary ELISA protocol to be used in accordance with the present invention is provided below:

Plate Preparation

1. Dilute the Capture Antibody to the working concentration in PBS without carrier protein. Immediately coat a 96-well microplate with 100 µL per well of the diluted Capture Antibody. Seal the plate and incubate overnight at room temperature.
2. Aspirate each well and wash with Wash Buffer, repeating the process two times for a total of three washes. Wash by filling each well with Wash Buffer (400 µL) using a squirt bottle, manifold dispenser, or autowasher. Complete removal of liquid at each step is essential for good performance. After the last wash, remove any remaining Wash Buffer by aspirating or by inverting the plate and blotting it against clean paper towels.
3. Block plates by adding 300 µL of Reagent Diluent to each well. Incubate at room temperature for a minimum of 1 hour.
4. Repeat the aspiration/wash as in step 2. The plates are now ready for sample addition.

Assay Procedure

1. Add 100 µL of sample or standards in Reagent Diluent, or an appropriate diluent, per well. Cover with an adhesive strip and incubate 2 hours at room temperature.
2. Repeat the aspiration/wash as in step 2 of Plate Preparation.
3. Add 100 µL of the Detection Antibody, diluted in Reagent Diluent, to each well. Cover with a new adhesive strip and incubate 2 hours at room temperature.
4. Repeat the aspiration/wash as in step 2 of Plate Preparation.
5. Add 100 µL of the working dilution of Streptavidin-HRP to each well. Cover the plate and incubate for 20 minutes at room temperature. Avoid placing the plate in direct light.
6. Repeat the aspiration/wash as in step 2.
7. Add 100 mL of Substrate Solution to each well. Incubate for 20 minutes at room temperature. Avoid placing the plate in direct light.
8. Add 50 µL of Stop Solution to each well. Gently tap the plate to ensure thorough mixing.
9. Determine the optical density of each well immediately, using a microplate reader set to 450 nm. If wavelength correction is available, set to 540 nm or 570 nm. If wavelength correction is not available, subtract readings at 540 nm or 570 nm from the readings at 450 nm. This subtraction will correct for optical imperfections in the plate. Readings made directly at 450 nm without correction may be higher and less accurate.

Generally, sandwich ELISAs (Enzyme-linked immunosorbent assay) for human sAXL can take advantage of various adaptions and modifications. For example, sAXL concentrations can be determined in serum samples of suspected liver cancer patients (preferably HCC patients), wherein the sample to be assessed is diluted 1:10 in phosphate buffered saline supplemented with 1% bovine serum albumin. For example, sAXL concentrations can be determined in serum samples of suspected liver cancer patients (preferably HCC patients), wherein the sample to be assessed is diluted 1:50 in phosphate buffered saline supplemented with 1% bovine serum albumin.

Interestingly, different sAXL values (amount/concentration) were obtained, when the serum sample was diluted 1:50 in the assay; see Example 2. As the following table shows, the results confirm the increase of sAXL in patient samples compared to control (e.g. samples from healthy persons).

| Dilution | Healthy Controls (IQR) | All HCC Patients (IQR) | HCC/ Healthy (IQR) |
| --- | --- | --- | --- |
| 1:10 | 13.388 (9.811-15.663) | 18.575 (14.316-23.045) | 1.39 (1.07-1.72) |
| 1:50 | 38.328 (30.670-43.653) | 63.437 (38.135-81.038) | 1.66 (0.99-2.11) |

Preferably, the amount of said one or more of soluble AXL, AFP and/or DKK-1 is determined by ELISA (like Sandwich ELISA).

In a preferred aspect, the present invention relates to a method for assessing whether a patient suffers from hepatocellular carcinoma or is prone to suffering from hepatocellular carcinoma, said method comprising
 determining the amount of soluble AXL in a sample from said patient; and
 assessing that said patient suffers from hepatocellular carcinoma or is prone to suffering from hepatocellular carcinoma when the amount of soluble AXL in said sample from the patient is increased in comparison to a control, wherein the amount of said one or more of soluble AXL, AFP and/or DKK-1 is determined by ELISA.

The control may be a control sample. The control sample may be a sample from a healthy person or from a hepatic fibrosis or from a liver cirrhosis patient.

In a certain aspect, the present invention relates to a method for assessing whether a patient suffers from hepatocellular carcinoma or is prone to suffering from hepatocellular carcinoma, said method comprising
 determining the amount of soluble AXL in a sample from said patient; and
 assessing that said patient suffers from hepatocellular carcinoma or is prone to suffering from hepatocellular carcinoma when the amount of soluble AXL in said sample from the patient is increased in comparison to a control, wherein the sample to be assessed is diluted 1:10.

The sample to be assessed may be diluted in phosphate buffered saline buffer. The sample to be assessed may be diluted in phosphate buffered saline buffer supplemented with 1% bovine serum albumin.

The present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL in said sample from the patient is increased in comparison to a control, wherein the sample to be assessed is diluted 1:50.

The sample to be assessed may be diluted in phosphate buffered saline buffer. The sample to be assessed may be diluted in phosphate buffered saline buffer supplemented with 1% bovine serum albumin.

In the methods herein, the amount of soluble AXL can be at least 1.05-fold, preferably at least 1.2-fold, at least 1.3-fold, at least 1.4-fold, at least 1.5-fold, more preferably at least 1.6-fold increased in comparison to a control.

The present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL in said sample from the patient is increased in comparison to a control, wherein said amount of soluble AXL in a sample from said patient is at least about 63 ng/ml, particularly about 63.44 ng/ml.

The present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL in said sample from the patient is increased in comparison to a control, wherein said amount of soluble AXL in a control is about 38 ng/ml, particularly about 38.33 ng/ml.

The data obtained by using a 1:10 and 1:50 dilution, respectively, can be converted as follows. Two methods of conversion are conceivable by regression analysis:

1. A simple conversion factor, yielding a Pearson-correlation of R=0.941

$$C_{1|60}=C_{1|10}*5.2264$$

2. A linear equation, resulting in a Pearson-correlation of R=1

$$C_{1|60}=C_{1|10}*4.8408-26.48$$

The present invention relates to a method for assessing whether a patient suffers from hepatocellular carcinoma or is prone to suffering from hepatocellular carcinoma, said method comprising
- determining the amount of soluble AXL in a sample from said patient; and
- assessing that said patient suffers from hepatocellular carcinoma or is prone to suffering from hepatocellular carcinoma when the amount of soluble AXL in said sample from the patient is increased in comparison to a control, wherein said amount of soluble AXL in a sample from said patient is about 18 ng/ml (like about 18.575 ng/ml).

In other words, the present invention relates to a method for assessing whether a patient suffers from hepatocellular carcinoma or is prone to suffering from hepatocellular carcinoma, said method comprising
- determining the concentration of soluble AXL in a sample from said patient; and
- assessing that said patient suffers from hepatocellular carcinoma or is prone to suffering from hepatocellular carcinoma when the concentration of soluble AXL in a sample from said patient is about 18 ng/ml (like about 18.575 ng/ml).

The present invention relates to a method for assessing whether a patient suffers from very early hepatocellular carcinoma or is prone to suffering from very early hepatocellular carcinoma, said method comprising
- determining the amount of soluble AXL in a sample from said patient; and
- assessing that said patient suffers from very early hepatocellular carcinoma or is prone to suffering from very early hepatocellular carcinoma when the amount of soluble AXL is increased in comparison to a control, wherein said amount of soluble AXL in a sample from said patient is about 18 ng/ml (like about 18.064 ng/ml).

In other words, the present invention relates to a method for assessing whether a patient suffers from very early hepatocellular carcinoma or is prone to suffering from very early hepatocellular carcinoma, said method comprising
- determining the concentration of soluble AXL in a sample from said patient; and
- assessing that said patient suffers from very early hepatocellular carcinoma or is prone to suffering from very early hepatocellular carcinoma when the concentration of soluble AXL in a sample from said patient is about 18 ng/ml (like about 18.064 ng/ml).

The present invention relates to a method for assessing whether a patient suffers from stage 0 hepatocellular carcinoma or is prone to suffering from stage 0 hepatocellular carcinoma, said method comprising
- determining the amount of soluble AXL in a sample from said patient; and
- assessing that said patient suffers from stage 0 hepatocellular carcinoma or is prone to suffering from stage 0 hepatocellular carcinoma when the amount of soluble AXL is increased in comparison to a control, wherein said amount of soluble AXL in a sample from said patient is about 18 ng/ml (like about 18.064 ng/ml).

In other words, the present invention relates to a method for assessing whether a patient suffers from stage 0 hepatocellular carcinoma or is prone to suffering from stage 0 hepatocellular carcinoma, said method comprising
- determining the concentration of soluble AXL in a sample from said patient; and
- assessing that said patient suffers from stage 0 hepatocellular carcinoma or is prone to suffering from stage 0 hepatocellular carcinoma when the concentration of soluble AXL in a sample from said patient is about 18 ng/ml (like about 18.064 ng/ml).

The present invention relates to a method for assessing whether a patient suffers from early hepatocellular carcinoma or is prone to suffering from early hepatocellular carcinoma, said method comprising
- determining the amount of soluble AXL in a sample from said patient; and assessing that said patient suffers from early hepatocellular carcinoma or is prone to suffering from early hepatocellular carcinoma when the amount of soluble AXL is increased in comparison to a control, wherein said amount of soluble AXL in a sample from said patient is about 16 ng/ml (like about 16.430 ng/ml).

In other words, the present invention relates to a method for assessing whether a patient suffers from early hepatocellular carcinoma or is prone to suffering from early hepatocellular carcinoma, said method comprising determining the concentration of soluble AXL in a sample from said patient; and assessing that said patient suffers from early hepatocellular carcinoma or is prone to suffering from early hepatocellular carcinoma when the concentration of soluble AXL in a sample from said patient is about 16 ng/ml (like about 16.430 ng/ml).

The present invention relates to a method for assessing whether a patient suffers from stage A hepatocellular carcinoma or is prone to suffering from stage A hepatocellular carcinoma, said method comprising determining the amount of soluble AXL in a sample from said patient; and assessing that said patient suffers from stage A hepatocellular carcinoma or is prone to suffering from stage A hepatocellular carcinoma when the amount of soluble AXL is increased in comparison to a control, wherein said amount of soluble AXL in a sample from said patient is about 16 ng/ml (like about 16.430 ng/ml).

In other words, the present invention relates to a method for assessing whether a patient suffers from stage A hepatocellular carcinoma or is prone to suffering from stage A hepatocellular carcinoma, said method comprising determining the concentration of soluble AXL in a sample from said patient; and assessing that said patient suffers from stage A hepatocellular carcinoma or is prone to suffering from stage A hepatocellular carcinoma when the concentration of soluble AXL in a sample from said patient is about 16 ng/ml (like about 16.430 ng/ml).

The present invention relates to a method for assessing whether a patient suffers from advanced hepatocellular carcinoma or is prone to suffering from advanced hepatocellular carcinoma, said method comprising determining the amount of soluble AXL in a sample from said patient; and assessing that said patient suffers from advanced hepatocellular carcinoma or is prone to suffering from advanced hepatocellular carcinoma when the amount of soluble AXL is increased in comparison to a control, wherein said amount of soluble AXL in a sample from said patient is higher than about 18 ng/ml (like 18.880 or higher).

In other words, the present invention relates to a method for assessing whether a patient suffers from advanced hepatocellular carcinoma or is prone to suffering from advanced hepatocellular carcinoma, said method comprising determining the concentration of soluble AXL in a sample from said patient; and assessing that said patient suffers from advanced hepatocellular carcinoma or is prone to suffering from advanced hepatocellular carcinoma when the concentration of soluble AXL in a sample from said patient is higher than about 18 ng/ml (like 18.880 or higher).

The present invention relates to a method for assessing whether a patient suffers from stage B, stage C or stage D hepatocellular carcinoma or is prone to suffering from stage B, stage C or stage D hepatocellular carcinoma, said method comprising determining the amount of soluble AXL in a sample from said patient; and assessing that said patient suffers from stage B, stage C or stage D hepatocellular carcinoma or is prone to suffering from stage B, stage C or stage D hepatocellular carcinoma when the amount of soluble AXL is increased in comparison to a control, wherein said amount of soluble AXL in a sample from said patient is higher than about 18 ng/ml (like 18.880 or higher).

In other words, the present invention relates to a method for assessing whether a patient suffers from stage B, stage C or stage D hepatocellular carcinoma or is prone to suffering from stage B, stage C or stage D hepatocellular carcinoma, said method comprising determining the concentration of soluble AXL in a sample from said patient; and assessing that said patient suffers from stage B, stage C or stage D hepatocellular carcinoma or is prone to suffering from stage B, stage C or stage D hepatocellular carcinoma when the concentration of soluble AXL in a sample from said patient is higher than about 18 ng/ml (like 18.880 or higher).

Figure 7:
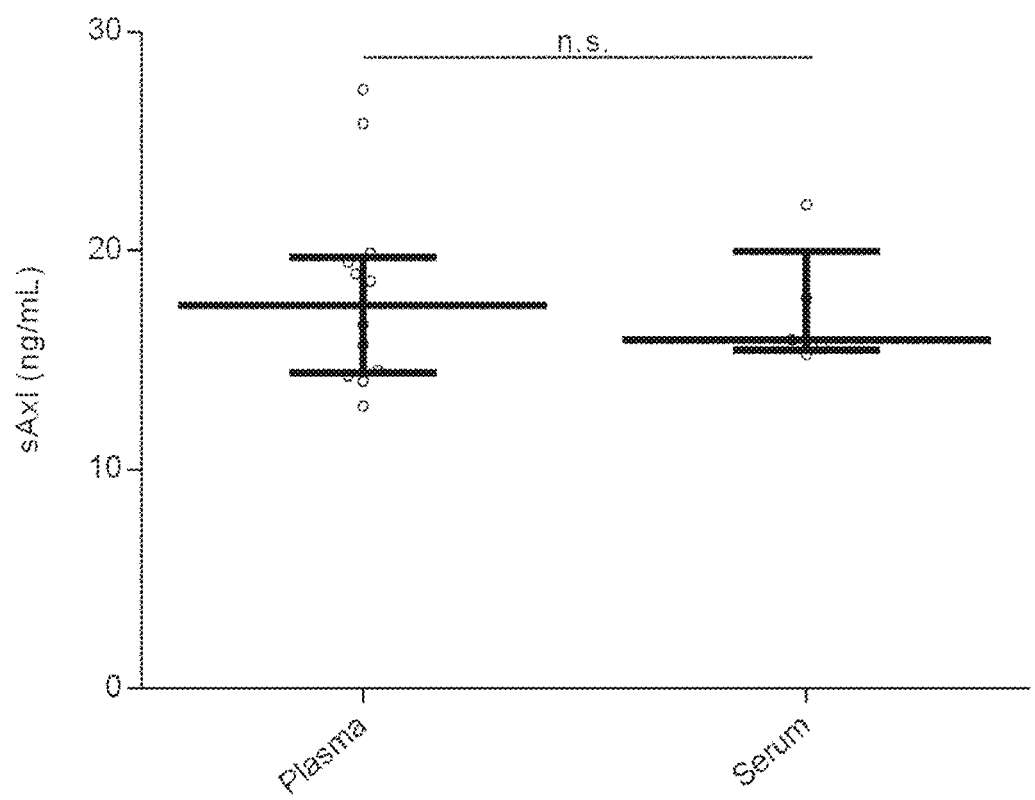

It is envisaged and preferred herein that the control/reference amount (or likewise concentration) of soluble AXL is about 13 ng/ml, particularly about 13.388 ng/ml In other words, the amount of soluble AXL in a control (sample) is about 13 ng/ml, particularly about 13.388 ng/ml As shown herein, amounts of sAXL in blood samples, like plasma samples and serum samples are comparable; see FIG. 7. Corresponding/comparable values can be obtained using peripheral blood (sample(s)). The values/amounts of samples of patients and controls provided above refer particularly to (a) blood (sample(s), like (a) serum (sample(s)), (a) plasma (sample(s)), or (a) peripheral blood (sample(s)).

FIG. 12 shows the analysis of sAXL concentrations in a urine and saliva sample in a healthy person. The control/reference amount (or likewise concentration) of soluble AXL in said sample was determined to be median 34.03 ng/ml in the urine sample and 0.375 ng/ml in the saliva sample.

A control/reference amount (or likewise concentration) of soluble AXL is about 20 to 40 ng/ml, for example, about 20 to 30 ng/ml, if (a) urine (sample(s)) is/are used. In other words, the amount of soluble AXL in (a) control urine (sample) is about 20 to 40 ng/ml, for example about 20 to 30 ng/ml.

A control/reference amount (or likewise concentration) of soluble AXL is about 0.2-0.4 ng/ml, for example 0.3-0.4 ng/ml, if (a) saliva (sample(s)) is/are used. In other words, the amount of soluble AXL in (a) control (a) saliva (sample(s)) is about 0.2-0.4 ng/ml.

If a urine or saliva sample of a patient suspected of suffering from liver cancer or suspected of being prone to suffering from liver cancer is analyzed, an amount or concentration above the threshold values of sAXL of a control (e.g. a control sample from a healthy person) indicates that the patient suffers from liver cancer or is prone to suffering from liver cancer. For example, an amount or concentration of sAXL in that is higher than about 20 to 40 ng/ml, for example, higher than about 20 to 30 ng/ml, particularly higher than about 30 ng/ml, in (a) urine (sample(s)) indicates that the patient suffers from liver cancer or is prone to suffering from liver cancer. For example, an amount or concentration of sAXL in that is higher than about 0.2-0.4 ng/ml, for example 0.3-0.4 ng/ml, particularly higher than about 0.4 ng/ml in (a) saliva (sample(s)) indicates that the patient suffers from liver cancer or is prone to suffering from liver cancer.

It is envisaged herein that the sample(s) from the patient and the control (sample(s)) are from the same source, e.g. both the patient sample(s) and the control (sample(s)) are from blood, like (a) serum (sample(s)), (a) plasma (sample(s)), (a) peripheral blood (sample(s)), or from (a) urine (sample(s)) or from (a) saliva (sample(s)).

It is generally preferred herein and in particular in the above mentioned embodiments of the present invention, that the sample from the patient is serum/a serum sample. Likewise, it is preferred that the control (sample) is serum/a serum sample. The following samples (e.g. from a patient to be assessed or a healthy individual) can be used in accordance with the present invention. The sample can be a blood sample. Also the use of a saliva sample or a urine sample is envisaged. The blood sample can, for example, be (a) serum (sample), (a) plasma (sample) or (a) peripheral blood (sample).

The sample can be obtained from a patient by routine techniques, for example, by biopsy. In the following an exemplary assay is described illustrating the preparation of (a) plasma (sample) or (a) serum (sample) to be used in the present invention.

For serum preparation, the collected blood sample from a patient to be assessed in accordance with the present invention (or a healthy control) can be allowed to clot at room temperature for less than 2 hours. The supernatant (designated serum) can be collected after centrifugation at 3000 rpm for 10 min, aliquoted for 0.5 ml/each and then stored at −80 C.

For plasma preparation, blood from a patient to be assessed in accordance with the present invention (or a healthy control) can be drawn into chilled blood collection tubes containing an anticoagulant mix of citrate, theophylline, adenosine, dipyridamole (CTAD) and immediately put on ice and further processed within 30 min. After an initial centrifugation step at 1000×g and 4° C. for 10 minutes, the plasma supernatant can be subjected to further centrifugation at 10000×g and 4° C. for 10 min to remove platelets. The supernatant can be stored in aliquots at −80° C. to avoid repeated cycles of freezing and thawing before analysis.

Because sAXL levels are generally comparable in both serum and plasma, the herein provided teaching applies at least to both serum and plasma; see Ekman, C. (2010) J Thromb Heamost 8: 838-844. doi: 10.1111/j.1538-7836.2010.03752.x.

The gist of the present invention lies in the surprising finding that liver cancer patients have an increased amount/concentration of soluble AXL (which can be determined in a sample from the patient). In the above described embodiments exemplary cut-off values (amounts/concentration) were defined based on median values of the patient cohort assessed in the clinical studies as shown in the appended Example.

Without deferring from the gist of the present invention other cut-off values can be used in the assessment or diagnosis of patients according the herein provided methods.

For example, interquartile ranges (IQR) can be used for assessing whether a patient suffers from liver cancer or is prone to suffering from liver cancer. The interquartile range (IQR) is a measure of statistical dispersion, being equal to the difference between the upper and lower quartiles.

In relation to very early HCC the interquartile range (IQR) was shown herein to be 14,385 to 22,623 ng/mL. In relation to early HCC the interquartile range (IQR) was shown herein to be 13,357 to 23,808 ng/mL As used herein, the amount/concentration of "about 18 ng/ml" in the assessment of very early HCC can refer to an amount/concentration of sAXL of 14,385 to 22,623 ng/mL (i.e. an amount/concentration of sAXL of about 14 to about 23 ng/ml). Likewise, the amount/concentration of "about 16 ng/ml" in the assessment of early HCC can refer to an amount/concentration of sAXL of 13,357 to 23,808 ng/mL (i.e. an amount/concentration of sAXL of about 13 to 24 ng/ml). In relation to advanced HCC the interquartile range (IQR) was shown herein to be 14,666 to 22,889 ng/mL. Likewise, the amount/concentration of "about 18 ng/ml" in the assessment of advanced HCC can refer to an amount/concentration of sAXL of 14,666 to 22,889 ng/mL (i.e. an amount/concentration of sAXL of about 14 to 23 ng/ml).

In relation to all HCC the interquartile range (IQR) was shown herein to be 14,316 to 23,045 ng/mL. Likewise, the amount/concentration of "about 18 ng/ml" in the assessment of all HCC can refer to an amount/concentration of sAXL of 14,316 to 23,045 ng/mL (i.e. an amount/concentration of sAXL of about 14 to 23 ng/ml).

The present invention relates to a method for assessing whether a patient suffers from very early hepatocellular carcinoma or is prone to suffering from very early hepatocellular carcinoma, said method comprising
  determining the amount of soluble AXL in a sample from said patient; and
  assessing that said patient suffers from very early hepatocellular carcinoma or is prone to suffering from very early hepatocellular carcinoma when the amount of soluble AXL is increased in comparison to a control, wherein said amount of soluble AXL in a sample from said patient is of from about 14 to about 23 ng/ml (like an amount of sAXL of from about 14 to about 23 ng/ml).

In other words, the present invention relates to a method for assessing whether a patient suffers from very early hepatocellular carcinoma or is prone to suffering from very early hepatocellular carcinoma, said method comprising
  determining the concentration of soluble AXL in a sample from said patient; and
  assessing that said patient suffers from very early hepatocellular carcinoma or is prone to suffering from very early hepatocellular carcinoma when the concentration of soluble AXL in a sample from said patient is of from about 14 to about 23 ng/ml (like a concentration of sAXL of from about 14 to about 23 ng/ml).

The present invention relates to a method for assessing whether a patient suffers from stage 0 hepatocellular carcinoma or is prone to suffering from stage 0 hepatocellular carcinoma, said method comprising
  determining the amount of soluble AXL in a sample from said patient; and
  assessing that said patient suffers from stage 0 hepatocellular carcinoma or is prone to suffering from stage 0 hepatocellular carcinoma when the amount of soluble AXL is increased in comparison to a control, wherein said amount of soluble AXL in a sample from said patient is of from about 14 to about 23 ng/ml (like an amount of sAXL of from about 14 to about 23 ng/ml).

In other words, the present invention relates to a method for assessing whether a patient suffers from stage 0 hepatocellular carcinoma or is prone to suffering from stage 0 hepatocellular carcinoma, said method comprising determining the concentration of soluble AXL in a sample from said patient; and assessing that said patient suffers from stage 0 hepatocellular carcinoma or is prone to suffering from stage 0 hepatocellular carcinoma when the concentration of soluble AXL in a sample from said patient is of from about 14 to about 23 ng/ml (like a concentration of sAXL of from about 14 to about 23 ng/ml).

The present invention relates to a method for assessing whether a patient suffers from early hepatocellular carcinoma or is prone to suffering from early hepatocellular carcinoma, said method comprising determining the amount of soluble AXL in a sample from said patient; and assessing that said patient suffers from early hepatocellular carcinoma or is prone to suffering from early hepatocellular carcinoma when the amount of soluble AXL is increased in comparison to a control, wherein said amount of soluble AXL in a sample from said patient is about of from 13 to 24 ng/ml (like an amount of from about 13,357 to 23,808 ng/mL).

In other words, the present invention relates to a method for assessing whether a patient suffers from early hepatocellular carcinoma or is prone to suffering from early hepatocellular carcinoma, said method comprising determining the concentration of soluble AXL in a sample from said patient; and assessing that said patient suffers from early hepatocellular carcinoma or is prone to suffering from early hepatocellular carcinoma when the concentration of soluble AXL in a sample from said patient is about of from 13 to 24 ng/ml (like a concentration of from about 13,357 to 23,808 ng/mL).

The present invention relates to a method for assessing whether a patient suffers from stage A hepatocellular carcinoma or is prone to suffering from stage A hepatocellular carcinoma, said method comprising determining the amount of soluble AXL in a sample from said patient; and assessing that said patient suffers from stage A hepatocellular carcinoma or is prone to suffering from stage A hepatocellular carcinoma when the amount of soluble AXL is increased in comparison to a control, wherein said amount of soluble AXL in a sample from said patient is about of from 13 to 24 ng/ml (like an amount of from about 13,357 to 23,808 ng/mL).

In other words, the present invention relates to a method for assessing whether a patient suffers from stage A hepatocellular carcinoma or is prone to suffering from stage A hepatocellular carcinoma, said method comprising determining the concentration of soluble AXL in a sample from said patient; and assessing that said patient suffers from stage A hepatocellular carcinoma or is prone to suffering from stage A hepatocellular carcinoma when the concentration of soluble AXL in a sample from said patient is about of from 13 to 24 ng/ml (like a concentration of from about 13,357 to 23,808 ng/mL).

Threshold amounts/concentrations of sAXL for a positive assessment/diagnosis can also be determined and used in accordance with the present invention based on the thresholds of ROC analyses. As shown in the appended example, two cut-offs for sAXL in HCC screening are provided, one offering exceptional sensitivity in the detection of very early and AFP-negative HCC (11.841 ng/mL) and a second one— exhibiting both high sensitivity and specificity (14.053 ng/mL)—that is suitable for diagnostic confirmation.

A patient can be assessed/diagnosed positive for HCC as defined and explained above, if the amount of sAXL in a sample is at least about 11 ng/ml, particularly about 11.841 ng/ml.

The present invention relates to a method for assessing whether a patient suffers from HCC or is prone to suffering from HCC, said method comprising determining the amount of soluble AXL in a sample from said patient; and assessing that said patient suffers from HCC or is prone to suffering from HCC when the amount of soluble AXL is at least about 11 ng/ml, particularly about 11.841 ng/ml.

This threshold is particularly useful in the diagnosis of very early and, optionally, AFP-negative HCC.

The present invention relates to a method for assessing whether a patient suffers from very early HCC or is prone to suffering from very early HCC, said method comprising determining the amount of soluble AXL in a sample from said patient; and assessing that said patient suffers from very early HCC or is prone to suffering from very early HCC when the amount of soluble AXL is at least about 11 ng/ml, particularly about 11.841 ng/ml.

The present invention relates to a method for assessing whether a patient suffers from very early HCC or is prone to suffering from very early HCC, said method comprising determining the amount of soluble AXL in a sample from said patient; and assessing that said patient suffers from very early HCC or is prone to suffering from very early HCC when the amount of soluble AXL is at least about 11 ng/ml, particularly about 11.841 ng/ml, the method further comprising determining the amount of AFP in a sample from said patient, wherein the patient is assessed AFP negative, for example, when the amount/concentration of AFP is below 20 ng/ml in a sample from said patient.

The definitions and explanations given herein above in context of diagnosing liver cancer apply mutatis mutandis in this context. For example, the definitions and explanations in relation to "patient" "determining the amount of sAXL", "sample", "sAXL", "HCC", "prone to suffering from HCC" and the like apply mutatis mutandis here.

A patient can be assessed/diagnosed positive for HCC as defined and explained above, if the amount of sAXL in a sample is at least about 14 ng/ml, particularly 14.053 ng/ml.

In a preferred embodiment, the present invention relates to a method for assessing whether a patient suffers from HCC or is prone to suffering from HCC, said method comprising determining the amount of soluble AXL in a sample from said patient; and assessing that said patient suffers from HCC or is prone to suffering from HCC when the amount of soluble AXL is at least about 14 ng/ml, particularly about 14.053 ng/ml ng/ml.

The definitions and explanations given herein above in context of diagnosing liver cancer apply mutatis mutandis in this context. For example, the definitions and explanations in relation to "patient" "determining the amount of sAXL", "sample", "sAXL", "HCC", "prone to suffering from HCC" and the like apply mutatis mutandis here.

The diagnostic methods of the present invention as explained and defined herein above are primarily useful to identify liver cancer patients or patients that are prone to suffering from liver cancer before any liver cancer therapy is applied to or contemplated for the patient(s). Exemplary liver cancer therapies are resection (of the tumor), Radio frequency ablation (RFA), transplantation, TACE, chemotherapy (like therapy with sorafenib, including to co-therapy with sorafenib, e.g. co-therapy with sorafenib and Mapk14 inhibitors (e.g. second-generation Mapk14 inhibitors such as skepinone-L and/or PH-797804)), as explained herein) or supportive care.

For example, the sample can be obtained from the patient before any liver cancer therapy has been applied and/or the assessment can be performed patient before any liver cancer therapy has been applied. Thereby, an unnecessary or detrimental therapy can be avoided (e.g. if the patient is assessed not to suffer from liver cancer). Alternatively, an appropriate therapy can be selected based on the exact classification of the cancer stage according to the present invention. For example, a patient can be selected for supportive care, if, for example, the patient is assessed for an advanced stage liver cancer.

The present invention relates to a method for assessing whether a patient suffers from liver cancer or is prone to suffering from liver cancer, said method comprising determining the amount of soluble AXL in a sample from said patient; and assessing that said patient suffers from liver cancer or is prone to suffering from liver cancer when the amount of soluble AXL is increased in comparison to a control, wherein the patient has not been treated by liver cancer therapy.

The methods of the present invention are also useful to monitor recurrence of liver cancer (i.e. as "monitoring markers") after liver cancer patients have been treated by liver cancer therapy as defined above (e.g. after resection, after liver transplantation and so on) In these aspects of the present invention, an increased amount of sAXL indicates recurrence of liver cancer.

For example, the sample can be obtained from the patient after liver cancer therapy has been applied and/or the assessment can be performed patient after liver cancer therapy has been applied. For example, a patient may have undergone liver cancer therapy and the methods provided herein are used to assess whether an increased amount of sAXL can be assessed in a patient sample at certain time intervals after termination of the therapy, e.g. after 1, 2, 3 and/or 4 weeks, after 1, 2, 3, 4, 5, 6, 7, 8, 9, 10, 11 and/or 12 months, 1, 2, 3, 4, 5, 6, 7, 8, 9 and/or 10 years after termination of the therapy. Thereby, a further/repeated unnecessary or detrimental therapy can be avoided (e.g. if the patient is, during monitoring, assessed not to suffer again from liver cancer). Alternatively, an appropriate therapy can be selected based on the exact classification of the cancer stage according to the present invention. For example, a patient can be selected for supportive care, if, for example, the patient is assessed for an advanced stage liver cancer.

The present invention relates to a method for assessing whether a patient suffers from liver cancer or is prone to suffering from liver cancer, said method comprising determining the amount of soluble AXL in a sample from said patient; and assessing that said patient suffers from liver cancer or is prone to suffering from liver cancer when the amount of soluble AXL is increased in comparison to a control, wherein the patient has been treated by liver cancer therapy.

The methods provided herein can also be used to monitor the efficacy of a liver cancer therapy. For example, a decrease of the amount of sAXL during the course of the therapy can indicate efficacy of the therapy. It is understood that a liver cancer patient has an increased amount of sAXL as defined herein (e.g. at least 14 ng/ml in a sample from the patient) prior to the start of a therapy. During or after treatment of the cancer, the tumor (cell(s)) driving the increase in the amount (or concentration) of sAXL is/are erased or otherwise depleted. Thus, a decrease in the amount or sAXL in a sample from a subject/patient during or after treatment of a liver cancer is indicative of the efficacy of the treatment.

If, for example, the amount of sAXL in a sample from a patient does not decrease during the course of the therapy, the liver cancer therapy is likely not effective. If, for example, the amount of sAXL in a sample from a patient does decrease during the course of the therapy, e.g. to a level of a healthy person (like about 13 ng/ml in a sample) the liver cancer therapy is likely effective. It is understood that there are various conceivable variations between "not effective" and "effective" wherein the methods of the present invention are useful.

In addition to sensitivity and specificity, further parameters like positive predictive values (PPV), negative predictive values (NPV) provide valuable information on the usefulness of a marker in clinical practice.

The term "positive predictive value" (PPV) refers to the proportion of true positives, i.e. the proportion of patients having a disease out of patients being diagnosed "positive" for the disease. If the PPV is low, a given diagnostic test will provide "false positives", i.e. patients which are diagnosed "positive" for a disease, do, in fact, not have the disease. Therefore, PPV is an important parameter to assess the reliability of a diagnostic test: the higher the PPV, the less likely a healthy person is misclassified as being sick. Thus, a high positive predictive value is of high relevance in clinical practice.

The term "negative predictive value" (NPV) refers to the proportion of patients with a negative test result who are correctly diagnosed. A high NPV value means that the test only rarely misclassifies a sick person as being healthy.

In case of high PPV values few patients are included that do not have cancer (few false positives) and in case of high NPV values few patients are excluded that do have cancer (few false negatives).

The following relates to soluble AXL (sAXL) to be used herein.

sAXL is the cleavage product of the receptor tyrosine kinase AXL. sAXL was first identified in 1995 by O'Bryan et al. (O'Bryan J. P. (1995) The Journal of Biological Chemistry 270:551-7) sAXL is defined as the extracellular domain of AXL, corresponding to the first (N-terminal) 440 amino acids of total AXL. The extracellular domain of AXL is proteolytically cleaved off leading to the release of sAXL consisting of the first 440 amino acids of the total Axl protein.

An exemplary nucleic acid sequence encodings total AXL and an exemplary amino acid sequence of total AXL is shown in SEQ ID NO: 1 and 2, respectively. An exemplary nucleic acid sequence encoding soluble AXL (sAXL) and an exemplary amino acid sequence of soluble AXL (sAXL) is shown in SEQ ID NO: 3 and 4, respectively. Also the use of (genetic) variants of sAXL is envisaged herein.

The soluble AXL to be used herein can be selected from the group consisting of (a) a polypeptide comprising an amino acid encoded by a nucleic acid molecule having the nucleic acid sequence as depicted in SEQ ID NO: 3;

(b) a polypeptide having an amino acid sequence as depicted in SEQ ID NO:4;

(c) a polypeptide encoded by a nucleic acid molecule encoding a peptide having an amino acid sequence as depicted in SEQ ID NO:4;
(d) a polypeptide comprising an amino acid encoded by a nucleic acid molecule hybridizing under stringent conditions to the complementary strand of nucleic acid molecules as defined in (a) or (c);
(e) a polypeptide having at least 70% identity to the polypeptide of any one of (a) to (d); and
(f) a polypeptide comprising an amino acid encoded by a nucleic acid molecule being degenerate as a result of the genetic code to the nucleotide sequence of a nucleic acid molecule as defined in (a), (c) and (d).

Preferably, sAXL to be used herein relates to
(a) a polypeptide comprising an amino acid encoded by a nucleic acid molecule having the nucleic acid sequence as depicted in SEQ ID NO: 3; or
(b) a polypeptide having an amino acid sequence as depicted in SEQ ID NO:4; or
(c) a polypeptide having at least 70% identity, most preferably at least 99% identity, to the polypeptide of (a) or (b).

Particularly preferably, sAXL to be used herein relates to
(a) a polypeptide comprising an amino acid encoded by a nucleic acid molecule having the nucleic acid sequence as depicted in SEQ ID NO: 3; or
(b) a polypeptide having an amino acid sequence as depicted in SEQ ID NO:4.

The herein provided method can further comprise assessing the amount of alpha-fetoprotein (AFP) in a sample from said patient. Assessing the amount of alpha-fetoprotein (AFP) can be performed prior to, simultaneously with or after assessing the amount of sAXL.

AFP is proteolytically processed during maturation, releasing an N-terminal signal peptide of 18 aminoacids and yielding mature AFP containing 591 amino acids. (Pucci P. (1991) Biochemistry 30:5061-5066.

AFP alone has been used in the art to diagnose HCC. Literature values of sensitivity and specificity of AFP for the detection of HCC range from 41-65% and 80-90% respectively (Daniele B. (2004) Gastroenterology 127(5 Suppl 1): S108-12). Furthermore, up to 50% of patients exhibit AFP-values below the most commonly used diagnostic cut-off of 20 ng/mL Farinati F. (2006) The American Journal of Gastroenterology 101: 524-32).

It is shown herein that sAXL allows the diagnosis of liver cancer patients even if the patients are AFP negative. Therefore, sAXL may be a valuable diagnostic tool in order to assess whether a patient suffers from liver cancer or is prone to suffering from liver cancer, if said patient is assessed as AFP negative. Usually, a patient is assessed AFP negative, when the amount/concentration of AFP is below 20 ng/ml in a sample from said patient.

The present invention is particularly useful if a patient is diagnosed positive for liver cancer, if both the amount of sAXL and of AFP is increased in comparison to a control. As described herein above in detail, sAXL is an excellent diagnostic marker, if used alone. The reliability/accuracy of the diagnostic test can be further increased, if a sample from a patient is assessed for an increase of the amount (or concentration of sAXL and AFP).

Accordingly, the methods of the present invention can comprise a step, wherein the patient is assessed to suffer from hepatocellular carcinoma or is prone to suffering from hepatocellular carcinoma when the amount of alpha-fetoprotein (AFP) is above a threshold value.

For example, it is shown herein that the median value of AFP in healthy controls is 3,000 ng/mL (IQR 2,090-3,980).

The median value of AFP in HCC patients was shown to be 33,550 (IQR 5,425-461,25). Accordingly, the above-mentioned threshold value can relate to an amount of alpha-fetoprotein (AFP) that is at least 5-fold, 6-fold, 7-fold, 8-fold, 9-fold, preferably 10-fold, more preferably 11-fold increased in comparison to a control.

Preferred in this context is an amount of alpha-fetoprotein (AFP) in a sample from the patient that is higher than about 20 ng/ml.

An exemplary nucleic acid sequence encoding AFP and an exemplary amino acid sequence of AFP is shown in SEQ ID NO: 5 and 6, respectively. Also the use of (genetic) variants of AFP/encoding an AFP protein is envisaged herein.

AFP to be used herein can be selected from the group consisting of
(a) a polypeptide comprising an amino acid encoded by a nucleic acid molecule having the nucleic acid sequence as depicted in SEQ ID NO: 5;
(b) a polypeptide having an amino acid sequence as depicted in SEQ ID NO:6;
(c) a polypeptide encoded by a nucleic acid molecule encoding a peptide having an amino acid sequence as depicted in SEQ ID NO:6;
(d) a polypeptide comprising an amino acid encoded by a nucleic acid molecule hybridizing under stringent conditions to the complementary strand of nucleic acid molecules as defined in (a) or (c);
(e) a polypeptide having at least 70% identity to the polypeptide of any one of (a) to (d); and
(f) a polypeptide comprising an amino acid encoded by a nucleic acid molecule being degenerate as a result of the genetic code to the nucleotide sequence of a nucleic acid molecule as defined in (a), (c) and (d).

Preferably, AFP to be used herein is
(a) a polypeptide comprising an amino acid encoded by a nucleic acid molecule having the nucleic acid sequence as depicted in SEQ ID NO: 5; or
(b) a polypeptide having an amino acid sequence as depicted in SEQ ID NO:6; or
(c) a polypeptide having at least 70% identity, most preferably at least 99% identity, to the polypeptide of (a) or (b).

Particularly preferably, AFP to be used herein is
(a) a polypeptide comprising an amino acid encoded by a nucleic acid molecule having the nucleic acid sequence as depicted in SEQ ID NO: 5; or
(b) a polypeptide having an amino acid sequence as depicted in SEQ ID NO:6.

The present invention is useful if a patient is diagnosed positive for liver cancer, if the amount of sAXL is increased in comparison to a control. The reliability/accuracy of the diagnostic test can be further increased, if a sample from a patient is assessed for an increase of the amount (or concentration) of sAXL in combination with an increase of the amount (or concentration) of AFP and/or an increase of the amount (or concentration) of DKK1.

Accordingly, the herein provided method can further comprise assessing the amount of Dickkopf-1 (DKK-1) in a sample from said patient.

DKK-1 is proteolytically processed during maturation, releasing an N-terminal signal peptide of 31 aminoacids and yielding mature DKK-1 containing 235 amino acids (Fedi P. (1999) J Biol Chem 274:19465-19472.

An exemplary nucleic acid sequence encoding DKK-1 and an exemplary amino acid sequence of DKK-1 is shown in SEQ ID NO: 7 and 8, respectively. Also the use of (genetic) variants of DKK-1/encoding a DKK-1 protein is envisaged herein.

The terms "sAXL", "AFP" and "DKK-1", respectively, refer primarily to proteins/polypeptides, i.e. to an sAXL protein/polypeptide, an AFP protein/polypeptide or an DKK-1 protein/polypeptide.

It is envisaged herein that the methods comprise a step, wherein said patient is assessed to suffer from liver cancer, like hepatocellular carcinoma, or is prone to suffering from liver cancer, like hepatocellular carcinoma, when the amount of Dickkopf-1 (DKK-1) is above a threshold value.

DKK-1 to be used herein can be selected from the group consisting of
(a) a polypeptide comprising an amino acid encoded by a nucleic acid molecule having the nucleic acid sequence as depicted in SEQ ID NO: 7;
(b) a polypeptide having an amino acid sequence as depicted in SEQ ID NO:8;
(c) a polypeptide encoded by a nucleic acid molecule encoding a peptide having an amino acid sequence as depicted in SEQ ID NO:8;
(d) a polypeptide comprising an amino acid encoded by a nucleic acid molecule hybridizing under stringent conditions to the complementary strand of nucleic acid molecules as defined in (a) or (c);
(e) a polypeptide having at least 70% identity to the polypeptide of any one of (a) to (d); and
(f) a polypeptide comprising an amino acid encoded by a nucleic acid molecule being degenerate as a result of the genetic code to the nucleotide sequence of a nucleic acid molecule as defined in (a), (c) and (d).

Preferably, DKK-1 to be used herein is
(a) a polypeptide comprising an amino acid encoded by a nucleic acid molecule having the nucleic acid sequence as depicted in SEQ ID NO: 7; or
(b) a polypeptide having an amino acid sequence as depicted in SEQ ID NO:8; or
(c) a polypeptide having at least 70% identity, most preferably at least 90% identity, to the polypeptide of (a) or (b).

Particularly preferably, DKK-1 to be used herein is
(a) a polypeptide comprising an amino acid encoded by a nucleic acid molecule having the nucleic acid sequence as depicted in SEQ ID NO: 7; or
(b) a polypeptide having an amino acid sequence as depicted in SEQ ID NO:8.

The amount of soluble AXL, AFP and/or DKK-1 can be determined by routine protein detections methods or assays, like ELISA (particularly Sandwich ELISA), immunohistochemistry (IHC), by immunoassay, gel- or blot-based methods, IHC, mass spectrometry, flow cytometry, or FACS.

sAXL can be measured in (a) sample(s) from patients (like serum or plasma from patients) which is/are devoid of cells or cellular particles due to centrifugation (e.g. at 1000×g for 10 minutes). The plasma supernatant can be subjected to further centrifugation e.g. at 10000×g and 4° C. for 10 min to remove platelets. Thus, it can be ensured that no or substantially no total AXL protein (i.e. non-cleaved AXL, as shown, for example in SEQ ID NO: 2) is present in the sample to be assessed.

As mentioned, a person skilled in the art is aware of standard methods to be used for determining or detecting/quantitating expression (and likewise the amount of the gene product) of soluble AXL, AFP and/or DKK-1 as defined herein. For example, the expression can be determined on the protein level by taking advantage of protein detection/quantitating techniques, like immunoagglutination, immunoprecipitation (e.g. immunodiffusion, immunelectrophoresis, immune fixation), western blotting techniques (e.g. (in situ) immuno histochemistry, (in situ) immuno cytochemistry, affinity chromatography, enzyme immunoassays), and the like. Amounts of purified polypeptide in solution can be determined by physical methods, e.g. photometry. Methods of quantifying a particular polypeptide in a mixture rely on specific binding, e.g. of antibodies. Specific detection and quantitation methods exploiting the specificity of antibodies comprise for example immunohistochemistry (in situ).

For example, concentration/amount of proteins in a cell, tissue or a non-human animal can be determined by enzyme linked-immunosorbent assay (ELISA), particularly Sandwich ELISA. Alternatively, Western Blot analysis or immunohistochemical staining can be performed. Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

Nucleic acid sequences with a certain level of identity to the herein provided human sequences can be identified by the skilled person using methods known in the art, e.g. by using hybridization assays or by using alignments, either manually or by using computer programs such as those mentioned herein below in connection with the definition of the term "hybridization" and degrees of homology/identity.

The nucleic acid sequence may be at least 70% identical to the nucleic acid sequence as shown in SEQ ID NO. 3, 5 or 7. More preferably, the nucleic acid sequence is at least 90%, 91%, 92%, 93%, 94%, 95%, 96%, 97% or 98% identical to the nucleic acid sequence as shown in SEQ ID NOs. 3, 5 or 7, wherein the higher values are preferred. Most preferably, the nucleic acid sequence is at least 99% identical to the nucleic acid sequence as shown in SEQ ID NO. 3, 5 or 7.

Hybridization assays for the characterization of nucleic acids with a certain level of identity to the nucleic acid sequences as provided herein are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as, for example, the highly stringent hybridization conditions of 0.1×SSC, 0.1% SDS at 65° C. or 2×SSC, 60° C., 0.1% SDS. Low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions.

In accordance with the present invention, the terms "homology" or "percent homology" or "identical" or "percent identity" or "percentage identity" or "sequence identity" in the context of two or more nucleic acid sequences refers to two or more sequences or subsequences that are the same, or that have a specified percentage of nucleotides that are the same (at least 70%, 75%, 80%, 85%, 90%, 91%, 92%, 93%, 94%, 95%, 96%, 97% or 98% identity, most preferably at least 99% identity), when compared and aligned for maximum correspondence over a window of comparison (preferably over the full length), or over a designated region as measured using a sequence comparison algorithm as known in the art, or by manual alignment and visual inspection. Sequences having, for example, 75% to 90% or greater sequence identity may be considered to be substantially identical. Such a definition also applies to the complement of a test sequence. Preferably the described identity exists over a region that is at least about 15 to 25 nucleotides in length, more preferably, over a region that is at least about 50 to 100 nucleotides in length and most preferably, over a region that is at least about 800 to 1200 nucleotides in length, preferably over the full length of the sequences as shown in SEQ ID NOs: 1, 3, 5 or 7. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

In order to determine whether an nucleotide residue in a nucleic acid sequence corresponds to a certain position in the nucleotide sequence of e.g. SEQ ID NOs: 3, 5 or 7, respectively, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of nucleotide sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum } BLAST \text{ score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those, which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

The explanations and definitions given herein above in respect of "homology/identity of nucleic acid sequences" apply, mutatis mutandis, to "amino acid sequences" of the proteins to be used herein as depicted in SEQ ID NO: 4, 6 or 8 as explained below.

SEQ ID NO: 4, 6 or 8 relate to exemplary amino acid sequences of soluble AXL, AFP and DKK-1, respectively.

The polypeptide to be used in accordance with the present invention may have at least 70% identity/similarity to the proteins having the amino acid sequence as, for example, depicted in SEQ ID NO: 4, 6 or 8, respectively. More preferably, the polypeptide has at least 90%, 91%, 92%, 93%, 94%, 95%, 96%, 97% or 98% identity/similarity to the proteins depicted in SEQ ID NO: 4, 6 or 8, respectively, wherein the higher values are preferred. Particularly and most preferred, the polypeptide has at least 99% homology to the protein as depicted in 4, 6 or 8.

Without deferring from the gist of the present invention also (functional) fragment(s) or (functional) derivatives of the herein provided polypeptides or proteins can be used, for example, (functional) fragment(s) or (functional) derivative(s) of soluble AXL, such as the one as shown in SEQ ID NO: 4, (functional) fragment(s) or (functional) derivative(s) of AFP, such as the one as shown in SEQ ID NO: 6, or (functional) fragment(s) or (functional) derivative (a) of DKK-1, such as the one as shown in SEQ ID NO. 8.

Thus, a (functional) fragment of the above polypeptide(s)/protein(s) can be any of the above specific polypeptides as shown in SEQ ID NOs: 4, 6 or 8, wherein one or more amino acids are deleted.

A (functional) derivative(s) of the above polypeptide(s)/protein(s) can be any of the above specific polypeptides as shown in SEQ ID NOs: 4, 6 or 8, wherein one or more amino acids are inserted, added or substituted.

The extracellular domain of Axl is proteolytically cleaved off leading to the release of sAxl consisting of the first 440 amino acids of the total Axl protein.

A fragment of an sAXL protein can consist of at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, or 420 and up to 430 contiguous amino acids of the amino acid sequence shown in SEQ ID NO: 4.

AFP is proteolytically processed during maturation, releasing an N-terminal signal peptide of 18 aminoacids and yielding mature AFP containing 591 amino acids. (Pucci P. (1991) Biochemistry 30:5061-5066.

A fragment of an AFP protein can consist of at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, or 580 and up to 590 contiguous amino acids of the amino acid sequence shown in SEQ ID NO: 6.

DKK-1 is proteolytically processed during maturation, releasing an N-terminal signal peptide of 31 aminoacids and yielding mature DKK-1 containing 235 amino acids (Fedi P. (1999) J Biol Chem 274:19465-19472.

A fragment of a DKK-1 protein can consist of at least 10, 20, 30, 40, 50, 60, 70, 80, 90, 100, 110, 120, 130, 140, 150, 160, 170, 180, 190, 200, 210, or 220 and up to 230 contiguous amino acids of the amino acid sequence shown in SEQ ID NO: 8.

The assessment of the amount of (genetic) variants of sAXL, optionally in combination with AFP and/or DKK-1 is envisaged in context of the present invention.

Exemplary (genetic) variants to be assessed in accordance with the present invention are described below.

The following shows exemplary polymorphisms of AXL protein(s). Soluble AXL protein is the extracellular domain of AXL, corresponding to the first (N-terminal) 440 amino acids of AXL. It is understood that the polymorphisms below relating to the first (N-terminal) 440 amino acids of AXL protein are therefore primarily relevant in the assessment of soluble AXL in accordance with the present invention. Polymorphisms of total AXL might be also relevant for the release of soluble AXL (AS 2-AS 883).

| Chr. Pos. | mRNA pos. | dbSNP rs# | Function | dbSNP allele | Protein residue | Codon | Amino acid |
|---|---|---|---|---|---|---|---|
| 41725302 | 195 | rs10411373 | missense | T | Val [V] | 2 | 2 |
| | | | contig reference | C | Ala [A] | 2 | 2 |
| 41725303 | 196 | rs149864098 | synonymous | A | Ala [A] | 3 | 2 |
| | | | contig reference | G | Ala [A] | 3 | 2 |
| 41725307 | 200 | rs182481095 | synonymous | A | Arg [R] | 1 | 4 |
| | | | contig reference | C | Arg [R] | 1 | 4 |
| 41725337 | 230 | rs112524750 | missense | A | Thr [T] | 1 | 14 |
| | | | contig reference | G | Ala [A] | 1 | 14 |
| 41725346 | 239 | rs371082541 | missense | G | Val [V] | 1 | 17 |
| | | | contig reference | T | Leu [L] | 1 | 17 |
| 41725350 | 243 | rs145867512 | missense | T | Val [V] | 2 | 18 |
| | | | contig reference | C | Ala [A] | 2 | 18 |
| 41726149 | | rs143482982 | | —/TCT | | | |
| 41726545 | 280 | rs201764420 | synonymous | A | Thr [T] | 3 | 30 |
| | | | contig reference | G | Thr [T] | 3 | 30 |
| 41726559 | 294 | rs201081309 | missense | T | Ile [I] | 2 | 35 |
| | | | contig reference | G | Ser [S] | 2 | 35 |
| 41726598 | 333 | rs200598880 | missense | A | Gln [Q] | 2 | 48 |
| | | | contig reference | G | Arg [R] | 2 | 48 |
| 41726603 | 338 | rs369684238 | missense | T | Phe [F] | 1 | 50 |
| | | | contig reference | C | Leu [L] | 1 | 50 |
| 41726608 | 343 | rs55767963 | synonymous | A | Thr [T] | 3 | 51 |
| | | | contig reference | G | Thr [T] | 3 | 51 |
| 41726611 | 346 | rs374467939 | synonymous | A | Gly [G] | 3 | 52 |
| | | | contig reference | C | Gly [G] | 3 | 52 |
| 41726627 | 362 | rs200868176 | missense | G | Val [V] | 1 | 58 |
| | | | contig reference | C | Leu [L] | 1 | 58 |
| 41726633 | 368 | rs144418422 | missense | T | Phe [F] | 1 | 60 |
| | | | contig reference | G | Val [V] | 1 | 60 |
| 41726650 | 385 | rs146598679 | synonymous | T | Pro [P] | 3 | 65 |
| | | | contig reference | C | Pro [P] | 3 | 65 |
| 41726659 | 394 | rs140935892 | synonymous | C | His [H] | 3 | 68 |
| | | | contig reference | T | His [H] | 3 | 68 |
| 41726667 | 402 | rs143071942 | missense | A | Gln [Q] | 2 | 71 |
| | | | contig reference | G | Arg [R] | 2 | 71 |
| 41726677 | 412 | rs55690306 | synonymous | A | Gln [Q] | 3 | 74 |
| | | | contig reference | G | Gln [Q] | 3 | 74 |
| 41726692 | 427 | rs372605787 | synonymous | A | Ala [A] | 3 | 79 |
| | | | contig reference | G | Ala [A] | 3 | 79 |
| 41727077 | 525 | rs35202236 | missense | T | Met [M] | 2 | 112 |
| | | | contig reference | C | Thr [T] | 2 | 112 |
| 41727126 | 574 | rs55682303 | synonymous | T | Ser [S] | 3 | 128 |
| | | | contig reference | C | Ser [S] | 3 | 128 |
| 41727243 | | rs35915914 | | (>6bp) | | | |
| 41727810 | 625 | rs148074357 | synonymous | T | Pro [P] | 3 | 145 |
| | | | contig reference | C | Pro [P] | 3 | 145 |
| 41727819 | 634 | rs61737384 | synonymous | A | Arg [R] | 3 | 148 |
| | | | contig reference | G | Arg [R] | 3 | 148 |

| Chr. Pos. | mRNA pos. | dbSNP rs# | Function | dbSNP allele | Protein residue | Codon | Amino acid |
|---|---|---|---|---|---|---|---|
| 41727820 | 635 | rs140091980 | missense | G | Ala [A] | 1 | 149 |
| | | | contig reference | A | Thr [T] | 1 | 149 |
| 41727824 | 639 | rs200505600 | missense | C | Ala [A] | 2 | 150 |
| | | | contig reference | T | Val [V] | 2 | 150 |
| 41727826 | 641 | rs375559004 | missense | A | Thr [T] | 1 | 151 |
| | | | contig reference | G | Ala [A] | 1 | 151 |
| 41727830 | 645 | rs377289020 | missense | T | Val [V] | 2 | 152 |
| | | | contig reference | C | Ala [A] | 2 | 152 |
| 41727866 | 681 | rs377308556 | missense | A | Glu [E] | 2 | 164 |
| | | | contig reference | G | Gly [G] | 2 | 164 |
| 41727868 | 683 | rs67729269 | frame shift | C | Arg [R] | 1 | 167 |
| | | | contig reference | — | Glu [E] | 1 | 167 |
| 41727872 | 687 | rs200541897 | missense | G | Arg [R] | 2 | 166 |
| | | | contig reference | C | Pro [P] | 2 | 166 |
| 41727886 | 701 | rs369500522 | synonymous | T | Leu [L] | 1 | 171 |
| | | | contig reference | C | Leu [L] | 1 | 171 |
| 41727897 | 712 | rs200002144 | synonymous | A | Leu [L] | 3 | 174 |
| | | | contig reference | C | Leu [L] | 3 | 174 |
| 41727911 | 726 | rs201959501 | missense | T | Leu [L] | 2 | 179 |
| | | | contig reference | C | Pro [P] | 2 | 179 |
| 41727913 | 728 | rs150285609 | synonymous | T | Leu [L] | 1 | 180 |
| | | | contig reference | C | Leu [L] | 1 | 180 |
| 41727916 | 731 | rs200904022 | missense | T | Ser [S] | 1 | 181 |
| | | | contig reference | G | Ala [A] | 1 | 181 |
| 41727920 | 735 | rs138094666 | missense | T | Met [M] | 2 | 182 |
| | | | contig reference | C | Thr [T] | 2 | 182 |
| 41727955 | 770 | rs34645731 | missense | A | Ile [I] | 1 | 194 |
| | | | contig reference | G | Val [V] | 1 | 194 |
| 41736900 | 805 | rs143934164 | synonymous | T | Cys [C] | 3 | 205 |
| | | | contig reference | C | Cys [C] | 3 | 205 |
| 41736901 | 806 | rs201799923 | missense | A | Lys [K] | 1 | 206 |
| | | | contig reference | G | Glu [E] | 1 | 206 |
| 41736908 | 813 | rs370473880 | missense | G | Arg [R] | 2 | 208 |
| | | | contig reference | A | His [H] | 2 | 208 |
| 41736921 | 826 | rs144284099 | synonymous | A | Gly [G] | 3 | 212 |
| | | | contig reference | G | Gly [G] | 3 | 212 |
| 41737105 | 875 | rs140448864 | missense | T | Cys [C] | 1 | 229 |
| | | | contig reference | C | Arg [R] | 1 | 229 |
| 41737137 | 907 | rs142452494 | synonymous | A | Thr [T] | 3 | 239 |
| | | | contig reference | G | Thr [T] | 3 | 239 |
| 41737141 | 911 | rs201678158 | synonymous | T | Leu [L] | 1 | 241 |
| | | | contig reference | C | Leu [L] | 1 | 241 |
| 41737170 | 940 | rs150914023 | synonymous | T | Ser [S] | 3 | 250 |
| | | | contig reference | C | Ser [S] | 3 | 250 |
| 41737200 | 970 | rs376785668 | synonymous | T | Leu [L] | 3 | 260 |
| | | | contig reference | G | Leu [L] | 3 | 260 |
| 41737851 | | rs369580083 | | (>6bp) | | | |
| | | | intron | (>6bp) | | | |
| 41737854 | | rs113264646 | | (>6bp) | | | |
| | | | intron | (>6bp) | | | |
| 41741280 | | rs58820138 | | (>6bp) | | | |
| | | | intron | (>6bp) | | | |
| 41743849 | 974 | rs139491068 | missense | A | Thr [T] | 1 | 262 |
| | | | contig reference | G | Ala [A] | 1 | 262 |
| 41743883 | 1008 | rs374699228 | missense | T | Val [V] | 2 | 273 |
| | | | contig reference | C | Ala [A] | 2 | 273 |
| 41743884 | 1009 | rs61737383 | synonymous | A | Ala [A] | 3 | 273 |
| | | | contig reference | G | Ala [A] | 3 | 273 |
| 41743910 | 1035 | rs191926606 | missense | T | Leu [L] | 2 | 282 |
| | | | contig reference | C | Pro [P] | 2 | 282 |
| 41743919 | 1044 | rs201003955 | missense | T | Leu [L] | 2 | 285 |
| | | | contig reference | C | Ser [S] | 2 | 285 |
| 41743925 | 1050 | rs370447193 | missense | G | Gly [G] | 2 | 287 |
| | | | contig reference | C | Ala [A] | 2 | 287 |
| 41743929 | 1054 | rs113249799 | synonymous | G | Ser [S] | 3 | 288 |
| | | | synonymous | T | Ser [S] | 3 | 288 |
| | | | contig reference | C | Ser [S] | 3 | 288 |
| 41743930 | 1055 | rs141302305 | missense | A | Met [M] | 1 | 289 |
| | | | contig reference | G | Val [V] | 1 | 289 |
| 41743949 | 1074 | rs199988157 | missense | A | Gln [Q] | 2 | 295 |
| | | | contig reference | G | Arg [R] | 2 | 295 |
| 41743952 | 1077 | rs112094962 | missense | C | Pro [P] | 2 | 296 |
| | | | contig reference | T | Leu [L] | 2 | 296 |
| 41743966 | 1091 | rs201596308 | missense | T | Ser [S] | 1 | 301 |
| | | | contig reference | C | Pro [P] | 1 | 301 |

-continued

| Chr. Pos. | mRNA pos. | dbSNP rs# | Function | dbSNP allele | Protein residue | Codon | Amino acid |
|---|---|---|---|---|---|---|---|
| 41743972 | 1097 | rs1061079 | missense | C | Pro [P] | 1 | 303 |
| | | | contig reference | A | Thr [T] | 1 | 303 |
| 41744001 | 1126 | rs367860043 | synonymous | G | Thr [T] | 3 | 312 |
| | | | contig reference | C | Thr [T] | 3 | 312 |
| 41744003 | 1128 | rs200936572 | missense | A | Asn [N] | 2 | 313 |
| | | | contig reference | G | Ser [S] | 2 | 313 |
| 41744032 | 1157 | rs199894470 | missense | A | Arg [R] | 1 | 323 |
| | | | contig reference | T | Trp [W] | 1 | 323 |
| 41744039 | 1164 | rs149706303 | missense | T | Leu [L] | 2 | 325 |
| | | | contig reference | C | Pro [P] | 2 | 325 |
| 41744048 | 1173 | rs376355256 | missense | T | Met [M] | 2 | 328 |
| | | | contig reference | C | Thr [T] | 2 | 328 |
| 41744049 | 1174 | rs56408665 | synonymous | A | Thr [T] | 3 | 328 |
| | | | contig reference | G | Thr [T] | 3 | 328 |
| 41744052 | 1177 | rs368468222 | synonymous | A | Pro [P] | 3 | 329 |
| | | | contig reference | G | Pro [P] | 3 | 329 |
| 41744059 | 1184 | rs372719583 | missense | A | Met [M] | 1 | 332 |
| | | | contig reference | G | Val [V] | 1 | 332 |
| 41744376 | 1186 | rs201262768 | synonymous | A | Val [V] | 3 | 332 |
| | | | contig reference | G | Val [V] | 3 | 332 |
| 41744392 | 1202 | rs1138335 | missense | A | Lys [K] | 1 | 338 |
| | | | contig reference | G | Glu [E] | 1 | 338 |
| 41744408 | 1218 | rs374067962 | missense | T | Met [M] | 2 | 343 |
| | | | contig reference | C | Thr [T] | 2 | 343 |
| 41744409 | 1219 | rs145562073 | synonymous | A | Thr [T] | 3 | 343 |
| | | | contig reference | G | Thr [T] | 3 | 343 |
| 41744410 | 1220 | rs148886744 | missense | T | Trp [W] | 1 | 344 |
| | | | contig reference | C | Arg [R] | 1 | 344 |
| 41744449 | 1259 | rs143593613 | missense | T | Trp [W] | 1 | 357 |
| | | | contig reference | C | Arg [R] | 1 | 357 |
| 41744453 | 1263 | rs138219571 | missense | T | Val [V] | 2 | 358 |
| | | | contig reference | C | Ala [A] | 2 | 358 |
| 41744462 | 1272 | rs141929169 | missense | C | Pro [P] | 2 | 361 |
| | | | contig reference | A | Gln [Q] | 2 | 361 |
| 41744708 | | rs150814982 | | —/GTT | | | |
| 41745071 | 1327 | rs199906180 | synonymous | C | Val [V] | 3 | 379 |
| | | | contig reference | G | Val [V] | 3 | 379 |
| 41745122 | 1378 | rs201734105 | synonymous | T | Asp [D] | 3 | 396 |
| | | | contig reference | C | Asp [D] | 3 | 396 |
| 41745135 | 1391 | rs71823923 | frame shift | C | [TS] | 1 | 401 |
| | | | contig reference | — | Asn [N] | 1 | 401 |
| 41748797 | 1485 | rs372019655 | missense | A | His [H] | 2 | 432 |
| | | | contig reference | C | Pro [P] | 2 | 432 |
| 41748818 | 1506 | rs117588892 | missense | T | Leu [L] | 2 | 439 |
| | | | contig reference | G | Trp [W] | 2 | 439 |
| 41748849 | 1537 | rs145779711 | synonymous | T | Val [V] | 3 | 449 |
| | | | contig reference | C | Val [V] | 3 | 449 |
| 41748850 | 1538 | rs138698106 | missense | A | Met [M] | 1 | 450 |
| | | | contig reference | G | Val [V] | 1 | 450 |
| 41748855 | 1543 | rs142750893 | synonymous | T | Ala [A] | 3 | 451 |
| | | | contig reference | C | Ala [A] | 3 | 451 |
| 41748891 | 1579 | rs200952166 | synonymous | T | Val [V] | 3 | 463 |
| | | | contig reference | C | Val [V] | 3 | 463 |
| 41748894 | 1582 | rs150756125 | missense | G | Gln [Q] | 3 | 464 |
| | | | contig reference | C | His [H] | 3 | 464 |
| 41748895 | 1583 | rs138883984 | missense | G | Gly [G] | 1 | 465 |
| | | | contig reference | C | Arg [R] | 1 | 465 |
| 41749530 | 1618 | rs149411519 | synonymous | C | Phe [F] | 3 | 476 |
| | | | contig reference | T | Phe [F] | 3 | 476 |
| 41749571 | 1659 | rs200850031 | missense | A | His [H] | 2 | 490 |
| | | | contig reference | G | Arg [R] | 2 | 490 |
| 41749572 | 1660 | rs202071701 | synonymous | T | Arg [R] | 3 | 490 |
| | | | contig reference | C | Arg [R] | 3 | 490 |
| 41749573 | 1661 | rs144824336 | missense | A | Met [M] | 1 | 491 |
| | | | contig reference | G | Val [V] | 1 | 491 |
| 41749606 | 1694 | rs377666344 | missense | A | Thr [T] | 1 | 502 |
| | | | contig reference | G | Ala [A] | 1 | 502 |
| 41752731 | | rs70950389 | | (>6bp) | | | |
| 41752916 | | rs138956703 | | —/CAA | | | |
| 41752917 | | rs148994728 | | —/AAC | | | |
| 41752921 | | rs72544845 | | —/AAC | | | |
| 41752922 | | rs3082707 | | —/AAC | | | |
| 41754427 | 1709 | rs17853029 | synonymous | T | Leu [L] | 1 | 507 |
| | | | contig reference | C | Leu [L] | 1 | 507 |
| 41754430 | 1712 | rs35538872 | missense | A | Ser [S] | 1 | 508 |
| | | | contig reference | G | Gly [G] | 1 | 508 |

-continued

| Chr. Pos. | mRNA pos. | dbSNP rs# | Function | dbSNP allele | Protein residue | Codon | Amino acid |
|---|---|---|---|---|---|---|---|
| 41754460 | 1742 | rs374709166 | missense | T | Trp [W] | 1 | 518 |
|  |  |  | contig reference | C | Arg [R] | 1 | 518 |
| 41754463 | 1745 | rs200466681 | missense | A | Asn [N] | 1 | 519 |
|  |  |  | contig reference | G | Asp [D] | 1 | 519 |
| 41754478 | 1760 | rs144179986 | missense | T | Trp [W] | 1 | 524 |
|  |  |  | contig reference | C | Arg [R] | 1 | 524 |
| 41754661 | 1810 | rs201416484 | synonymous | C | Ala [A] | 3 | 540 |
|  |  |  | contig reference | T | Ala [A] | 3 | 540 |
| 41754708 | 1857 | rs374586885 | missense | G | Gly [G] | 2 | 556 |
|  |  |  | contig reference | C | Ala [A] | 2 | 556 |
| 41754718 | 1867 | rs372248009 | synonymous | A | Thr [T] | 3 | 559 |
|  |  |  | contig reference | G | Thr [T] | 3 | 559 |
| 41758164 |  | rs111441971 |  | —/TGA |  |  |  |
|  |  |  | intron | —/TGA |  |  |  |
| 41758302 | 1921 | rs372826434 | synonymous | A | Ala [A] | 3 | 577 |
|  |  |  | contig reference | G | Ala [A] | 3 | 577 |
| 41758332 | 1951 | rs370684779 | synonymous | T | Asn [N] | 3 | 587 |
|  |  |  | contig reference | C | Asn [N] | 3 | 587 |
| 41758347 | 1966 | rs146060336 | synonymous | T | Ile [I] | 3 | 592 |
|  |  |  | contig reference | C | Ile [I] | 3 | 592 |
| 41758775 | 1992 | rs374737642 | missense | T | Leu [L] | 2 | 601 |
|  |  |  | contig reference | G | Arg [R] | 2 | 601 |
| 41758786 | 2003 | rs140047155 | missense | T | Ser [S] | 1 | 605 |
|  |  |  | contig reference | C | Pro [P] | 1 | 605 |
| 41758858 | 2075 | rs67987188 | frame shift | G | Gly [G] | 1 | 630 |
|  |  |  | contig reference | — | Asp [D] | 1 | 630 |
| 41758862 | 2079 | rs1138336 | missense | C | Ala [A] | 2 | 630 |
|  |  |  | missense | G | Gly [G] | 2 | 630 |
|  |  |  | contig reference | A | Asp [D] | 2 | 630 |
| 41759514 | 2100 | rs202051448 | missense | T | Ile [I] | 2 | 637 |
|  |  |  | contig reference | C | Thr [T] | 2 | 637 |
| 41759545 | 2131 | rs79369530 | synonymous | T | Ile [I] | 3 | 647 |
|  |  |  | contig reference | C | Ile [I] | 3 | 647 |
| 41759577 | 2163 | rs367869435 | missense | A | Lys [K] | 2 | 658 |
|  |  |  | contig reference | G | Arg [R] | 2 | 658 |
| 41759578 | 2164 | rs372570874 | synonymous | G | Arg [R] | 3 | 658 |
|  |  |  | contig reference | A | Arg [R] | 3 | 658 |
| 41759593 | 2179 | rs5828095 | frame shift | — | Trp [W] | 3 | 664 |
|  |  |  | contig reference | C | Leu [L] | 3 | 664 |
| 41759593 | 2179 | rs150624962 | synonymous | T | Asp [D] | 3 | 663 |
|  |  |  | contig reference | C | Asp [D] | 3 | 663 |
| 41759599 | 2185 | rs138641156 | synonymous | A | Ala [A] | 3 | 665 |
|  |  |  | contig reference | G | Ala [A] | 3 | 665 |
| 41759805 |  | rs10618949 |  | —/CCC |  |  |  |
| 41760297 |  | rs67742741 |  | —/AAG |  |  |  |
|  |  |  | intron | —/AAG |  |  |  |
| 41760299 |  | rs56662977 |  | —/GAA |  |  |  |
|  |  |  | intron | —/GAA |  |  |  |
| 41761997 |  | rs67443177 |  | (>6bp) |  |  |  |
|  |  |  | intron | (>6bp) |  |  |  |
| 41762006 |  | rs71177704 |  | (>6bp) |  |  |  |
|  |  |  | intron | (>6bp) |  |  |  |
| 41762366 | 2209 | rs200876332 | missense | T | Asp [D] | 3 | 673 |
|  |  |  | contig reference | G | Glu [E] | 3 | 673 |
| 41762370 | 2213 | rs139134087 | missense | T | Leu [L] | 1 | 675 |
|  |  |  | contig reference | A | Met [M] | 1 | 675 |
| 41762404 | 2247 | rs369032589 | missense | G | Arg [R] | 2 | 686 |
|  |  |  | contig reference | A | Lys [K] | 2 | 686 |
| 41762429 | 2272 | rs201240568 | nonsense | A | [Ter[*]] | 3 | 694 |
|  |  |  | contig reference | C | Tyr [Y] | 3 | 694 |
| 41762439 | 2282 | rs371618406 | missense | T | Cys [C] | 1 | 698 |
|  |  |  | contig reference | C | Arg [R] | 1 | 698 |
| 41762483 | 2326 | rs140101050 | synonymous | T | Leu [L] | 3 | 712 |
|  |  |  | contig reference | A | Leu [L] | 3 | 712 |
| 41762511 | 2354 | rs200253980 | missense | A | Asn [N] | 1 | 722 |
|  |  |  | contig reference | G | Asp [D] | 1 | 722 |
| 41763406 | 2368 | rs147631147 | synonymous | T | Phe [F] | 3 | 726 |
|  |  |  | contig reference | C | Phe [F] | 3 | 726 |
| 41763426 | 2388 | rs368437223 | missense | C | Thr [T] | 2 | 733 |
|  |  |  | contig reference | T | Ile [I] | 2 | 733 |
| 41763458 | 2420 | rs372169583 | missense | A | Met [M] | 1 | 744 |
|  |  |  | contig reference | G | Val [V] | 1 | 744 |
| 41763469 | 2431 | rs117626938 | missense | A | Arg [R] | 3 | 747 |
|  |  |  | synonymous | T | Ser [S] | 3 | 747 |
|  |  |  | contig reference | C | Ser [S] | 3 | 747 |

-continued

| Chr. Pos. | mRNA pos. | dbSNP rs# | Function | dbSNP allele | Protein residue | Codon | Amino acid |
|---|---|---|---|---|---|---|---|
| 41763471 | 2433 | rs146263330 | missense | G | Gly [G] | 2 | 748 |
| | | | contig reference | A | Glu [E] | 2 | 748 |
| 41763489 | 2451 | rs201238916 | missense | A | His [H] | 2 | 754 |
| | | | contig reference | G | Arg [R] | 2 | 754 |
| 41763492 | 2454 | rs17856940 | missense | G | Arg [R] | 2 | 755 |
| | | | contig reference | A | Gln [Q] | 2 | 755 |
| 41763501 | 2463 | rs200271277 | missense | A | His [H] | 2 | 758 |
| | | | contig reference | G | Arg [R] | 2 | 758 |
| 41763505 | 2467 | rs376741284 | synonymous | C | Leu [L] | 3 | 759 |
| | | | contig reference | G | Leu [L] | 3 | 759 |
| 41763512 | 2474 | rs147769214 | missense | A | Thr [T] | 1 | 762 |
| | | | contig reference | C | Pro [P] | 1 | 762 |
| 41763517 | 2479 | rs148833322 | synonymous | A | Ala [A] | 3 | 763 |
| | | | contig reference | G | Ala [A] | 3 | 763 |
| 41765473 | 2512 | rs376416855 | synonymous | A | Ser [S] | 3 | 774 |
| | | | contig reference | G | Ser [S] | 3 | 774 |
| 41765475 | 2514 | rs201956398 | missense | A | Gln [Q] | 2 | 775 |
| | | | contig reference | G | Arg [R] | 2 | 775 |
| 41765486 | 2525 | rs143486475 | missense | G | Val [V] | 1 | 779 |
| | | | contig reference | C | Leu [L] | 1 | 779 |
| 41765513 | 2552 | rs1004955 | missense | G | Ala [A] | 1 | 788 |
| | | | contig reference | A | Thr [T] | 1 | 788 |
| 41765523 | 2562 | rs199709000 | missense | A | Gln [Q] | 2 | 791 |
| | | | contig reference | G | Arg [R] | 2 | 791 |
| 41765530 | 2569 | rs148013323 | synonymous | C | Asp [D] | 3 | 793 |
| | | | contig reference | T | Asp [D] | 3 | 793 |
| 41765538 | 2577 | rs141502789 | missense | C | Thr [T] | 2 | 796 |
| | | | contig reference | A | Asn [N] | 2 | 796 |
| 41765561 | 2600 | rs145805143 | missense | A | Thr [T] | 1 | 804 |
| | | | contig reference | G | Ala [A] | 1 | 804 |
| 41765575 | 2614 | rs61737386 | synonymous | T | Asp [D] | 3 | 808 |
| | | | contig reference | C | Asp [D] | 3 | 808 |
| 41765601 | 2640 | rs186884585 | missense | C | Ala [A] | 2 | 817 |
| | | | contig reference | A | Glu [E] | 2 | 817 |
| 41765617 | 2656 | rs116041107 | synonymous | C | Pro [P] | 3 | 822 |
| | | | contig reference | T | Pro [P] | 3 | 822 |
| 41765628 | 2667 | rs377757427 | missense | T | Val [V] | 2 | 826 |
| | | | contig reference | G | Gly [G] | 2 | 826 |
| 41765633 | 2672 | rs146164767 | missense | T | Ser [S] | 1 | 828 |
| | | | contig reference | G | Ala [A] | 1 | 828 |
| 41765652 | 2691 | rs369947891 | missense | G | Arg [R] | 2 | 834 |
| | | | contig reference | C | Pro [P] | 2 | 834 |
| 41765694 | 2733 | rs61737385 | missense | T | Val [V] | 2 | 848 |
| | | | contig reference | C | Ala [A] | 2 | 848 |
| 41765695 | 2734 | rs140014970 | synonymous | A | Ala [A] | 3 | 848 |
| | | | contig reference | G | Ala [A] | 3 | 848 |
| 41765743 | 2782 | rs199598417 | synonymous | A | Thr [T] | 3 | 864 |
| | | | contig reference | C | Thr [T] | 3 | 864 |
| 41765750 | 2789 | rs200112365 | missense | A | Thr [T] | 1 | 867 |
| | | | contig reference | C | Pro [P] | 1 | 867 |
| 41765752 | 2791 | rs61737388 | synonymous | T | Pro [P] | 3 | 867 |
| | | | contig reference | C | Pro [P] | 3 | 867 |
| 41765762 | 2801 | rs201717829 | missense | A | Thr [T] | 1 | 871 |
| | | | contig reference | G | Ala [A] | 1 | 871 |
| 41765776 | 2815 | rs372938197 | synonymous | G | Ser [S] | 3 | 875 |
| | | | contig reference | C | Ser [S] | 3 | 875 |
| 41765795 | 2834 | rs376230166 | missense | C | Gln [Q] | 1 | 882 |
| | | | contig reference | G | Glu [E] | 1 | 882 |
| 41765799 | 2838 | rs201188110 | missense | C | Ala [A] | 2 | 883 |
| | | | contig reference | A | Asp [D] | 2 | 883 |

The following shows exemplary polymorphisms of AFP protein(s) to be assessed in accordance with the present invention.

| Chr. Pos. | mRNA pos. | dbSNP rs# | Function | dbSNP allele | Protein residue | Codon | Amino acid |
|---|---|---|---|---|---|---|---|
| 74302005 | 73 | rs200781949 | nonsense | A | [Ter[*]] | 2 | 9 |
| | | | contig reference | T | Leu [L] | 2 | 9 |
| 74302006 | 74 | rs201668475 | missense | T | Phe [F] | 3 | 9 |
| | | | contig reference | A | Leu [L] | 3 | 9 |

-continued

| Chr. Pos. | mRNA pos. | dbSNP rs# | Function | dbSNP allele | Protein residue | Codon | Amino acid |
|---|---|---|---|---|---|---|---|
| 74302011 | 79 | rs372320842 | missense | C | Ser [S] | 2 | 11 |
|  |  |  | contig reference | T | Phe [F] | 2 | 11 |
| 74302025 | 93 | rs369819257 | missense | G | Ala [A] | 1 | 16 |
|  |  |  | contig reference | A | Thr [T] | 1 | 16 |
| 74302030 | 98 | rs150335619 | missense | C | Asp [D] | 3 | 17 |
|  |  |  | contig reference | A | Glu [E] | 3 | 17 |
| 74302064 | 132 | rs202199587 | missense | A | Thr [T] | 1 | 29 |
|  |  |  | contig reference | G | Ala [A] | 1 | 29 |
| 74303902 | 196 | rs146576905 | missense | A | Tyr [Y] | 2 | 50 |
|  |  |  | contig reference | T | Phe [F] | 2 | 50 |
| 74303959 | 253 | rs139089703 | missense | T | Val [V] | 2 | 69 |
|  |  |  | contig reference | A | Asp [D] | 2 | 69 |
| 74303962 | 256 | rs367831004 | missense | T | Val [V] | 2 | 70 |
|  |  |  | contig reference | C | Ala [A] | 2 | 70 |
| 74303963 | 257 | rs371149488 | synonymous | G | Ala [A] | 3 | 70 |
|  |  |  | contig reference | A | Ala [A] | 3 | 70 |
| 74306372 | 371 | rs375543359 | synonymous | T | Tyr [Y] | 3 | 108 |
|  |  |  | contig reference | C | Tyr [Y] | 3 | 108 |
| 74306373 | 372 | rs115932512 | missense | C | Arg [R] | 1 | 109 |
|  |  |  | contig reference | G | Gly [G] | 1 | 109 |
| 74306398 | 397 | rs368290434 | missense | C | Thr [T] | 2 | 117 |
|  |  |  | contig reference | G | Ser [S] | 2 | 117 |
| 74306404 | 403 | rs372500027 | missense | G | Gly [G] | 2 | 119 |
|  |  |  | contig reference | A | Glu [E] | 2 | 119 |
| 74306405 | 404 | rs143015198 | missense | C | Asp [D] | 3 | 119 |
|  |  |  | contig reference | G | Glu [E] | 3 | 119 |
| 74306428 | 427 | rs367965385 | missense | T | Val [V] | 2 | 127 |
|  |  |  | contig reference | C | Ala [A] | 2 | 127 |
| 74306447 | 446 | rs200305333 | synonymous | G | Pro [P] | 3 | 133 |
|  |  |  | contig reference | A | Pro [P] | 3 | 133 |
| 74306466 | 465 | rs371770284 | missense | A | Lys [K] | 1 | 140 |
|  |  |  | contig reference | C | Gln [Q] | 1 | 140 |
| 74306476 | 475 | rs374723455 | missense | C | Ala [A] | 2 | 143 |
|  |  |  | contig reference | A | Glu [E] | 2 | 143 |
| 74306488 | 487 | rs368968696 | missense | A | Asn [N] | 2 | 147 |
|  |  |  | contig reference | G | Ser [S] | 2 | 147 |
| 74306501 | 500 | rs113645421 | synonymous | C | Tyr [Y] | 3 | 151 |
|  |  |  | contig reference | T | Tyr [Y] | 3 | 151 |
| 74306527 | 526 | rs148186203 | missense | T | Ile [I] | 2 | 160 |
|  |  |  | contig reference | A | Asn [N] | 2 | 160 |
| 74307295 |  | rs35201987 |  | (>6bp) |  |  |  |
|  |  |  | intron | (>6bp) |  |  |  |
| 74308036 | 553 | rs143076376 | missense | A | Lys [K] | 2 | 169 |
|  |  |  | contig reference | G | Arg [R] | 2 | 169 |
| 74308055 | 572 | rs369195112 | synonymous | C | Ala [A] | 3 | 175 |
|  |  |  | contig reference | A | Ala [A] | 3 | 175 |
| 74308060 | 577 | rs151308004 | missense | G | Arg [R] | 2 | 177 |
|  |  |  | contig reference | C | Thr [T] | 2 | 177 |
| 74308088 | 605 | rs146140853 | synonymous | T | Asp [D] | 3 | 186 |
|  |  |  | contig reference | C | Asp [D] | 3 | 186 |
| 74308089 | 606 | rs35765619 | missense | C | Gln [Q] | 1 | 187 |
|  |  |  | contig reference | A | Lys [K] | 1 | 187 |
| 74308116 | 633 | rs142136082 | missense | A | Lys [K] | 1 | 196 |
|  |  |  | contig reference | G | Glu [E] | 1 | 196 |
| 74308124 | 641 | rs35924362 | synonymous | C | Ala [A] | 3 | 198 |
|  |  |  | contig reference | A | Ala [A] | 3 | 198 |
| 74309085 | 684 | rs371502429 | synonymous | C | Leu [L] | 1 | 213 |
|  |  |  | contig reference | T | Leu [L] | 1 | 213 |
| 74309097 | 696 | rs146456647 | missense | G | Gly [G] | 1 | 217 |
|  |  |  | contig reference | A | Ser [S] | 1 | 217 |
| 74309112 | 711 | rs200092580 | missense | A | Asn [N] | 1 | 222 |
|  |  |  | contig reference | C | His [H] | 1 | 222 |
| 74309160 | 759 | rs200267486 | missense | C | Leu [L] | 1 | 238 |
|  |  |  | contig reference | A | Ile [I] | 1 | 238 |
| 74310712 | 763 | rs373540770 | missense | T | Ile [I] | 2 | 239 |
|  |  |  | contig reference | C | Thr [T] | 2 | 239 |
| 74310754 | 805 | rs139295532 | missense | G | Ser [S] | 2 | 253 |
|  |  |  | contig reference | C | Thr [T] | 2 | 253 |
| 74310768 | 819 | rs41265657 | missense | G | Val [V] | 1 | 258 |
|  |  |  | contig reference | C | Leu [L] | 1 | 258 |
| 74310774 | 825 | rs141239137 | missense | G | Val [V] | 1 | 260 |
|  |  |  | contig reference | C | Leu [L] | 1 | 260 |
| 74310793 | 844 | rs144243983 | missense | G | Arg [R] | 2 | 266 |
|  |  |  | contig reference | A | His [H] | 2 | 266 |
| 74313193 | 905 | rs28482344 | synonymous | T | Ser [S] | 3 | 286 |
|  |  |  | contig reference | C | Ser [S] | 3 | 286 |

| Chr. Pos. | mRNA pos. | dbSNP rs# | Function | dbSNP allele | Protein residue | Codon | Amino acid |
|---|---|---|---|---|---|---|---|
| 74313216 | 928 | rs144523159 | missense | T | Ile [I] | 2 | 294 |
| | | | contig reference | C | Thr [T] | 2 | 294 |
| 74313220 | 932 | rs147848862 | synonymous | A | Leu [L] | 3 | 295 |
| | | | contig reference | G | Leu [L] | 3 | 295 |
| 74313228 | 940 | rs369341269 | missense | T | Ile [I] | 2 | 298 |
| | | | contig reference | A | Lys [K] | 2 | 298 |
| 74313308 | 1020 | rs369690102 | missense | C | Arg [R] | 1 | 325 |
| | | | contig reference | G | Gly [G] | 1 | 325 |
| 74313336 | 1048 | rs368783558 | missense | C | Ser [S] | 2 | 334 |
| | | | contig reference | T | Leu [L] | 2 | 334 |
| 74313380 | 1092 | rs188021984 | missense | G | Val [V] | 1 | 349 |
| | | | contig reference | A | Ile [I] | 1 | 349 |
| 74313389 | 1101 | rs376333213 | missense | T | Ser [S] | 1 | 352 |
| | | | contig reference | G | Ala [A] | 1 | 352 |
| 74315056 | 1110 | rs376112674 | missense | C | Leu [L] | 1 | 355 |
| | | | contig reference | G | Val [V] | 1 | 355 |
| 74315060 | 1114 | rs200626144 | missense | G | Arg [R] | 2 | 356 |
| | | | contig reference | A | His [H] | 2 | 356 |
| 74315164 | 1218 | rs373915432 | missense | T | Phe [F] | 1 | 391 |
| | | | contig reference | C | Leu [L] | 1 | 391 |
| 74315786 | 1272 | rs142607267 | missense | G | Glu [E] | 1 | 409 |
| | | | contig reference | C | Gln [Q] | 1 | 409 |
| 74315801 | 1287 | rs374322791 | nonsense | T | [Ter[*]] | 1 | 414 |
| | | | contig reference | C | Arg [R] | 1 | 414 |
| 74315806 | 1292 | rs150964344 | synonymous | T | Ser [S] | 3 | 415 |
| | | | contig reference | C | Ser [S] | 3 | 415 |
| 74315809 | 1295 | rs200050605 | nonsense | A | [Ter[*]] | 3 | 416 |
| | | | contig reference | C | Cys [C] | 3 | 416 |
| 74315850 | 1336 | rs367853668 | missense | T | Val [V] | 2 | 430 |
| | | | contig reference | C | Ala [A] | 2 | 430 |
| 74316338 | 1343 | rs181827990 | synonymous | T | Leu [L] | 3 | 432 |
| | | | contig reference | C | Leu [L] | 3 | 432 |
| 74316373 | 1378 | rs374243731 | missense | T | Leu [L] | 2 | 444 |
| | | | contig reference | C | Ser [S] | 2 | 444 |
| 74316376 | 1381 | rs140788572 | missense | T | Leu [L] | 2 | 445 |
| | | | contig reference | C | Ser [S] | 2 | 445 |
| 74316377 | 1382 | rs1894264 | synonymous | A | Ser [S] | 3 | 445 |
| | | | contig reference | G | Ser [S] | 3 | 445 |
| 74316381 | 1386 | rs199981870 | synonymous | T | Leu [L] | 1 | 447 |
| | | | contig reference | C | Leu [L] | 1 | 447 |
| 74316394 | 1399 | rs138531623 | missense | T | Ile [I] | 2 | 451 |
| | | | contig reference | C | Thr [T] | 2 | 451 |
| 74316395 | 1400 | rs140208686 | synonymous | T | Thr [T] | 3 | 451 |
| | | | contig reference | C | Thr [T] | 3 | 451 |
| 74316405 | 1410 | rs142451188 | frame shift | C | Ser [S] | 1 | 456 |
| | | | contig reference | — | Ala [A] | 1 | 456 |
| 74316431 | 1436 | rs145185829 | synonymous | G | Gln [Q] | 3 | 463 |
| | | | contig reference | A | Gln [Q] | 3 | 463 |
| 74316434 | 1439 | rs186121476 | synonymous | T | Leu [L] | 3 | 464 |
| | | | contig reference | C | Leu [L] | 3 | 464 |
| 74316453 | 1458 | rs369442700 | missense | A | Thr [T] | 1 | 471 |
| | | | contig reference | G | Ala [A] | 1 | 471 |
| 74316461 | 1466 | rs115622472 | synonymous | T | Gly [G] | 3 | 473 |
| | | | contig reference | C | Gly [G] | 3 | 473 |
| 74316465 | 1470 | rs149411760 | missense | A | Arg [R] | 1 | 475 |
| | | | contig reference | G | Gly [G] | 1 | 475 |
| 74316469 | 1474 | rs376466369 | missense | T | Val [V] | 2 | 476 |
| | | | contig reference | C | Ala [A] | 2 | 476 |
| 74318118 | 1476 | rs367619656 | missense | A | Thr [T] | 1 | 477 |
| | | | contig reference | G | Ala [A] | 1 | 477 |
| 74318132 | 1490 | rs371460704 | synonymous | T | Ile [I] | 3 | 481 |
| | | | contig reference | C | Ile [I] | 3 | 481 |
| 74318133 | 1491 | rs200196094 | missense | A | Arg [R] | 1 | 482 |
| | | | contig reference | G | Gly [G] | 1 | 482 |
| 74318135 | 1493 | rs144799463 | synonymous | G | Gly [G] | 3 | 482 |
| | | | contig reference | A | Gly [G] | 3 | 482 |
| 74318138 | 1496 | rs368477992 | missense | G | Gln [Q] | 3 | 483 |
| | | | contig reference | C | His [H] | 3 | 483 |
| 74318150 | 1508 | rs376621037 | missense | T | Ser [S] | 3 | 487 |
| | | | contig reference | A | Arg [R] | 3 | 487 |
| 74318159 | 1517 | rs148131848 | missense | T | Ile [I] | 3 | 490 |
| | | | contig reference | G | Met [M] | 3 | 490 |
| 74318175 | 1533 | rs372972529 | missense | A | Ser [S] | 1 | 496 |
| | | | contig reference | G | Gly [G] | 1 | 496 |
| 74318176 | 1534 | rs201210663 | missense | A | Asp [D] | 2 | 496 |
| | | | contig reference | G | Gly [G] | 2 | 496 |

-continued

| Chr. Pos. | mRNA pos. | dbSNP rs# | Function | dbSNP allele | Protein residue | Codon | Amino acid |
|---|---|---|---|---|---|---|---|
| 74318177 | 1535 | rs35920062 | synonymous | C | Gly [G] | 3 | 496 |
| | | | contig reference | T | Gly [G] | 3 | 496 |
| 74318222 | 1580 | rs200600473 | synonymous | T | Cys [C] | 3 | 511 |
| | | | contig reference | C | Cys [C] | 3 | 511 |
| 74318260 | 1618 | rs150629509 | missense | T | Leu [L] | 2 | 524 |
| | | | contig reference | C | Pro [P] | 2 | 524 |
| 74318292 | 1650 | rs191136122 | missense | G | Glu [E] | 1 | 535 |
| | | | contig reference | A | Lys [K] | 1 | 535 |
| 74318293 | 1651 | rs183385957 | missense | G | Arg [R] | 2 | 535 |
| | | | contig reference | A | Lys [K] | 2 | 535 |
| 74318296 | 1654 | rs140758670 | missense | T | Val [V] | 2 | 536 |
| | | | contig reference | A | Asp [D] | 2 | 536 |
| 74318310 | 1668 | rs144607501 | missense | A | Lys [K] | 1 | 541 |
| | | | contig reference | C | Gln [Q] | 1 | 541 |
| 74318320 | 1678 | rs369625484 | missense | T | Val [V] | 2 | 544 |
| | | | contig reference | C | Ala [A] | 2 | 544 |
| 74318321 | 1679 | rs147439366 | synonymous | A | Ala [A] | 3 | 544 |
| | | | contig reference | G | Ala [A] | 3 | 544 |
| 74318329 | 1687 | rs114970091 | missense | T | Met [M] | 2 | 547 |
| | | | contig reference | C | Thr [T] | 2 | 547 |
| 74318340 | 1698 | rs191300110 | nonsense | T | [Ter[*]] | 1 | 551 |
| | | | contig reference | G | Glu [E] | 1 | 551 |
| 74319137 | | rs374827933 | | —/AGA | | | |
| | | | intron | —/AGA | | | |
| 74319482 | 1700 | rs377430589 | synonymous | A | Glu [E] | 3 | 551 |
| | | | contig reference | G | Glu [E] | 3 | 551 |
| 74319515 | 1733 | rs192631782 | synonymous | G | Gln [Q] | 3 | 562 |
| | | | contig reference | A | Gln [Q] | 3 | 562 |
| 74319538 | 1756 | rs7790 | missense | G | Gly [G] | 2 | 570 |
| | | | contig reference | C | Ala [A] | 2 | 570 |
| 74319588 | 1806 | rs149074640 | missense | A | Lys [K] | 1 | 587 |
| | | | contig reference | G | Glu [E] | 1 | 587 |
| 74319597 | 1815 | rs142115366 | missense | A | Ile [I] | 1 | 590 |
| | | | contig reference | G | Val [V] | 1 | 590 |
| 74320984 | 1864 | rs201376665 | missense | A | Asp [D] | 2 | 606 |
| | | | contig reference | C | Ala [A] | 2 | 606 |
| 74320989 | 1869 | rs146692547 | missense | A | Arg [R] | 1 | 608 |
| | | | contig reference | G | Gly [G] | 1 | 608 |

The following shows exemplary polymorphisms of DKK-1 protein(s) to be assessed in accordance with the present invention.

| Chr. Pos. | mRNA pos. | dbSNP rs# | Function | dbSNP allele | Protein residue | Codon | Amino acid |
|---|---|---|---|---|---|---|---|
| 54074197 | 157 | rs199874560 | missense | T | Ile [I] | 3 | 1 |
| | | | contig reference | G | Met [M] | 3 | 1 |
| 54074240 | 200 | rs140471040 | missense | C | Leu [L] | 1 | 16 |
| | | | contig reference | A | Met [M] | 1 | 16 |
| 54074269 | 229 | rs200786704 | synonymous | C | Pro [P] | 3 | 25 |
| | | | contig reference | T | Pro [P] | 3 | 25 |
| 54074272 | 232 | rs183906578 | synonymous | T | Leu [L] | 3 | 26 |
| | | | contig reference | G | Leu [L] | 3 | 26 |
| 54074284 | 244 | rs200283314 | synonymous | T | Ser [S] | 3 | 30 |
| | | | contig reference | C | Ser [S] | 3 | 30 |
| 54074305 | 265 | rs368619028 | synonymous | T | Leu [L] | 3 | 37 |
| | | | contig reference | C | Leu [L] | 3 | 37 |
| 54074315 | 275 | rs145640971 | missense | A | Thr [T] | 1 | 41 |
| | | | contig reference | G | Ala [A] | 1 | 41 |
| 54074375 | 335 | rs372730677 | missense | C | Arg [R] | 1 | 61 |
| | | | contig reference | A | Ser [S] | 1 | 61 |
| 54074380 | 340 | rs34795541 | frame shift | — | Arg [R] | 3 | 63 |
| | | | contig reference | C | Ala [A] | 3 | 63 |
| 54074405 | 365 | rs146628250 | missense | A | Arg [R] | 1 | 71 |
| | | | contig reference | G | Gly [G] | 1 | 71 |
| 54074690 | 405 | rs201617558 | missense | T | Leu [L] | 2 | 84 |
| | | | contig reference | C | Pro [P] | 2 | 84 |
| 54074743 | 458 | rs377469990 | missense | A | Ser [S] | 1 | 102 |
| | | | contig reference | C | Arg [R] | 1 | 102 |
| 54074755 | 470 | rs141115379 | missense | A | Thr [T] | 1 | 106 |
| | | | contig reference | G | Ala [A] | 1 | 106 |

-continued

| Chr. Pos. | mRNA pos. | dbSNP rs# | Function | dbSNP allele | Protein residue | Codon | Amino acid |
|---|---|---|---|---|---|---|---|
| 54074757 | 472 | rs2241529 | synonymous | G | Ala [A] | 3 | 106 |
|  |  |  | contig reference | A | Ala [A] | 3 | 106 |
| 54074776 | 491 | rs372651276 | missense | A | Thr [T] | 1 | 113 |
|  |  |  | contig reference | G | Ala [A] | 1 | 113 |
| 54074797 | 512 | rs138915253 | missense | T | Cys [C] | 1 | 120 |
|  |  |  | contig reference | C | Arg [R] | 1 | 120 |
| 54074798 | 513 | rs149268042 | missense | T | Leu [L] | 2 | 120 |
|  |  |  | contig reference | G | Arg [R] | 2 | 120 |
| 54074800 | 515 | rs146946503 | missense | C | Arg [R] | 1 | 121 |
|  |  |  | contig reference | T | Cys [C] | 1 | 121 |
| 54074806 | 521 | rs138015066 | missense | T | Cys [C] | 1 | 123 |
|  |  |  | contig reference | C | Arg [R] | 1 | 123 |
| 54074811 | 526 | rs201074100 | synonymous | T | His [H] | 3 | 124 |
|  |  |  | contig reference | C | His [H] | 3 | 124 |
| 54074843 | 558 | rs375574588 | missense | G | Ser [S] | 2 | 135 |
|  |  |  | contig reference | A | Asn [N] | 2 | 135 |
| 54076059 | 565 | rs201884496 | missense | G | Met [M] | 3 | 137 |
|  |  |  | contig reference | A | Ile [I] | 3 | 137 |
| 54076088 | 594 | rs371367754 | missense | A | Gln [Q] | 2 | 147 |
|  |  |  | contig reference | G | Arg [R] | 2 | 147 |
| 54076112 | 618 | rs374712846 | missense | G | Ser [S] | 2 | 155 |
|  |  |  | contig reference | C | Thr [T] | 2 | 155 |
| 54076118 | 624 | rs143388912 | missense | A | Asn [N] | 2 | 157 |
|  |  |  | missense | T | Ile [I] | 2 | 157 |
|  |  |  | contig reference | G | Ser [S] | 2 | 157 |
| 54076180 | 686 | rs61757609 | missense | C | Leu [L] | 1 | 178 |
|  |  |  | contig reference | A | Met [M] | 1 | 178 |
| 54076322 | 710 | rs200984065 | missense | T | Cys [C] | 1 | 186 |
|  |  |  | contig reference | G | Gly [G] | 1 | 186 |
| 54076337 | 725 | rs200238542 | missense | T | Trp [W] | 1 | 191 |
|  |  |  | contig reference | C | Arg [R] | 1 | 191 |
| 54076425 | 813 | rs373503166 | missense | T | Phe [F] | 2 | 220 |
|  |  |  | contig reference | G | Cys [C] | 2 | 220 |
| 54076438 | 826 | rs200588937 | synonymous | A | Arg [R] | 3 | 224 |
|  |  |  | contig reference | G | Arg [R] | 3 | 224 |
| 54076452 | 840 | rs147143909 | missense | G | Arg [R] | 2 | 229 |
|  |  |  | contig reference | A | His [H] | 2 | 229 |
| 54076453 | 841 | rs148686867 | synonymous | C | His [H] | 3 | 229 |
|  |  |  | contig reference | T | His [H] | 3 | 229 |
| 54076460 | 848 | rs11001564 | missense | A | Lys [K] | 1 | 232 |
|  |  |  | contig reference | G | Glu [E] | 1 | 232 |
| 54076503 | 891 | rs141377301 | missense | A | Gln [Q] | 2 | 246 |
|  |  |  | contig reference | G | Arg [R] | 2 | 246 |
| 54076504 | 892 | rs200532552 | synonymous | T | Arg [R] | 3 | 246 |
|  |  |  | contig reference | G | Arg [R] | 3 | 246 |
| 54076509 | 897 | rs370680630 | missense | G | Arg [R] | 2 | 248 |
|  |  |  | contig reference | A | Gln [Q] | 2 | 248 |
| 54076522 | 910 | rs150770986 | missense | A | Gln [Q] | 3 | 252 |
|  |  |  | contig reference | T | His [H] | 3 | 252 |

A (functional) derivative(s) of the above polypeptide(s)/protein(s) can be the polypeptide as shown in SEQ ID NO: 4, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 and up to 47 amino acids are inserted, added or substituted. Preferred herein are substitutions. Preferably, a (functional) derivative(s) of the above polypeptide(s)/protein(s) is a polypeptide as shown in SEQ ID NO: 4, wherein 1 amino acid is substituted.

A (functional) derivative(s) of the above polypeptide(s)/protein(s) can be the polypeptide as shown in SEQ ID NO: 6, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 and up to 67 amino acids are inserted, added or substituted. Preferred herein are substitutions. Preferably, a (functional) derivative(s) of the above polypeptide(s)/protein(s) is the polypeptide as shown in SEQ ID NO: 6, wherein 1 amino acid is substituted.

A (functional) derivative(s) of the above polypeptide(s)/protein(s) can be the polypeptide as shown in SEQ ID NO: 8, wherein at least 1, 2, 3, 4, 5, 6, 7, 8, 9, 10, 11, 12, 13, 14, 15, 16, 17, 18, 19, 20, 21, 22, 23, 24, 25, 26, 27 and up to 28 amino acids are inserted, added or substituted. Preferred herein are substitutions. Preferably, a (functional) derivative(s) of the above polypeptide(s)/protein(s) is the polypeptide as shown in SEQ ID NO: 8, wherein 1 amino acid is substituted.

A (functional) derivative(s) of the polypeptide as shown in SEQ ID NO: 2 can be a polypeptide, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91 and up to 92 amino acids of the polypeptide as shown in SEQ ID NO: 2 are inserted, added or substituted. Preferred herein are substitutions. Preferably, a (functional) derivative(s) of the above polypeptide(s)/protein(s) is a polypeptide as shown in SEQ ID NO: 2, wherein 1 amino acid is substituted.

The fragment or derivative preferably has the same (or essentially the same) biological activity as the full length polypeptide from which it is derived, the full length polypeptide having the amino acid sequence as shown in SEQ ID NO: 4, 6 or 8. In this sense, the fragment or derivative is a "functional" fragment or "functional" derivative to be used herein.

The herein provided polypeptide (as shown, for example, in SEQ ID NO: 2, 4 or 8) may have one or more amino acids deleted, inserted, added and/or substituted provided that the polypeptide maintains essentially the biological activity which is characteristic of the polypeptides from which it is derived.

Preferably, any such deletions, insertions, additions and/or substitutions (in this context particularly substitutions) are conservative, i.e. amino acids are substituted by amino acids having the same or similar characteristics. For example, a hydrophobic amino acid will preferably be substituted by another hydrophobic amino acid and so on.

Furthermore, the present invention provides a kit useful for carrying out the methods of the invention. The present invention relates to a kit for use in the herein provided methods. The present invention relates to the use of a kit in the herein provided methods.

The kit can comprise (a) binding molecule(s) specifically binding to soluble AXL, AFP and/or DKK-1.

The kit to be used herein primarily comprises (a) binding molecule(s) specifically binding to soluble AXL. Said kit can further comprise (a) binding molecule(s) specifically binding to AFP and/or (a) binding molecule(s) specifically binding to DKK-1.

The kit can comprise (a) binding molecule(s) specifically binding to soluble AXL. The kit can comprise (a) binding molecule(s) specifically binding to AFP. The kit can comprise (a) binding molecule(s) specifically binding to DKK-1.

The kit can comprise (a) binding molecule(s) specifically binding to soluble AXL and (a) binding molecule(s) specifically binding to AFP. The kit can comprise (a) binding molecule(s) specifically binding to soluble AXL and (a) binding molecule(s) specifically binding to DKK-1. The kit can comprise (a) binding molecule(s) specifically binding to soluble AXL, (a) binding molecule(s) specifically binding to AFP and (a) binding molecule(s) specifically binding DKK-1.

The "binding molecule(s)" is/are preferably an antibody.

The kit may comprise (a) binding molecule(s) required for specifically determining the presence or amount of soluble AXL, and, optionally, (a) binding molecule(s) required for specifically determining the presence or amount of AFP and/or DKK-1. Moreover, the present invention also relates to the use of (a) binding molecule(s) required for specifically determining the presence or amount of soluble AXL and, optionally, (a) binding molecule(s) required for specifically determining the presence or amount of AFP and/or DKK-1 as defined herein for the preparation of a kit for carrying out the methods of this invention.

On the basis of the teaching of this invention, the skilled person knows which compound(s) is (are) required for specifically determining the presence of presence or amount of soluble AXL and, optionally, AFP and/or DKK-1 as defined herein. For example, such compound(s) may be (a) "binding molecule(s)", like, for example, (an) antibody(ies) and/or (an) aptamer(s) specific for at least soluble AXL, and, optionally, AFP and/or DKK-1 as described herein. The kit (to be prepared in context) of this invention may be a diagnostic kit.

The kit (to be prepared in context) of this invention may further comprise or be provided with (an) instruction manual(s). For example, said instruction manual(s) may guide the skilled person (how) to determine the (reference/control) level or amount of soluble AXL and, optionally, AFP and/or DKK-1 as defined herein and/or (how) to diagnose liver cancer. Said instruction manual(s) may comprise guidance to use or apply the herein provided methods or uses. The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) binding molecule(s) that may be required for specifically determining the presence or amount of soluble AXL and, optionally, AFP and/or DKK-1 as defined herein.

The following exemplary kits can be used in accordance with the present invention.

For example, a kit to be used herein can be designed for use in ELISA, particularly Sandwich ELISA.

A kit to be used herein can accordingly comprise one capture antibody and one detection antibody, if one antigen is to be detected (e.g. one capture antibody specifically binding to sAXL and one detection antibody specifically binding to sAXL).

A kit to be used herein can comprise two capture and two detection antibodies, if two antigens are to be detected (e.g. one capture antibody specifically binding to sAXL, one capture antibody specifically binding to AFP, one detection antibody specifically binding to sAXL, and one detection antibody specifically binding to AFP; or one capture antibody specifically binding to sAXL, one capture antibody specifically binding to DKK-1, one detection antibody specifically binding to sAXL, and one detection antibody specifically binding to DKK-1).

Two capture and two detection antibodies can be used in a sandwich ELISA to measure levels of sAXL and AFP. The kit can further comprise recombinant sAXL and AFP (standards), microplates, wash buffer (Tween/phosphate buffered saline [PBS]), reagent diluent (bovine serum albumin/PBS), streptavidin-horseradish peroxidase, substrate solution (Hydrogen peroxide/tetramethylbenzidine) and stop solution (sulfuric acid).

Two capture and two detection antibodies can be used in a sandwich ELISA to measure levels of sAXL and Dickkopf-1 (DKK1). The kit can comprise recombinant sAXL and DKK1 (standards), microplates, wash buffer (Tween/phosphate buffered saline [PBS]), reagent diluent (bovine serum albumin/PBS), streptavidin-horseradish peroxidase, substrate solution (Hydrogen peroxide/tetramethylbenzidine) and stop solution (sulfuric acid).

The present invention relates to (a) binding molecule(s) for use in the herein provided methods. The present invention provides (a) binding molecule(s) useful for carrying out the methods of the invention. The present invention relates to the use of (a) binding molecule(s) in the herein provided methods.

Herein contemplated are antibodies that specifically bind to the above provided and defined soluble AXL and, optionally, AFP and/or DKK-1 protein(s). Such antibodies can be used for diagnostic purposes in accordance with the present invention.

It is envisaged herein that the antibodies can specifically bind to (functional) fragments or (functional) derivatives of the soluble AXL, AFP and/or DKK-1 protein(s) as defined herein, for example also to polypeptides having at least 70% or more identity to herein soluble AXL, AFP and/or DKK-1 protein(s) protein(s).

Accordingly, the present invention relates to the use of these antibodies in the methods of the present invention.

Therefore, the present invention relates, inter alia, to the use of the herein above described binding molecule(s), such as antibody/antibodies, specifically binding to or specifically recognizing soluble AXL, and, optionally, AFP and/or DKK-1 protein(s) for assessing whether a patient suffers from liver cancer or is prone to suffering from a liver cancer.

The present invention also relates to an antibody/antibodies as defined above or a composition comprising said antibody/antibodies for the preparation of a diagnostic kit (for use in the methods of the present invention).

The antibody may be a polyclonal antibody, a monoclonal antibody, a full antibody (immunoglobulin), a F(ab)-fragment, a F(ab)$_2$-fragment, a single-chain antibody, a chimeric antibody, a CDR-grafted antibody, a bivalent antibody-construct, a bispecific single chain antibody, a synthetic antibody or a cross-cloned antibody and the like.

Also commercially available antibodies can be used in accordance with the present invention. The following tables provide an overview of exemplary, commercially available antibodies that specifically bind to AXL, AFP and DKK-1 and that can be used herein.

The following table shows exemplary, commercially available antibodies that specifically bind to sAXL and that can be used herein:

| Supplier Catalog# | Host Species | Reactivity | Type | Antigen |
|---|---|---|---|---|
| antibodies-online 89 antibodies | | | | |
| ABIN391876 | Rabbit | Human | Polyclonal | |
| ABIN391878 | Rabbit | Human | Polyclonal | |
| ABIN391877 | Rabbit | Human | Polyclonal | |
| ABIN965631 | Rabbit | Human, Mouse, Rat | Polyclonal | |
| ABIN965632 | | Human, Mouse, Rat | Polyclonal | |
| ABIN965630 | Mouse | Human | Monoclonal | Purified recombinant extracellular fragment of human AXL fused with hIgGFc tag expressed in HEK293 cell line. |
| ABIN659480 | Mouse | Human | Monoclonal | Purified recombinant extracellular fragment of human AXL fused with hIgGFc tag expressed in HEK293 cell line. |
| ABIN482649 | Rabbit | Human, Mouse, Rat | Polyclonal | |
| ABIN756022 | Rabbit | Human, Mouse, Rat, Bovine, Canine, Horse, Porcine | Polyclonal | |
| ABIN931416 | Mouse | Human | Monoclonal | AXL antibody was raised in Mouse using purified recombinant extracellular fragment of human AXL fused with hIgGFc tag expressed in HEK293 cell line as the immunogen |
| ABIN968974 | Mouse | Human | Monoclonal | Purified recombinant extracellular fragment of human AXL fused with hIgGFc tag expressed in HEK293 cell line. |

-continued

| Supplier Catalog# | Host Species | Reactivity | Type | Antigen |
|---|---|---|---|---|
| ABIN560017 | Mouse | Human | Monoclonal | AXL (AAH32229, 30 a.a.~140 a.a) partial recombinant protein with GST tag. MW of the GST tag alone is 26 KDa. Immunogen sequence: TQAEESPFVGNPGNITGARG LTGTLRCQLQVQGEPPEVHW LRDGQILELADSTQTQVPLG EDEQDDWIVVSQLRITSLQL SDTGQYQCLVFLGHQTFVSQ PGYVGLEGLPY |
| ABIN756037 | Rabbit | Human, Mouse, Rat, Bovine, Canine, Horse, Porcine | Polyclonal | |
| ABIN960094 | Rabbit | Human | Polyclonal | |
| ABIN567451 | Rabbit | Human | Polyclonal | |
| ABIN790566 | Mouse | Human | Monoclonal | Purified recombinant extracellular fragment of human AXL fused with hIgGFc tag expressed in HEK293 cell line. |
| ABIN929112 | Rabbit | Human | Polyclonal | |
| ABIN1034404 | Rabbit | Human, Mouse, Rat | | |
| ABIN1496791 | Mouse | Human | Monoclonal | Purified recombinant extracellular fragment of human AXL fused with hIgGFc tag expressed in HEK293 cell line. |
| ABIN359785 | Rabbit | Human | Polyclonal | |
| ABIN397222 | Rabbit | Human | Polyclonal | |
| ABIN543959 | Rabbit | Human | Polyclonal | |
| ABIN756024 | Rabbit | Human, Mouse, Rat, Bovine, Canine, Horse, Porcine | Polyclonal | |
| ABIN756031 | Rabbit | Human, Mouse, Rat, Bovine, Canine, Horse, Porcine | Polyclonal | |
| ABIN756039 | Rabbit | Human, Mouse, Rat, Bovine, Canine, Horse, Porcine | Polyclonal | |

-continued

| Supplier Catalog# | Host Species | Reactivity | Type | Antigen |
|---|---|---|---|---|
| ABIN756046 | Rabbit | Human, Mouse, Rat, Bovine, Canine, Horse, Porcine | Polyclonal | |
| ABIN958039 | Goat | Human | Polyclonal | |
| ABIN1340809 | Rabbit | Human | | |
| ABIN1356844 | Rabbit | Human, Mouse, Rat | Polyclonal | |
| ABIN1363703 | Rabbit | Human, Mouse, Rat | Polyclonal | |
| ABIN1479746 | Rabbit | Human | Polyclonal | |
| ABIN203791 | Rabbit | Human | Polyclonal | |
| ABIN359784 | Rabbit | Human | Polyclonal | |
| ABIN359786 | Rabbit | Human | Polyclonal | |
| ABIN397223 | Rabbit | Human | Polyclonal | |
| ABIN397224 | Rabbit | Human | Polyclonal | |
| ABIN439646 | Rabbit | Human | Polyclonal | |
| ABIN492797 | Rabbit | Human, Mouse, Rat, Simian | Polyclonal | |
| ABIN513651 | Mouse | Human | Monoclonal | AXL (AAH32229, 30 a.a.~140 a.a) partial recombinant protein with GST tag. MW of the GST tag alone is 26 KDa. Immunogen sequence: TQAEESPFVGNPGNITGARG LTGTLRCQLQVQGEPPEVHW LRDGQILELADSTQTQVPLG EDEQDDWIVVSQLRITSLQL SDTGQYQCLVFLGHQTFVSQ PGYVGLEGLPY |
| ABIN543958 | Rabbit | Human | Polyclonal | |
| ABIN560016 | Mouse | Human | Polyclonal | |
| ABIN756025 | Rabbit | Human, Mouse, Rat, Bovine, Canine, Horse, Porcine | Polyclonal | |
| ABIN756026 | Rabbit | Human, Mouse, Rat, Bovine, Canine, Horse, Porcine | Polyclonal | |
| ABIN756027 | Rabbit | Human, Mouse, | Polyclonal | |

| Supplier Catalog# | Host Species | Reactivity | Type | Antigen |
|---|---|---|---|---|
| | | Rat, Bovine, Canine, Horse, Porcine | | |
| ABIN756028 | Rabbit | Human, Mouse, Rat, Bovine, Canine, Horse, Porcine | Polyclonal | |
| ABIN756029 | Rabbit | Human, Mouse, Rat, Bovine, Canine, Horse, Porcine | Polyclonal | |
| ABIN756032 | Rabbit | Human, Mouse, Rat, Bovine, Canine, Horse, Porcine | Polyclonal | |
| ABIN756033 | Rabbit | Human, Mouse, Rat, Bovine, Canine, Horse, Porcine | Polyclonal | |
| ABIN756034 | Rabbit | Human, Mouse, Rat, Bovine, Canine, Horse, Porcine | Polyclonal | |
| ABIN756035 | Rabbit | Human, Mouse, Rat, Bovine, Canine, Horse, Porcine | Polyclonal | |
| ABIN790950 | Rabbit | Human | Polyclonal | |
| ABIN802656 | Rabbit | Human | Polyclonal | |
| ABIN884290 | Rabbit | Human, Mouse, Rat, Bovine, Canine, Horse, Porcine | Polyclonal | |
| ABIN884291 | Rabbit | Human, Mouse, Rat, Bovine, Canine, Horse, Porcine | Polyclonal | |
| ABIN884292 | Rabbit | Human, Mouse, | Polyclonal | |

-continued

| Supplier Catalog# | Host Species | Reactivity | Type | Antigen |
|---|---|---|---|---|
| | | Rat, Bovine, Canine, Horse, Porcine | | |
| ABIN884293 | Rabbit | Human, Mouse, Rat, Bovine, Canine, Horse, Porcine | Polyclonal | |
| ABIN884294 | Rabbit | Human, Mouse, Rat, Bovine, Canine, Horse, Porcine | Polyclonal | |
| ABIN947603 | Rabbit | Human | Polyclonal | |
| ABIN958040 | Rabbit | Human | Polyclonal | |
| ABIN121670 | Goat | Human | Polyclonal | |
| ABIN439645 | Rabbit | Human | Polyclonal | |
| ABIN513649 | Mouse | Human | Polyclonal | |
| ABIN513650 | Rabbit | Human | Polyclonal | |
| ABIN537947 | Rabbit | Human, Mouse, Rat, Bovine, Canine | Polyclonal | |
| ABIN537948 | Rabbit | Human, Mouse, Rat, Bovine, Canine | Polyclonal | |
| ABIN551283 | Rabbit | Human | Polyclonal | |
| ABIN554714 | Rabbit | Human | Polyclonal | |
| ABIN568776 | Rabbit | Human, Mouse, Rat | Polyclonal | |
| ABIN575652 | Rabbit | Human | Polyclonal | |
| ABIN756030 | Rabbit | Human, Mouse, Rat, Bovine, Canine, Horse, Porcine | Polyclonal | |
| ABIN756040 | Rabbit | Human, Mouse, Rat, Bovine, Canine, Horse, Porcine | Polyclonal | |
| ABIN756041 | Rabbit | Human, Mouse, Rat, Bovine, | Polyclonal | |

| Supplier Catalog# | Host Species | Reactivity | Type | Antigen |
|---|---|---|---|---|
| | | Canine, Horse, Porcine | | |
| ABIN756042 | Rabbit | Human, Mouse, Rat, Bovine, Canine, Horse, Porcine | Polyclonal | |
| ABIN756043 | Rabbit | Human, Mouse, Rat, Bovine, Canine, Horse, Porcine | Polyclonal | |
| ABIN756044 | Rabbit | Human, Mouse, Rat, Bovine, Canine, Horse, Porcine | Polyclonal | |
| ABIN756045 | Rabbit | Human, Mouse, Rat, Bovine, Canine, Horse, Porcine | Polyclonal | |
| ABIN756047 | Rabbit | Human, Mouse, Rat, Bovine, Canine, Horse, Porcine | Polyclonal | |
| ABIN756048 | Rabbit | Human, Mouse, Rat, Bovine, Canine, Horse, Porcine | Polyclonal | |
| ABIN756049 | Rabbit | Human, Mouse, Rat, Bovine, Canine, Horse, Porcine | Polyclonal | |
| ABIN756050 | Rabbit | Human, Mouse, Rat, Bovine, Canine, Horse, Porcine | Polyclonal | |
| ABIN880064 | Rabbit | Human, Mouse, Rat, Bovine, Canine, Horse, Porcine | Polyclonal | |

-continued

| Supplier | Catalog# | Host Species | Reactivity | Type | Antigen |
|---|---|---|---|---|---|
| | ABIN880065 | Rabbit | Human, Mouse, Rat, Bovine, Canine, Horse, Porcine | Polyclonal | |
| | ABIN880066 | Rabbit | Human, Mouse, Rat, Bovine, Canine, Horse, Porcine | Polyclonal | |
| | ABIN880067 | Rabbit | Human, Mouse, Rat, Bovine, Canine, Horse, Porcine | Polyclonal | |
| | ABIN880068 | Rabbit | Human, Mouse, Rat, Bovine, Canine, Horse, Porcine | Polyclonal | |
| | ABIN947602 | Mouse | Human | Polyclonal | |
| | ABIN957275 | Rabbit | Human | Polyclonal | |
| | ABIN957276 | Rabbit | Human | Polyclonal | |
| | ABIN957277 | Rabbit | Human | Polyclonal | |
| R & D Systems 9 antibodies | | | | | |
| | AF154 | Goat | Human | Polyclonal | |
| | AF2228 | Rabbit | Human | Polyclonal | |
| | MAB154 | Mouse | Human | Monoclonal | Mouse myeloma cell line NS0-derived recombinant human Axl, Met1-Pro440 |
| | FAB154A | Mouse | Human | Monoclonal | Mouse myeloma cell line NS0-derived recombinant human Axl, Met1-Pro440 |
| | FAB154C | Mouse | Human | Monoclonal | Mouse myeloma cell line NS0-derived recombinant human Axl, Met1-Pro440 |
| | FAB154G | Mouse | Human | Monoclonal | Mouse myeloma cell line NS0-derived recombinant human Axl, Met1-Pro440 |
| | FAB154N | Mouse | Human | Monoclonal | Mouse myeloma cell line NS0-derived recombinant human Axl, Met1-Pro440 |

-continued

| Supplier Catalog# | Host Species | Reactivity | Type | Antigen |
|---|---|---|---|---|
| FAB154P | Mouse | Human | Monoclonal | Mouse myeloma cell line NS0-derived recombinant human Axl, Met1-Pro440 |
| BAF154 | Goat | Human | Polyclonal | |
| Abnova Corporation 13 antibodies | | | | |
| PAB2998 | Rabbit | Human | Polyclonal | |
| H00000558-M01 | Mouse | Human | Monoclonal | AXL (AAH32229, 30 a.a.~140 a.a) partial recombinant protein with GST tag. MW of the GST tag alone is 26 KDa. |
| H00000558-D01 | Rabbit | Human | Polyclonal | |
| MAB10498 | Mouse | Human | Monoclonal | Recombinant hIgGFc tag fusion protein corresponding to extracellular fragment of human AXL. |
| H00000558-M02 | Mouse | Human | Monoclonal | AXL (AAH32229, 30 a.a. ~140 a.a) partial recombinant protein with GST tag. MW of the GST tag alone is 26 KDa. |
| PAB2999 | Rabbit | Human | Polyclonal | |
| PAB15888 | Rabbit | Human | Polyclonal | |
| PAB0803 | Rabbit | Human | Polyclonal | |
| PAB0804 | Rabbit | Human | Polyclonal | |
| H00000558-B01 | Mouse | Human | Polyclonal | |
| H00000558-B01P | Mouse | Human | Polyclonal | |
| H00000558-D01P | Rabbit | Human | Polyclonal | |
| H00000558-A01 | Mouse | Human | Polyclonal | |
| Aviva Systems Biology 2 antibodies | | | | |
| OAAB04648 | | Human | Polyclonal | |
| ARP59004_P050 | Rabbit | Human | Polyclonal | |
| Acris Antibodies GmbH 8 antibodies | | | | |
| AM31820SU-N | Mouse | Human | Monoclonal | AXL antibody was raised against purified recombinant extracellular fragment of human AXL fused with hIgGFc tag expressed in HEK293 cell line. |

-continued

| Supplier Catalog# | Host Species | Reactivity | Type | Antigen |
|---|---|---|---|---|
| AP14269PU-N | Rabbit | Human | Polyclonal | |
| AM06326SU-N | Mouse | Human | Monoclonal | AXL antibody was raised against purified recombinant extracellular fragment of human AXL fused with hIgGFc tag expressed in HEK293 cell line. |
| AP14268PU-N | Rabbit | Human | Polyclonal | |
| AP14270PU-N | Rabbit | Human | Polyclonal | |
| AP21586PU-N | Rabbit | Human, Mouse, Rat | Polyclonal | |
| AP09905PU-N | Rabbit | Human, Mouse, Rat, Simian | Polyclonal | |
| SP1392P | Goat | Human, Mouse | Polyclonal | |
| Thermo Fisher Scientific Pierce 6 antibodies | | | | |
| PA5-14566 | Rabbit | Human | Polyclonal | |
| MA5-15504 | Mouse | Human | Monoclonal | Purified recombinant extracellular fragment of human AXL fused with hIgGFc tag expressed in HEK293 cell line. |
| PA5-14567 | Rabbit | Human | Polyclonal | |
| PA5-28850 | Rabbit | Human | Polyclonal | |
| PA5-17039 | Rabbit | Human | Polyclonal | |
| PA5-23254 | Rabbit | Human, Mouse, Rat | Polyclonal | |
| Cell Signaling Technology, Inc 2 antibodies | | | | |
| 3269 | Rabbit | Human, Simian | Polyclonal | |
| 4977 | Rabbit | Human, Mouse, Rat, Hamster, Simian | Polyclonal | |
| Novus Biologicals 12 antibodies | | | | |
| H00000558-M01 | Mouse | Human | Monoclonal | AXL (AAH32229, 30 a.a.~140 a.a) partial recombinant protein with GST tag. MW of the GST tag alone is 26 KDa. |

-continued

| Supplier | Catalog# | Host Species | Reactivity | Type | Antigen |
|---|---|---|---|---|---|
| | H00000558-M02 | Mouse | Human | Monoclonal | AXL (AAH32229, 30 a.a.~140 a.a) partial recombinant protein with GST tag. MW of the GST tag alone is 26 KDa. |
| | NBP2-15530 | Rabbit | Human | Polyclonal | |
| | H00000558-B01 | Mouse | Human | Polyclonal | |
| | H00000558-D01P | Rabbit | Human | Polyclonal | |
| | NBP1-22964 | Rabbit | Human | Polyclonal | |
| | NBP1-22965 | Rabbit | Human | Polyclonal | |
| | NBP1-83073 | Rabbit | Human | Polyclonal | |
| | NBP2-24497 | Rabbit | Human, Mouse, Rat | Polyclonal | |
| | H00000558-D01 | Rabbit | Human | Polyclonal | |
| | H00000558-A01 | Mouse | Human | Polyclonal | |
| | H00000558-B01P | Mouse | Human | Polyclonal | |
| GeneTex 3 antibodies | | | | | |
| | GTX83125 | Mouse | Human | Monoclonal | Purified recombinant extracellular fragment of human AXL fused with hIgGFc tag expressed in HEK293 cell line. |
| | GTX101345 | Rabbit | Human | Polyclonal | |
| | GTX108560 | Rabbit | Human | Polyclonal | |
| LifeSpan BioSciences, Inc. 17 antibodies | | | | | |
| | LS-C150029 | Rabbit | Human | Polyclonal | |
| | LS-B6124 | Mouse | Human | Monoclonal | Purified recombinant extracellular fragment of human AXL fused with hIgGFc tag expressed in HEK293 cell line. |
| | LS-C198665 | Rabbit | Human, Mouse, Rat | Polyclonal | |
| | LS-B7213 | Rabbit | Human, Mouse, Rat | Polyclonal | |
| | LS-C100248 | Rabbit | Human | Polyclonal | |
| | LS-C149853 | Goat | Human | Polyclonal | |
| | LS-C196729 | Mouse | Human | Monoclonal | AXL (AAH32229, aa30-140 partial recombinant protein with GST tag. |

-continued

| Supplier Catalog# | Host Species | Reactivity | Type | Antigen |
|---|---|---|---|---|
| | | | | MW of the GST tag alone is 26 KDa. |
| LS-C100246 | Rabbit | Human | Polyclonal | |
| LS-C100247 | Rabbit | Human | Polyclonal | |
| LS-C116926 | Rabbit | Human | Polyclonal | |
| LS-C164301 | Rabbit | Human | Polyclonal | |
| LS-C136999 | Rabbit | Human | Polyclonal | |
| LS-C35081 | Rabbit | Human | Polyclonal | |
| LS-C148881 | Rabbit | Human, Mouse, Rat, Bovine, Canine, Horse, Porcine, Simian | Polyclonal | |
| LS-C148882 | Rabbit | Human, Simian | Polyclonal | |
| LS-C148955 | Rabbit | Human, Mouse, Rat, Canine, Hamster, Horse, Simian | Polyclonal | |
| LS-C3874 | Goat | Human | Polyclonal | |
| Bethyl Laboratories, Inc. 2 antibodies | | | | |
| A302-168A | Rabbit | Human | Polyclonal | |
| A302-167A | Rabbit | Human | Polyclonal | |
| Proteintech Group 1 antibody | | | | |
| 13196-1-AP | Rabbit | Human, Mouse, Rat | Polyclonal | |
| RabMAbs 3 antibodies | | | | |
| T2564 | | Human | Polyclonal | |
| T2566 | | Human | Polyclonal | |
| T2565 | | Human | Polyclonal | |
| Creative Biomart 14 antibodies | | | | |
| CPBT-28351RH | Rabbit | Human | Polyclonal | |
| CPBT-28353RH | Rabbit | Human | Polyclonal | |
| CAB-7805MH | Mouse | Human | Monoclonal | Purified recombinant extracellular fragment of human AXL fused with hIgGFc tag expressed in HEK293 cell line. |

-continued

| Supplier Catalog# | Host Species | Reactivity | Type | Antigen |
|---|---|---|---|---|
| CABT-16589MH | Mouse | Human | Monoclonal | AXL (AAH32229, 30 a.a.~140 a.a) partial recombinant protein with GST tag. MW of the GST tag alone is 26 KDa. |
| CABT-26985MH | Mouse | Human | Monoclonal | Human recombinant Axl (extracellular region). |
| CABT-16590MH | Mouse | Human | Monoclonal | AXL (AAH32229, 30 a.a.~140 a.a) partial recombinant protein with GST tag. MW of the GST tag alone is 26 KDa. |
| CPB-1412RH | Rabbit | Human | Polyclonal | |
| CPB-1414RH | Rabbit | Human | Polyclonal | |
| CABT-26984MH | Mouse | Human | Monoclonal | Recombinant fragment, corresponding to amino acids 30-140 of Human Axl |
| CPBT-28352RH | Rabbit | Human | Polyclonal | |
| CPBT-49690RH | Rabbit | Human | Polyclonal | |
| CPBT-49691RH | Rabbit | Human | Polyclonal | |
| DPABT-H18838 | Rabbit | Human | Polyclonal | |
| DPABT-H7983 | Rabbit | Human | Polyclonal | |
| Atlas Antibodies 1 antibody | | | | |
| HPA037422 | Rabbit | Human | Polyclonal | |
| United States Biological 22 antibodies | | | | |
| 032344-AP | Rabbit | Human | Polyclonal | |
| 032344-APC | Rabbit | Human | Polyclonal | |
| 032344-Biotin | Rabbit | Human | Polyclonal | |
| 032344-FITC | Rabbit | Human | Polyclonal | |
| 032344-HRP | Rabbit | Human | Polyclonal | |
| 032344-PE | Rabbit | Human | Polyclonal | |
| 32344 | Rabbit | Human | Polyclonal | |
| A4776-10A | Rabbit | Human | Polyclonal | |
| A4776-10A-AP | Rabbit | Human | Polyclonal | |
| A4776-10A-APC | Rabbit | Human | Polyclonal | |

-continued

| Supplier Catalog# | Host Species | Reactivity | Type | Antigen |
|---|---|---|---|---|
| A4776-10A-Biotin | Rabbit | Human | Polyclonal | |
| A4776-10A-FITC | Rabbit | Human | Polyclonal | |
| A4776-10A-HRP | Rabbit | Human | Polyclonal | |
| A4776-10A-PE | Rabbit | Human | Polyclonal | |
| 032343-AP | Rabbit | Human | Polyclonal | |
| 032343-APC | Rabbit | Human | Polyclonal | |
| 032343-Biotin | Rabbit | Human | Polyclonal | |
| 032343-FITC | Rabbit | Human | Polyclonal | |
| 032343-HRP | Rabbit | Human | Polyclonal | |
| 032343-PE | Rabbit | Human | Polyclonal | |
| 32343 | Rabbit | Human | Polyclonal | |
| A4776-10B | Rabbit | Human | Polyclonal | |
| EMD Millipore 1 antibody | | | | |
| ABN275 | Rabbit | Human | Polyclonal | |
| Abbiotec 1 antibody | | | | |
| 252873 | Mouse | Human | Monoclonal | Purified recombinant extracellular fragment of human AXL fused with hIgGFc tag expressed in HEK293 cell line. |
| Sigma-Aldrich 2 antibodies | | | | |
| A2441 | | Human, Mouse | Polyclonal | |
| WH0000558M1 | | Human | Monoclonal | AXL (AAH32229, a.a. 30-140) partial recombinant protein with GST tag. MW of the GST tag alone is 26 kDa. |

The following table shows exemplary, commercially available antibodies that specifically bind to AFP and that can be used herein:

| Supplier | Catalog# | Host Species | Reactivity | Type |
|---|---|---|---|---|
| antibodies-online 494 antibodies | ABIN394088 | Mouse | Human | Monoclonal |
| | ABIN388198 | Rabbit | Human | Polyclonal |
| | ABIN388199 | Rabbit | Human | Polyclonal |
| | ABIN659001 | Mouse | Human | Monoclonal |
| | ABIN488831 | Mouse | Human, Canine, Simian | Monoclonal |
| | ABIN93623 | Mouse | Human | Monoclonal |
| | ABIN93887 | Mouse | Human | Monoclonal |
| | ABIN189009 | Rabbit | Human | Monoclonal |
| | ABIN488832 | Mouse | Human | Monoclonal |

-continued

| Supplier | Catalog# | Host Species | Reactivity | Type |
|---|---|---|---|---|
| | ABIN488836 | Mouse | Human | Monoclonal |
| | ABIN488837 | Mouse | Human | Monoclonal |
| | ABIN488838 | Mouse | Human | Monoclonal |
| | ABIN93596 | Mouse | Human | Monoclonal |
| | ABIN93599 | Mouse | Human | Monoclonal |
| | ABIN93624 | Mouse | Human | Monoclonal |
| | ABIN256754 | Rabbit | Human, Rat | Polyclonal |
| | ABIN410914 | Mouse | Human | Monoclonal |
| | ABIN410915 | Mouse | Human | Monoclonal |
| | ABIN410925 | Mouse | Human | Monoclonal |
| | ABIN559807 | Mouse | Human | Monoclonal |
| | ABIN601310 | Chicken/Avian | Human | Polyclonal |
| | ABIN120681 | Mouse | Human | Monoclonal |
| | ABIN120683 | Mouse | Human | Monoclonal |
| | ABIN370517 | Rabbit | Human | Polyclonal |
| | ABIN649261 | Rabbit | Human | Monoclonal |
| | ABIN93889 | Mouse | Human | Monoclonal |
| | ABIN649262 | Rabbit | Human | Monoclonal |
| | ABIN649285 | Rabbit | Human, Rat | Monoclonal |
| | ABIN659538 | Mouse | Human | Monoclonal |
| | ABIN707801 | Rabbit | Human, Mouse, Bovine, Canine, Horse, Porcine, Rabbit | Polyclonal |
| | ABIN707803 | Rabbit | Human, Mouse, Bovine, Canine, Horse, Porcine, Rabbit | Polyclonal |
| | ABIN957725 | Mouse | Human | Monoclonal |
| | ABIN957778 | Rabbit | Human | Polyclonal |
| | ABIN960474 | Rabbit | Human | Polyclonal |
| | ABIN962039 | Rabbit | Human | Polyclonal |
| | ABIN969492 | Mouse | Human | Monoclonal |
| | ABIN114623 | Mouse | Human, Canine, Porcine | Monoclonal |
| | ABIN115282 | Rabbit | Human | Polyclonal |
| | ABIN1385277 | Rabbit | Human | Polyclonal |
| | ABIN189010 | Rabbit | Human | Monoclonal |
| | ABIN197693 | Rabbit | Human | Polyclonal |
| | ABIN197737 | Rabbit | Human | Polyclonal |
| | ABIN488830 | Mouse | Human | Monoclonal |
| | ABIN488833 | Mouse | Human | Monoclonal |
| | ABIN488834 | Mouse | Human | Monoclonal |
| | ABIN488835 | Mouse | Human | Monoclonal |
| | ABIN722901 | Mouse | Human | Monoclonal |
| | ABIN722916 | Mouse | Human | Monoclonal |
| | ABIN863470 | Mouse | Human | Monoclonal |
| | ABIN863471 | Mouse | Human | Monoclonal |
| | ABIN932517 | Mouse | Human | Monoclonal |
| | ABIN93597 | Mouse | Human | Monoclonal |
| | ABIN93598 | Mouse | Human | Monoclonal |
| | ABIN1099958 | Rabbit | Human | Monoclonal |
| | ABIN1385264 | Rabbit | Human | Polyclonal |
| | ABIN1496485 | Mouse | Human | Monoclonal |
| | ABIN151158 | Rabbit | Human | Polyclonal |
| | ABIN410810 | Mouse | Human | Monoclonal |
| | ABIN410878 | Mouse | Human | Monoclonal |
| | ABIN410879 | Mouse | Human | Monoclonal |
| | ABIN452558 | Mouse | Human | Monoclonal |
| | ABIN452559 | Mouse | Human | Monoclonal |
| | ABIN536867 | Mouse | Human | Monoclonal |
| | ABIN595041 | Mouse | Human | Monoclonal |
| | ABIN863305 | Mouse | Human | Monoclonal |
| | ABIN863310 | Mouse | Human | Monoclonal |
| | ABIN1031219 | Rabbit | Human, Mouse, Rat | Polyclonal |
| | ABIN1077783 | Rabbit | Human | Polyclonal |
| | ABIN1082868 | Rabbit | Human | Polyclonal |
| | ABIN1105330 | Mouse | Human | Monoclonal |
| | ABIN1105331 | Mouse | Human, Canine | Monoclonal |
| | ABIN1172460 | Rabbit | Human | Polyclonal |
| | ABIN1302059 | Mouse | Human | Monoclonal |
| | ABIN1302213 | Mouse | Human | Monoclonal |
| | ABIN1356494 | Rabbit | Human, Mouse, Rat | Polyclonal |
| | ABIN1363353 | Rabbit | Human, Mouse, Rat | Polyclonal |
| | ABIN1396374 | Rabbit | Human | Polyclonal |
| | ABIN1396710 | Rabbit | Human | Polyclonal |
| | ABIN1414251 | Rabbit | Human | Polyclonal |
| | ABIN1414587 | Rabbit | Human | Polyclonal |
| | ABIN145542 | Mouse | Human | Monoclonal |
| | ABIN145787 | Mouse | Human | Monoclonal |

-continued

| Supplier | Catalog# | Host Species | Reactivity | Type |
|---|---|---|---|---|
| | ABIN1496211 | Rabbit | Human | Polyclonal |
| | ABIN1496486 | Mouse | Human | Monoclonal |
| | ABIN1496487 | Mouse | Human | Monoclonal |
| | ABIN1496488 | Mouse | Human | Monoclonal |
| | ABIN206984 | Mouse | Human | Monoclonal |
| | ABIN208445 | Mouse | Human | Monoclonal |
| | ABIN216909 | Rabbit | Human | Polyclonal |
| | ABIN234254 | Mouse | Human | Monoclonal |
| | ABIN269156 | Mouse | Human | Monoclonal |
| | ABIN269271 | Mouse | Human | Monoclonal |
| | ABIN290656 | Mouse | Human | Monoclonal |
| | ABIN297273 | Mouse | Human | Monoclonal |
| | ABIN301830 | Goat | Human | Polyclonal |
| | ABIN301831 | Rabbit | Human | Polyclonal |
| | ABIN305094 | Mouse | Human | Monoclonal |
| | ABIN308975 | Mouse | Human | Monoclonal |
| | ABIN308976 | Mouse | Human | Monoclonal |
| | ABIN329760 | Mouse | Human | Monoclonal |
| | ABIN331267 | Mouse | Human | Monoclonal |
| | ABIN331268 | Mouse | Human | Monoclonal |
| | ABIN356915 | Rabbit | Human | Polyclonal |
| | ABIN401832 | Mouse | Human | Monoclonal |
| | ABIN462564 | Mouse | Human | Monoclonal |
| | ABIN532784 | Mouse | Human | Monoclonal |
| | ABIN532832 | Mouse | Human | Monoclonal |
| | ABIN534386 | Mouse | Human | Monoclonal |
| | ABIN534387 | Mouse | Human | Monoclonal |
| | ABIN544035 | Rabbit | Human | Polyclonal |
| | ABIN545955 | Rabbit | Human | Polyclonal |
| | ABIN577142 | Mouse | Human | Monoclonal |
| | ABIN609591 | Mouse | Human | Monoclonal |
| | ABIN609592 | Mouse | Human | Monoclonal |
| | ABIN609593 | Mouse | Human | Monoclonal |
| | ABIN609594 | Mouse | Human | Monoclonal |
| | ABIN614453 | Mouse | Human | Monoclonal |
| | ABIN669396 | Rabbit | Human, Mouse, Rat | Polyclonal |
| | ABIN669398 | Rabbit | Human, Mouse, Rat | Polyclonal |
| | ABIN722903 | Mouse | Human | Monoclonal |
| | ABIN722910 | Mouse | Human | Monoclonal |
| | ABIN722918 | Mouse | Human | Monoclonal |
| | ABIN722925 | Mouse | Human | Monoclonal |
| | ABIN783673 | Rabbit | Human, Mouse, Rat | Polyclonal |
| | ABIN865696 | Mouse | Human, Mouse, Rat | |
| | ABIN950379 | Rabbit | Human | Polyclonal |
| | ABIN959532 | Mouse | Human | Monoclonal |
| | ABIN99154 | Mouse | Human | Monoclonal |
| | ABIN1032206 | Mouse | Human | |
| | ABIN1034217 | Rabbit | Human, Mouse | |
| | ABIN1105325 | Mouse | Human | Monoclonal |
| | ABIN1105326 | Rabbit | Human, Bovine, Canine, Porcine | Monoclonal |
| | ABIN1105328 | Rabbit | Human, Bovine, Canine, Porcine | Monoclonal |
| | ABIN1105329 | Mouse | Human | Monoclonal |
| | ABIN1105332 | Mouse | Human, Mouse | Monoclonal |
| | ABIN1105333 | Rabbit | Human, Bovine, Canine, Porcine | Monoclonal |
| | ABIN110609 | | Human | Polyclonal |
| | ABIN110610 | | Human | Polyclonal |
| | ABIN111085 | Mouse | Human | Monoclonal |
| | ABIN1112839 | Rabbit | Human | Polyclonal |
| | ABIN1340692 | Rabbit | Human | |
| | ABIN1340693 | Rabbit | Human | |
| | ABIN1386358 | Rabbit | Human, Mouse, Rat | Polyclonal |
| | ABIN1396706 | Rabbit | Human | Polyclonal |
| | ABIN1396707 | Rabbit | Human | Polyclonal |
| | ABIN1396708 | Rabbit | Human | Polyclonal |
| | ABIN1396709 | Rabbit | Human | Polyclonal |
| | ABIN1396711 | Rabbit | Human | Polyclonal |
| | ABIN1414582 | Rabbit | Human | Polyclonal |
| | ABIN1414583 | Rabbit | Human | Polyclonal |
| | ABIN1414584 | Rabbit | Human | Polyclonal |
| | ABIN1414585 | Rabbit | Human | Polyclonal |
| | ABIN1431006 | Rabbit | Human | Polyclonal |
| | ABIN1431007 | Rabbit | Human | Polyclonal |
| | ABIN1431008 | Rabbit | Human | Polyclonal |
| | ABIN1431009 | Rabbit | Human | Polyclonal |

| Supplier | Catalog# | Host Species | Reactivity | Type |
|---|---|---|---|---|
| | ABIN1431010 | Rabbit | Human | Polyclonal |
| | ABIN1494248 | Mouse | Human | Monoclonal |
| | ABIN1494249 | Mouse | Human | Monoclonal |
| | ABIN1494462 | Rabbit | Human | Polyclonal |
| | ABIN1494463 | Rabbit | Human | Polyclonal |
| | ABIN1496489 | Mouse | Human | Monoclonal |
| | ABIN1496490 | Mouse | Human | Monoclonal |
| | ABIN1496491 | Mouse | Human | Monoclonal |
| | ABIN187924 | Rabbit | Human, Porcine, Sheep | Polyclonal |
| | ABIN190145 | Mouse | Human | Polyclonal |
| | ABIN190146 | Mouse | Human | Polyclonal |
| | ABIN190147 | Mouse | Human | Polyclonal |
| | ABIN207057 | Mouse | Human | Monoclonal |
| | ABIN211449 | Mouse | Human | Monoclonal |
| | ABIN232988 | Rabbit | Human | Polyclonal |
| | ABIN234261 | Mouse | Human | Monoclonal |
| | ABIN234262 | Mouse | Human | Monoclonal |
| | ABIN263680 | Mouse | Human | Monoclonal |
| | ABIN309030 | Rabbit | Human | Polyclonal |
| | ABIN329756 | Mouse | Human | Monoclonal |
| | ABIN329759 | Rabbit | Human | Polyclonal |
| | ABIN329770 | Mouse | Human | Monoclonal |
| | ABIN356479 | Rabbit | Human | Polyclonal |
| | ABIN356480 | Rabbit | Human | Polyclonal |
| | ABIN356914 | Rabbit | Human | Polyclonal |
| | ABIN373013 | Rabbit | Human | Polyclonal |
| | ABIN373014 | Rabbit | Human | Polyclonal |
| | ABIN381781 | Rabbit | Human | Polyclonal |
| | ABIN387328 | Rabbit | Human | Polyclonal |
| | ABIN387329 | Rabbit | Human | Polyclonal |
| | ABIN387419 | Rabbit | Human | Polyclonal |
| | ABIN443655 | Rabbit | Human | Polyclonal |
| | ABIN492751 | Rabbit | Human | Polyclonal |
| | ABIN513167 | Rabbit | Human | Polyclonal |
| | ABIN513169 | Mouse | Human | Monoclonal |
| | ABIN533580 | Mouse | Human, Canine, Porcine | Monoclonal |
| | ABIN535306 | Mouse | Human | Monoclonal |
| | ABIN535582 | Mouse | Human | Monoclonal |
| | ABIN535599 | Mouse | Human | Monoclonal |
| | ABIN535600 | Mouse | Human | Monoclonal |
| | ABIN535601 | Mouse | Human | Monoclonal |
| | ABIN544034 | Rabbit | Human | Polyclonal |
| | ABIN573921 | Chicken/Avian | Human | Polyclonal |
| | ABIN574588 | Rabbit | Human | Polyclonal |
| | ABIN595028 | Rabbit | Human | Polyclonal |
| | ABIN595029 | Goat | Human | Polyclonal |
| | ABIN595030 | Mouse | Human | Monoclonal |
| | ABIN595039 | Mouse | Human | Monoclonal |
| | ABIN595040 | Rabbit | Human | Polyclonal |
| | ABIN601306 | Mouse | Human | Monoclonal |
| | ABIN601308 | Mouse | Human | Monoclonal |
| | ABIN601309 | Mouse | Human | Monoclonal |
| | ABIN609596 | Mouse | Human | Monoclonal |
| | ABIN659000 | Mouse | Human | Monoclonal |
| | ABIN669397 | Rabbit | Human, Mouse, Rat | Polyclonal |
| | ABIN669399 | Rabbit | Human, Mouse, Rat | Polyclonal |
| | ABIN669400 | Rabbit | Human, Mouse, Rat | Polyclonal |
| | ABIN669401 | Rabbit | Human, Mouse, Rat | Polyclonal |
| | ABIN669402 | Rabbit | Human, Mouse, Rat | Polyclonal |
| | ABIN669403 | Rabbit | Human, Mouse, Rat | Polyclonal |
| | ABIN669406 | Rabbit | Human, Mouse, Rat | Polyclonal |
| | ABIN669407 | Rabbit | Human, Mouse, Rat | Polyclonal |
| | ABIN669408 | Rabbit | Human, Mouse, Rat | Polyclonal |
| | ABIN669409 | Rabbit | Human, Mouse, Rat | Polyclonal |
| | ABIN669410 | Rabbit | Human, Mouse, Rat | Polyclonal |
| | ABIN707802 | Rabbit | Human, Mouse, Bovine, Canine, Horse, Porcine, Rabbit | Polyclonal |
| | ABIN707804 | Rabbit | Human, Mouse, Bovine, Canine, Horse, Porcine, Rabbit | Polyclonal |
| | ABIN707805 | Rabbit | Human, Mouse, Bovine, Canine, Horse, Porcine, Rabbit | Polyclonal |
| | ABIN707806 | Rabbit | Human, Mouse, Bovine, Canine, Horse, Porcine, Rabbit | Polyclonal |

-continued

| Supplier | Catalog# | Host Species | Reactivity | Type |
|---|---|---|---|---|
| | ABIN707807 | Rabbit | Human, Mouse, Bovine, Canine, Horse, Porcine, Rabbit | Polyclonal |
| | ABIN707808 | Rabbit | Human, Mouse, Bovine, Canine, Horse, Porcine, Rabbit | Polyclonal |
| | ABIN707810 | Rabbit | Human, Mouse, Bovine, Canine, Horse, Porcine, Rabbit | Polyclonal |
| | ABIN707811 | Rabbit | Human, Mouse, Bovine, Canine, Horse, Porcine, Rabbit | Polyclonal |
| | ABIN707812 | Rabbit | Human, Mouse, Bovine, Canine, Horse, Porcine, Rabbit | Polyclonal |
| | ABIN707813 | Rabbit | Human, Mouse, Bovine, Canine, Horse, Porcine, Rabbit | Polyclonal |
| | ABIN707814 | Rabbit | Human, Mouse, Bovine, Canine, Horse, Porcine, Rabbit | Polyclonal |
| | ABIN707815 | Rabbit | Human, Mouse, Bovine, Canine, Horse, Porcine, Rabbit | Polyclonal |
| | ABIN781997 | Mouse | Human | Monoclonal |
| | ABIN782501 | Rabbit | Human | Polyclonal |
| | ABIN800467 | Rabbit | Human | Polyclonal |
| | ABIN800468 | Rabbit | Human | Polyclonal |
| | ABIN881775 | Rabbit | Human, Mouse | Polyclonal |
| | ABIN881776 | Rabbit | Human, Mouse, Rat, Chicken/Avian | Polyclonal |
| | ABIN881777 | Rabbit | Human, Mouse, Rat, Bovine, Simian | Polyclonal |
| | ABIN881778 | Rabbit | Human, Mouse, Rat, Bovine, Canine, Chicken/Avian | Polyclonal |
| | ABIN881779 | Rabbit | Human, Mouse, Rat, Bovine, Canine, Horse, Simian | Polyclonal |
| | ABIN881780 | Rabbit | Human, Mouse, Rat, Bovine, Canine, Chicken/Avian, Sheep | Polyclonal |
| | ABIN881781 | Rabbit | Human, Mouse, Rat, Bovine, Canine, Chicken/Avian, Porcine, Sheep | Polyclonal |
| | ABIN881782 | Rabbit | Human, Mouse, Rat | Polyclonal |
| | ABIN881783 | Rabbit | Human, Mouse, Rat, Porcine, Sheep | Polyclonal |
| | ABIN958023 | Chicken/Avian | Human | Polyclonal |
| | ABIN1032207 | Mouse | Human | |
| | ABIN1099959 | Mouse | Human | Monoclonal |
| | ABIN1105327 | Mouse | Human | Monoclonal |
| | ABIN114622 | Mouse | Human, Canine, Porcine | Monoclonal |
| | ABIN115281 | Rabbit | Human | Polyclonal |
| | ABIN1340691 | Rabbit | Human | |
| | ABIN137059 | Mouse | Human, Canine, Porcine | Polyclonal |
| | ABIN138246 | Mouse | Human | Monoclonal |
| | ABIN1388143 | Rabbit | Human, Mouse, Rat | Polyclonal |
| | ABIN1388144 | Rabbit | Human, Mouse, Rat | Polyclonal |
| | ABIN1388145 | Rabbit | Human, Mouse, Rat | Polyclonal |
| | ABIN1388146 | Rabbit | Human, Mouse, Rat | Polyclonal |
| | ABIN1388147 | Rabbit | Human, Mouse, Rat | Polyclonal |
| | ABIN1388148 | Rabbit | Human, Mouse, Rat | Polyclonal |
| | ABIN1396370 | Rabbit | Human | Polyclonal |
| | ABIN1396371 | Rabbit | Human | Polyclonal |
| | ABIN1396372 | Rabbit | Human | Polyclonal |
| | ABIN1396373 | Rabbit | Human | Polyclonal |
| | ABIN1396375 | Rabbit | Human | Polyclonal |
| | ABIN1406031 | Rabbit | Human, Mouse, Rat | Polyclonal |
| | ABIN1406032 | Rabbit | Human, Mouse, Rat | Polyclonal |
| | ABIN1406033 | Rabbit | Human, Mouse, Rat | Polyclonal |
| | ABIN1406034 | Rabbit | Human, Mouse, Rat | Polyclonal |
| | ABIN1406035 | Rabbit | Human, Mouse, Rat | Polyclonal |
| | ABIN1406036 | Rabbit | Human, Mouse, Rat | Polyclonal |
| | ABIN140707 | Rabbit | Human | Polyclonal |
| | ABIN1414246 | Rabbit | Human | Polyclonal |
| | ABIN1414247 | Rabbit | Human | Polyclonal |
| | ABIN1414248 | Rabbit | Human | Polyclonal |
| | ABIN1414249 | Rabbit | Human | Polyclonal |

-continued

| Supplier | Catalog# | Host Species | Reactivity | Type |
|---|---|---|---|---|
| | ABIN1414250 | Rabbit | Human | Polyclonal |
| | ABIN1414586 | Rabbit | Human | Polyclonal |
| | ABIN141941 | Rabbit | Human | Polyclonal |
| | ABIN1423876 | Rabbit | Human, Mouse, Rat | Polyclonal |
| | ABIN1423877 | Rabbit | Human, Mouse, Rat | Polyclonal |
| | ABIN1423878 | Rabbit | Human, Mouse, Rat | Polyclonal |
| | ABIN1423879 | Rabbit | Human, Mouse, Rat | Polyclonal |
| | ABIN1423880 | Rabbit | Human, Mouse, Rat | Polyclonal |
| | ABIN1430726 | Rabbit | Human | Polyclonal |
| | ABIN1430727 | Rabbit | Human | Polyclonal |
| | ABIN1430728 | Rabbit | Human | Polyclonal |
| | ABIN1430729 | Rabbit | Human | Polyclonal |
| | ABIN1430730 | Rabbit | Human | Polyclonal |
| | ABIN143305 | Rabbit | Human | Polyclonal |
| | ABIN143308 | Rabbit | Human | Polyclonal |
| | ABIN143791 | Mouse | Human | Monoclonal |
| | ABIN143804 | Mouse | Human | Monoclonal |
| | ABIN144666 | Mouse | Human, Canine, Porcine | Polyclonal |
| | ABIN145396 | Mouse | Human | Monoclonal |
| | ABIN147103 | Rabbit | Human | Polyclonal |
| | ABIN148583 | Rabbit | Human | Polyclonal |
| | ABIN149445 | Chicken/Avian | Human | Polyclonal |
| | ABIN1496212 | Rabbit | Human | Polyclonal |
| | ABIN1496492 | Mouse | Human | Monoclonal |
| | ABIN1496493 | Mouse | Human | Monoclonal |
| | ABIN1496494 | Mouse | Human | Monoclonal |
| | ABIN1502055 | Mouse | Human | Monoclonal |
| | ABIN1502066 | Mouse | Human | Monoclonal |
| | ABIN1502067 | Mouse | Human | Monoclonal |
| | ABIN191205 | Mouse | Human | Monoclonal |
| | ABIN191206 | Mouse | Human | Monoclonal |
| | ABIN197694 | Rabbit | Human | Polyclonal |
| | ABIN208441 | Mouse | Human | Monoclonal |
| | ABIN208442 | Mouse | Human | Monoclonal |
| | ABIN208444 | Mouse | Human | Monoclonal |
| | ABIN208447 | Mouse | Human | Monoclonal |
| | ABIN208448 | Mouse | Human | Monoclonal |
| | ABIN210027 | Mouse | Human | Monoclonal |
| | ABIN210395 | Mouse | Human | Monoclonal |
| | ABIN210396 | Mouse | Human | Monoclonal |
| | ABIN210397 | Mouse | Human | Monoclonal |
| | ABIN210398 | Mouse | Human | Monoclonal |
| | ABIN216910 | Rabbit | Human | Polyclonal |
| | ABIN230782 | Rabbit | Human | Polyclonal |
| | ABIN232991 | Mouse | Human | Monoclonal |
| | ABIN234255 | Mouse | Human | Monoclonal |
| | ABIN234256 | Mouse | Human | Monoclonal |
| | ABIN234258 | Mouse | Human | Monoclonal |
| | ABIN234263 | Mouse | Human | Monoclonal |
| | ABIN236740 | Rabbit | Human | Polyclonal |
| | ABIN253528 | Mouse | Human | Monoclonal |
| | ABIN253531 | Mouse | Human | Monoclonal |
| | ABIN256040 | Mouse | Human | Monoclonal |
| | ABIN259575 | Mouse | Human | Monoclonal |
| | ABIN263679 | Mouse | Human | Monoclonal |
| | ABIN265658 | Mouse | Human | Monoclonal |
| | ABIN266580 | Mouse | Human | Monoclonal |
| | ABIN269422 | Rabbit | Human | Polyclonal |
| | ABIN272323 | Mouse | Human, Canine, Porcine | Monoclonal |
| | ABIN283897 | Mouse | Human | Monoclonal |
| | ABIN283898 | Mouse | Human | Monoclonal |
| | ABIN292772 | Mouse | Human | Monoclonal |
| | ABIN294630 | Mouse | Human | Monoclonal |
| | ABIN298981 | Mouse | Human | Monoclonal |
| | ABIN298982 | Mouse | Human | Monoclonal |
| | ABIN307022 | Mouse | Human, Canine, Porcine | Monoclonal |
| | ABIN316175 | Chicken/Avian | Human | Polyclonal |
| | ABIN316649 | Mouse | Human | Monoclonal |
| | ABIN317211 | Mouse | Human | Monoclonal |
| | ABIN329765 | Mouse | Human | Monoclonal |
| | ABIN329767 | Rabbit | Human | Polyclonal |
| | ABIN329771 | Mouse | Human | Monoclonal |
| | ABIN329775 | Mouse | Human | Monoclonal |
| | ABIN336969 | Rabbit | Human | Polyclonal |
| | ABIN336970 | Rabbit | Human | Polyclonal |
| | ABIN336971 | Rabbit | Human | Polyclonal |
| | ABIN343616 | | Human | Monoclonal |

-continued

| Supplier | Catalog# | Host Species | Reactivity | Type |
|---|---|---|---|---|
| | ABIN343661 | Rabbit | Human | Polyclonal |
| | ABIN344964 | Mouse | Human | Monoclonal |
| | ABIN344974 | Mouse | Human | Monoclonal |
| | ABIN345184 | Mouse | Human | Monoclonal |
| | ABIN346550 | Goat | Human | Polyclonal |
| | ABIN349909 | Mouse | Human | Monoclonal |
| | ABIN349910 | Mouse | Human | Monoclonal |
| | ABIN355152 | Mouse | Human | Monoclonal |
| | ABIN355153 | Mouse | Human | Monoclonal |
| | ABIN363524 | Goat | Human | Polyclonal |
| | ABIN379910 | Chicken/Avian | Human | Polyclonal |
| | ABIN385326 | Mouse | Human | Monoclonal |
| | ABIN385327 | Mouse | Human | Monoclonal |
| | ABIN385328 | Mouse | Human | Monoclonal |
| | ABIN402465 | Mouse | Human | Monoclonal |
| | ABIN449451 | Mouse | Human | Polyclonal |
| | ABIN452557 | Mouse | Human | Monoclonal |
| | ABIN458119 | Rabbit | Human | Polyclonal |
| | ABIN473154 | Mouse | Human | Monoclonal |
| | ABIN473205 | Mouse | Human | Monoclonal |
| | ABIN473208 | Rabbit | Human | Polyclonal |
| | ABIN473214 | Goat | Human | Polyclonal |
| | ABIN473220 | Rabbit | Human | Polyclonal |
| | ABIN513166 | Mouse | Human | Polyclonal |
| | ABIN513168 | Rabbit | Human | Polyclonal |
| | ABIN532096 | Mouse | Human | Polyclonal |
| | ABIN532244 | Mouse | Human | Monoclonal |
| | ABIN532245 | Mouse | Human | Monoclonal |
| | ABIN533279 | Mouse | Human | Monoclonal |
| | ABIN533316 | Mouse | Human | Monoclonal |
| | ABIN533317 | Mouse | Human | Monoclonal |
| | ABIN533318 | Mouse | Human | Monoclonal |
| | ABIN533319 | Mouse | Human | Monoclonal |
| | ABIN533462 | Mouse | Human | Monoclonal |
| | ABIN535305 | Mouse | Human | Monoclonal |
| | ABIN535598 | Mouse | Human | Monoclonal |
| | ABIN537017 | Mouse | Human | Monoclonal |
| | ABIN541114 | Rabbit | Human | Polyclonal |
| | ABIN543128 | Rabbit | Human | Polyclonal |
| | ABIN548484 | Goat | Human | Polyclonal |
| | ABIN548485 | Goat | Human | Polyclonal |
| | ABIN572996 | Mouse | Human | Monoclonal |
| | ABIN574521 | Rabbit | Human | Polyclonal |
| | ABIN574692 | Mouse | Human | Monoclonal |
| | ABIN595026 | Mouse | Human | Monoclonal |
| | ABIN595027 | Mouse | Human | Monoclonal |
| | ABIN595032 | Mouse | Human | Monoclonal |
| | ABIN595033 | Mouse | Human | Monoclonal |
| | ABIN595034 | Mouse | Human | Monoclonal |
| | ABIN595035 | Mouse | Human | Monoclonal |
| | ABIN595036 | Mouse | Human | Monoclonal |
| | ABIN595037 | Mouse | Human | Monoclonal |
| | ABIN595038 | Mouse | Human | Monoclonal |
| | ABIN595042 | Goat | Human | Polyclonal |
| | ABIN595044 | Rabbit | Human | Polyclonal |
| | ABIN601307 | Rabbit | Human | Polyclonal |
| | ABIN603190 | Mouse | Human | Monoclonal |
| | ABIN603191 | Goat | Human | Polyclonal |
| | ABIN603192 | Goat | Human | Polyclonal |
| | ABIN603193 | Chicken/Avian | Human | Polyclonal |
| | ABIN608998 | Mouse | Human | Monoclonal |
| | ABIN609595 | Rabbit | Human | Polyclonal |
| | ABIN613071 | Rabbit | Human | Polyclonal |
| | ABIN613072 | Rabbit | Human | Polyclonal |
| | ABIN613541 | Rabbit | Human | Polyclonal |
| | ABIN613542 | Rabbit | Human | Polyclonal |
| | ABIN638535 | Mouse | Human | |
| | ABIN642662 | Rabbit | Human | |
| | ABIN643062 | Mouse | Human | |
| | ABIN643107 | Rabbit | Human | |
| | ABIN643108 | Rabbit | Human | |
| | ABIN669404 | Rabbit | Human, Mouse, Rat | Polyclonal |
| | ABIN707809 | Rabbit | Human, Mouse, Bovine, Canine, Horse, Porcine, Rabbit | Polyclonal |
| | ABIN722904 | Mouse | Human | Monoclonal |
| | ABIN722905 | Mouse | Human | Monoclonal |

-continued

| Supplier | Catalog# | Host Species | Reactivity | Type |
|---|---|---|---|---|
| | ABIN722906 | Mouse | Human | Monoclonal |
| | ABIN722907 | Mouse | Human | Monoclonal |
| | ABIN722908 | Mouse | Human | Monoclonal |
| | ABIN722909 | Mouse | Human | Monoclonal |
| | ABIN722911 | Mouse | Human | Monoclonal |
| | ABIN722912 | Mouse | Human | Monoclonal |
| | ABIN722913 | Mouse | Human | Monoclonal |
| | ABIN722914 | Mouse | Human | Monoclonal |
| | ABIN722919 | Mouse | Human | Monoclonal |
| | ABIN722920 | Mouse | Human | Monoclonal |
| | ABIN722921 | Mouse | Human | Monoclonal |
| | ABIN722922 | Mouse | Human | Monoclonal |
| | ABIN722923 | Mouse | Human | Monoclonal |
| | ABIN722924 | Mouse | Human | Monoclonal |
| | ABIN722926 | Mouse | Human | Monoclonal |
| | ABIN722927 | Mouse | Human | Monoclonal |
| | ABIN722928 | Mouse | Human | Monoclonal |
| | ABIN722929 | Mouse | Human | Monoclonal |
| | ABIN781998 | Mouse | Human | Monoclonal |
| | ABIN781999 | Mouse | Human | Monoclonal |
| | ABIN782000 | Mouse | Human | Monoclonal |
| | ABIN800062 | Goat | Human | Polyclonal |
| | ABIN800076 | Rabbit | Human | Polyclonal |
| | ABIN809957 | Goat | Human | Polyclonal |
| | ABIN873515 | Mouse | Human | Monoclonal |
| | ABIN873516 | Mouse | Human | Polyclonal |
| | ABIN873517 | Mouse | Human | Monoclonal |
| | ABIN873518 | Mouse | Human | Monoclonal |
| | ABIN873519 | Mouse | Human | Monoclonal |
| | ABIN873520 | Mouse | Human | Monoclonal |
| | ABIN873521 | Mouse | Human | Polyclonal |
| | ABIN873522 | Mouse | Human | Monoclonal |
| | ABIN873523 | Mouse | Human | Monoclonal |
| | ABIN873524 | Mouse | Human | Monoclonal |
| | ABIN950378 | Rabbit | Human | Polyclonal |
| | ABIN958575 | Rabbit | Human | Polyclonal |
| | ABIN965540 | Rabbit | Human | Polyclonal |
| | ABIN99155 | Mouse | Human | Monoclonal |
| | ABIN99157 | Mouse | Human | Monoclonal |
| | ABIN108664 | Goat | Human | Polyclonal |
| | ABIN1099956 | Mouse | Human | Monoclonal |
| | ABIN1099957 | Mouse | Human | Monoclonal |
| | ABIN141631 | Goat | Human | Polyclonal |
| | ABIN342178 | Mouse | Human | Monoclonal |
| | ABIN344972 | Mouse | Human | Monoclonal |
| | ABIN344975 | Mouse | Human | Monoclonal |
| | ABIN344976 | Mouse | Human | Monoclonal |
| | ABIN345185 | Mouse | Human | Monoclonal |
| | ABIN346713 | Goat | Human | Polyclonal |
| | ABIN378849 | Mouse | Human | Monoclonal |
| | ABIN378850 | Mouse | Human | Monoclonal |
| | ABIN379319 | Mouse | Human | Monoclonal |
| | ABIN458101 | Rabbit | Human | Polyclonal |
| | ABIN570397 | Mouse | Human | Monoclonal |
| | ABIN577143 | Mouse | Human | Monoclonal |
| | ABIN595031 | Mouse | Human | Monoclonal |
| | ABIN619292 | Goat | Human | Polyclonal |
| | ABIN865537 | Mouse | Human | Monoclonal |
| | ABIN865538 | Mouse | Human | Monoclonal |
| | ABIN865539 | Mouse | Human | Monoclonal |
| | ABIN926302 | Goat | Human | Polyclonal |
| | ABIN926304 | Goat | Human | Polyclonal |
| | ABIN929459 | Goat | Human | Polyclonal |
| | ABIN957826 | Rabbit | Human | Polyclonal |
| | ABIN99156 | Mouse | Human | Monoclonal |
| Abnova Corporation 41 antibodies | H00000174-M01 | Mouse | Human | Monoclonal |
| | PAB3074 | Rabbit | Human | Polyclonal |
| | PAB3075 | Rabbit | Human | Polyclonal |
| | MAB2685 | Mouse | Human | Monoclonal |
| | MAB2686 | Mouse | Human | Monoclonal |
| | H00000174-D01 | Rabbit | Human | Polyclonal |
| | MAB1822 | Mouse | Human | Monoclonal |
| | MAB9896 | Mouse | Human | Monoclonal |
| | MAB0906 | Mouse | Human | Monoclonal |
| | MAB0954 | Mouse | Human | Monoclonal |

-continued

| Supplier | Catalog# | Host Species | Reactivity | Type |
|---|---|---|---|---|
| | H00000174-B01 | Mouse | Human | Polyclonal |
| | H00000174-D01P | Rabbit | Human | Polyclonal |
| | H00000174-M04 | Mouse | Human | Monoclonal |
| | MAB1508 | Mouse | Human | Monoclonal |
| | PAB19287 | Rabbit | Human | Polyclonal |
| | MAB5322 | Mouse | Human | Monoclonal |
| | PAB11180 | Rabbit | Human | Polyclonal |
| | MAB6776 | Mouse | Human | Monoclonal |
| | MAB3669 | Mouse | Human | Monoclonal |
| | MAB4003 | Mouse | Human | Monoclonal |
| | MAB4005 | Mouse | Human | Monoclonal |
| | MAB4007 | Mouse | Human | Monoclonal |
| | MAB5294 | Mouse | Human | Monoclonal |
| | PAB14517 | Rabbit | Human | Polyclonal |
| | MAB0195 | Mouse | Human | Monoclonal |
| | MAB0350 | Mouse | Human | Monoclonal |
| | MAB0351 | Mouse | Human | Monoclonal |
| | MAB1545 | Mouse | Human | Monoclonal |
| | MAB1546 | Mouse | Human | Monoclonal |
| | MAB1547 | Mouse | Human | Monoclonal |
| | MAB1548 | Mouse | Human | Monoclonal |
| | MAB1697 | Mouse | Human | Monoclonal |
| | MAB3668 | Mouse | Human | Monoclonal |
| | MAB4002 | Mouse | Human | Monoclonal |
| | MAB5473 | Mouse | Human | Monoclonal |
| | MAB6534 | Mouse | Human | Monoclonal |
| | MAB6535 | Mouse | Human | Monoclonal |
| | MAB8258 | Mouse | Human | Monoclonal |
| | PAB2166 | Rabbit | Human | Polyclonal |
| | PAB7937 | Goat | Human | Polyclonal |
| | PAB7938 | Goat | Human | Polyclonal |
| Novus Biologicals 56 antibodies | H00000174-M01 | Mouse | Human | Monoclonal |
| | NBP2-03084 | Mouse | Human, Canine, Simian | Monoclonal |
| | NBP2-03085 | Mouse | Human | Monoclonal |
| | NBP2-03090 | Mouse | Human | Monoclonal |
| | NBP2-03091 | Mouse | Human | Monoclonal |
| | NBP2-03206 | Mouse | Human | Monoclonal |
| | NB100-1611 | Rabbit | Human | Polyclonal |
| | NB100-79895 | Rabbit | Human, Rat | Polyclonal |
| | NBP1-48255 | Mouse | Human | Monoclonal |
| | NBP1-48256 | Mouse | Human | Monoclonal |
| | NBP1-48257 | Mouse | Human | Monoclonal |
| | NBP1-76275 | Rabbit | Human, Mouse, Rat | Polyclonal |
| | NBP2-03083 | Mouse | Human | Monoclonal |
| | NBP2-03087 | Mouse | Human | Monoclonal |
| | NBP2-03088 | Mouse | Human | Monoclonal |
| | NBP2-03089 | Mouse | Human | Monoclonal |
| | NBP2-03410 | Mouse | Human | Monoclonal |
| | NBP2-03411 | Mouse | Human | Monoclonal |
| | 25440002 | Rabbit | Human | Polyclonal |
| | NB500-524 | Mouse | Human | Monoclonal |
| | NB500-643 | Mouse | Human | Monoclonal |
| | H00000174-B01 | Mouse | Human | Polyclonal |
| | H00000174-D01P | Rabbit | Human | Polyclonal |
| | NBP2-22197 | Mouse | Human | Monoclonal |
| | 33970002 | Rabbit | Human | Polyclonal |
| | 33990002 | Rabbit | Human | Polyclonal |
| | NBP1-48252 | Mouse | Human | Monoclonal |
| | NBP1-48253 | Mouse | Human | Monoclonal |
| | NBP1-48254 | Mouse | Human | Monoclonal |
| | NBP2-03086 | Mouse | Human | Monoclonal |
| | NLS2566 | Rabbit | Human | Polyclonal |
| | H00000174-D01 | Rabbit | Human | Polyclonal |
| | 33950002 | Rabbit | Human | Polyclonal |
| | 33980002 | Rabbit | Human | Polyclonal |
| | H00000174-M04 | Mouse | Human | Monoclonal |
| | NB120-10025 | Mouse | Human | Monoclonal |
| | NBP1-35286-0.1ml | Rabbit | Human | Polyclonal |

-continued

| Supplier | Catalog# | Host Species | Reactivity | Type |
|---|---|---|---|---|
| | NBP1-42181 | Mouse | Mouse, Rat | Monoclonal |
| | NBP2-12516-0.1ml | Rabbit | Human | Monoclonal |
| | NB110-2533 | Mouse | Human | Monoclonal |
| | NB110-2533APC | Mouse | Human | Monoclonal |
| | NB110-2533FR | Mouse | Human | Monoclonal |
| | NB110-2533G | Mouse | Human | Monoclonal |
| | NB110-2533IR | Mouse | Human | Monoclonal |
| | NB110-2533PCP | Mouse | Human | Monoclonal |
| | NB110-2533PE | Mouse | Human | Monoclonal |
| | NB110-2533UV | Mouse | Human | Monoclonal |
| | NB110-2533V | Mouse | Human | Monoclonal |
| | NB110-2533V2 | Mouse | Human | Monoclonal |
| | NB110-2533V3 | Mouse | Human | Monoclonal |
| | NB110-7961 | Mouse | Human | Monoclonal |
| | NB120-10072 | Mouse | Human | Monoclonal |
| | NB600-1237 | Goat | Human | Polyclonal |
| | NBP1-22571-0.5ml | Mouse | Human, Canine, Porcine | Monoclonal |
| | NBP2-23510 | Mouse | Human | Monoclonal |
| | NBP2-23511 | Mouse | Human | Monoclonal |
| GeneTex 37 antibodies | GTX84954 | Mouse | Human, Canine, Simian | Monoclonal |
| | GTX84947 | Mouse | Human | Monoclonal |
| | GTX84948 | Mouse | Human | Monoclonal |
| | GTX84949 | Mouse | Human | Monoclonal |
| | GTX84953 | Mouse | Human | Monoclonal |
| | GTX23980 | Mouse | Human | Monoclonal |
| | GTX61406 | Rabbit | Human | Monoclonal |
| | GTX61379 | Rabbit | Human, Mouse, Rat | Polyclonal |
| | GTX84950 | Mouse | Human | Monoclonal |
| | GTX84951 | Mouse | Human | Monoclonal |
| | GTX84952 | Mouse | Human | Monoclonal |
| | GTX84955 | Mouse | Human | Monoclonal |
| | GTX19529 | Rabbit | Human | Polyclonal |
| | GTX60214 | Mouse | Human | Monoclonal |
| | GTX60215 | Mouse | Human | Monoclonal |
| | GTX61429 | Rabbit | Human | Monoclonal |
| | GTX63974 | Rabbit | Human | Monoclonal |
| | GTX77527 | Goat | Human | Polyclonal |
| | GTX83261 | Mouse | Human | Monoclonal |
| | GTX14224 | Chicken/Avian | Human | Polyclonal |
| | GTX44459 | Mouse | Human | Monoclonal |
| | GTX44462 | Mouse | Human | Monoclonal |
| | GTX10071 | Mouse | Human | Monoclonal |
| | GTX10072 | Mouse | Human | Monoclonal |
| | GTX17240 | Mouse | Human, Canine, Porcine | Monoclonal |
| | GTX20839 | Mouse | Human, Canine, Porcine | Monoclonal |
| | GTX20920 | Rabbit | Human | Polyclonal |
| | GTX28276 | Mouse | Human | Monoclonal |
| | GTX29372 | Rabbit | Human | Polyclonal |
| | GTX42797 | Mouse | Human | Monoclonal |
| | GTX42798 | Mouse | Human | Monoclonal |
| | GTX44460 | Mouse | Human | Monoclonal |
| | GTX44461 | Mouse | Human | Monoclonal |
| | GTX44466 | Mouse | Human | Monoclonal |
| | GTX74240 | Rabbit | Human, Rabbit | Polyclonal |
| | GTX74241 | Rabbit | Human, Rabbit | Polyclonal |
| | GTX75466 | Mouse | Human | Monoclonal |
| OriGene 19 antibodies | TA501782 | Mouse | Human, Canine, Simian | Monoclonal |
| | TA501783 | Mouse | Human | Monoclonal |
| | TA501788 | Mouse | Human | Monoclonal |
| | TA501789 | Mouse | Human | Monoclonal |
| | TA501925 | Mouse | Human | Monoclonal |
| | TA500010 | Mouse | Human | Monoclonal |
| | TA500011 | Mouse | Human, Canine | Monoclonal |
| | TA500258 | Mouse | Human, Canine, Simian | Monoclonal |
| | TA501780 | Mouse | Human | Monoclonal |

-continued

| Supplier | Catalog# | Host Species | Reactivity | Type |
|---|---|---|---|---|
| | TA501785 | Mouse | Human | Monoclonal |
| | TA501786 | Mouse | Human | Monoclonal |
| | TA501787 | Mouse | Human | Monoclonal |
| | TA502169 | Mouse | Human | Monoclonal |
| | TA502170 | Mouse | Human | Monoclonal |
| | TA500007 | Mouse | Human | Monoclonal |
| | TA500008 | Mouse | Human | Monoclonal |
| | TA500009 | Mouse | Human | Monoclonal |
| | TA501784 | Mouse | Human | Monoclonal |
| | TA501814 | Mouse | Human | Monoclonal |
| R&D Systems 7 antibodies | MAB1368 | Mouse | Human, Mouse | Monoclonal |
| | MAB1369 | Mouse | Human | Monoclonal |
| | AF1369 | Chicken/Avian | Human | Polyclonal |
| | BAF1369 | Chicken/Avian | Human | Polyclonal |
| | IC1368G | Mouse | Human, Mouse | Monoclonal |
| | IC1368P | Mouse | Human, Mouse | Monoclonal |
| | MAB13691 | Mouse | Human | Monoclonal |
| Proteintech Group 1 antibody | 14550-1-AP | Rabbit | Human, Mouse, Rat | Polyclonal |
| LifeSpan BioSciences, Inc. 173 antibodies | LS-C196625 | Mouse | Human | Monoclonal |
| | LS-C115684 | Mouse | Human, Canine, Simian | Monoclonal |
| | LS-C152488 | Rabbit | Human | Monoclonal |
| | LS-B3881 | Mouse | Human | Monoclonal |
| | LS-B6366 | Rabbit | Human | Polyclonal |
| | LS-B6424 | Mouse | Human | Monoclonal |
| | LS-B7157 | Rabbit | Human | Polyclonal |
| | LS-C123533 | Chicken/Avian | Human | Polyclonal |
| | LS-C49754 | Rabbit | Human | Monoclonal |
| | LS-B6902 | Rabbit | Human | Polyclonal |
| | LS-B8109 | Rabbit | Human, Mouse, Rat | Polyclonal |
| | LS-C115689 | Mouse | Human | Monoclonal |
| | LS-C115690 | Mouse | Human | Monoclonal |
| | LS-C115769 | Mouse | Human | Monoclonal |
| | LS-C98143 | Rabbit | Human | Polyclonal |
| | LS-C45881 | Mouse | Human | Monoclonal |
| | LS-C62142 | Mouse | Human | Monoclonal |
| | LS-C62143 | Mouse | Human | Monoclonal |
| | LS-C129023 | Mouse | Human | Monoclonal |
| | LS-C149880 | Chicken/Avian | Human | Polyclonal |
| | LS-C171037 | Mouse | Human | Monoclonal |
| | LS-C49779 | Rabbit | Human | Monoclonal |
| | LS-C88735 | Rabbit | Human, Porcine, Sheep | Polyclonal |
| | LS-C88767 | Rabbit | Human | Polyclonal |
| | LS-C115683 | Mouse | Human | Monoclonal |
| | LS-C121806 | Mouse | Human, Canine | Monoclonal |
| | LS-C121807 | Mouse | Human | Monoclonal |
| | LS-C121808 | Mouse | Human, Mouse | Monoclonal |
| | LS-C121809 | Mouse | Human | Monoclonal |
| | LS-C146581 | Mouse | Human | Monoclonal |
| | LS-C156293 | Mouse | Human | Monoclonal |
| | LS-C156294 | Mouse | Human | Monoclonal |
| | LS-C170881 | Rabbit | Human | Polyclonal |
| | LS-C171036 | Mouse | Human | Monoclonal |
| | LS-C172398 | Mouse | Human | Monoclonal |
| | LS-C172401 | Mouse | Human | Monoclonal |
| | LS-C172508 | Mouse | Human | Monoclonal |
| | LS-C172509 | Mouse | Human | Monoclonal |
| | LS-C174841 | Mouse | Human | Monoclonal |
| | LS-C33093 | Rabbit | Human | Polyclonal |
| | LS-C66001 | Mouse | Human | Monoclonal |
| | LS-C66003 | Chicken/Avian | Human | Polyclonal |
| | LS-C6786 | Mouse | Human | Monoclonal |
| | LS-C98144 | Rabbit | Human | Polyclonal |
| | LS-C115881 | Rabbit | Human, Mouse, Rat | Polyclonal |
| | LS-C121811 | Mouse | Human | Monoclonal |
| | LS-C123531 | Mouse | Human | Monoclonal |
| | LS-C123532 | Mouse | Human | Monoclonal |
| | LS-C129010 | Rabbit | Human | Polyclonal |
| | LS-C129011 | Goat | Human | Polyclonal |
| | LS-C129012 | Mouse | Human | Monoclonal |
| | LS-C129021 | Mouse | Human, Mouse | Monoclonal |
| | LS-C129022 | Rabbit | Human, Mouse | Polyclonal |
| | LS-C188999 | Rabbit | Human | Polyclonal |
| | LS-C194156 | Mouse | Human | Monoclonal |
| | LS-C194157 | Mouse | Human | Monoclonal |
| | LS-C194158 | Mouse | Human | Monoclonal |

-continued

| Supplier | Catalog# | Host Species | Reactivity | Type |
|---|---|---|---|---|
| | LS-C194159 | Mouse | Human | Monoclonal |
| | LS-C194160 | Mouse | Human | Monoclonal |
| | LS-C194161 | Mouse | Human | Monoclonal |
| | LS-C194366 | Mouse | Human | Monoclonal |
| | LS-C195176 | Rabbit | Human | Polyclonal |
| | LS-C41594 | Mouse | Human | Monoclonal |
| | LS-C46045 | Mouse | Human | Monoclonal |
| | LS-C49722 | Rabbit | Human | Polyclonal |
| | LS-C49723 | Rabbit | Human | Polyclonal |
| | LS-C65997 | Mouse | Human | Monoclonal |
| | LS-C66000 | Rabbit | Human | Polyclonal |
| | LS-C66011 | Mouse | Human | Monoclonal |
| | LS-C6780 | Rabbit | Human | Polyclonal |
| | LS-C11494 | Rabbit | Human | Polyclonal |
| | LS-C11598 | Mouse | Human | Monoclonal |
| | LS-C121211 | Mouse | Human | Monoclonal |
| | LS-C121810 | Rabbit | Human | Polyclonal |
| | LS-C123529 | Mouse | Human | Monoclonal |
| | LS-C123530 | Rabbit | Human | Polyclonal |
| | LS-C125594 | Mouse | Human | Monoclonal |
| | LS-C125595 | Goat | Human | Polyclonal |
| | LS-C125596 | Goat | Human | Polyclonal |
| | LS-C125597 | Chicken/Avian | Human | Polyclonal |
| | LS-C129008 | Mouse | Human | Monoclonal |
| | LS-C129009 | Mouse | Human | Monoclonal |
| | LS-C129014 | Mouse | Human | Monoclonal |
| | LS-C129015 | Mouse | Human | Monoclonal |
| | LS-C129016 | Mouse | Human | Monoclonal |
| | LS-C129017 | Mouse | Human | Monoclonal |
| | LS-C129018 | Mouse | Human | Monoclonal |
| | LS-C129019 | Mouse | Human | Monoclonal |
| | LS-C129020 | Mouse | Human | Monoclonal |
| | LS-C129024 | Goat | Human | Polyclonal |
| | LS-C129026 | Rabbit | Human | Polyclonal |
| | LS-C141810 | Mouse | Human | Monoclonal |
| | LS-C141923 | Mouse | Human | Monoclonal |
| | LS-C147749 | Rabbit | Human | Polyclonal |
| | LS-C153042 | | Human, Mouse | Monoclonal |
| | LS-C170867 | Rabbit | Human | Polyclonal |
| | LS-C171038 | Mouse | Human | Monoclonal |
| | LS-C189000 | Mouse | Human, Canine, Porcine | Monoclonal |
| | LS-C189534 | Mouse | Human, Canine, Horse, Porcine | Monoclonal |
| | LS-C190799 | Mouse | Human, Canine, Porcine | Monoclonal |
| | LS-C190800 | Rabbit | Human | Polyclonal |
| | LS-C194155 | Mouse | Human | Monoclonal |
| | LS-C194317 | Mouse | Human | Monoclonal |
| | LS-C194318 | Mouse | Human | Monoclonal |
| | LS-C194572 | Mouse | Human | Monoclonal |
| | LS-C194573 | Mouse | Human | Monoclonal |
| | LS-C33095 | Rabbit | Human | Polyclonal |
| | LS-C41894 | Rabbit | Human | Polyclonal |
| | LS-C41896 | Mouse | Human | Monoclonal |
| | LS-C51824 | Mouse | Human | Monoclonal |
| | LS-C51825 | Mouse | Human | Monoclonal |
| | LS-C58288 | Mouse | Human | Monoclonal |
| | LS-C58289 | Mouse | Human | Monoclonal |
| | LS-C62287 | Rabbit | Human | Polyclonal |
| | LS-C66002 | Rabbit | Human | Polyclonal |
| | LS-C66006 | Mouse | Human, Canine, Porcine | Monoclonal |
| | LS-C66007 | Mouse | Human | Monoclonal |
| | LS-C66008 | Rabbit | Human | Polyclonal |
| | LS-C66010 | Mouse | Human | Monoclonal |
| | LS-C66012 | Mouse | Human | Monoclonal |
| | LS-C6778 | Mouse | Human | Monoclonal |
| | LS-C6779 | Mouse | Human | Monoclonal |
| | LS-C6781 | Mouse | Human | Monoclonal |
| | LS-C6782 | Mouse | Human | Monoclonal |
| | LS-C6783 | Mouse | Human | Monoclonal |
| | LS-C6784 | Mouse | Human | Monoclonal |
| | LS-C6785 | Mouse | Human | Monoclonal |
| | LS-C6788 | Mouse | Human | Monoclonal |
| | LS-C6789 | Mouse | Human | Monoclonal |
| | LS-C6790 | Rabbit | Human | Polyclonal |
| | LS-C6791 | Mouse | Human | Monoclonal |
| | LS-C6792 | Mouse | Human | Monoclonal |
| | LS-C6793 | Mouse | Human | Monoclonal |

| Supplier | Catalog# | Host Species | Reactivity | Type |
|---|---|---|---|---|
| | LS-C6794 | Mouse | Human | Monoclonal |
| | LS-C6795 | Mouse | Human | Monoclonal |
| | LS-C6796 | Mouse | Human, Canine, Porcine | Monoclonal |
| | LS-C6797 | Mouse | Human, Canine, Porcine | Monoclonal |
| | LS-C6800 | Mouse | Human | Monoclonal |
| | LS-C6801 | Rabbit | Human | Polyclonal |
| | LS-C6802 | Goat | Human | Polyclonal |
| | LS-C6804 | Mouse | Human | Monoclonal |
| | LS-C6807 | Rabbit | Human | Polyclonal |
| | LS-C83853 | Goat | Human | Polyclonal |
| | LS-C84209 | Mouse | Human | Monoclonal |
| | LS-C84244 | Mouse | Human | Monoclonal |
| | LS-C84749 | Mouse | Human | Monoclonal |
| | LS-C85649 | Goat | Human | Polyclonal |
| | LS-C85668 | Rabbit | Human | Polyclonal |
| | LS-C86900 | Goat | Human | Polyclonal |
| | LS-C87960 | Mouse | Human, Canine, Porcine | Monoclonal |
| | LS-C92513 | Mouse | Human | Monoclonal |
| | LS-C92514 | Mouse | Human | Monoclonal |
| | LS-C96179 | Chicken/Avian | Human | Polyclonal |
| | LS-C129013 | Mouse | Human | Monoclonal |
| | LS-C147748 | Rabbit | Human | Polyclonal |
| | LS-C153016 | Mouse | Human | Monoclonal |
| | LS-C153017 | Mouse | Human | Monoclonal |
| | LS-C194074 | Mouse | Human | Monoclonal |
| | LS-C195074 | Goat | Human | Polyclonal |
| | LS-C195076 | Goat | Human | Polyclonal |
| | LS-C195211 | Goat | Human | Polyclonal |
| | LS-C195212 | Goat | Human | Polyclonal |
| | LS-C195272 | Rabbit | Human | Polyclonal |
| | LS-C195324 | Mouse | Human | Monoclonal |
| | LS-C196556 | Goat | Human | Polyclonal |
| | LS-C83363 | Mouse | Human | Monoclonal |
| | LS-C84242 | Mouse | Human | Monoclonal |
| | LS-C84245 | Mouse | Human | Monoclonal |
| | LS-C84246 | Mouse | Human | Monoclonal |
| | LS-C84750 | Mouse | Human | Monoclonal |
| | LS-C87155 | Goat | Human | Polyclonal |
| | LS-C95394 | Mouse | Human, Mouse, Rat, Bovine, Canine, Feline, Porcine | Monoclonal |
| | LS-C95672 | Mouse | Human | Monoclonal |
| Thermo Fisher Scientific Pierce 23 antibodies | MA5-12754 | Mouse | Human, Canine, Porcine | Monoclonal |
| | MA5-16321 | Rabbit | Human | Monoclonal |
| | PA5-11480 | Rabbit | Human | Polyclonal |
| | PA5-11481 | Rabbit | Human | Polyclonal |
| | MA1-19178 | Mouse | Human | Monoclonal |
| | PA5-16658 | Rabbit | Human, Porcine | Polyclonal |
| | PA5-16801 | Rabbit | Human | Polyclonal |
| | MA5-15562 | Mouse | Human | Monoclonal |
| | MA1-19342 | Mouse | Human | Monoclonal |
| | MA5-14665 | Mouse | Human | Monoclonal |
| | MA5-14666 | Mouse | Human | Monoclonal |
| | MIA1301 | Mouse | Human | Monoclonal |
| | MIA1305 | Mouse | Human | Monoclonal |
| | PA5-21004 | Rabbit | Human, Mouse, Rat | Polyclonal |
| | MA1-35008 | Mouse | Human | Monoclonal |
| | MA1-35438 | Mouse | Human | Monoclonal |
| | PA1-35997 | Goat | Human | Polyclonal |
| | PA1-37063 | Rabbit | Human | Polyclonal |
| | HYB 097-04-02 | Mouse | Human | Monoclonal |
| | HYB 097-06-02 | Mouse | Human | Monoclonal |
| | MA1-22694 | Mouse | Human | Monoclonal |
| | MA1-35436 | Mouse | Human | Monoclonal |
| | PA1-36036 | Rabbit | Human | Polyclonal |
| Acris Antibodies GmbH 45 antibodies | AM20476PU-N | Mouse | Human | Monoclonal |
| | AP11398PU-N | Rabbit | Human | Polyclonal |
| | AP31741PU-N | Rabbit | Human | Polyclonal |
| | AM31985PU-M | Rabbit | Human, Bovine, Canine, Porcine | Polyclonal (Antigen purified) |
| | AM31985PU-N | Rabbit | Human, Bovine, Canine, Porcine | Polyclonal (Antigen purified) |
| | AM31985PU-S | Rabbit | Human, Bovine, Canine, Porcine | Polyclonal (Antigen purified) |
| | AP15341PU-M | Rabbit | Human | Polyclonal |
| | AP15341PU-N | Rabbit | Human | Polyclonal |
| | AP15341PU-S | Rabbit | Human | Polyclonal |
| | AP26245PU-N | Rabbit | Human, Mouse, Rat | Polyclonal |

-continued

| Supplier | Catalog# | Host Species | Reactivity | Type |
|---|---|---|---|---|
| | SM3089P | Mouse | Human | Monoclonal |
| | AM06377PU-N | Mouse | Human | Monoclonal |
| | AM09236HR-N | Mouse | Human | Monoclonal |
| | AP11397PU-N | Rabbit | Human | Polyclonal |
| | AM09236PU-N | Mouse | Human | Monoclonal |
| | AM09237PU-N | Mouse | Human | Monoclonal |
| | AM20588PU-N | Mouse | Human | Monoclonal |
| | AP10421PU-N | Rabbit | Human | Polyclonal |
| | AM32229PU-N | Mouse | Human | Monoclonal |
| | AM32230PU-N | Mouse | Human, Canine | Monoclonal |
| | SM3090P | Mouse | Human | Monoclonal |
| | AM00787PU-N | Mouse | Human | Monoclonal |
| | AM05441PU-S | Mouse | Human | Monoclonal |
| | AM31383PU-N | Mouse | Human | Monoclonal |
| | AM32231PU-N | Mouse | Human, Mouse | Monoclonal |
| | AP08129PU-N | Rabbit | Human | Polyclonal |
| | AP08129PU-S | Rabbit | Human | Polyclonal |
| | AP09883PU-N | Rabbit | Human | Polyclonal |
| | BM2155 | Mouse | Human | Monoclonal |
| | AM00786PU-N | Mouse | Human | Monoclonal |
| | AM05441PU-N | Mouse | Human | Monoclonal |
| | AM0573PU-N | Mouse | Human | Monoclonal |
| | AM31384PU-N | Mouse | Human | Monoclonal |
| | AM31385PU-N | Mouse | Human | Monoclonal |
| | AM31386PU-N | Mouse | Human | Monoclonal |
| | DM129 | Mouse | Human, Canine, Porcine | Monoclonal |
| | DM129-05 | Mouse | Human, Canine, Porcine | Monoclonal |
| | DM129P | Mouse | Human, Canine, Porcine | Monoclonal |
| | DP001 | Rabbit | Human | Polyclonal |
| | DP001-05 | Rabbit | Human | Polyclonal |
| | AP09883CP-N | | | Polyclonal |
| | AP11397CP-N | | | Polyclonal |
| | AP11398CP-N | | | Polyclonal |
| | AP26245CP-N | | | |
| | BA1024 | | | |
| Aviva | OAAB01176 | | Human | Polyclonal |
| Systems | OAAB01177 | | Human | Polyclonal |
| Biology | OAMA01352 | Mouse | | Monoclonal |
| 21 antibodies | OAMA01433 | Mouse | Human | Monoclonal |
| | OAMA02494 | Mouse | Human | Monoclonal |
| | OAMA01341 | Mouse | | Monoclonal |
| | OAMA01358 | Mouse | | Monoclonal |
| | OASA00927 | | Human | Monoclonal |
| | OASA00928 | | Human | Monoclonal |
| | OASA00929 | | Human | Monoclonal |
| | OASA00930 | | Human | Monoclonal |
| | OASA00931 | | Human | Monoclonal |
| | OASA00932 | | Human | Monoclonal |
| | OASA07398 | | Human | Polyclonal |
| | OASA07399 | | Human | Polyclonal |
| | OASA07400 | | Human | Polyclonal |
| | OAMA00870 | Mouse | | Monoclonal |
| | OAMA00881 | Mouse | | Monoclonal |
| | OAMA01340 | Mouse | | Monoclonal |
| | OAMA01434 | Mouse | Human | Monoclonal |
| | OAMA03505 | Rabbit | | Polyclonal |
| Cell Signaling Technology, | 3903 | Mouse | Human | Monoclonal |
| Inc | 7741 | Mouse | Human, Mouse | Monoclonal |
| 7 antibodies | 7765 | Mouse | Human, Mouse | Monoclonal |
| | 2137 | Rabbit | Human, Mouse | Polyclonal |
| | 4448 | Rabbit | Human | Monoclonal |
| | 7800 | Mouse | Human, Mouse | Monoclonal |
| | 7877 | Mouse | Human, Mouse | Monoclonal |
| Atlas | HPA010607 | Rabbit | Human | Polyclonal |
| Antibodies | HPA023600 | Rabbit | Human | Polyclonal |
| 2 antibodies | | | | |
| RabMAbs | 5667-1 | | Human | Monoclonal |
| 9 antibodies | 1791-1 | | Human | Monoclonal |
| | ab133617 | | Human | Monoclonal |
| | 1757-1 | | Human | Polyclonal |
| | 1816-1 | | Human | Monoclonal |
| | ab169552 | | Human | Monoclonal |
| | ab45147 | | Human | Monoclonal |
| | ab46799 | | Human | Polyclonal |
| | ab52940 | | Human | Monoclonal |
| ProSci | 5869 | Rabbit | | Polyclonal |
| 1 antibody | | | | |

| Supplier | Catalog# | Host Species | Reactivity | Type |
| --- | --- | --- | --- | --- |
| Spring | E2950 | Rabbit | | Polyclonal |
| Bioscience | E2952 | Rabbit | | Polyclonal |
| 8 antibodies | E2954 | Rabbit | | Polyclonal |
| | M4540 | Rabbit | | Monoclonal |
| | M4542 | Rabbit | | Monoclonal |
| | M4544 | Rabbit | | Monoclonal |
| | E2951 | Rabbit | | Polyclonal |
| | M4541 | Rabbit | | Monoclonal |
| Creative | CABT-49289MH | Mouse | Human | Monoclonal |
| Biomart | CABT-49291MH | Mouse | Human | Monoclonal |
| 128 antibodies | CPBT-65854RH | Rabbit | Human | Polyclonal |
| | CPBT-65855RH | Rabbit | Human | Polyclonal |
| | CABT-49286MH | Mouse | Human | Monoclonal |
| | CABT-49287MH | Mouse | Human | Monoclonal |
| | CABT-12597MH | Mouse | Human | Monoclonal |
| | CABT-22539MH | Mouse | Human | Monoclonal |
| | CABT-26481MH | Mouse | Human | Monoclonal |
| | CABT-26482MH | Mouse | Human | Monoclonal |
| | CABT-49285MH | Mouse | Human | Monoclonal |
| | CAB-10500MH | Mouse | Human | Monoclonal |
| | CAB-10501MH | Mouse | Human | Monoclonal |
| | CAB-7415MH | Mouse | Human | Monoclonal |
| | CAB-7416RH | Rabbit | Human | Monoclonal |
| | CAB-8309MH | Mouse | Human | Monoclonal |
| | CAB-8310MH | Mouse | Human | Monoclonal |
| | CABT-21235MH | Mouse | Human | Monoclonal |
| | CABT-21237MH | Mouse | Human | Monoclonal |
| | CABT-22458MH | Mouse | Human | Monoclonal |
| | CABT-22459MH | Mouse | Human | Monoclonal |
| | CABT-22561MH | Mouse | Human | Monoclonal |
| | CABT-23406MH | Mouse | Human | Monoclonal |
| | CABT-26350MH | Mouse | Human | Monoclonal |
| | CABT-26483RH | Rabbit | Human | Monoclonal |
| | CABT-50796MH | Mouse | Human | Monoclonal |
| | CPBT-66602RH | Rabbit | Human | Polyclonal |
| | DMABT-H17336 | Mouse | Human | Monoclonal |
| | DMABT-H27239 | Mouse | Human | Monoclonal |
| | DMABT-H27239H | Mouse | Human | Monoclonal |
| | DMABT-H27240 | Mouse | Human | Monoclonal |
| | DMABT-H27240H | Mouse | Human | Monoclonal |
| | DMABT-H27243 | Mouse | Human | Monoclonal |
| | DMABT-H27243H | Mouse | Human | Monoclonal |
| | DMABT-H27244 | Mouse | Human | Monoclonal |

| Supplier | Catalog# | Host Species | Reactivity | Type |
| --- | --- | --- | --- | --- |
| | DMABT-H27244H | Mouse | Human | Monoclonal |
| | DPABT-H30321 | Rabbit | Human | Polyclonal |
| | DPABT-H31426 | Rabbit | Human | Polyclonal |
| | CAB-1029MH | Mouse | Human | Monoclonal |
| | CAB-1890MH | Mouse | Human | Monoclonal |
| | CAB-7412MH | Mouse | Human | Monoclonal |
| | CAB-7413MH | Mouse | Human | Monoclonal |
| | CAB-7414MH | Mouse | Human | Monoclonal |
| | CAB-7417RH | Rabbit | Human | Monoclonal |
| | CABT-12598MH | Mouse | Human | Monoclonal |
| | CABT-21825MD | Mouse | Canine | Monoclonal |
| | CABT-22494MH | Mouse | Human | Monoclonal |
| | CABT-22510MH | Mouse | Human | Monoclonal |
| | CABT-22511MH | Mouse | Human | Monoclonal |
| | CABT-22512MH | Mouse | Human | Monoclonal |
| | CABT-22538MH | Mouse | Human | Monoclonal |
| | CABT-26382MH | Mouse | Human | Monoclonal |
| | CPB-1966RH | Rabbit | Human | Polyclonal |
| | CPBT-26085GH | Goat | Human | Polyclonal |
| | CPBT-26088DH | | Human | Polyclonal |
| | CPBT-26475RH | Rabbit | Human | Polyclonal |
| | CPBT-26476RH | Rabbit | Human | Polyclonal |
| | CPBT-27489RH | Rabbit | Human | Polyclonal |
| | CPBT-27490RH | Rabbit | Human | Polyclonal |
| | CPBT-27492RH | Rabbit | Human | Polyclonal |
| | CPBT-51203RH | Rabbit | Human | Polyclonal |
| | DMABT-H12999 | Mouse | Human | Monoclonal |
| | DMABT-H19951 | Mouse | Human | Monoclonal |
| | DMABT-H20087 | Rabbit | Human | Monoclonal |
| | DMABT-H2297MH | Mouse | Human | Monoclonal |
| | DMABT-H23319 | Mouse | Human | Monoclonal |
| | DMABT-H26982 | Rabbit | Human | Monoclonal |
| | DMABT-H27058 | Mouse | Human | Monoclonal |
| | DMABT-H27058H | Mouse | Human | Monoclonal |
| | DMABT-H27238 | Mouse | Human | Monoclonal |
| | DMABT-H27238H | Mouse | Human | Monoclonal |
| | DMABT-H27242 | Mouse | Human | Monoclonal |
| | DMABT-H27242H | Mouse | Human | Monoclonal |
| | DMABT-H28902 | Mouse | Human | Monoclonal |
| | CAB-8306MH | Mouse | Human | Monoclonal |

| Supplier | Catalog# | Host Species | Reactivity | Type |
|---|---|---|---|---|
| | CABT-21211MH | Mouse | Human | Monoclonal |
| | CABT-21218MH | Mouse | Human | Monoclonal |
| | CABT-21219MH | Mouse | Human | Monoclonal |
| | CABT-21258MH | Mouse | Human | Monoclonal |
| | CABT-21260MH | Mouse | Human | Monoclonal |
| | CABT-21261MH | Mouse | Human | Monoclonal |
| | CABT-21262MH | Mouse | Human | Monoclonal |
| | CABT-21263MH | Mouse | Human | Monoclonal |
| | CABT-21817MH | Mouse | Human | Monoclonal |
| | CABT-22493MH | Mouse | Human | Monoclonal |
| | CABT-22509MH | Mouse | Human | Monoclonal |
| | CABT-22551MH | Mouse | Human | Monoclonal |
| | CABT-22552MH | Mouse | Human | Monoclonal |
| | CABT-23355MH | Mouse | Human | Monoclonal |
| | CABT-26351MH | Mouse | Human | Monoclonal |
| | CABT-26352MH | Mouse | Human | Monoclonal |
| | CABT-26353MH | Mouse | Human | Monoclonal |
| | CABT-26354MH | Mouse | Human | Monoclonal |
| | CABT-26479MH | Mouse | Human | Monoclonal |
| | CABT-26480MH | Mouse | Human | Monoclonal |
| | CABT-26484MH | Mouse | Human | Monoclonal |
| | CABT-26485MH | Mouse | Human | Monoclonal |
| | CPBT-26084RH | Rabbit | Human | Polyclonal |
| | CPBT-26086RH | Rabbit | Human | Polyclonal |
| | CPBT-26087RH | Rabbit | Human | Polyclonal |
| | CPBT-26089CH | Chicken/Avian | Human | Polyclonal |
| | CPBT-27493RH | Rabbit | Human | Polyclonal |
| | CPBT-27494RH | Rabbit | Human | Polyclonal |
| | CPBT-27495RH | Rabbit | Human | Polyclonal |
| | DMABT-H12951 | Mouse | Human | Monoclonal |
| | DMABT-H13000 | Mouse | Human | Monoclonal |
| | DMABT-H13001 | Mouse | Human | Monoclonal |
| | DMABT-H13002 | Mouse | Human | Monoclonal |
| | DMABT-H19316 | Mouse | Human | Monoclonal |
| | DMABT-H2034MH | Mouse | Human | Monoclonal |
| | DMABT-H2035MH | Mouse | Human | Monoclonal |
| | DMABT-H2298MH | Mouse | Human | Monoclonal |
| | DMABT-H23320 | Mouse | Human | Monoclonal |

-continued

| Supplier | Catalog# | Host Species | Reactivity | Type |
|---|---|---|---|---|
| | DMABT-H27057 | Mouse | Human | Monoclonal |
| | DMABT-H27057H | Mouse | Human | Monoclonal |
| | DMABT-H27237 | Mouse | Human | Monoclonal |
| | DMABT-H27237H | Mouse | Human | Monoclonal |
| | DPABT-H20127 | Rabbit | Human | Polyclonal |
| | DPABT-H30185 | Rabbit | Human | Polyclonal |
| | DPABT-H7653 | Rabbit | Human | Polyclonal |
| | DMAB31688 | Mouse | Human | Monoclonal |
| | DMABT-H11141 | Mouse | Human | Monoclonal |
| | DMABT-H15361 | Mouse | Human | Monoclonal |
| | DMABT-H17337 | Mouse | Human | Monoclonal |
| | DPAB31433 | Goat | Human | Polyclonal |
| | DPABT-H7654 | Rabbit | Human | Polyclonal |
| | DPABT-H7655 | Rabbit | Human | Polyclonal |
| | DPABT-H7656 | Rabbit | Human | Polyclonal |
| Enzo Life Sciences 4 antibodies | ALX-801-090-1 | | | Monoclonal |
| | ADI-905-827-100 | | | Monoclonal |
| | BPD-HYB-097-04-02 | | | Monoclonal |
| | BPD-HYB-097-04-1 | | | Monoclonal |
| Boster Immunoleader Biotechnology 1 antibody | MA1001 | Mouse | Human | Monoclonal |
| Sigma-Aldrich 10 antibodies | WH0000174M1 | | Human | Monoclonal |
| | A8452 | | Human, Canine, Porcine | Monoclonal |
| | HPA010607 | | Human | Polyclonal |
| | HPA023600 | | Human | Polyclonal |
| | SAB3300008 | | Human | Monoclonal |
| | SAB3300009 | | Human | Monoclonal |
| | SAB3300011 | | Human | Monoclonal |
| | GW22680 | | Human | Polyclonal |
| | SAB3300007 | | Human | Monoclonal |
| | SAB3300010 | | Human | Monoclonal |
| Abbiotec 7 antibodies | 252138 | Rabbit | Human | Polyclonal |
| | 251708 | Mouse | Human | Monoclonal |
| | 254328 | Rabbit | Human, Mouse, Rat | Polyclonal |
| | 250329 | Mouse | Human | Monoclonal |
| | 250330 | Mouse | Human | Monoclonal |
| | 250333 | Mouse | Human | Monoclonal |
| | 252931 | Mouse | Human | Monoclonal |
| GenWay 23 antibodies | 18-272-198097 | Rabbit | Human | Polyclonal |
| | 18-272-196788 | Rabbit | Human | Polyclonal |
| | 18-272-196879 | Rabbit | Human | Polyclonal |
| | 18-272-197737 | Rabbit | Human | Polyclonal |
| | 18-272-198146 | Rabbit | | Polyclonal |
| | 18-272-198349 | Rabbit | Human, Rabbit | Polyclonal |
| | 18-783-76299 | Rabbit | Human | Polyclonal |
| | 18-783-76300 | Rabbit | Human | Polyclonal |
| | 18-783-76301 | Rabbit | Human | Polyclonal |
| | 20-511-240061 | | | Monoclonal |
| | 20-511-240065 | | | Monoclonal |
| | 20-783-71081 | Mouse | Human | Monoclonal |
| | 20-783-71082 | Mouse | Human | Monoclonal |
| | 20-783-72957 | Mouse | Human | Monoclonal |
| | 20-783-73288 | Mouse | Human | Monoclonal |
| | 18-272-198481 | Goat | | Polyclonal |
| | 18-511-244032 | Rabbit | | Polyclonal |

| Supplier | Catalog# | Host Species | Reactivity | Type |
|---|---|---|---|---|
| | 20-511-240057 | Mouse | | Monoclonal |
| | 20-511-240058 | Mouse | | Monoclonal |
| | 20-511-240060 | Mouse | | Monoclonal |
| | 20-511-240069 | Mouse | | Monoclonal |
| | 20-511-240084 | Mouse | | Monoclonal |
| | 20-511-240099 | Mouse | | Monoclonal |
| eBioscience, An Affymetrix Company 4 antibodies | 14-6583-80 | Mouse | Human | Monoclonal |
| | 14-6583-82 | Mouse | Human | Monoclonal |
| | 53-6583-80 | Mouse | Human | Monoclonal |
| | 53-6583-82 | Mouse | Human | Monoclonal |
| YO Proteins | 564 | Goat | | Polyclonal |
| AB 2 antibodies | 605 | Rabbit | | Polyclonal |
| United States Biological 10 antibodies | 123047 | Rabbit | Human | Polyclonal |
| | 030748-AP | Mouse | Human | Monoclonal |
| | 030748-APC | Mouse | Human | Monoclonal |
| | 030748-Biotin | Mouse | Human | Monoclonal |
| | 030748-FITC | Mouse | Human | Monoclonal |
| | 030748-HRP | Mouse | Human | Monoclonal |
| | 030748-PE | Mouse | Human | Monoclonal |
| | 123048 | Rabbit | Human | Polyclonal |
| | 30748 | Mouse | Human | Monoclonal |
| | F4100-02B | Mouse | Human | Monoclonal |
| EMD Millipore 1 antibody | MABD78 | | Human | Monoclonal |

The following table shows exemplary, commercially available antibodies that specifically bind to DKK-1 and that can be used herein:

| Supplier | Catalog# | Host Species | Reactivity | Type |
|---|---|---|---|---|
| Abnova Corporation 19 antibodies | | | | |
| | H00022943-M11 | Mouse | Human | Monoclonal |
| | H00022943-M08 | Mouse | Human | Monoclonal |
| | H00022943-D01P | Rabbit | Human | Polyclonal |
| | PAB6672 | Goat | Human | Polyclonal |
| | H00022943-M10 | Mouse | Human | Monoclonal |
| | H00022943-M12 | Mouse | Human | Monoclonal |
| | H00022943-M01 | Mouse | Human | Monoclonal |
| | H00022943-M02 | Mouse | Human | Monoclonal |
| | H00022943-M04 | Mouse | Human | Monoclonal |
| | H00022943-M05 | Mouse | Human | Monoclonal |
| | PAB16291 | Rabbit | Human | Polyclonal |
| | PAB16292 | Rabbit | Human | Polyclonal |
| | PAB19539 | Rabbit | Human | Polyclonal |
| | PAB8677 | Rabbit | Mouse | Polyclonal |
| | H00022943-A01 | Mouse | Human | Polyclonal |
| | H00022943-M06 | Mouse | Human | Monoclonal |
| | H00022943-M07 | Mouse | Human | Monoclonal |
| | H00022943-M09 | Mouse | Human | Monoclonal |
| | H00022943-M19 | Mouse | Human | Monoclonal |
| Novus Biologicals 22 antibodies | | | | |
| | NBP1-95560 | Rabbit | Human, Rat | Monoclonal |
| | H00022943-M11 | Mouse | Human | Monoclonal |
| | H00022943-M08 | Mouse | Human | Monoclonal |
| | H00022943-M10 | Mouse | Human | Monoclonal |
| | H00022943-D01P | Rabbit | Human | Polyclonal |
| | H00022943-M01 | Mouse | Human | Monoclonal |
| | H00022943-M02 | Mouse | Human | Monoclonal |
| | H00022943-M04 | Mouse | Human | Monoclonal |
| | H00022943-M05 | Mouse | Human | Monoclonal |

-continued

| Supplier | Catalog# | Host Species | Reactivity | Type |
|---|---|---|---|---|
| | H00022943-M06 | Mouse | Human, Mouse | Monoclonal |
| | H00022943-M12 | Mouse | Human | Monoclonal |
| | NB100-1450 | Goat | Human | Polyclonal |
| | NBP1-47391 | Mouse | Human | Monoclonal |
| | NB110-40442 | Rabbit | Human | Polyclonal |
| | NB110-40443 | Rabbit | Human | Polyclonal |
| | NBP1-45519 | Rabbit | Human, Mouse, Rat | Polyclonal |
| | NBP1-59321 | Rabbit | Human, Mouse, Rat, Bovine, Canine, Goat, Guinea Pig, Porcine, Rabbit | Polyclonal |
| | NBP2-24701 | Rabbit | Human, Mouse | Polyclonal |
| | H00022943-A01 | Mouse | Human | Polyclonal |
| | H00022943-M07 | Mouse | Human | Monoclonal |
| | H00022943-M09 | Mouse | Human | Monoclonal |
| | H00022943-M19 | Mouse | Human | Monoclonal |
| antibodies-online 83 antibodies | | | | |
| | ABIN524880 | Mouse | Human | Monoclonal |
| | ABIN659473 | Mouse | Human | Monoclonal |
| | ABIN966001 | Mouse | Human | Monoclonal |
| | ABIN653551 | Rabbit | Human | Polyclonal |
| | ABIN310967 | Rabbit | Human, Mouse, Rat, Bovine, Canine, Chicken/Avian, Porcine, Rabbit, *Xenopus* | Polyclonal |
| | ABIN395287 | Mouse | Human | Monoclonal |
| | ABIN395339 | Mouse | Human | Monoclonal |
| | ABIN185275 | Goat | Human | Polyclonal |
| | ABIN296913 | Goat | Human | Polyclonal |
| | ABIN678158 | Rabbit | Human, Mouse, Rat | Polyclonal |
| | ABIN678160 | Rabbit | Human, Mouse, Rat | Polyclonal |
| | ABIN1106989 | Mouse | Human | Monoclonal |
| | ABIN932523 | Mouse | Human | Monoclonal |
| | ABIN1048501 | Rabbit | Human | Polyclonal |
| | ABIN1048502 | Rabbit | Human | Polyclonal |
| | ABIN213403 | Rabbit | Human | Polyclonal |
| | ABIN213404 | Rabbit | Human | Polyclonal |
| | ABIN223506 | Rabbit | Human, Mouse, Rat | Polyclonal |
| | ABIN524877 | Mouse | Human | Monoclonal |
| | ABIN792165 | Rabbit | Human | Monoclonal |
| | ABIN303030 | Goat | Human | Polyclonal |
| | ABIN403090 | Goat | Human | Polyclonal |
| | ABIN504692 | Goat | Human | Polyclonal |
| | ABIN1343090 | Rabbit | Human | |
| | ABIN1343091 | Rabbit | Human | |
| | ABIN1488240 | Rabbit | Human | Polyclonal |
| | ABIN1497842 | Mouse | Human | Monoclonal |
| | ABIN250268 | Goat | Human | Polyclonal |
| | ABIN321363 | Rabbit | Human | Polyclonal |
| | ABIN466182 | Mouse | Human | Monoclonal |
| | ABIN466183 | Mouse | Human | Monoclonal |
| | ABIN466744 | Mouse | Human | Monoclonal |
| | ABIN524872 | Mouse | Human | Polyclonal |
| | ABIN524874 | Mouse | Human | Monoclonal |
| | ABIN524875 | Mouse | Human | Monoclonal |
| | ABIN524876 | Mouse | Human | Monoclonal |
| | ABIN524879 | Mouse | Human | Monoclonal |
| | ABIN524881 | Mouse | Human | Monoclonal |
| | ABIN547332 | Goat | Human | Polyclonal |
| | ABIN564970 | Mouse | Human | Monoclonal |
| | ABIN564971 | Mouse | Human | Monoclonal |
| | ABIN564972 | Mouse | Human, Mouse | Monoclonal |
| | ABIN678159 | Rabbit | Human, Mouse, Rat | Polyclonal |
| | ABIN678165 | Rabbit | Human, Mouse, Rat | Polyclonal |
| | ABIN678167 | Rabbit | Human, Mouse, Rat | Polyclonal |

-continued

| Supplier | Catalog# | Host Species | Reactivity | Type |
|---|---|---|---|---|
| | ABIN678172 | Rabbit | Human, Mouse, Rat | Polyclonal |
| | ABIN894061 | Rabbit | Human, Mouse, Rat | Polyclonal |
| | ABIN894062 | Rabbit | Human, Mouse, Rat | Polyclonal |
| | ABIN894064 | Rabbit | Human, Mouse, Rat, Simian | Polyclonal |
| | ABIN951911 | Rabbit | Human | Polyclonal |
| | ABIN969085 | Mouse | Human | Monoclonal |
| | ABIN135007 | Rabbit | Human | Polyclonal |
| | ABIN203684 | Rabbit | Human | Polyclonal |
| | ABIN207754 | Rabbit | Human | Polyclonal |
| | ABIN232224 | Rabbit | Human | Polyclonal |
| | ABIN302392 | Rabbit | Human, Mouse | Polyclonal |
| | ABIN302393 | Rabbit | Human | Polyclonal |
| | ABIN332738 | Rabbit | Human | Polyclonal |
| | ABIN374460 | Goat | Human | Polyclonal |
| | ABIN403091 | Rabbit | Human | Polyclonal |
| | ABIN403092 | Rabbit | Human | Polyclonal |
| | ABIN524873 | Rabbit | Human | Polyclonal |
| | ABIN524878 | Mouse | Human | Monoclonal |
| | ABIN524882 | Mouse | Human | Monoclonal |
| | ABIN549212 | Rabbit | Human | Polyclonal |
| | ABIN556374 | Rabbit | Human | Polyclonal |
| | ABIN558934 | Rabbit | Human | Polyclonal |
| | ABIN568929 | Rabbit | Human | Polyclonal |
| | ABIN609517 | Rabbit | Human | Polyclonal |
| | ABIN643515 | Rabbit | Human | |
| | ABIN678161 | Rabbit | Human, Mouse, Rat | Polyclonal |
| | ABIN678162 | Rabbit | Human, Mouse, Rat | Polyclonal |
| | ABIN678163 | Rabbit | Human, Mouse, Rat | Polyclonal |
| | ABIN678164 | Rabbit | Human, Mouse, Rat | Polyclonal |
| | ABIN678166 | Rabbit | Human, Mouse, Rat | Polyclonal |
| | ABIN678168 | Rabbit | Human, Mouse, Rat | Polyclonal |
| | ABIN678169 | Rabbit | Human, Mouse, Rat | Polyclonal |
| | ABIN678170 | Rabbit | Human, Mouse, Rat | Polyclonal |
| | ABIN678171 | Rabbit | Human, Mouse, Rat | Polyclonal |
| | ABIN769903 | Rabbit | Human | Polyclonal |
| | ABIN894060 | Rabbit | Human, Mouse, Rat | Polyclonal |
| | ABIN894063 | Rabbit | Human, Mouse, Rat | Polyclonal |
| | ABIN552651 | Rabbit | Human | Polyclonal |
| R&D Systems | | | | |
| 4 antibodies | | | | |
| | AF1096 | Goat | Human | Polyclonal |
| | BAF1096 | Goat | Human | Polyclonal |
| | MAB10962 | Mouse | Human | Monoclonal |
| | MAB1096 | Mouse | Human | Monoclonal |
| Santa Cruz Biotechnology | | | | |
| 1 antibody | | | | |
| | sc-25516 | Rabbit | Human | Polyclonal |
| GeneTex | | | | |
| 3 antibodies | | | | |
| | GTX62902 | Rabbit | Human, Rat | Monoclonal |
| | GTX89683 | Goat | Human, Rat, Bovine, Canine, Porcine | Polyclonal |
| | GTX59723 | Rabbit | Human, Mouse, Rat | Polyclonal |

-continued

| Supplier | Catalog# | Host Species | Reactivity | Type |
|---|---|---|---|---|
| EMD Millipore 1 antibody | | | | |
| | ABS375 | Rabbit | Human | Polyclonal |
| LifeSpan BioSciences, Inc. | | | | |
| 18 antibodies | | | | |
| | LS-B8698 | Rabbit | Human, Rat | Monoclonal |
| | LS-B194 | Goat | Human, Mouse, Bovine, Canine, Goat, Horse, Porcine, Simian | Polyclonal |
| Proteintech Group 1 antibody | | | | |
| | 21112-1-AP | Rabbit | Human, Mouse, Rat | Polyclonal |
| Acris Antibodies GmbH | | | | |
| 13 antibodies | | | | |
| | AP07519PU-N | Goat | Human | Polyclonal |
| | AP51269PU-N | Rabbit | Human | Polyclonal |
| | AM06319SU-N | Mouse | Human | Monoclonal |
| | AP06880PU-N | Rabbit | Human, Mouse | Polyclonal |
| | AP06881PU-N | Rabbit | Human | Polyclonal |
| | AP16265PU-N | Goat | Human | Polyclonal |
| | AP21737PU-N | Rabbit | Human | Polyclonal |
| | AR09148PU-N | | | |
| | AR09148PU-S | | | |
| | AR20019PU-N | | | |
| | AR20019PU-S | | | |
| | AR50894PU-N | | | |
| | AR50894PU-S | | | |
| Creative Biomart 34 antibodies | | | | |
| | CPBT-66557RH | Rabbit | Human | Polyclonal |
| | CABT-14702MH | Mouse | Human | Monoclonal |
| | CABT-14705MH | Mouse | Human | Monoclonal |
| | CABT-30811MH | Mouse | Human | Monoclonal |
| | CABT-30812RH | Rabbit | Human | Monoclonal |
| | CAB-6491MH | Mouse | Human | Monoclonal |
| | CAB-6492MH | Mouse | Human | Monoclonal |
| | CABT-37916MH | Mouse | Human | Monoclonal |
| | CAB-6490MH | Mouse | Human | Monoclonal |
| | CABT-14696MH | Mouse | Human | Monoclonal |
| | CABT-14697MH | Mouse | Human | Monoclonal |
| | CABT-14698MH | Mouse | Human | Monoclonal |
| | CABT-14699MH | Mouse | Human | Monoclonal |
| | CABT-14700MH | Mouse | Human | Monoclonal |
| | CABT-14701MH | Mouse | Human | Monoclonal |
| | CABT-14704MH | Mouse | Human | Monoclonal |
| | CABT-14706MH | Mouse | Human | Monoclonal |
| | CPBT-52755RH | Rabbit | Human | Polyclonal |
| | DMABT-H13591 | Mouse | Human | Monoclonal |
| | CAB-9420MH | Mouse | Human | Monoclonal |
| | CABT-14703MH | Mouse | Human | Monoclonal |
| | CABT-14707MH | Mouse | Human | Monoclonal |
| | CABT-30810MH | Mouse | Human | Monoclonal |
| | CPB-1552RH | Rabbit | Human | Polyclonal |
| | CPBT-32910RH | Rabbit | Human | Polyclonal |
| | CPBT-52878RH | Rabbit | Human | Polyclonal |
| | DMABT-H13589 | Mouse | Human | Monoclonal |
| | DPABT-H15818 | Rabbit | Human | Polyclonal |
| | DPABT-H17202 | Rabbit | Human | Polyclonal |
| | DPABT-H17959 | Rabbit | Human | Polyclonal |
| | DPABT-H9517 | Rabbit | Human | Polyclonal |
| | DPABT-H9519 | Rabbit | Human | Polyclonal |
| | CAB-765MH | Mouse | Human | Monoclonal |
| | CAB11524RH | Rabbit | Human | Monoclonal |
| RabMAbs 2 antibodies | | | | |
| | 3435-1 | | Human | Monoclonal |
| | ab109416 | | Human | Monoclonal |

-continued

| Supplier | Catalog# | Host Species | Reactivity | Type |
|---|---|---|---|---|
| Aviva Systems Biology | | | | |
| 4 antibodies | | | | |
| | OAAB06195 | | Human | Polyclonal |
| | ARP48015_T100 | Rabbit | Human, Mouse, Rat, Bovine, Canine, Chicken/Avian, Porcine, Rabbit | Polyclonal |
| | OAEB01181 | Goat | Human, Rat, Bovine, Canine, Porcine | Polyclonal |
| | OASA07692 | | Human | Polyclonal |
| Thermo Fisher Scientific Pierce | | | | |
| 6 antibodies | | | | |
| | MA5-15497 | Mouse | Human | Monoclonal |
| | PA1-9037 | Goat | Human | Polyclonal |
| | PA5-26604 | Rabbit | Human | Polyclonal |
| | PA5-32721 | Rabbit | Human | Polyclonal |
| | PA5-32722 | Rabbit | Human, Porcine | Polyclonal |
| | PA5-23187 | Rabbit | Human | Polyclonal |
| Atlas Antibodies | | | | |
| 1 antibody | | | | |
| | HPA018995 | Rabbit | Human | Polyclonal |
| Boster Immunoleader Biotechnology | | | | |
| 1 antibody | | | | |
| | PA1462 | Rabbit | Human, Mouse, Rat | Polyclonal |
| Everest Biotech | | | | |
| 1 antibody | | | | |
| | EB06457 | Goat | Human, Rat, Bovine, Canine, Porcine | Polyclonal |
| Abiocode, Inc. | | | | |
| 1 antibody | | | | |
| | R0840-1 | Rabbit | Human | Polyclonal |
| Cell Signaling Technology, Inc | | | | |
| 1 antibody | | | | |
| | 4687 | Rabbit | Human | Polyclonal |
| Sigma-Aldrich | | | | |
| 7 antibodies | | | | |
| | HPA018995 | | Human | Polyclonal |
| | SAB2500314 | | Human | Polyclonal |
| | SAB2900059 | | Human | Polyclonal |
| | SAB2900060 | | Human | Polyclonal |
| | WH0022943M1 | | Human, Mouse, Rat | Monoclonal |
| | AV48015 | | Human | Polyclonal |
| | D3195 | | Human | Polyclonal |
| United States Biological | | | | |
| 10 antibodies | | | | |
| | 034657-AP | Rabbit | Human | Polyclonal |
| | 034657-APC | Rabbit | Human | Polyclonal |
| | 034657-Biotin | Rabbit | Human | Polyclonal |
| | 034657-FITC | Rabbit | Human | Polyclonal |
| | 034657-HRP | Rabbit | Human | Polyclonal |
| | 034657-PE | Rabbit | Human | Polyclonal |
| | 125867 | Rabbit | Human | Polyclonal |
| | 34657 | Rabbit | Human | Polyclonal |

-continued

| Supplier | Catalog# | Host Species | Reactivity | Type |
|---|---|---|---|---|
| GenWay | D3810-01Q | Rabbit | Human | Polyclonal |
| | D3810-01R | Rabbit | Human | Polyclonal |
| | 2 antibodies | | | |
| Abbiotec | 18-003-44544 | Rabbit | Human, Rat, Canine | Polyclonal |
| | 18-783-75539 | Rabbit | Human | Polyclonal |
| | 1 antibody | | | |
| | 252866 | Mouse | Human | Monoclonal |

Polyclonal or monoclonal antibodies or other antibodies (derived therefrom) can be routinely prepared using, inter alia, standard immunization protocols; see Ed Harlow, David Lane, (December 1988), Antibodies: A Laboratory Manual, Cold Spring Harbor Laboratory; or Ed Harlow, David Lane, (December 1998), Portable Protocols (Using Antibodies): A Laboratory Manual $2^{nd}$ edition, Cold Spring Harbor Laboratory.

For example, immunization may involve the intraperitoneal or subcutaneous administration of the soluble AXL, AFP and/or DKK-1 protein(s)/polypeptide (and/or fragments, isoforms, homologues, derivatives thereof and so on) as defined herein to a mammal (e.g. rodents such as mice, rats, hamsters and the like). Preferably, fragments of soluble AXL, AFP and/or DKK-1 protein(s) are used.

Methods for the preparation and screening of antibodies specifically binding to an antigen are known in the art. Such methods can be used in accordance with the present invention. For example, antibodies recognizing the soluble AXL, AFP and/or DKK-1 protein(s) may be affinity purified. ELISA is commonly used for screening sera and/or assaying affinity column fractions. Western Blots can be used to demonstrate that the antibody can detect the actual protein of interest and to evaluate whether the antibody only recognizes the protein of interest, or if it cross-reacts with other proteins.

A person skilled in the art is in the position to apply and to adapt the teaching of these documents for the generation and validation of antibodies specifically binding to or specifically recognizing the polypeptides as defined herein in context of the present invention.

The following relates to sAXL in the prognosis of patients.

As discussed herein above and shown in the appended example, among all HCC stages, patients exhibiting high AXL show a significantly decreased overall survival (median 25.37 mo, p=0.018) as compared to those with low AXL serum levels (median 88.56 mo; FIG. 5B). This decrease was even more pronounced among advanced HCC patients (high AXL median 11.37 mo, low AXL median 39.63 mo, p=0.007; FIG. 5C). These data suggest that sAXL levels reflect disease progression. High sAXL correlated with decreased overall survival (25.37 mo, p=0.018) as compared to low sAXL (88.56 mo).

Accordingly, it is shown herein that sAXL is useful as a prognostic marker.

The present invention relates to a method of assessing a prognosis of a patient, said method comprising
determining in a sample from said patient the amount of sAXL; and
assessing that the patient has an increased predisposition to an adverse outcome, when the amount of sAXL is increased in comparison to a control, wherein the patient suffers from liver cancer, is prone to suffering from liver cancer or is suspected of suffering from liver cancer.

The definitions and explanations given herein above in context of diagnosing liver cancer apply mutatis mutandis in context of assessing the prognosis of a patient. For example, the definitions and explanations in relation to "patient" "determining the amount of sAXL", "sample", "sAXL", "increase", "control", "liver cancer", "prone to suffering from liver cancer" and the like apply mutatis mutandis here.

In accordance with the above, the present invention relates to the use of soluble AXL (optionally in combination with AFP and/or DKK-1) for assessing a prognosis of a patient wherein the patient suffers from liver cancer, is prone to suffering from liver cancer or is suspected of suffering from liver cancer. The definitions and explanations given herein above in context of diagnosing liver cancer apply mutatis mutandis in context of assessing the prognosis of a patient. For example, the definitions and explanations in relation to "patient" "determining the amount of sAXL", "sample", "sAXL", "increase", "control", "liver cancer", "prone to suffering from liver cancer" and the like apply mutatis mutandis here. Moreover, the specific explanations and definitions provided herein below in relation to assessing a prognosis of a patient apply here mutatis mutandis.

sAXL is primarily useful in the prognosis of patients suffering from liver cancer, i.e. patients that have been diagnosed positive for liver cancer and/or patients that have undergone anti-liver cancer therapy. In particular, sAXL is useful in this context in assessing the prognosis of a patient, wherein the patient suffers from as advanced liver cancer, such as advanced hepatocellular carcinoma.

The amount of sAXL in a patient sample, alone or in combination with one or more additional prognostic makers, can provide prognostic information useful for e.g. predicting near-term morbidity and/or mortality. Thus, the materials and procedures described herein can be used to identify those patients that are at acute risk for one or more serious complications, including the risk of death, resulting from liver cancer, and to guide the clinician in treatment of such patients.

The term "assessing a prognosis" as used herein refers to methods by which one can predict the course or outcome of a condition in a patient. The term "prognosis" does not refer to the ability to predict the course or outcome of a condition with 100% accuracy, or even that a given course or outcome is more likely to occur than not. Instead, a person skilled in the art will understand that the term "prognosis" refers to an increased probability that a certain course or outcome will occur; that is, that a course or outcome is more likely to occur in a patient exhibiting a given characteristic, such as the presence or level of a prognostic indicator (like increased amount of sAXL), when compared to those individuals not exhibiting the characteristic (like control/reference samples).

For example, as described hereinafter, a liver cancer patient exhibiting a high sAXL amount (like about 18 ng/ml or higher, e.g. about 18.575 ng/ml or higher) may be more likely to suffer from an adverse outcome than an liver cancer patient exhibiting a low sAXL amount (like lower than about 18 ng/ml, e.g. lower than about 18.575 ng/ml).

For example, in individuals not exhibiting the condition, the chance of a certain course or outcome may be 3%. In such a case; the increased probability that the course or outcome will occur would be any number greater than 3%.

A prognosis is often assessed by examining one or more "prognostic indicators." These are markers, the presence or amount of which in a patient (or a sample obtained from the patient) signal a probability that a given course or outcome will occur. For example, a preferred prognostic indicator in the present invention is sAXL.

As discussed herein, sAXL is present in patients suffering from liver cancer (or patients prone to suffering from liver cancer or patients suspected of suffering from liver cancer). When sAXL reaches a sufficiently high level/amount/concentration in samples obtained from such patients, the sAXL level/amount/concentration signals that the patient is at an increased probability for morbidity or death, in comparison to a similar patient exhibiting a lower sAXL level/amount/concentration. A level of a prognostic indicator, such as sAXL, that signals an increased probability for morbidity or death is referred to as being associated with an "increased predisposition to an adverse outcome".

A threshold level of a prognostic indicator can be established, and the level of the indicator in a patient sample can simply be compared to the threshold level. For example, an sAXL level of about 18 ng/ml in a patient sample can be established as a level at which a patient is at an increased disposition for morbidity or death. As used herein, the term "adverse outcome" can refer to morbidity or death. In this context, the "control" can refer to a sample from a healthy individual or an individual having an sAXL amount/level/concentration of below 18 ng/ml.

In context of assessing a prognosis of a patient, the liver cancer is preferably hepatocellular carcinoma, particularly advanced hepatocellular carcinoma, like stage B, C or D hepatocellular carcinoma.

The present invention relates to a method of assessing a prognosis of a patient, said method comprising
   determining in a sample from said patient the amount of sAXL; and
   assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma.

The present invention relates to a method of assessing a prognosis of a patient, said method comprising
   determining in a sample from said patient the amount of sAXL; and
   assessing that the patient has an increased predisposition to an adverse outcome, when the level of sAXL is increased in comparison to a control, wherein the patient suffers from advanced hepatocellular carcinoma (like stage B, C or D hepatocellular carcinoma), is prone to suffering from advanced hepatocellular carcinoma (like stage B, C or D hepatocellular carcinoma) or is suspected of suffering from advanced hepatocellular carcinoma (like stage B, C or D hepatocellular carcinoma).

In context of assessing a prognosis of a patient, the amount of soluble AXL in a sample from said patient can be higher than about 18 ng/ml.

The present invention relates to a method of assessing a prognosis of a patient, said method comprising
   determining in a sample from said patient the amount of sAXL; and
   assessing that the patient has an increased predisposition to an adverse outcome, when the amount of sAXL is increased in comparison to a control, wherein the patient suffers from liver cancer, is prone to suffering from liver cancer or is suspected of suffering from liver cancer,
wherein the amount of soluble AXL in a sample from said patient is higher than about 18 ng/ml.

In other words, the present invention relates to a method of assessing a prognosis of a patient, said method comprising
   determining in a sample from said patient the amount of sAXL; and
   assessing that the patient has an increased predisposition to an adverse outcome, when the amount of soluble AXL in a sample from said patient is higher than about 18 ng/ml,
wherein the patient suffers from liver cancer, is prone to suffering from liver cancer or is suspected of suffering from liver cancer.

The present invention relates to a method of assessing a prognosis of a patient, said method comprising
   determining in a sample from said patient the amount of sAXL; and
   assessing that the patient has an increased predisposition to an adverse outcome, when the amount of sAXL is increased in comparison to a control,
wherein the patient suffers from hepatocellular carcinoma, is prone to suffering from hepatocellular carcinoma or is suspected of suffering from hepatocellular carcinoma, wherein the amount of soluble AXL in a sample from said patient is higher than about 18 ng/ml.

In other words, the present invention relates to a method of assessing a prognosis of a patient, said method comprising
   determining in a sample from said patient the amount of sAXL; and
   assessing that the patient has an increased predisposition to an adverse outcome, when the amount of soluble AXL in a sample from said patient is higher than about 18 ng/ml,
wherein the patient suffers from hepatocellular carcinoma, is prone to suffering from hepatocellular carcinoma or is suspected of suffering from hepatocellular carcinoma.

The present invention relates to a method of assessing a prognosis of a patient, said method comprising
   determining in a sample from said patient the amount of sAXL; and
   assessing that the patient has an increased predisposition to an adverse outcome, when the level of sAXL is increased in comparison to a control,
wherein the patient suffers from advanced hepatocellular carcinoma (like stage B, C or D hepatocellular carcinoma), is prone to suffering from advanced hepatocellular carcinoma (like stage B, C or D hepatocellular carcinoma) or is suspected of suffering from advanced hepatocellular carcinoma (like stage B, C or D hepatocellular carcinoma), wherein the amount of soluble AXL in a sample from said patient is higher than about 18 ng/ml.

In other words, the present invention relates to a method of assessing a prognosis of a patient, said method comprising determining in a sample from said patient the amount of sAXL; and assessing that the patient has an increased predisposition to an adverse outcome, when the amount of soluble AXL in a sample from said patient is higher than about 18 ng/ml, wherein the patient suffers from advanced hepatocellular carcinoma (like stage B, C or D hepatocellular carcinoma), is prone to suffering from advanced hepatocellular carcinoma (like stage B, C or D hepatocellular carcinoma) or is suspected of suffering from advanced hepatocellular carcinoma (like stage B, C or D hepatocellular carcinoma).

In context of assessing a prognosis of a patient it is preferred that the patient suffers from liver cancer, preferably hepatocellular carcinoma, particularly advanced hepatocellular carcinoma (like stage B, C or D hepatocellular carcinoma).

Preferably, the amount of said one or more of soluble AXL, AFP and/or DKK-1 is determined by ELISA (like Sandwich ELISA).

As explained above, sandwich ELISAs (Enzyme-linked immunosorbent assay) for human sAXL can take advantage of various adaptions and modifications. For example, sAXL concentrations can be determined in serum samples of suspected liver cancer patients (preferably HCC patients), wherein the sample to be assessed is diluted 1:10 in phosphate buffered saline supplemented with 1% bovine serum albumin. For example, sAXL concentrations can be determined in serum samples of suspected liver cancer patients (preferably HCC patients), wherein the sample to be assessed is diluted 1:50 in phosphate buffered saline supplemented with 1% bovine serum albumin; see Example 2. These aspects apply similarly to the herein provided prognostic methods.

In a preferred aspect, the present invention relates to a method of assessing a prognosis of a patient, said method comprising determining in a sample from said patient the amount of sAXL; and assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma, wherein the amount of said soluble AXL is determined by ELISA.

The control may be a control sample. The control sample may be a sample from a healthy person or from a hepatic fibrosis or from a liver cirrhosis patient.

In a certain aspect, the present invention relates to a method of assessing a prognosis of a patient, said method comprising determining in a sample from said patient the amount of sAXL; and assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma, wherein the sample to be assessed is diluted 1:10.

The sample to be assessed may be diluted in phosphate buffered saline buffer. The sample to be assessed may be diluted in phosphate buffered saline buffer supplemented with 1% bovine serum albumin.

In a certain aspect, the present invention relates to a method of assessing a prognosis of a patient, said method comprising determining in a sample from said patient the amount of sAXL; and assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma, wherein the sample to be assessed is diluted 1:50.

The sample to be assessed may be diluted in phosphate buffered saline buffer. The sample to be assessed may be diluted in phosphate buffered saline buffer supplemented with 1% bovine serum albumin.

In the methods herein, the amount of soluble AXL can be at least 1.05-fold, preferably at least 1.2-fold, at least 1.3-fold, at least 1.4-fold, at least 1.5-fold, more preferably at least 1.6-fold increased in comparison to a control.

In a certain aspect, the present invention relates to a method of assessing a prognosis of a patient, said method comprising determining in a sample from said patient the amount of sAXL; and assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma, wherein said amount of soluble AXL in a sample from said patient is at least about 63 ng/ml, particularly about 63.44 ng/ml.

In a certain aspect, the present invention relates to a method of assessing a prognosis of a patient, said method comprising determining in a sample from said patient the amount of sAXL; and assessing that the patient has an increased predisposition to an adverse outcome, when the level of sAXL is increased in comparison to a control, wherein the patient suffers from hepatocellular carcinoma, is prone to suffering from hepatocellular carcinoma or is suspected of suffering from hepatocellular carcinoma, wherein said amount of soluble AXL in a control is about 38 ng/ml, particularly about 38.33 ng/ml.

The patient can have one or more risk factors, like one or more of hepatitis B, hepatitis C, cirrhosis of the liver, alcoholism, smoking and/or genetic polymorphisms.

The one or more risk factor may also be one or more of overweight, obesity, type 2 diabetes, metabolic syndrome, hepatitis B, hepatitis C, aflatoxin, hemochromatosis and/or Wilson's disease.

The explanations and definitions given herein above in relation to diagnosing liver cancer (i.e. assessing whether a patients suffers from liver cancer or is prone to suffering from liver cancer) apply, mutatis mutandis, in this context.

Soluble AXL to be used herein can be selected from the group consisting of (a) a polypeptide comprising an amino acid encoded by a nucleic acid molecule having the nucleic acid sequence as depicted in SEQ ID NO: 3;
(b) a polypeptide having an amino acid sequence as depicted in SEQ ID NO:4;
(c) a polypeptide encoded by a nucleic acid molecule encoding a peptide having an amino acid sequence as depicted in SEQ ID NO:4;
(d) a polypeptide comprising an amino acid encoded by a nucleic acid molecule hybridizing under stringent conditions to the complementary strand of nucleic acid molecules as defined in (a) or (c);
(e) a polypeptide having at least 70% identity to the polypeptide of any one of (a) to (d); and
(f) a polypeptide comprising an amino acid encoded by a nucleic acid molecule being degenerate as a result of the genetic code to the nucleotide sequence of a nucleic acid molecule as defined in (a), (c) and (d).

Non-limiting methods and techniques for determining the amount of soluble AXL (and, optionally, AFP and/or DKK-1) are, protein detection/quantifying techniques, like ELISA (particularly Sandwich ELISA), immunohistochemistry (IHC), by immunoassay, gel- or blot-based methods, IHC, mass spectrometry, flow cytometry, or FACS. These and other techniques have been described herein above in detail. The explanations and definitions given herein above in relation to diagnosing liver cancer (i.e. assessing whether a patients suffers from liver cancer or is prone to suffering from liver cancer) apply, mutatis mutandis, in this context.

The skilled artisan will understand that the plurality of prognostic indicators (like sAXL, AFP and/or DKK-1) need not be determined in the same sample, or even at the same time. For example, one prognostic indicator may not appear in samples until some time has passed from the onset of liver cancer. Combining, for example, the amount of sAXL with the amount of AFP and/or DKK1 may provide an increased predictive value in comparison to either measurement alone.

The sample may be a blood sample, like a serum sample, a plasma sample or a peripheral blood sample. Preferably, the blood sample is serum. The definitions and explanations given herein above in relation to a "sample" apply mutatis mutandis here.

Preferably, the patient is a human patient.

Also provided herein is a kit for use in the above described method for use in the herein provided assessment of a prognosis of a patient. The present invention relates to the use of a kit in above described method for assessing the prognosis of a patient.

The kit can comprise a binding molecule specifically binding to soluble AXL.

The binding molecule is preferably an antibody.

Also envisaged herein is a binding molecule, such as antibody, for use in the herein provided assessment of the prognosis of a patient.

The definitions and explanations given herein above in relation to "Kits", "binding molecules", "antibodies" and the like apply mutatis mutandis here.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of." Thus, the terms "comprising"/"including"/ "having" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

If not defined otherwise herein, the term "about" refers to ±10%, preferably ±1%.

The present invention is further described by reference to the following non-limiting figures and examples.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

The Figures Show:

FIGS. 1A-B. Study Profile

FIG. 1 shows the results of extensive clinical studies with participants from centers in Austria, the Czech Republic and China. Thus, the diagnostic accuracy of sAXL in a large-scale study, including patients from four different cancer centers located in Europe and Asia was assessed. 518 participants were enrolled in the study presented herein (FIG. 1A). Additionally, 30 liver cirrhosis patients were included, so that in total 548 participants were enrolled in the study (FIG. 1B). Serum levels of sAXL were assessed in 311 HCC, 10 breast cancer, 10 ovarian cancer and 62 colorectal cancer patients as well as 125 healthy donors 30 liver cirrhosis patients by enzyme-linked immunosorbent assay (ELISA). Diagnostic accuracy of sAXL was assessed by receiver operating characteristics (ROC) curve analysis and compared to the known marker α-fetoprotein (AFP).

Figure 2A:
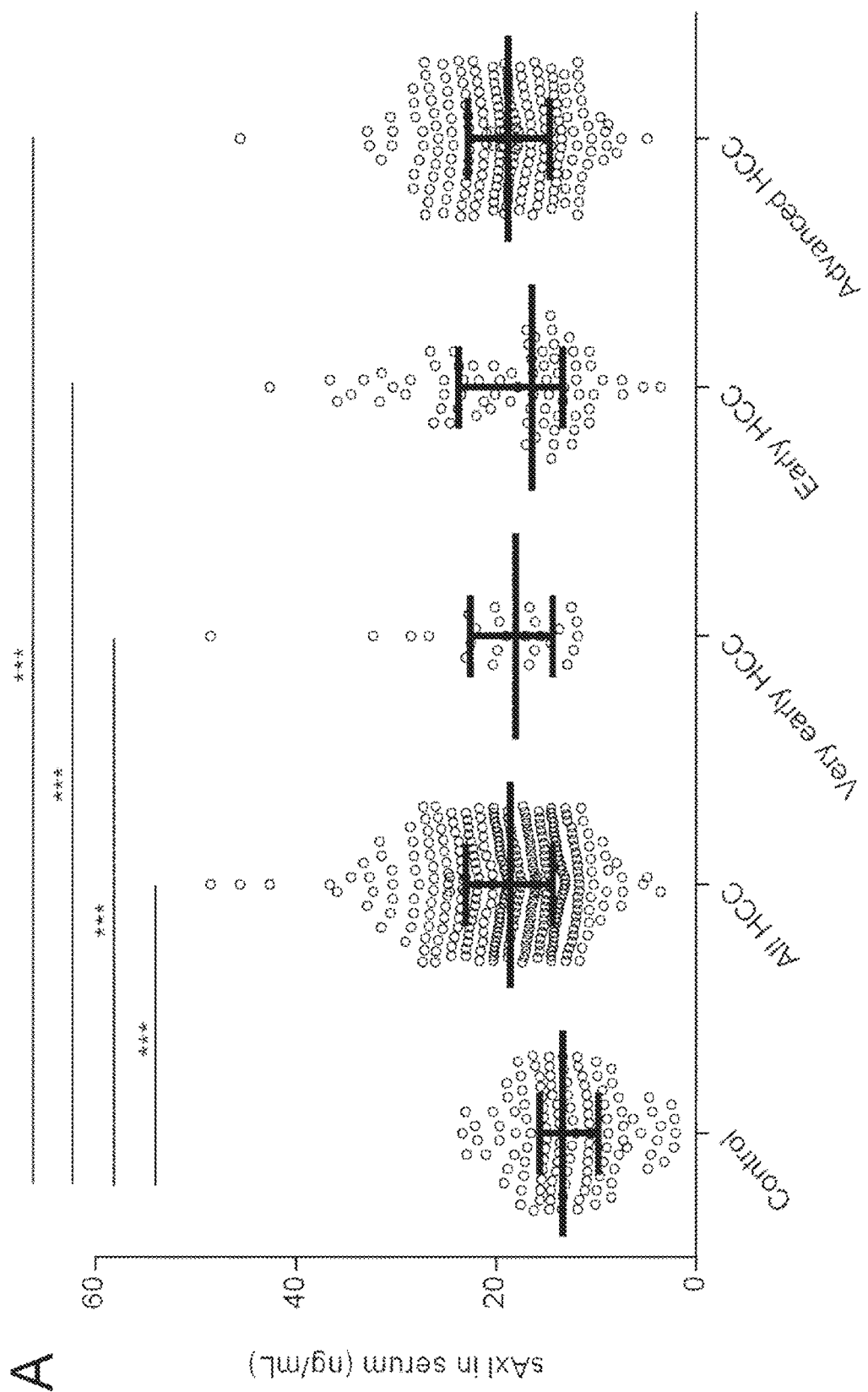
Figure 2B:
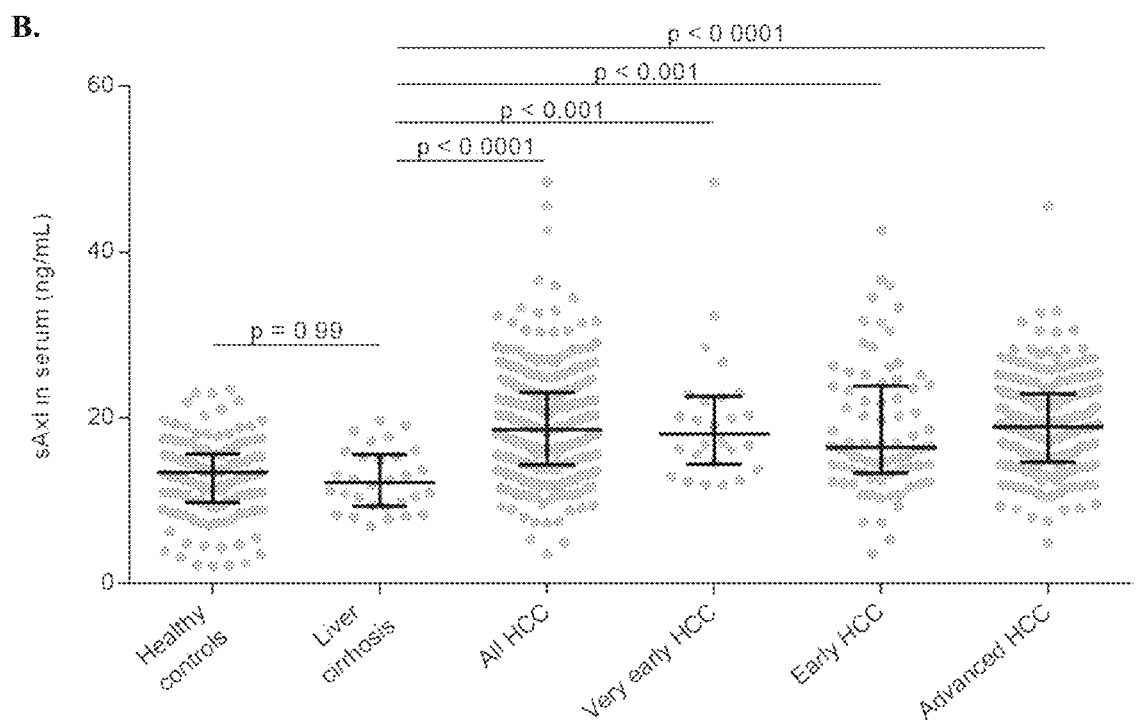
Figure 2C:
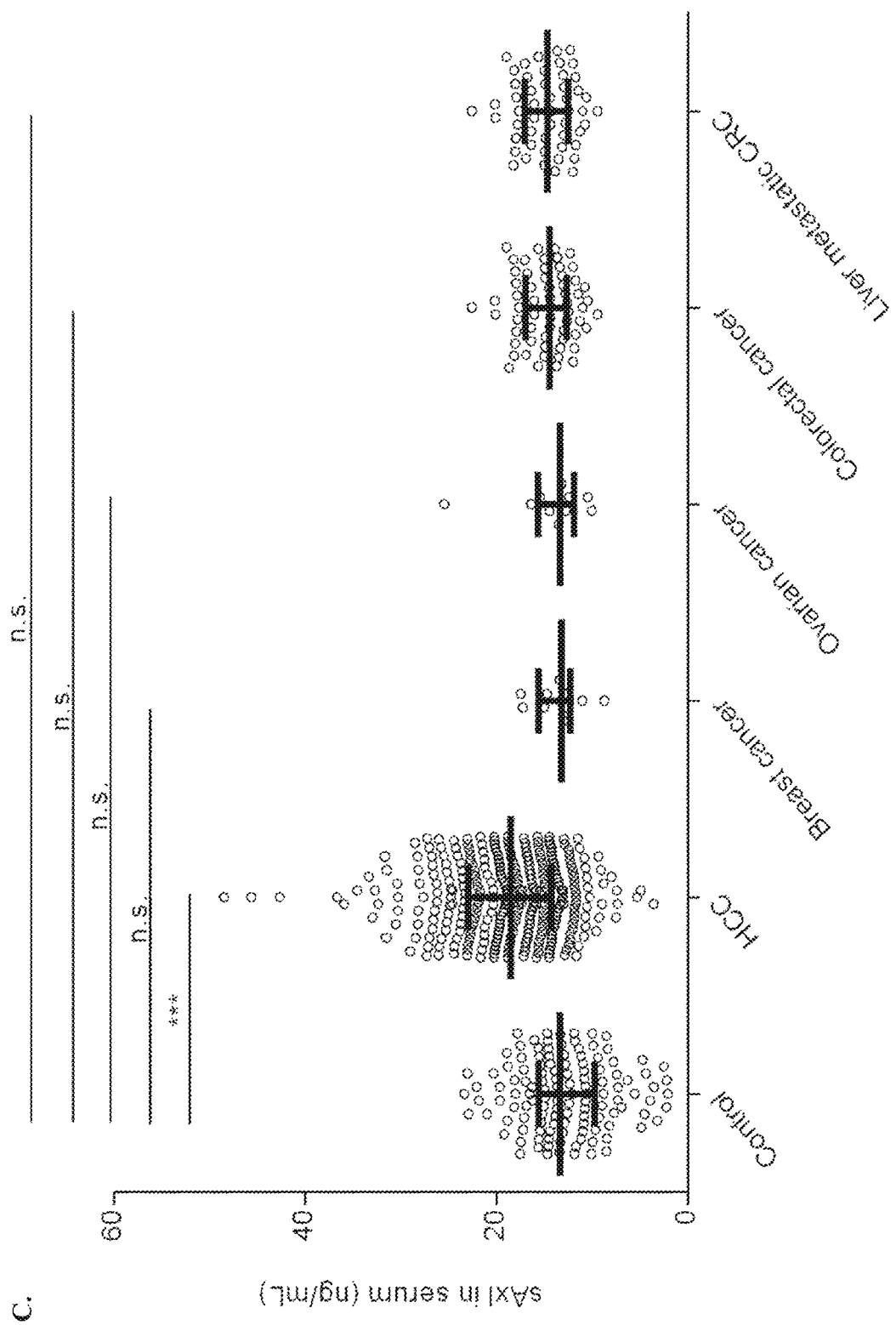

FIGS. 2A-C. sAXL levels in HCC patients.

(A) sAXL serum concentrations in controls (n=125) and patient serum samples (n=311) with very early (BCLC 0; n=26), early (BCLC A; n=78) and advanced HCC (BCLC >A; n=200) as assessed by ELISA. Horizontal bars indicate median levels with interquartile ranges. (p<0.0001; Mann-Whitney U test). (B) FIG. 2B shows the results of (A) with the exception that Cirrhotic controls ("Liver cirrhosis") were included and compared statistically. (C) Correlation of sAXL release with other cancer entities. HCC, hepatocellular carcinoma; CRC, colorectal carcinoma; n.s., non-significant; ***, p<0.001.

FIGS. 3A-B. sAXL levels in invasive and metastatic HCC.

(A) Correlation of high sAXL release with vascular invasion. (B) Relation between lymph node metastasis and high sAXL serum levels. High sAXL was defined as >18.575 ng/mL. LN, lymph node; **, p<0.01; * p<0.05

FIGS. 4A-H. Detection of HCC by sAXL.

(A) ROC curve expressing sensitivity and specificity at various cut-off levels and evaluating the diagnostic performance of AFP, sAXL and a combination of both in healthy controls (n=65) versus (vs.) HCC patients (n=311). Numbers in brackets represent the area under the curve. (B) True positive rate of AFP, sAXL or a combination of both in all HCC and of sAXL in AFP-negative HCC. Diagnostic cut-off for AFP was 20 ng/mL. Diagnostic cut-off for sAxl was 14.053. (C) True positive values for sAxl among all AFP-negative HCC in 4B were recalculated in the course of a refined analysis, resulting in a change from 88.3 to 73%. (D) ROC curves of AFP, sAXL or both in very early HCC patients (n=26). (E) True positive rate of AFP, sAXL or both in very early HCC and of sAXL in AFP-negative HCC. Diagnostic cut-off for AFP was 20 ng/mL. Diagnostic cut-off for sAxl was 11.841 ng/mL. (F) In FIG. 4F the threshold of 11.841 ng/mL for very early HCC patients (BCLC 0) was completely removed and sensitivity (true positives) was recalculated using the threshold for all HCC (14.053 ng/mL). (G) ROC curves of AFP, sAXL or both in early HCC (n=78). (H) Diagnostic accuracy of sAXL in AFP-negative HCC (n=138). HCC, hepatocellular carcinoma; AFP-, AFP-negative.

FIGS. 5A-C. sAXL and survival of HCC patients.

(A) Rate of change in sAXL serum levels in patients with stable (n=6) or progressing disease (n=5). (B) Kaplan-meier plot showing the overall survival of all HCC patients with high (>18.575 ng/mL) and low sAXL serum levels (n=122). (C) Overall survival among advanced HCC patients exhibiting high/low AXL (n=86). Numbers in brackets represent median survival in months. STA, stable disease; PRO, progressing disease; HCC, hepatocellular carcinoma; **, p<0.01; * p<0.05.

Figure 6A:
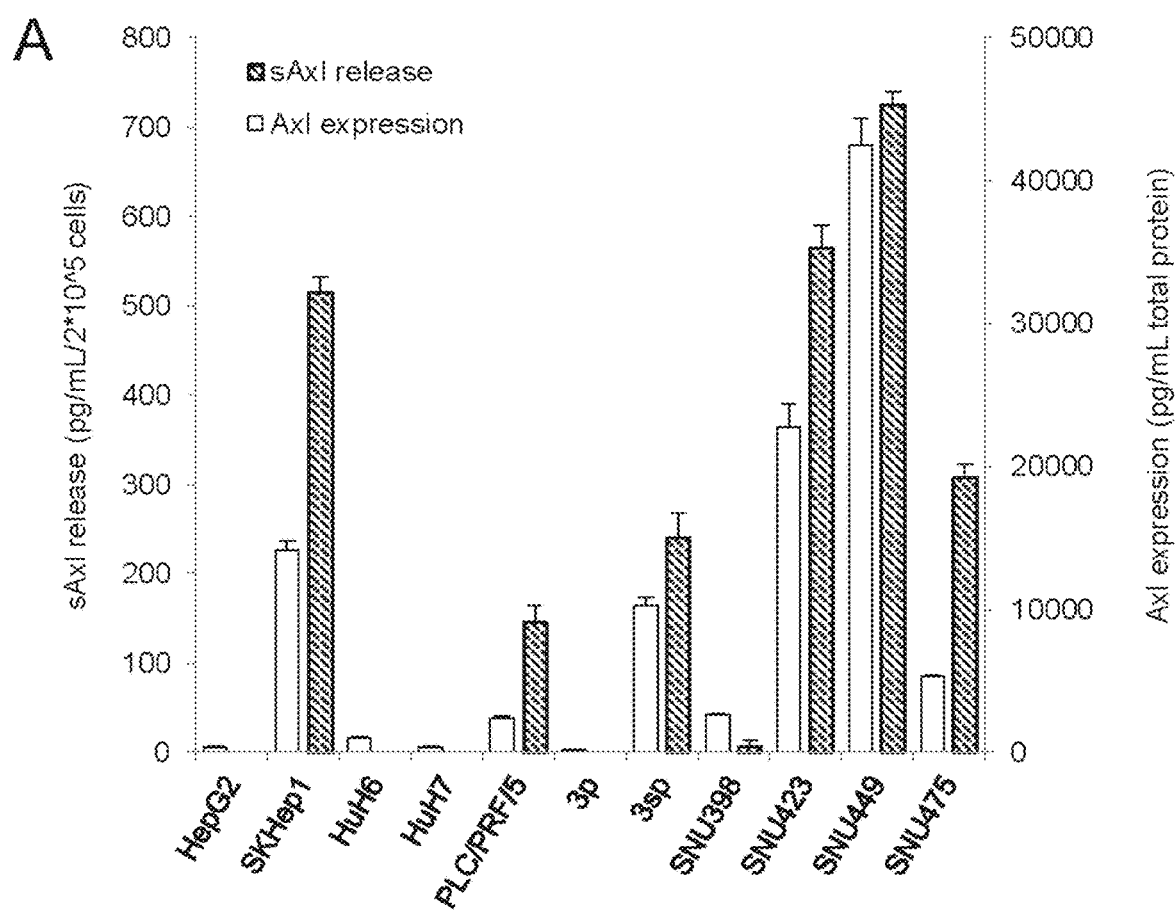
Figure 6B:
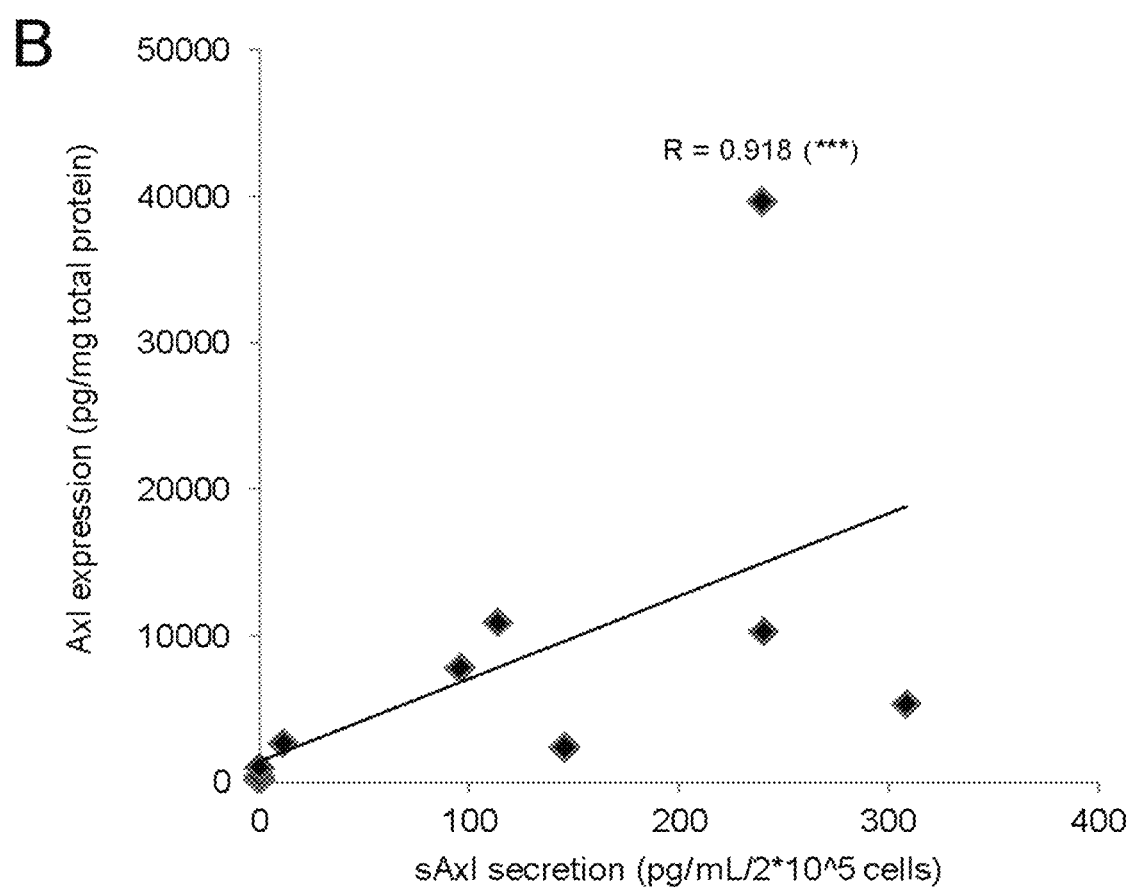

FIGS. 6A-B. Expression and release of AXL by hepatoma cell lines.

(A) Assessment of intracellular AXL expression and release of sAXL in 11 hepatoma cell lines by ELISA. Data are expressed as mean±s.d. (B) Relation of total AXL protein expression and sAXL production. R, Pearson correlation; ***, p<0.001.

FIG. 7. sAXL levels in plasma and serum.

sAXL levels in serum and anticoagulant treated plasma samples from Vienna. Horizontal bars indicate median levels with interquartile ranges. n.s., not significant.

FIGS. 8A-E. Detection of HCC by sAXL in all centers examined.

(A) Median sAXL serum concentrations in each center included in this study. (B-E) ROC curves expressing sensitivity and specificity and evaluating the diagnostic performance of AFP, sAXL and a combination of both in healthy controls (n=65) versus HCC patients in Shanghai, Hong Kong, Brno and Vienna, respectively. Numbers in brackets represent the area under the curve. SHG, Shanghai. HK, Hong Kong. BNR, Brno. VIE, Vienna. ***, p<0.001.

FIG. 9. Detection of advanced HCC by sAXL.

ROC curve expressing sensitivity and specificity at various cut-off levels and evaluating the diagnostic performance of AFP, sAXL and a combination of both in healthy controls (n=65) versus advanced HCC patients (n=200). Numbers in brackets represent the area under the curve. HCC, hepatocellular carcinoma.

FIGS. 10A-D. ROC analysis was performed in HCC versus cirrhotic controls.

In differential diagnosis of HCC versus liver cirrhosis, sAxl (AUC 0.815) outperformed AFP (AUC 0.771) and showed increased sensitivity (78%) as compared to AFP (55.3%; FIGS. 10A and 10B; Table 2). sAxl also displayed much higher accuracy (AUC 0.838) and sensitivity (80.8%) in discriminating between very early HCC and liver cirrhosis as compared to AFP (AUC 0.662; sensitivity 42.3%; FIGS. 10C and 10D; Table 2). Remarkably, combination of both markers enhanced diagnostic accuracy in all HCC (AUC 0.891; sensitivity 85.1%; specificity 80%) and in very early HCC (AUC 0.901; sensitivity 88.5%; specificity 76.7%) vs. cirrhotic controls (FIGS. 10A-10D; Table 2). In summary, these data suggest that sAxl is a highly accurate diagnostic marker for very early and AFP-negative HCC, and that sAxl alone or in combination with AFP allows discrimination between very early HCC and liver cirrhosis.

Figure 11C:
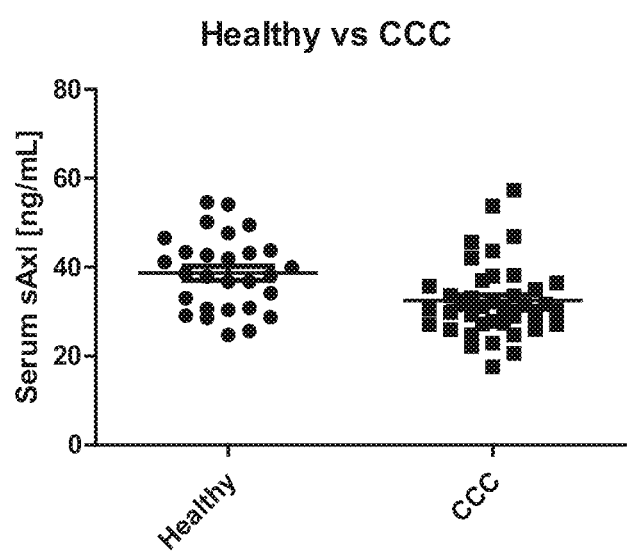

FIGS. 11A-C. sAxl levels in pathological liver or bile conditions.

(A) sAxl serum concentrations in healthy controls (n=28), HCC (n=20), NAFLD/NASH (n=78), cystic fibrosis (n=31), autoimmune hepatitis (n=28), alcohol abuse (n=6), HBV (n=12), primary biliary cirrhosis (n=15) or primary sclerosing cholangitis (n=25) patient samples as assessed by ELISA. Horizontal bars indicate median levels with interquartile ranges. (B) sAxl serum concentrations in healthy controls (n=28), HCC (n=20), CCC (n=21), hepatic fibrosis (n=92) or cirrhosis (n=13) patients. HCC, hepatocellular carcinoma; NAFLD/NASH, non-alcoholic fatty liver disease/non-alcoholic steatohepatitis; CF, cystic fibrosis; AI hepatitis, autoimmune hepatitis; HBV, hepatitis B virus; PBC, primary biliary cirrhosis; PSC, primary sclerosing cholangitis; CCC, cholangiocellular carcinoma. ELISAs were performed at a serum dilution of 1:50. (C) sAxl is not increased in CCC patients (median 30.90 ng/mL, n=40) as compared to healthy control (median 38.33 ng/mL, n=28) .Serum samples in (C) were analyzed at a dilution of 1:50.

FIGS. 12A-B. Detection of sAxl in human body fluids.

sAxl levels were assessed in serum, (A) urine and (B) saliva samples of one healthy volunteer by ELISA. Concentrations were above the detection limit in every case. Data are expressed as mean s.d. ELISAs were performed at a serum dilution of 1:10.

FIGS. 13A-C. Stability of sAxl in serum samples of HCC patients.

Serum samples of HCC patients were subjected to freeze (snap freeze in liquid nitrogen) and thaw cycles (C0, no freezing; C5, 5 freeze and thaw cycles; C10, 10 freeze and thaw cycles) and were either immediately analyzed (t0) or analyzed after 3, 7, 11 or 14 days on 4° C. (t3, t7, t11, t14) for sAxl levels by ELISA. (A) patient 1, (B) patient 2 and (C) patient 3. ELISAs were performed at a serum dilution of 1:50.

Figure 14:
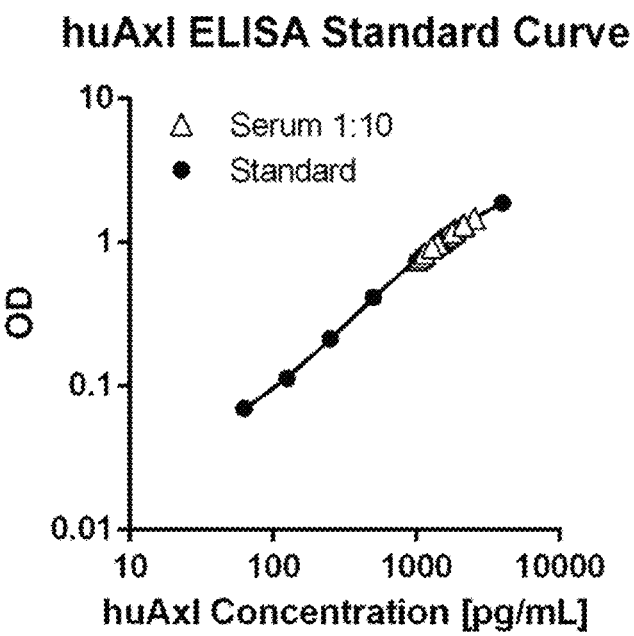

FIG. 14. sAXL standard curve.

FIG. 14 shows the determination of sAXL concentrations in serum by ELISA. In the course of assay establishment, the current literature was consulted, most notably Ekman et al. (2010), who had previously determined sAxl concentrations in serum by ELISA at tenfold dilution (see Ekman et al. Clinical biochemistry. 2010; 43(10-11):873-6). This approach was followed herein and the measured sAxl concentrations were well within the linear portion of the standard curve.

Figure 15:
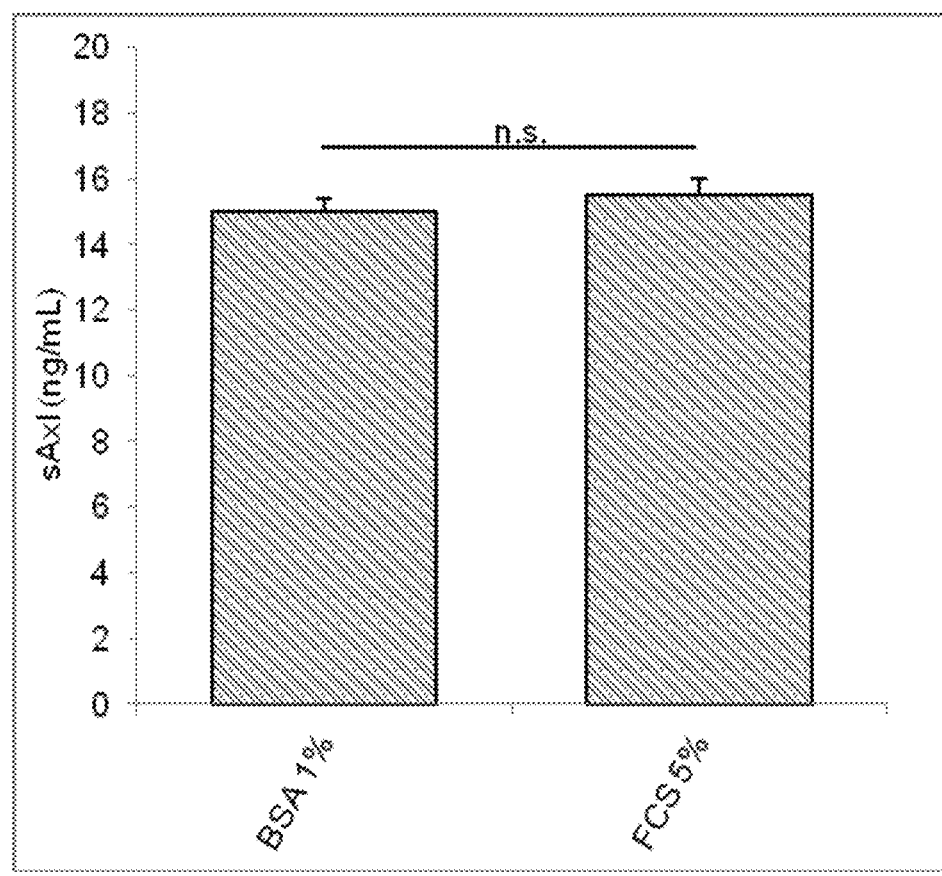

FIG. 15. Comparison of buffers.

Samples and standards diluted 1:10 in PBS and supplemented with 1% bovine serum albumin (BSA) or diluted 1:10 in PBS with 5% fetal calf serum (FCS) were assayed and compared.

Figure 16:
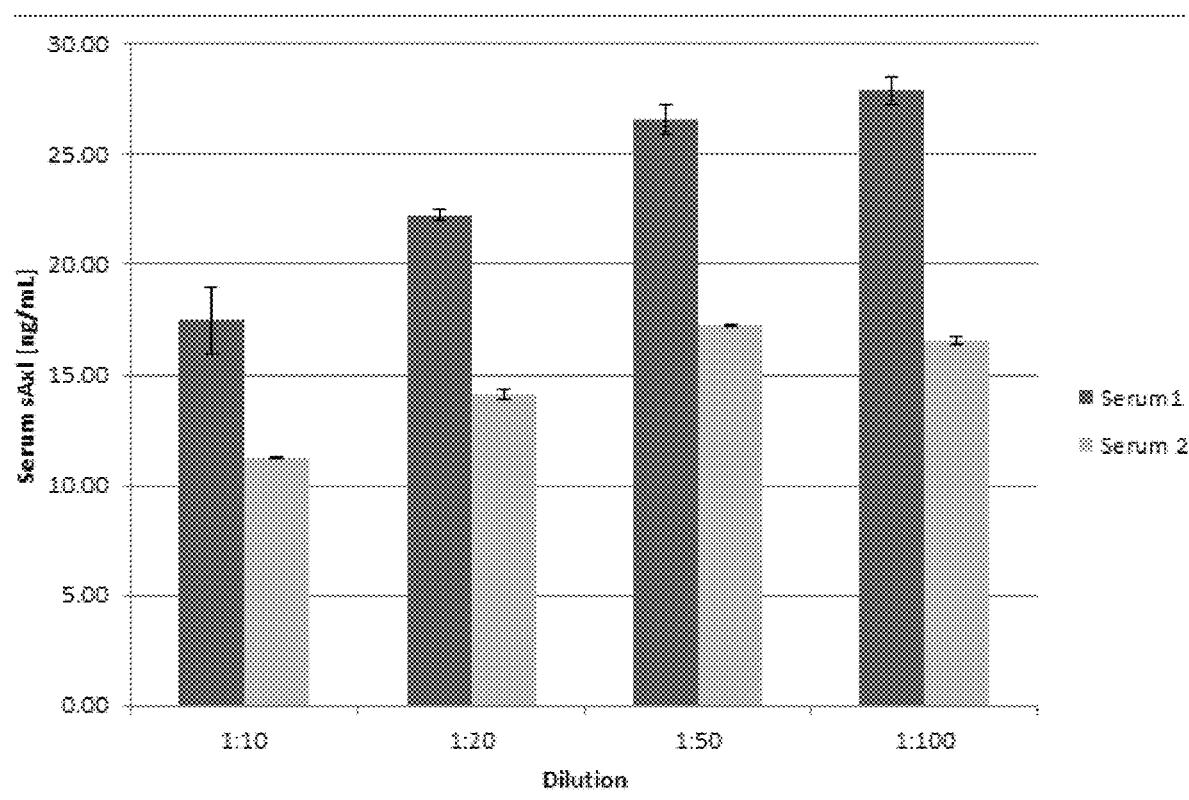

FIG. 16. Increase of sAXL concentration depending on serum dilutions.

FIG. 16 shows the increase of sAxl using serum dilutions of 1:10, 1:20, 1:50 and 1:100.

Figure 17:
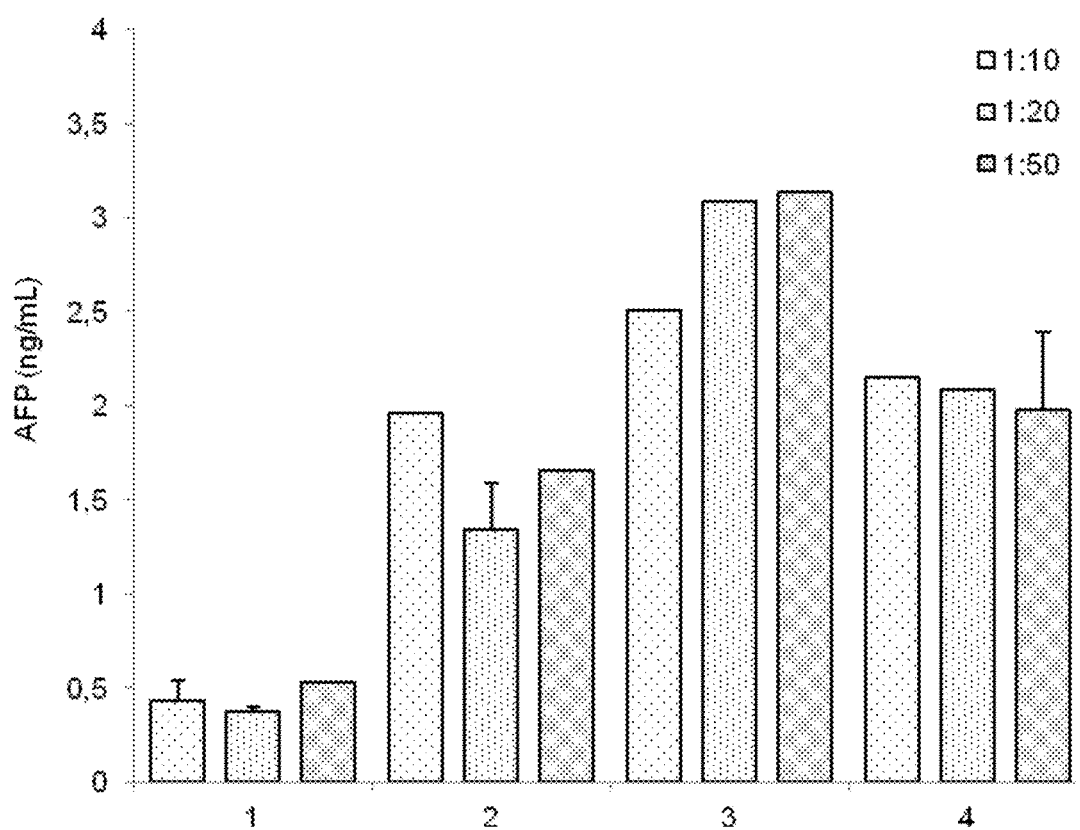

FIG. 17. AFP concentration using various serum dilutions.

AFP concentrations were determined by ELISA in 16 sera of patients with cystic fibrosis, diluted 1:10, 1:20 and 1:50 in PBS supplemented with 1% BSA.

The Examples illustrate the invention.

EXAMPLE 1: MULTICENTER ANALYSIS OF SOLUBLE AXL REVEALS DIAGNOSTIC VALUE FOR EARLY STAGE HEPATOCELLULAR CARCINOMA

Methods

Study Population

Serum samples from HCC patients (n=311) as well as healthy controls (n=125) and liver cirrhosis controls were collected in the Eastern Hepatobiliary Surgery Hospital (Shanghai, China; HCC, n=151; controls, n=66), the Vienna General Hospital (Vienna, Austria; HCC, n=18; healthy controls, n=31; liver cirrhosis controls, n=30), and the Masaryk Memorial Cancer Institute (Brno, Czech Republic; HCC, n=22; controls, n=9) from 2011 to 2013 as well as in the Li Ka Shing Faculty of Medicine (Hong Kong, China; HCC, n=100; controls, n=20) from 1999 to 2001 (FIG. 1). AFP levels were determined at time of diagnosis via enzyme-linked immunosorbent assay (ELISA). In addition, serum samples from breast (n=10), ovarian (n=10) and colorectal (n=62) cancer (CRC) patients were obtained. All samples were collected prior to therapeutic intervention, with the exception of those from Brno, where 17 patients were included that have undergone treatment but still exhibited stable or progressing disease. For 11 of these Brno patients, multiple samples were collected at different time points ranging from two months to two years post diagnosis. Samples from Vienna were partially collected as plasma into anticoagulant-coated tubes (13 of 18 samples). All samples were centrifuged and stored at −80° C. until testing. The study protocol was approved by the Chinese, Austrian as well as Czech Ethics Committees. Informed consent was obtained both from patients and healthy controls. All patients were diagnosed by ultrasound, computer tomography or magnetic resonance imaging, AFP and liver enzyme serology, and histopathologically confirmed by 2 individual pathologists after surgical resection. Patients with liver malignancies of different cellular origin, such as cholangiocellular carinomas were excluded. Age- and sex-matched healthy controls were recruited from routine physical examination. Exclusion criteria were alterations in liver serology, viral or non-viral liver disease as well as other malignancies. Clinical information about age, gender, TNM stage, cirrhosis, hepatitis virus infection, tumor size, number of tumors, vascular involvement, lymph node metastasis and AFP level determined at diagnosis was available (Table 3). Follow-up survival data was available for 122 HCC patients. In the case of CRC, liver metastasis status was known and positive in 52 of 62 patients. Patients were classified into very early, early and advanced HCC according to the established Barcelona Clinic Liver Cancer (BCLC) classification. Very early HCCs (n=26) were defined as BCLC stage 0 (single nodule<2 cm) and early HCCs (n=78) as BCLC stage A (single nodule<5 cm or 3 nodules<3 cm). BCLC stage B, C and D (large, multiple nodules, vascular invasion or extrahepatic secondary tumors) were classified as advanced HCCs (n=200) (Llovet J. M. (1999) Seminars in Liver Disease 19:329-38).

Enzyme-Linked Immunosorbent Assay (ELISA)

Sandwich ELISAs for human sAXL were carried out from December, 2012 to October, 2013 according to the manufacturer's protocol (R&D Systems Inc., USA) by independent researchers in each center included in this study (Vienna and Brno, Shanghai and Hong Kong). They had no access to patients' clinical information. The human Axl DuoSet ELISA kit, Catalog Number: DY154, Lot Number 1285322 (using a standard: 130 ng/ml) was used. sAXL concentrations were further determined in serum samples of HCC patients diluted 1:10 in phosphate buffered saline supplemented with 1% bovine serum albumin. A seven point, 4 parameter logistic standard curve using 2-fold dilutions of recombinant human AXL (R&D Systems Inc., USA) was generated for every plate, confirming a dynamic range from 62.5 pg/mL to 4000 pg/mL. Quantification was performed with the GraphPad Prism 5.0 software (GraphPad Software, USA). Data are expressed as the median value with interquartile ranges.

Receiver Operating Characteristic (ROC)

ROC curves were generated by plotting sensitivity against the false positive rate for sAXL and AFP using IBM SPSS software v20.0 (IBM Corp., USA). In addition, a variable combining both markers was generated by binary logistic regression through an iterative maximum likelihood procedure, according to the equation:

$$\ln\left(\frac{p}{1-p}\right) = a_1 * sAxl + a_2 * AFP + b$$

Equations for all comparisons are provided in Table 4. Diagnostic performance was evaluated by ROC curve analysis and quantified using the area under the curve (AUC) with 95% confidence interval (CI). Optimal cut-off values for sAXL were selected at concentrations exhibiting the highest sum of sensitivity and specificity (Yourden's Index (J)). For AFP, the clinically well-established cut-off value of 20 ng/mL was used (El-Serag H. B. (2011) Therapeutic Advances in Gastroenterology 4:5-10).

Statistical Analysis

Data sets were compared using the IBM SPSS software v20.0 (IBM Corp., USA) and Medcalc version 12.5 (MedCalc Software, Belgium). Two-sided Mann-Whitney U tests were used for continuous data and two-sided Fisher's exact tests for categorical data. Survival curves were compared with the Gehan-Breslow-Wilcoxon test. Correlations between intracellular and released AXL were established by Pearson product-moment correlation (R). *P values<0.05, P<0.01 or *P<0.001 were considered statistically significant.

Cell Lines

The following human hepatoma cell lines were cultured in their respective media at 37° C. and 5% $CO_2$: 3p, 3sp, SNU398, SNU423, SNU449 and SNU475 cells in RPMI supplemented with 10% fetal calf serum (FCS); PLC/PRF/5 and HuH7 cells in DMEM plus 10% FCS; HepG2 and SKHep 1 in EMEM with 10% FCS; HuH6 in RPMI plus 4% FCS. Cells were routinely screened for the absence of *mycoplasma*.

Enzyme-Linked Immunosorbent Assay (ELISA) to Detect Total AXL and sAXL in Cell Culture Sandwich ELISAs to detect human AXL in cell culture were performed in Vienna according to the manufacturer's protocol (R&D Systems Inc., USA). Briefly, levels of released sAxl and total cellular Axl were assessed in cell culture supernatants or total protein extracts of human HCC cell lines. Supernatants were collected after incubation of subconfluent cells in serum-free RPMI medium for 24 hours. Cells were counted after harvesting of supernatants and results from the ELISA were normalized to cell numbers. Total protein concentration was adjusted to 100 µg/mL before carrying out the ELISA of whole cell extracts. A seven point, 4 parameter logistic standard curve using 2-fold dilutions of recombinant human Axl (R&D Systems Inc., USA) was generated for every plate, confirming a dynamic range from 62.5 pg/mL to 4000 pg/mL. Quantification was performed with the GraphPad Prism 5.0 software (GraphPad Software, USA). Data are expressed as the median value with interquartile ranges.

Statistical Analysis

Data sets were compared using IBM SPSS software v20.0 (IBM Corp., USA) and Medcalc version 12.5 (MedCalc Software, Belgium). Two-sided Mann-Whitney U tests or multiplicity adjusted Kruskal-Wallis tests were used for continuous data and two-sided Fisher's exact tests for categorical data. Survival curves were compared with the Gehan-Breslow-Wilcoxon test. *P values<0.05, P<0.01 or *P<0.001 were considered statistically significant. Correlations between total and released Axl were established by Pearson product-moment correlation (R). ***P value<0.001 was considered statistically significant.

Results

Established human HCC cell lines were examined for expression of intracellular AXL in cell extracts and for release of sAXL into cell culture supernatants by ELISA. Well differentiated 3p, HepG2, HuH6 and HuH7 hepatoma cells displayed low to undetectable amounts of AXL (FIG. 6A). In contrast, 7 out of 11 hepatoma cell lines (64%) exhibited significant expression of AXL, which was highest in poorly differentiated SNU423 and SNU449 cells. By comparison of cellular AXL and sAXL levels, we observed a close correlation of AXL expression and sAXL release in almost all HCC cell lines (FIG. 6A). 10 out of 11 HCC cell lines showed closely corresponding AXL and sAXL values, while only SNU398 cells revealed a slight decrease of sAXL concentration relative to AXL expression (FIG. 6A). As expected, cells that failed to express significant AXL were devoid of sAXL production. Together, these data provide strong evidence that sAXL levels reflect intracellular AXL expression in human hepatoma cells (R=0.918, Pearson's correlation; p<0.001; FIG. 6B).

Next the question was addressed whether enhanced sAXL levels can be detected in HCC patients. Therefore, sera of 311 HCC patients were analyzed for sAXL levels by ELISA. Anticoagulant-treated blood samples from Vienna (13 out of 18) did not show any alteration in sAXL levels as compared to serum samples, confirming previous findings (FIG. 7)[19]. Patients were grouped into very early, early and advanced HCC according to established BCLC criteria. HCC patients exhibiting sAXL concentrations above the median value (18.575 ng/mL) were considered "high sAXL" cases, whereas lower concentrations were classified as "low sAXL". Cirrhotic controls did not display significantly higher sAxl concentrations (12.169 ng/ml) as compared to healthy controls (13.388 ng/ml). Importantly, significantly increased median levels of sAXL were found in all HCC (18.575 ng/mL), very early HCC (18.064 ng/mL) and early HCC (16.430 ng/mL) as compared to healthy controls (13.388 ng/mL; p<0.0001; FIG. 2A) or cirrhotic controls. A further rise in sAXL levels was observed in late HCC (18.880 ng/mL). The increase in HCC patients was significant across all centers included in this study (FIG. 8A and Table 5; Shanghai, 16.82 ng/mL; Hong Kong, 20.03 ng/mL; Brno, 19.95 ng/mL; Vienna 17.08 ng/mL).

In addition, significant differences in sAXL concentrations were detected between HCC in the presence or absence of vessel invasion or lymph node metastasis (FIG. 3A). In particular, 54.9% of HCC accompanied by vascular invasion exhibited high levels of sAXL, while 58.6% of non-invasive HCC cases showed low sAXL (FIG. 3A; Table 1; p<0.05). Similarly, 70.6% of HCC patients with lymph node metastasis showed augmented sAXL levels, whereas 54.7% of patients without spreading into lymph nodes exhibited low sAXL (p<0.001; FIG. 3B; Table 1). No changes in sAXL amounts could be determined in HCC with different status of hepatitis B, hepatitis C or cirrhosis (Table 1).

In addition, sAXL serum concentrations were assessed in a cohort of breast, ovarian and CRC patients. Notably, sAXL serum levels remained unchanged in patients suffering from these carcinomas as compared to healthy controls. Importantly, no changes in serum sAXL were detected in CRC patients exhibiting liver metastases (FIG. 2B). These data suggest that sAXL levels specifically detect early and late stage HCC in patients' sera, either alone or associated with entry into blood vessels or lymph nodes.

Further, the diagnostic value of sAXL in HCC was assessed by comparison with the established serum marker AFP. ROC curve analysis revealed a comparable diagnostic performance of sAXL (AUC 0.834 [0.792-0.870]) and AFP (AUC 0.868 [0.829-0.900]) in all HCC patients, whereas sensitivity was higher for sAXL (78.1%) at the optimal cut-off of 14.053 ng/mL as compared to AFP (55.3%) at the clinically used cut-off of 20 ng/mL (FIG. 4A; 4B; 4C; Table 2). Again, diagnostic performance of sAXL was high across all centers included in this study (FIG. 8B-E; Shanghai, AUC 0.789 [0.727-0.852]; Hong Kong, AUC, 0.901 [0.855-0.947]; Brno, AUC 0.866 [0.777-0.955]; Vienna AUC 0.854 [0.773-0.935]).

Remarkably, sAXL outperformed AFP in detecting very early HCC (sAXL, AUC 0.848 [0.757-0.914]; AFP, AUC 0.797 [0.699-0.874]). Again, sensitivity of sAXL was much higher (100%) at a cut-off of 11.841 ng/mL than of AFP (38.5%; FIG. 4D; 4E; 4F; Table 2).

In order to assess the combination of both markers, the predicted probability was calculated via binary logistic regression. Combined analysis of sAXL and AFP revealed an exceptional accuracy of 0.937 [0.907-0.959] with a sensitivity of 84.5% and a specificity of 92.3% in detecting HCC (FIG. 4A; 4B; 4C; Table 2). This was shown to be valid throughout all stages, with AUC 0.936 [0.864-0.976] in very early HCC, AUC 0.921 [0.864-0.952] in early HCC and AUC 0.943 [0.908-0.968] in advanced stage HCC (FIG. 4D; 4G and FIG. 9).

In AFP-negative HCC, sAXL was also indicated as a valid marker for HCC detection (AUC 0.803 [0.741-0.855]; FIG. 4H) with a sensitivity of 88.3% and a specificity of 56.9% at a cut-off level of 11.841 ng/mL (FIG. 4B; Table 2), allowing to overcome the absence of the diagnostic marker AFP.

Among very early, AFP-negative patients, sAXL showed even higher sensitivity of 100% and specificity of 56.9% at a cut-off of 11.841 ng/mL (FIG. 4E; table 2). In summary, these data suggest that sAXL is a highly accurate diagnostic marker for very early and AFP-negative HCC.

In differential diagnosis of HCC versus liver cirrhosis, sAxl (AUC 0.815) also outperformed AFP (AUC 0.771) and showed increased sensitivity (78%) as compared to AFP (55.3%; FIGS. 10a and 10b; Table 2). sAxl also displayed much higher accuracy (AUC 0.838) and sensitivity (80.8%) in discriminating between very early HCC and liver cirrhosis as compared to AFP (AUC 0.662; sensitivity 42.3%; FIGS. 10c and 10d; Table 2). Remarkably, combination of both markers enhanced diagnostic accuracy in all HCC (AUC 0.891; sensitivity 85.1%; specificity 80%) and in very early HCC (AUC 0.901; sensitivity 88.5%; specificity 76.7%) vs. cirrhotic controls (FIGS. 10a-10d; Table 2). In summary, these data suggest that sAxl is a highly accurate diagnostic marker for very early and AFP-negative HCC, and that sAxl alone or in combination with AFP allows discrimination between very early HCC and liver cirrhosis.

Furthermore, a prognostic role of sAXL was addressed by analyzing samples from different time points post diagnosis of patients undergoing treatment, ranging from two months to two years. The data revealed a significantly higher rate of change of sAXL levels in patients exhibiting tumor progression (median 33.518 pg/mL/day, n=5) as compared to those showing stable disease (median 3.06 pg/mL/day, n=6, p=0.0043; FIG. 5A).

Furthermore, analysis of patient's survival was performed by comparison of high AXL versus low AXL HCC. Among all HCC stages, patients exhibiting high AXL show a significantly decreased overall survival (median 25.37 mo, p=0.018) as compared to those with low AXL serum levels (median 88.56 mo; FIG. 5B). This decrease was even more pronounced among advanced HCC patients (high AXL median 11.37 mo, low AXL median 39.63 mo, p=0.007; FIG. 5C). These data suggest that sAXL levels reflect disease progression.

Alterations of sAxl levels in human sera have been documented with different outcomes in a number of pathological conditions including cancer (Gustafsson et al. Clin Cancer Res 2009; 15: 4742-9; Ekman et al. Clin Biochem 2010; 43: 110-4). One study reported a reduction of sAxl in sera of renal cell carcinoma patients as compared to healthy controls, suggesting that the contribution of tumor-released sAxl might be too low to significantly alter total sAxl serum concentrations (Gustafsson et al., loc. cit.). In contrast, we now show that most cultured HCC cell lines produce sAxl and that sAxl serum levels of HCC patients are significantly higher as compared to healthy and cirrhotic controls, indicating that HCC-derived sAxl is a major contributor to the overall sAxl serum concentration (FIG. 2AB). Importantly, cirrhotic controls do not exhibit higher sAxl concentrations as compared to healthy controls and cirrhotic HCC patients show no increase versus noncirrhotic patients arguing against a significant contribution of myofibroblast-derived sAxl (FIG. 2AB; Table 1). Similarly, patients suffering from breast, ovarian or colorectal cancer show no changes in sAxl levels either, underlining a specific role of sAxl as a biomarker of HCC (FIG. 2C). Remarkably, liver metastasis of colon cancer does not alter sAxl serum levels, allowing a clear discrimination between HCC and secondary hepatic malignancy (FIG. 2C) (Tzeng et al. J Gastrointest Surg 2013; 17: 195-201; quiz p -2).

Axl signaling regulates cellular processes relevant for tumorigenesis such as proliferation, survival and chemoresistance as well as those involved in tumor progression including migration and invasion (Korshunov, Clin Sci (Loud) 2012; 122: 361-8). Therefore, multiple Axl-specific functions might be involved in all stages of HCC. Accordingly, we detected increased sAxl levels already in very early as well as in advanced stages HCC. Due to the lack of suitable biomarkers, most HCCs remain undetected until they reach advanced stages. This greatly reduces treatment options as compared to very early HCC where liver resection and percutaneous ablation are the therapies of choice, leading to a high 5-year survival of 70% (Lin et al. Liver Cancer 2012; 1: 144-58). Despite its limited performance, AFP has been extensively used as a biomarker for HCC (Paul et al. Oncology 2007; 72 Suppl 1: 117-23). Many diagnostic thresholds for AFP have been proposed, ranging from 10 to 2000 ng/mL. We applied the most commonly used value of 20 ng/mL to mimic the most probable clinical situation (Shen et al. Lancet Oncol 2012; 13: 817-26; El-Serag and Davila, Therap Adv Gastroenterol 2011; 4: 5-10; da Costa et al. Int J Cancer 2015; 136: 172-81; Zhou et al. Hepatogastroenterology 2012; 59: 840-3). Furthermore, we followed a threshold independent approach by ROC curve analysis. In this context, sAxl exhibits higher performance as compared to AFP in detecting very early HCC. Importantly, combination of both biomarkers shows exceptional accuracy (FIG. 4D; Table 2).

Additionally, almost half (45%) of all patients included in this study exhibited AFP levels below the clinically used cutoff and thus would not have been identified. Among very early HCC, this proportion is even worse (58%) and in these patients, sAxl shows high performance in detecting HCC (FIG. 4F; Table 2). It has to be noted that AFP alone exhibits higher specificity (100% in very early HCC) and PPV as compared to sAxl (69.2%). Similarly, the combination of both markers also results in a decrease of specificity (92.3%) as compared to AFP alone; however, this slight reduction represents only a small trade-off as compared to the vast gain in sensitivity (80.8% for sAxl/AFP versus 38.5% for AFP alone in very early HCC), which is highly desired in diagnostic screening procedures.

For monitoring of high-risk groups, accurate differential diagnosis of HCC versus other risk factors, most notably cirrhosis, is desired Fattovich et al. Gastroenterology 2004; 127: S35-50). sAxl shows higher performance as compared to AFP in discriminating between cirrhotic controls and very early HCC, resulting in higher sensitivity. Combination of both markers again leads to an increase in accuracy with very high sensitivity and specificity (FIGS. 10c and 10d; Table 2). Since etiology of HCC strongly differs between China and Europe, we recruited patients from both regions. sAxl was shown to be increased in HCC patients from all centers, further underlining its potential as a biomarker of HCC (FIG. 8). Remarkably, the combined median sAxl levels of HCC patients recruited in Asian centers (18.762 ng/mL) did not differ from those in Europe (18.450 ng/mL). Nevertheless, a bias due to differences in etiology is conceivable, as a higher proportion of Chinese HCC patients were included in this study and cirrhotic controls were exclusively collected in Vienna. Thus, these data can be verified in a prospective study conducted according to the guidelines of highest quality management and including further controls, such as hepatitis and fibrosis patients as well as cirrhotic patients from Chinese centers and additional HCC patients from Europe.

With respect to AFP, we observed higher median levels in Chinese patients as compared to Europe. This might be caused by the inclusion of a higher number of very advanced HCC cases (TNM >5) from Asia, which were completely absent in Europe, possibly due to regional differences in HCC surveillance and stage at diagnosis (Llovet et al. Liver Transpl 2004; 10:S115-5120). sAxl concentrations are slightly higher in advanced HCC cases as compared to early HCCs, although not statistically significant.

In addition, high sAxl serum concentrations are associated with vascular invasion and lymph node metastasis (FIG. 3; Table 1), suggesting a prominent role of Axl in HCC progression. Accordingly, patients exhibiting high sAxl show decreased overall survival as compared to those having low levels (FIGS. 5b and 5c). Furthermore, patients escaping therapy during tumor progression show an increased rate of change in sAxl levels as compared to patients with stable disease (FIG. 5a). Thus, sAxl may also serve as a candidate prognostic and surveillance marker for HCC.

In summary, we report that sAxl shows high sensitivity in detecting early stages of HCC, as compared to AFP alone. Combination of sAxl and AFP further increases performance and shows high accuracy in differential diagnosis between HCC and hepatic cirrhosis. Additionally, sAxl performs well in AFP-negative HCC patients. Therefore, sAxl represents a valuable biomarker for routine screening of very early HCC. As sAxl levels are elevated in very early as well as in advanced HCC, various Axl-mediated functions might be relevant in the different stages of HCC.

If diagnosed at early stages, patients with hepatocellular carcinoma (HCC) can receive curative therapies, whereas therapeutic options at later stages are very limited. Here, we addressed the potential of soluble Axl (sAxl) as a biomarker of early HCC by analyzing levels of sAxl in 311 HCC and 237 control serum samples from centers in Europe and China. Serum concentrations of sAxl were significantly increased in HCC (18.575 ng/mL) as compared to healthy (13.388 ng/mL) or cirrhotic (12.169 ng/mL) controls. Receiver operating characteristic curve analysis of sAxl in very early stage HCC patients (BCLC 0) showed an area under the curve (AUC) of 0.848, with a sensitivity of 76.9% and a specificity of 69.2%. a-Fetoprotein (AFP)-negative HCC patients displayed an AUC of 0.803, with sensitivity and specificity of 73% and 70.8%. Combination of sAxl and AFP improved diagnostic accuracy to 0.936 in very early HCC patients and to 0.937 in all HCC. Differential diagnosis of very early HCC versus liver cirrhosis showed a combined performance for sAxl and AFP of 0.901 with a sensitivity of 88.5% and a specificity of 76.7%. Furthermore, sAxl levels failed to be elevated in primary ovarian, colorectal and breast carcinomas as well as in secondary hepatic malignancies derived from colon. In summary, sAxl outperforms AFP in detecting very early HCC as compared to healthy or cirrhotic controls and shows high diagnostic accuracy for AFP-negative patients. sAxl is specific for HCC and useful as a biomarker for routine clinical use.

If diagnosed at early stages, patients with hepatocellular carcinoma (HCC) can receive curative therapies, whereas therapeutic options at later stages are limited. Detection of early stage hepatocellular carcinoma by measuring serum a-fetoprotein (AFP) however exhibits only moderate sensitivity. This study shows that serum concentrations of soluble Axl (sAxl) are increased in very early, early and advanced HCC as well as in AFP-negative HCC patients, as compared to cirrhotic controls. Assessment of sAxl levels allows accurate differential diagnosis of very early HCC versus cirrhosis and other types of cancer. Therefore sAxl is a promising diagnostic biomarker for routine clinical use.

TABLE 1

Correlation of sAXL serum levels with various clinicopathological parameters
Table 1. Correlation of sAxl serum levels with various clinicopathological parameters

| Variable | Number of cases | sAxl High | sAxl Low | OR | CI 95% | p |
|---|---|---|---|---|---|---|
| Age (years) | | | | | | |
| <55 | 162 | 73 (45.1%) | 89 (54.9%) | 1.497 | 0.939-2.388 | 0.098 |
| ≥55 | 127 | 70 (55.1%) | 57 (44.9%) | | | |
| Gender | | | | | | |
| Male | 256 | 125 (48.8%) | 131 (51.2%) | 1.354 | 0.753-2.434 | 0.373 |
| Female | 55 | 31 (56.4%) | 24 (43.6%) | | | |
| HBV status | | | | | | |
| Negative | 33 | 13 (39.4%) | 20 (60.6%) | 1.578 | 0.750-3.318 | 0.267 |
| Positive | 237 | 120 (50.6%) | 117 (49.4%) | | | |
| HCV status | | | | | | |
| Negative | 275 | 137 (49.8%) | 138 (50.2%) | 0.863 | 0.283-2.635 | 1.000 |
| Positive | 13 | 6 (46.2%) | 7 (53.8%) | | | |
| Cirrhosis | | | | | | |
| No | 53 | 18 (34.0%) | 35 (66.0%) | 1.734 | 0.906-3.318 | 0.110 |
| Yes | 157 | 74 (47.1%) | 83 (52.9%) | | | |
| Vascular invasion | | | | | | |
| No | 145 | 60 (41.4%) | 85 (58.6%) | 1.728 | 1.018-2.932 | 0.045* |
| Yes | 91 | 50 (54.9%) | 41 (45.1%) | | | |

TABLE 1-continued

Correlation of sAXL serum levels with various clinicopathological parameters
Table 1. Correlation of sAxl serum levels with various clinicopathological parameters

|  | Number of cases | sAxl High | sAxl Low | OR | CI 95% | p |
|---|---|---|---|---|---|---|
| Lymph node metastasis | | | | | | |
| No | 256 | 116 (45.3%) | 140 (54.7%) | 2.897 | 1.511-5.552 | 0.001*** |
| Yes | 51 | 36 (70.6%) | 15 (29.4%) | | | |

CI, confidence interval.
OR, odds ratio.
HBV, hepatitis B virus.
HCV, hepatitis C virus.
***p < 0.001.
*p < 0.05.
low sAxl < 18.575 ng/mL < high sAxl.

TABLE 2

Performance of sAXL and AFP in the detection of HCC
Table 2. Performance of sAxl and AFP in the detection of HCC

|  | AUC (95% CI) | Sensitivity (%) | Specificity (%) | PPV (%) | NPV (%) | Youden's index |
|---|---|---|---|---|---|---|
| All HCC | | | | | | |
| AFP | 0.868 (0.829-0.900) | 55.3 | 100 | 100 | 69.1 | 0.55 |
| sAxl | 0.834 (0.792-0.870) | 78.1 | 70.8 | 72.8 | 76.4 | 0.49 |
| sAxl + AFP | 0.937 (0.907-0.959) | 84.5 | 92.3 | 91.6 | 85.6 | 0.77 |
| Very early HCC | | | | | | |
| AFP | 0.797 (0.699-0.874) | 38.5 | 100 | 100 | 61.9 | 0.39 |
| sAxl | 0.848 (0.757-0.914) | 100 | 56.9 | 69.9 | 100 | 0.57 |
| sAxl + AFP | 0.936 (0.864-0.976) | 80.8 | 92.3 | 91.3 | 82.8 | 0.73 |
| All AFP negative HCC | | | | | | |
| sAxl | 0.803 (0.741-0.855) | 88.3 | 56.9 | 67.2 | 82.9 | 0.45 |
| Very early AFP negative HCC | | | | | | |
| sAxl | 0.863 (0.767-0.929) | 100 | 56.9 | 69.9 | 100 | 0.57 |

AUC, area under the curve.
CI, confidence interval.
PPV, positive predictive value.
NPV, negative predictive value.
HCC, hepatocellular carcinoma.
AFP, α-fetoprotein.
Diagnostic cut-off for AFP was 20 ng/mL.
Diagnostic cut-offs for sAxl in all HCC and very early HCC were 14.053 and 11.841 ng/mL respectively.

Additional Table 2: Performance of sAXL and AFP in the detection of HCC

Values for all AFP-negative HCC were recalculated resulting in a decrease in sensitivity and an increase in specificity. The threshold for very early HCC (11.841 ng/mL) was removed and values were recalculated using 14.053 ng/mL. This results in changes of sensitivity, specificity, PPV and NPV for very early HCC versus healthy controls. It is of note that threshold-independent AUC values are unaffected. The table was also extended to include diagnostic performance of sAxl versus cirrhotic controls.

TABLE 2

Performance of sAxl and AFP in the detection of HCC

|  | AUC (95% CI) | Sensitivity (%) | Specificity (%) | PPV (%) | NPV (%) | Youden's index |
|---|---|---|---|---|---|---|
| All HCC vs. HC | | | | | | |
| AFP | 0.868 (0.829-0.900) | 55.3 | 100 | 100 | 69.1 | 0.55 |
| sAxl | 0.834 (0.792-0.870) | 78.1 | 70.8 | 72.8 | 76.4 | 0.49 |
| sAxl + AFP | 0.937 (0.907-0.959) | 84.5 | 92.3 | 91.6 | 85.6 | 0.77 |

TABLE 2-continued

Performance of sAxl and AFP in the detection of HCC

| | AUC (95% CI) | Sensitivity (%) | Specificity (%) | PPV (%) | NPV (%) | Youden's index |
|---|---|---|---|---|---|---|
| Very early HCC vs. HC | | | | | | |
| AFP | 0.797 (0.699-0.874) | 38.5 | 100 | 100 | 61.9 | 0.39 |
| sAxl | 0.848 (0.757-0.914) | 76.9 | 69.2 | 71.4 | 75.0 | 0.46 |
| sAxl + AFP | 0.936 (0.864-0.976) | 80.8 | 92.3 | 91.3 | 82.8 | 0.73 |
| All AFP negative HCC vs. HC | | | | | | |
| sAxl | 0.803 (0.741-0.855) | 73 | 70.8 | 71.4 | 72.4 | 0.44 |
| Very early AFP negative HCC vs. HC | | | | | | |
| sAxl | 0.863 (0.767-0.929) | 80 | 69.2 | 72.2 | 77.6 | 0.49 |
| All HCC vs. LC | | | | | | |
| AFP | 0.771 (0.710-0.833) | 55.3 | 93.3 | 89.2 | 67.6 | 0.49 |
| sAxl | 0.815 (0.747-0.884) | 78 | 66.7 | 70.1 | 75.2 | 0.45 |
| sAxl + AFP | 0.891 (0.847-0.936) | 85.1 | 80.0 | 81.0 | 84.3 | 0.65 |
| Very early HCC vs. LC | | | | | | |
| AFP | 0.662 (0.513-0.810) | 42.3 | 93.3 | 86.3 | 61.8 | 0.36 |
| sAxl | 0.838 (0.738-0.939) | 80.8 | 66.7 | 70.8 | 77.6 | 0.48 |
| sAxl + AFP | 0.901 (0.823-0.979) | 88.5 | 76.7 | 79.2 | 87.0 | 0.65 |
| All AFP negative HCC vs. LC | | | | | | |
| sAxl | 0.780 (0.698-0.861) | 73 | 66.7 | 68.7 | 71.2 | 0.40 |
| Very early AFP negative HCC vs. LC | | | | | | |
| sAxl | 0.858 (0.746-0.969) | 86.7 | 66.7 | 72.3 | 83.4 | 0.53 |

AUC, area under the curve; CI, confidence interval; PPV, positive predictive value; NPV, negative predictive value; HCC, hepatocellular carcinoma; AFP, α-fetoprotein; HC, healthy controls; LC, liver cirrhosis.
Diagnostic cutoffs for AFP and sAxl were 20 ng/mL and 14.053 ng/mL, respectively.

TABLE 3

(supporting table 1): Demographic and clinicopathological characteristics of the study population
Supporting Table 1: Demographic and clinicopathological characteristics of the study population

| Variable | | Number of cases | % | Valid % |
|---|---|---|---|---|
| Age (years) | | | | |
| Valid | <55 | 162 | 52.1 | 56.1 |
| | ≥55 | 127 | 40.8 | 43.9 |
| Missing | | 22 | 7.1 | |
| Total | | 311 | 100 | 100 |
| Gender | | | | |
| Valid | Male | 256 | 82.3 | 82.3 |
| | Female | 55 | 17.7 | 17.7 |
| Total | | 311 | 100 | 100 |
| HBV status | | | | |
| Valid | Negative | 33 | 10.6 | 12.2 |
| | Positive | 237 | 76.2 | 87.8 |
| Missing | | 41 | 13.2 | |
| Total | | 311 | 100 | 100 |
| HCV status | | | | |
| Valid | Negative | 275 | 88.4 | 95.5 |
| | Positive | 13 | 4.2 | 4.5 |
| Missing | | 23 | 7.4 | |
| Total | | 311 | 100 | 100 |
| Cirrhosis | | | | |
| Valid | Negative | 53 | 17 | 25.2 |
| | Positive | 157 | 50.5 | 74.8 |
| Missing | | 101 | 32.5 | |
| Total | | 311 | 100 | 100 |
| Vascular invasion | | | | |
| Valid | Negative | 145 | 46.6 | 61.4 |
| | Positive | 91 | 29.3 | 38.6 |
| Missing | | 75 | 24.1 | |
| Total | | 311 | 100 | 100 |

TABLE 3-continued (supporting table 1): Demographic and clinicopathological characteristics of the study population
Supporting Table 1: Demographic and clinicopathological characteristics of the study population

| Variable | | Number of cases | % | Valid % |
|---|---|---|---|---|
| Lymph node metastasis | | | | |
| Valid | Negative | 256 | 82.3 | 83.4 |
| | Positive | 51 | 16.4 | 16.6 |
| Missing | | 4 | 1.3 | |
| Total | | 311 | 100 | 100 |

HBV, hepatitis B virus.
HCV, hepatitis C virus.

TABLE 4

(supporting tabel 2): Regression equations for the combinations of sAxl and AFP
Supporting Table 2: Regression equations for the combinations of sAxl and AFP

| | $a_1$ (sAxl) | $a_2$ (AFP) | b |
|---|---|---|---|
| All HCC | 0.248 | 0.383 | −4.402 |
| Very early | 0.309 | 0.300 | −7.357 |
| Early HCC | 0.211 | 0.469 | −5.367 |
| Advanced HCC | 0.247 | 0.366 | −4.885 |
| SHG | 0.201 | 0.380 | −4.164 |
| HK | 0.356 | 0.479 | −8.260 |
| BRN | 0.337 | 0.558 | −9.000 |
| VIE | 0.294 | 0.167 | −6.501 |

HCC, hepatocellular carcinoma.
AFP, α-fetoprotein.
SHG, Shanghai.
HK., Hong Kong.
BRN, Brno.
VIE, Vienna.
Probabilities for combination of sAxl and AFP were calculated according to the equation:

$$\ln\left(\frac{p}{1-p}\right) = \alpha_1 * \text{sAxl} + \alpha_2 * \text{AFP} + b$$

Additional Table 4 (Supporting Table 2): Regression Equations for the Combinations of sAXL and AFP.

Additional Table 4 corresponds to Table 4 with the exception that equations for cirrhotic controls were included.

Supporting Information Table S2: Regression equations for the combinations of sAxl and AFP

| | $a_1$ (sAxl) | $a_2$ (AFP) | b |
|---|---|---|---|
| All HCC vs. HC | 0.248 | 0.383 | −4.402 |
| All HCC vs. LC | 0.220 | 0.043 | −1.952 |
| Very early HCC vs. HC | 0.309 | 0.300 | −7.357 |
| Very early HCC vs. LC | 0.330 | 0.036 | −5.941 |
| Early HCC vs. HC | 0.211 | 0.469 | −5.367 |
| Advanced HCC vs. HC | 0.247 | 0.366 | −4.885 |
| SHG | 0.201 | 0.380 | −4.164 |
| HK | 0.356 | 0.479 | −8.260 |
| BRN | 0.337 | 0.558 | −9.000 |
| VIE | 0.294 | 0.167 | −6.501 |

HCC, hepatocellular carcinoma.
AFP, α-fetoprotein.
SHG, Shanghai.
HK., Hong Kong.
BRN, Brno.
VIE, Vienna.
Probabilities for combination of sAxl and AFP were calculated according to the equation:

$$\ln\left(\frac{p}{1-p}\right) = \alpha_1 * \text{sAxl} + \alpha_2 * \text{AFP} + b$$

TABLE 5

(supporting table 3): sAXL and AFP serum concentrations of the study population
Supporting Table 3: sAxl and AFP serum concentrations of the study population

| | Number of cases | Median (IQR) ng/mL | Mean (s.d.) ng/mL |
|---|---|---|---|
| sAxl | | | |
| Controls | 125 | 13.388 (9.811-15.663) | 12.834 (4.781) |
| All HCC | 311 | 18.575 (14.316-23.045) | 19.079 (6.456) |
| Very early HCC | 26 | 18.064 (14.385-22.623) | 19.779 (7.881) |
| Early HCC | 78 | 16.438 (13.357-23.808) | 18.617 (7.754) |
| Advanced HCC | 200 | 18.880 (14.666-22.889) | 19.144 (5.771) |
| AFP-negative HCC | 137 | 17.231 (13.855-21.380) | 18.112 (6.463) |
| SHG | 171 | 16.820 (13.216-22.130) | 18.250 (7.255) |
| HK | 100 | 20.027 (16.815-24.148) | 20.443 (4.985) |
| BRN | 22 | 19.952 (14.243-25.084) | 20.265 (4.985) |
| VIE | 18 | 17.078 (15.084-19.594) | 17.930 (3.944) |
| AFP | | | |
| Controls | 65 | 3.000 (2.090-3.980) | 3.233 (1.499) |
| All HCC | 309 | 33.550 (5.425-461.25) | 9301 (42540) |
| Very early HCC | 26 | 8.900 (3.550-8.900) | 144.5 (365.8) |
| Early HCC | 78 | 13.650 (5.425-205.0) | 890.3 (2542) |
| Advanced HCC | 197 | 80.50 (6.870-1164) | 14169 (52590) |
| AFP-negative HCC | 137 | 4.6 (3.0-7.818) | 6.040 (4.361) |
| SHG | 170 | 30.90 (4.750-460.0) | 10387 (49991) |
| HK | 99 | 134.0 (10.00-1930) | 11025 (36343) |
| BRN | 21 | 8.60 (3.60-100.8) | 310.0 (1020) |
| VIE | 18 | 6.164 (2.001-42.57) | 59.24 (153.3) |

HCC, hepatocellular carcinoma.
AFP, α-fetoprotein.
IQR, inter-quartile range.
S.d., standard deviation.
SHG, Shanghai.
HK, Hong Kong.
BRN, Brno.
VIE, Vienna.

Additional Table 5 (Supporting Table 3): sAXL and AFP Serum Concentrations of the Study Population Additional Table 5 corresponds to Table 5 with the exception that median and mean values for cirrhotic controls were added.

Supporting Information Table S3: sAxl and AFP serum concentrations of the study population

| | Number of cases | Median (IQR) ng/mL | Mean (s.d.) ng/mL |
|---|---|---|---|
| sAxl | | | |
| Healthy controls | 125 | 13.388 (9.811-15.663) | 12.834 (4.781) |
| Liver cirrhosis | 30 | 12.169 (9.345-15.542) | 12.550 (3.708) |
| All HCC | 311 | 18.575 (14.316-23.045) | 19.079 (6.456) |
| Very early HCC | 26 | 18.064 (14.385-22.623) | 19.779 (7.881) |
| Early HCC | 78 | 16.438 (13.357-23.808) | 18.617 (7.754) |
| Advanced HCC | 200 | 18.880 (14.666-22.889) | 19.144 (5.771) |
| AFP-negative HCC | 137 | 17.231 (13.855-21.380) | 18.112 (6.463) |
| SHG | 171 | 16.820 (13.216-22.130) | 18.250 (7.255) |
| HK | 100 | 20.027 (16.815-24.148) | 20.443 (4.985) |
| BRN | 22 | 19.952 (14.243-25.084) | 20.265 (4.985) |
| VIE | 18 | 17.078 (15.084-19.594) | 17.930 (3.944) |
| AFP | | | |
| Healthy controls | 65 | 3.000 (2.090-3.980) | 3.233 (1.499) |
| Liver cirrhosis | 30 | 4.600 (2.950-4.600) | 7.037 (6.646) |
| All HCC | 309 | 33.550 (5.425-461.25) | 9301 (42540) |
| Very early HCC | 26 | 8.900 (3.550-8.900) | 144.5 (365.8) |
| Early HCC | 78 | 13.650 (5.425-205.0) | 890.3 (2542) |
| Advanced HCC | 197 | 80.50 (6.870-1164) | 14169 (52590) |
| AFP-negative HCC | 137 | 4.6 (3.0-7.818) | 6.040 (4.361) |
| SHG | 170 | 30.90 (4.750-460.0) | 10387 (49991) |
| HK | 99 | 134.0 (10.00-1930) | 11025 (36343) |
| BRN | 21 | 8.60 (3.60-100.8) | 310.0 (1020) |
| VIE | 18 | 6.164 (2.001-42.57) | 59.24 (153.3) |

HCC, hepatocellular carcinoma.
AFP, α-fetoprotein.
IQR, inter-quartile range.
S.d., standard deviation.
SHG, Shanghai.
HK, Hong Kong.
BRN, Brno.
VIE, Vienna.

References for the following tables: Greene F. L. (2002) AJCC cancer staging manual, 6th edn. Springer, 435p; Bruix J. (2011) American Association for the Study of Liver Diseases. http://www.aasld.org/practiceguidelines 2011; O'Neil B. H., (2007) Oncologist 12:1425-1432.

| TNM stage | I | II | IIIA | IIIB | IIIC | IV | Missing | Total |
|---|---|---|---|---|---|---|---|---|
| SHG | 101 | 34 | 29 | 0 | 5 | 2 | 0 | 171 |
| HK | 41 | 14 | 6 | 0 | 33 | 4 | 2 | 100 |
| BRN | 8 | 2 | 7 | 0 | 2 | 3 | 0 | 22 |
| VIE | 4 | 12 | 2 | 0 | 0 | 0 | 0 | 18 |
| Total | 154 | 62 | 44 | 0 | 40 | 9 | 2 | 311 |

SHG, Shanghai.
HK., Hongkong.
BRN, Brno.
VIE, Vienna.
TNM status of HCC patient cohorts.

| | BCLC0 | BCLCA | BCLC > A | Missing | Total |
|---|---|---|---|---|---|
| SHG | 15 | 51 | 101 | 4 | 171 |
| HK | 9 | 20 | 69 | 2 | 100 |
| BRN | 0 | 4 | 17 | 1 | 22 |
| VIE | 2 | 3 | 13 | 0 | 18 |
| Total | 26 | 78 | 200 | 7 | 311 |

BCLC, Barcelona Clinic Liver Cancer.
SHG, Shanghai.
HK., Hongkong.
BRN, Brno.
VIE, Vienna.
BCLC status of HCC patient cohorts.

AFP in Very Early and Early HCC (See Table Below)

| AFP | Number of cases | % AFP-negative | Median (IQR) ng/mL | Mean (s.d.) ng/mL |
|---|---|---|---|---|
| Controls | 65 | 100 | 3.000 (2.090-3.980) | 3.233 (1.499) |
| All HCC | 309 | 44.7 | 33.550 (5.425-461.25) | 9301 (42540) |
| Very early HCC | 26 | 57.7 | 8.900 (3.550-8.900) | 144.5 (365.8) |
| Early HCC | 78 | 53.8 | 13.650 (5.425-205.0) | 890.3 (2542) |
| Advanced HCC | 197 | 38.6 | 80.50 (6.870-1164) | 14169 (52590) |
| AFP-negative HCC | 137 | 100 | 4.6 (3.0-7.818) | 6.040 (4.361) |
| SHG | 170 | 45.9 | 30.90 (4.750-460.0) | 10387 (49991) |
| HK | 99 | 35.4 | 134.0 (10.00-1930) | 11025 (36343) |
| BRN | 21 | 57.1 | 8.60 (3.60-100.8) | 310.0 (1020) |
| VIE | 18 | 66.7 | 6.164 (2.001-42.57) | 59.24 (153.3) |

HCC, hepatocellular carcinoma.
AFP, alpha fetoprotein.
IQR, inter-quartile range.
S.d., standard deviation.
SHG, Shanghai.
HK, Hongkong.
BRN, Brno.
VIE, Vienna.
AFP-negative was defined as <20 ng/mL.
AFP status of HCC patients and controls

EXAMPLE 2: SAXL IN THE DIFFERENTIAL DIAGNOSIS OF CHRONIC LIVER DISEASE

Long-term exposure to hepatotoxins such as alcohol, sustained fat rich diet leading to obesity or chronic viral infection cause hepatitis and non-alcoholic steatohepatitis which can frequently progress to fibrosis and cirrhosis, commonly designated as chronic liver disease (CLD). The risk of developing hepatocellular carcinoma (HCC) increases during CLD progression.

Herein sAxl levels in various etiologies of CLD were determined in order to assess whether sAxl levels allow accurate differential diagnosis of HCC versus autoimmune hepatitis (AI hepatitis), infection with hepatitis B virus (HBV), non-alcoholic fatty liver disease/non-alcoholic steatohepatitis (NAFLD/NASH), cystic fibrosis (CF), primary sclerosing cholangitis (PSC) and primary biliary cirrhosis (PBC). Thus, sAxl levels in serum samples of 264 patients suffering on chronic liver disease (CLD) versus HCC were analyzed.

Materials and Methods
sAXL

The ELISA kit used in the studies herein for the analysis of sAXL was not validated in the prior art for analysis of serum samples, and no recommendation for dilution of serum is given in the manual provided. However, the ELISA Development Guide, available through the manufacturer's website advises "to dilute serum and plasma samples [ . . . ] at least 2-fold in an appropriate buffer to overcome matrix effects". The human Axl DuoSet ELISA kit, Catalog Number: DY154, Lot Number 1285322 (using a standard: 130 ng/ml) was employed herein, for example, for dilution studies. For further studies (see FIG. 11, FIG. 16) a standard with 150 ng/ml was used (Lot Number changed to 134007).

In the course of assay establishment, the current literature was consulted, most notably Ekman et al. (2010), who had previously determined sAxl concentrations in serum by ELISA at tenfold dilution (see Ekman et al. Clinical biochemistry. 2010; 43(10-11):873-6). This approach was followed herein and the measured sAxl concentrations were well within the linear portion of the standard curve; see FIG. 14.

Animal serum is recommended as a possible diluent in the manufacturer's manual. Therefore the same samples and standards diluted 1:10 in PBS supplemented with 1% bovine serum albumin (BSA) and in PBS with 5% fetal calf serum (FCS) were assayed and compared. The obtained concentrations for BSA (15.023 ng/mL) and FCS (15.51 ng/mL) were very comparable and in order to avoid artefacts from inter-batch variability, we decided to use 1% BSA as a dilution buffer; see FIG. 15.

Despite the manufacturer's recommendations, further dilution experiments revealed a matrix-effect at ten-fold dilution. Linearity of dilution was achieved at 1:50 resulting in a shift of measured analyte concentrations; see, for illustrative purposes, FIG. 16. FIG. 16 shows the increase of sAxl using serum dilutions of 1:10, 1:20, 1:50 and 1:100. The analyzed samples were obtained from two healthy persons. In light of these more refined analyses, a dilution of 1:50 was chosen in the experiments below and in the stability tests disclosed in Example 3.

Since the unbiased concentration would still be within the linear portion of the standard curve at a 1:10 dilution, it is concluded that matrix effects such as heterophile antibodies may affect the assay (Tate and Ward; Interferences in immunoassay. The Clinical biochemist Reviews/Australian Association of Clinical Biochemists. 2004; 25(2):105-20.). The resulting shift of sAxl concentrations seems to be proportional and sAxl ratios between healthy individuals and HCC patients remain constant at both 1:10 and 1:50 dilutions.

Interestingly, no matrix effect was observed for AFP by ELISA. AFP concentrations were determined by ELISA in 16 sera of patients with cystic fibrosis, diluted 1:10, 1:20 and 1:50 in PBS supplemented with 1% BSA. In 12 out of 16 cases, AFP levels were below the detection threshold (0.1 ng/mL). For the remaining samples, (n=4), differences between dilutions were non-significant; see FIG. 17. Data are expressed as mean±SD. From these data it is concluded that no matrix effect occurs for AFP by ELISA.

ELISAs were performed by two independent researchers. They had no access to patients' clinical data. For detection of sAxl levels in sera of healthy controls (n=28) or HCC (n=20), NAFLD/NASH (n=78), CF (n=31), AI hepatitis (n=28), alcohol abuse (n=6), HBV (n=12), PBC (n=15), PSC (n=25), fibrosis (n=92) and cirrhosis (n=13) patients, samples were diluted 1:50 in phosphate buffered saline supplemented with 1% bovine serum albumin (FIG. 11). ELISAs for detection and comparison of sAxl in human body fluids (serum, saliva, urine; FIG. 12) of one health volunteer were carried out at a dilution of 1:10 in phosphate buffered saline supplemented with 1% bovine serum albumin. A seven point, 4 parameter logistic standard curve using 2-fold dilutions of recombinant human Axl (R&D Systems Inc., USA) was generated for every plate, confirming a dynamic range from 62.5 pg/mL to 4000 pg/mL. Quantification was performed with the GraphPad Prism 5.0 software (GraphPad Software, USA). Data from multiple patients (FIG. 11) are expressed as the median value with interquartile ranges. Data from one single volunteer (FIG. 12) are expressed as mean±s.d.

AFP

In a majority of cases, AFP concentrations were determined externally in the respective clinical facilities at the time of diagnosis by validated methods, approved by regulatory authorities. In the case of missing data (n=16), AFP values were determined or re-evaluated in-house by ELISA (R&D Systems Inc., USA).

In contrast to the assay used in Example 1, the serum sample was diluted 1:50. As the following table shows, the results confirm the increase of sAXL in patient samples compared to control (e.g. samples from healthy persons).

| Dilution | Healthy Controls (IQR) | All HCC Patients (IQR) | HCC/Healthy (IQR) |
|---|---|---|---|
| 1:10 | 13.388 (9.811-15.663) | 18.575 (14.316-23.045) | 1.39 (1.07-1.72) |
| 1:50 | 38.328 (30.670-43.653) | 63.437 (38.135-81.038) | 1.66 (0.99-2.11) |

The data obtained by using a 1:10 and 1:50 dilution, respectively, can be converted as follows. According to current data, two methods of conversion are conceivable by regression analysis:

3. A simple conversion factor, yielding a Pearson-correlation of R=0.941

$C_{1l50}=C_{1l10}*3.2264=$

4. A linear equation, resulting in a Pearson-correlation of R=1

$C_{1l80}=C_{1l10}*4.8408-26.48$

Results sAxl in the Differential Diagnosis of Chronic Liver Disease

Remarkably, sAxl was not significantly increased in AI hepatitis (median 41.99 ng/mL, n=28), chronic alcohol intoxication (median 41.96 ng/mL, n=6), CF (median 45.21 ng/mL, n=31), HBV (median 40.29 ng/mL, n=12), NAFLD/NASH (median 47.11 ng/mL, n=78), PBC (median 34.03 ng/mL, n=15) and PSC (median 36.03 ng/mL, n=25) as compared to healthy control (median 38.33 ng/mL, n=28) (FIG. 11A). As expected, sAxl levels were significantly elevated in HCC (median 63.44 ng/mL, n=20) as compared to healthy control.

Stratification of CLD subgroups into fibrotic and cirrhotic patients further revealed that sAxl levels are not significantly elevated in fibrosis (median 40.32 ng/mL, n=92,) and cirrhosis (median 47.11 ng/mL, n=13) as compared to healthy control (median 38.33 ng/mL, n=28) (FIG. 11B).

From these data it is concluded that sAxl exhibits a high diagnostic accuracy for HCC patients without recognizing other CLDs.

Further, it was analyzed whether sAxl is elevated not only in HCC but also in another type liver cancer termed cholangiocellular carcinoma (CCC). CCC derives from cholangiocytes and accounts for about 10% of all liver cancers. Analysis of serum samples from CCC patients revealed that sAxl is not significantly increased (median 32.73 ng/mL, n=21) as compared to healthy (median 38.33 ng/mL, n=28) or fibrotic (median 40.32 ng/mL, n=92,) or cirrhotic controls (median 47.11 ng/mL, n=13) (FIG. 11B).

Additionally, the analysis of sAxl values of CCC patients was extended to a total patient number of 40 (n=40). It was confirmed that sAxl is not increased in CCC patients; see FIG. 11C.

sAxl can be Detected in Urine and Saliva

As shown herein above, sAxl can be detected in serum and plasma samples of patients. Therefore, it was assessed whether sAxl can be determined by ELISA in other body fluids such as urine and saliva which would be of relevance for routine screening of sAXL levels in CLD patients. As samples of urine and saliva from CLD patients were not available, urine and saliva from one healthy donor was analyzed using the ELISA assay described in Example 1, including a 1:10 dilution of the sample. Interestingly, sAxl can be significantly detected in both urine and saliva. Noteworthy, sAxl is detected at a higher level in urine (median 34.03 ng/mL) as compared to serum (median 14.77 ng/mL) (FIG. 12A) while sAxl is lower in saliva (median 0.375 ng/mL) (FIG. 12B). As an exceptional deviation, the serum median value of 14.77 ng/ml is higher than that determined in Example 1 in relation to healthy controls (13.388 ng/ml). Yet, the median value of 14.77 ng/ml is still lower compared to values of HCC patients (18.575 for all HCC patients).

EXAMPLE 3: SAXL IS STABLE IN SERUM SAMPLES

A study was performed in order to validate the stability of sAxl for routine analytical procedures by partially following ICH Q2 quality control guidelines. As handling of serum samples is of paramount importance for the accuracy of a diagnostic biomarker, it was analyzed whether sAxl is a stable biomarker that is not rapidly degraded after taking blood and generating the serum of patients. Therefore, the stability of sAxl in serum samples of HCC patients after a certain number of freeze and thaw cycles with subsequent storage at 4° C. for up to 14 days was determined. The ELISA measurements were performed as set out in Example 2 with the exception that a standard with 150 ng/ml was used (Lot Number changed to 134007). Analysis of 3 representative serum samples of HCC patients showed that sAxl levels do not significantly decrease even after 10 freeze and thaw cycle and storage for 14 days (FIG. 13A-C). These data suggest that sAxl is stable even under stress conditions and can be employed for routine clinical use as well as for retrospective test replications.

The present invention refers to the following nucleotide and amino acid sequences:

The sequences provided herein are available in the NCBI database and can be retrieved from www.ncbi.nlm.nih.gov/sites/entrez?db=gene; Theses sequences also relate to annotated and modified sequences. Usually, the RNA sequence is shown as cDNA sequence in the NCBI database (see, for example, SEQ ID No. 1, 5 and 7). The present invention also provides techniques and methods wherein homologous sequences, and variants of the concise sequences provided herein are used. Preferably, such "variants" are genetic variants.

REFERENCES

1. Ferlay J, Shin H R, Bray F, Forman D, Mathers C, Parkin D M. Estimates of worldwide burden of cancer in 2008: GLOBOCAN 2008. *International journal of cancer Journal international du cancer* 2010; 127:2893-917.
2. Llovet J M, Bustamante J, Castells A, et al. Natural history of untreated nonsurgical hepatocellular carcinoma: rationale for the design and evaluation of therapeutic trials. *Hepatology* 1999; 29:62-7.
3. Singal A G, Marrero J A. Recent advances in the treatment of hepatocellular carcinoma. *Current opinion in gastroenterology* 2010; 26:189-95.
4. Altekruse S F, McGlynn K A, Reichman M E. Hepatocellular carcinoma incidence, mortality, and survival trends in the United States from 1975 to 2005. *Journal of clinical oncology: official journal of the American Society of Clinical Oncology* 2009; 27:1485-91.
5. Singal A, Volk M L, Waljee A, et al. Meta-analysis: surveillance with ultrasound for early-stage hepatocellular carcinoma in patients with cirrhosis. *Alimentary pharmacology & therapeutics* 2009; 30:37-47.
6. Paul S B, Gulati M S, Sreenivas V, et al. Evaluating patients with cirrhosis for hepatocellular carcinoma: value of clinical symptomatology, imaging and alpha-fetoprotein. *Oncology* 2007; 72 Suppl 1:117-23.
7. Marrero J A, Feng Z, Wang Y, et al. Alpha-fetoprotein, des-gamma carboxyprothrombin, and lectin-bound alpha-fetoprotein in early hepatocellular carcinoma. *Gastroenterology* 2009; 137:110-8.
8. Durazo F A, Blatt L M, Corey W G, et al. Des-gamma-carboxyprothrombin, alpha-fetoprotein and AFP-L3 in patients with chronic hepatitis, cirrhosis and hepatocellular carcinoma. *Journal of gastroenterology and hepatology* 2008; 23:1541-8.

9. Shen Q, Fan J, Yang X R, et al. Serum DKK1 as a protein biomarker for the diagnosis of hepatocellular carcinoma: a large-scale, multicentre study. *The lancet oncology* 2012; 13:817-26.
10. Carr B I, Kanke F, Wise M, Satomura S. Clinical evaluation of lens culinaris agglutinin-reactive alpha-fetoprotein and des-gamma-carboxy prothrombin in histologically proven hepatocellular carcinoma in the United States. *Digestive diseases and sciences* 2007; 52:776-82.
11. El-Serag H B, Davila J A. Surveillance for hepatocellular carcinoma: in whom and how? *Therapeutic advances in gastroenterology* 2011; 4:5-10.
12. Pinato D J, Mauri F A, Lloyd T, et al. The expression of AXL receptor tyrosine kinase influences the tumour phenotype and clinical outcome of patients with malignant pleural mesothelioma. *British journal of cancer* 2013; 108:621-8.
13. Gjerdrum C, Tiron C, Hoiby T, et al. AXL is an essential epithelial-to-mesenchymal transition-induced regulator of breast cancer metastasis and patient survival. *Proceedings of the National Academy of Sciences of the United States of America* 2010; 107:1124-9.
14. Ishikawa M, Sonobe M, Nakayama E, et al. Higher Expression of Receptor Tyrosine Kinase AXL, and Differential Expression of its Ligand, Gas6, Predict Poor Survival in Lung Adenocarcinoma Patients. *Annals of surgical oncology* 2012; Epub ahead of print.
15. Linger R M, Keating A K, Earp H S, Graham D K. Taking aim at Mer and AXL receptor tyrosine kinases as novel therapeutic targets in solid tumors. *Expert opinion on therapeutic targets* 2010; 14:1073-90.
16. Korshunov V A. AXL-dependent signalling: a clinical update. *Clin Sci* (Loud) 2012; 122:361-8.
17. O'Bryan J P, Fridell Y W, Koski R, Varnum B, Liu E T. The transforming receptor tyrosine kinase, AXL, is post-translationally regulated by proteolytic cleavage. *The Journal of biological chemistry* 1995; 270:551-7.
18. Weinger J G, Omani K M, Marsden K, Raine C S, Shafit-Zagardo B. Up-regulation of soluble AXL and Mer receptor tyrosine kinases negatively correlates with Gas6 in established multiple sclerosis lesions. *The American journal of pathology* 2009; 175:283-93.
19. Ekman C, Stenhoff J, Dahlback B. Gas6 is complexed to the soluble tyrosine kinase receptor AXL in human blood. *Journal of thrombosis and haemostasis: JTH* 2010; 8:838-44.
20. Llovet J M, Bru C, Bruix J. Prognosis of hepatocellular carcinoma: the BCLC staging classification. *Seminars in liver disease* 1999; 19:329-38.
21. Tsou A P, Wu K M, Tsen T Y, et al. Parallel hybridization analysis of multiple protein kinase genes: identification of gene expression patterns characteristic of human hepatocellular carcinoma. *Genomics* 1998; 50:331-40.
22. Giannelli G, Bergamini C, Fransvea E, Marinosci F, Quaranta V, Antonaci S. Human hepatocellular carcinoma (HCC) cells require both alpha3beta1 integrin and matrix metalloproteinases activity for migration and invasion. *Laboratory investigation; a journal of technical methods and pathology* 2001; 81:613-27.
23. Kim J R, Kim C H. Association of a high activity of matrix metalloproteinase-9 to low levels of tissue inhibitors of metalloproteinase-1 and -3 in human hepatitis B-viral hepatoma cells. *The international journal of biochemistry & cell biology* 2004; 36:2293-306.
24. Gustafsson A, Martuszewska D, Johansson M, et al. Differential expression of AXL and Gas6 in renal cell carcinoma reflecting tumor advancement and survival. *Clinical cancer research: an official journal of the American Association for Cancer Research* 2009; 15:4742-9.
25. Ekman C, Site D F, Gottsater A, Lindblad B, Dahlback B. Plasma concentrations of growth arrest specific protein 6 and the soluble form of its tyrosine kinase receptor AXL as markers of large abdominal aortic aneurysms. *Clinical biochemistry* 2010; 43:110-4.
26. Tzeng C W, Aloia T A. Colorectal liver metastases. *Journal of gastrointestinal surgery: official journal of the Society for Surgery of the Alimentary Tract* 2013; 17:195-201; quiz p-2.
27. Lin S, Hoffmann K, Schemmer P. Treatment of Hepatocellular Carcinoma: A Systematic Review. *Liver cancer* 2012; 1:144-58.
28. Asiedu M K, Beauchamp-Perez F D, Ingle J N, Behrens M D, Radisky D C, Knutson K L. AXL induces epithelial-to-mesenchymal transition and regulates the function of breast cancer stem cells. *Oncogene* 2013; Epub ahead of print.
29. van Zijl F, Zulehner G, Petz M, et al. Epithelial-mesenchymal transition in hepatocellular carcinoma. *Future Oncol* 2009; 5:1169-79.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A method for treating a human patient suspected of having a liver tumor, said method comprising the steps of:
   (a) testing a sample of the patient having or suspected of having a liver tumor, the sample comprising a bodily fluid of the patient, to determine whether the sample has an elevated level of soluble extracellular domain of AXL (soluble extracellular sAXL) in comparison to a control;
   (b) administering a liver cancer therapy to the patient whose bodily fluid was determined to have an elevated level of sAXL in step (a).

2. The method of claim 1, the amount of said soluble AXL and/or control being determined by ELISA, Sandwich ELISA, immunohistochemistry (IHC), immunoassay, gel- or blot-based methods, IHC, mass spectrometry, flow cytometry, or FACS.

3. The method of claim 1, the patient having hepatocellular carcinoma.

4. The method of claim 1, said patient having been determined to have an elevated serum level of soluble AXL of at least 14 ng/ml.

5. The method of claim 3, said hepatocellular carcinoma being stage 0 hepatocellular carcinoma.

6. The method of claim 4, said elevated serum level being about 18 ng/ml.

7. The method of claim 3, said hepatocellular carcinoma being stage A hepatocellular carcinoma.

8. The method of claim 4 said elevated serum level of soluble AXL being about 16 ng/ml.

9. The method of claim 3, said hepatocellular carcinoma being stage B, C or D hepatocellular carcinoma.

10. The method of claim 4, said elevated serum level of soluble AXL being higher than 18 ng/ml.

11. The method of claim 4, the serum level of soluble AXL in the control being about 13 ng/ml.

12. The method of claim 1, the bodily fluid comprising blood.

13. The method of claim 1, the bodily fluid comprising plasma.

14. The method of claim 1, the bodily fluid comprising serum.

15. The method of claim 14, the serum sample of said patient having been determined to have an amount of alpha-fetoprotein (AFP) higher than 20 ng/ml.

16. The method of claim 1, the sAXL being:
   (i) a soluble extracellular sAXL encoded by a nucleic acid molecule having the nucleic acid sequence as depicted in SEQ ID NO: 3;
   (ii) soluble extracellular soluble sAXL as depicted in SEQ ID NO:4;
   (iii) soluble extracellular sAXL encoded by a nucleic acid molecule encoding a peptide having an amino acid sequence as depicted in SEQ ID NO:4;
   (iv) soluble extracellular sAXL encoded by a nucleic acid molecule hybridizing under stringent conditions to the complementary strand of nucleic acid molecules as defined in (i) or (iii);
   (v) soluble extracellular sAXL that is at least 90% identical to the sAXL of any one of (i) to (iv); or
   (vi) soluble extracellular sAXL encoded by a nucleic acid molecule being degenerate as a result of the genetic code to the nucleotide sequence of a nucleic acid molecule as defined in (i), (iii) or (iv).

* * * * *

```
SEQUENCE LISTING

<160> NUMBER OF SEQ ID NOS: 9

<210> SEQ ID NO 1
<211> LENGTH: 4750
<212> TYPE: DNA
<213> ORGANISM: Homo sapiens

<400> SEQUENCE: 1
gtgagggaag gaggcagggg tgctgagaag gcggctgctg ggcagagccg gtggcaaggg      60 cctccectgc cgctgtgcca ggcaggcagt gccaaatccg gggagcctgg agctggggg     120 agggccgggg acagcccggc cctgccccct ccccgctgg gagcccaaca acttctgagg     180
aaagtttggc acccatggcg tggcggtgcc ccaggatggg cagggtcccg ctggcctggt     240
gcttggcgct gtgcggctgg gcgtgcatgg cccccagggg cacgcaggct gaagaaagtc     300
```

```
ccttcgtggg caacccaggg aatatcacag gtgcccgggg actcacgggc acccttcggt    360
gtcagctcca ggttcaggga gagcccccg aggtacattg gcttcgggat ggacagatcc     420
tggagctcgc ggacagcacc cagacccagg tgccctggg tgaggatgaa caggatgact     480
ggatagtggt cagccagctc agaatcacct ccctgcagct ttccgacacg ggacagtacc    540
agtgtttggt gtttctggga catcagacct tcgtgtccca gcctggctat gttgggctgg    600
agggcttgcc ttacttcctg gaggagcccg aagacaggac tgtggccgcc aacccccct    660 tcaacctgag ctgccaagct cagggacccc cagagcccgt ggacctactc tggctccagg    720
atgctgtccc cctggccacg gctccaggtc acggccccca gcgcagcctg catgttccag    780
ggctgaacaa gacatcctct ttctcctgcg aagcccataa cgccaagggg gtcaccacat    840
cccgcacagc caccatcaca gtgctccccc agcagcccg taacctccac ctggtctccc     900
gccaacccac ggagctggag gtggcttgga ctccaggcct gagcggcatc taccccctga    960
cccactgcac cctgcaggct gtgctgtcag acgatgggat gggcatccag gcgggagaac    1020
cagacccccc agaggagccc ctcacctcgc aagcatccgt gccccccat cagcttcggc     1080 taggcagcct ccatcctcac accccttatc acatccgcgt ggcatgcacc agcagccagg    1140
gcccctcatc ctggacccac tggcttcctg tggagacgcc ggagggagtg cccctgggcc    1200
cccctgagaa cattagtgct acgcggaatg ggagccaggc cttcgtgcat ggcaagagc     1260 cccgggcgcc cctgcagggt accctgttag ggtaccggct ggcgtatcaa ggccaggaca    1320
ccccagaggt gctaatggac ataggctaa ggcaagaggt gaccctggag ctgcaggggg     1380
acgggtctgt gtccaatctg acagtgtgtg tggcagccta cactgctgct ggggatggac    1440
cctggagcct cccagtaccc ctggaggcct ggcgcccagg gcaagcacag ccagtccacc    1500
agctggtgaa ggaaccttca actcctgcct tctcgtggcc ctggtggtat gtactgctag    1560
gagcagtcgt ggccgctgcc tgtgtcctca tcttggctct cttccttgtc caccggcgaa    1620
agaaggagac ccgttatgga gaagtgtttg aaccaacagt ggaaagaggt gaactggtag    1680
tcaggtaccg cgtgcgcaag tcctacagtc gtcggaccac tgaagctacc ttgaacagcc    1740
tgggcatcag tgaagagctg aaggagaagc tgcgggatgt gatggtggac cggcacaagg    1800
tggccctggg gaagactctg ggagagggag agtttggagc tgtgatggaa ggccagctca    1860
accaggacga ctccatcctc aaggtggctg tgaagacgat gaagattgcc atctgcacga    1920
ggtcagagct ggaggatttc ctgagtgaag cggtctgcat gaaggaattt gaccatccca    1980
acgtcatgag gctcatcggt gtctgtttcc agggttctga acgagagagc ttcccagcac    2040
ctgtggtcat cttacctttc atgaaacatg gagacctaca cagcttcctc ctctattccc    2100 ggctcggga ccagccagtg tacctgccca ctcagatgct agtgaagttc atggcagaca    2160
tcgccagtgg catggagtat ctgagtacca agagattcat caccgggac ctggcggcca    2220 ggaactgcat gctgaatgag aacatgtccg tgtgtgtggc ggacttcggg ctctccaaga    2280
agatctacaa tgggactac taccgccagg acgtatcgc caagatgcca gtcaagtgga    2340
ttgccattga gagtctagct gaccgtgtct acaccagcaa gagcgatgtg tggtccttcg    2400
gggtgacaat gtgggagatt gccacaagag gccaaacccc atatccgggc gtggagaaca    2460
gcgagattta tgactatctg cgccagggaa atcgcctgaa gcagcctgcg gactgtctgg    2520
atggactgta tgccttgatg tcgcggtgct gggagctaaa tcccaggac cggccaagtt     2580 ttacagagct gcgggaagat ttggagaaca cactgaaggc cttgcctcct gcccaggagc    2640
```

| | | |
|---|---|---|
| ctgacgaaat cctctatgtc aacatggatg agggtggagg ttatcctgaa ccccctggag | | 2700 |
| ctgcaggagg agctgacccc ccaacccagc cagaccctaa ggattcctgt agctgcctca | | 2760 |
| ctgcggctga ggtccatcct gctggacgct atgtcctctg cccttccaca acccctagcc | | 2820 |
| ccgctcagcc tgctgatagg ggctccccag cagccccagg gcaggaggat ggtgcctgag | | 2880 |
| acaaccctcc acctggtact ccctctcagg atccaagcta agcactgcca ctggggaaaa | | 2940 |
| ctccaccttc ccactttccc accccacgcc ttatccccac ttgcagccct gtcttcctac | | 3000 |
| ctatcccacc tccatcccag acaggtccct cccttctct gtgcagtagc atcaccttga | | 3060 |
| aagcagtagc atcaccatct gtaaaaggaa ggggttggat tgcaatatct gaagccctcc | | 3120 |
| caggtgttaa cattccaaga ctctagagtc caaggtttaa agagtctaga ttcaaaggtt | | 3180 |
| ctaggtttca aagatgctgt gagtctttgg ttctaaggac ctgaaattcc aaagtctcta | | 3240 |
| attctattaa agtgctaagg ttctaaggcc tacttttttt ttttttttt tttttttttt | | 3300 |
| ttttgcgata gagtctcact gtgtcaccca ggctggagtg cagtggtgca atctcgcctc | | 3360 |
| actgcaacct tcacctaccg agttcaagtg attttcctgc cttggcctcc caagtagctg | | 3420 |
| ggattacagg tgtgtgccac cacacccggc taattttat attttagta gagacagggt | | 3480 |
| ttcaccatgt tggccaggct ggtctaaaac tcctgacctc aagtgatctg cccacctcag | | 3540 |
| cctcccaaag tgctgagatt acaggcatga gccactgcac tcaaccttaa gacctactgt | | 3600 |
| tctaaagctc tgacattatg tggttttaga ttttctggtt ctaacatttt tgataaagcc | | 3660 |
| tcaaggtttt aggttctaaa gttctaagat tctgatttta ggagctaagg ctctatgagt | | 3720 |
| ctagatgttt attcttctag agttcagagt ccttaaaatg taagattata gattctaaag | | 3780 |
| attctatagt tctagacatg gaggttctaa ggcctaggat tctaaaatgt gatgttctaa | | 3840 |
| ggctctgaga gtctagattc tctggctgta aggctctaga tcataaggct tcaaaatgtt | | 3900 |
| atcttctcaa gttctaagat tctaatgatg atcaattata gtttctgagg ctttatgata | | 3960 |
| atagattctc ttgtataaga tcctagatcc taagggtcga aagctctaga atctgcaatt | | 4020 |
| caaaagttcc aagagtctaa agatggagtt tctaaggtcc ggtgttctaa gatgtgatat | | 4080 |
| tctaagactt actctaagat cttagattct ctgtgtctaa gattctagat cagatgctcc | | 4140 |
| aagattctag atgattaaat aagattctaa cggtctgttc tgtttcaagg cactctagat | | 4200 |
| tccattggtc caagattccg gatcctaagc atctaagtta taagactctc acactcagtt | | 4260 |
| gtgactaact agacaccaaa gttctaataa tttctaatgt tggacacctt taggttctt | | 4320 |
| gctgcattct gcctctctag gaccatggtt aagagtccaa gaatccacat ttctaaaatc | | 4380 |
| ttatagttct aggcactgta gttctaagac tcaaatgttc taagtttcta agattctaaa | | 4440 |
| ggtccacagg tctagactat taggtgcaat ttcaaggttc taaccctata ctgtagtatt | | 4500 |
| ctttggggtg ccctctcct tcttagctat cattgcttcc tcctcccaa ctgtgggggt | | 4560 |
| gtgccccctt caagcctgtg caatgcatta gggatgcctc cttccccgca ggggatggac | | 4620 |
| gatctcccac ctttcgggcc atgttgcccc cgtgagccaa tccctcacct tctgagtaca | | 4680 |
| gagtgtggac tctggtgcct ccagaggggc tcaggtcaca taaaactttg tatatcaacg | | 4740 |
| agaaaaaaaa | | 4750 |

<210> SEQ ID NO 2
<211> LENGTH: 894
<212> TYPE: PRT
<213> ORGANISM: Homo sapiens

<400> SEQUENCE: 2

-continued

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
            85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
            165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
            245                 250                 255

His Cys Thr Leu Gln Ala Val Leu Ser Asp Asp Gly Met Gly Ile Gln
        260                 265                 270

Ala Gly Glu Pro Asp Pro Pro Glu Glu Pro Leu Thr Ser Gln Ala Ser
    275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
            325                 330                 335

Pro Glu Asn Ile Ser Ala Thr Arg Asn Gly Ser Gln Ala Phe Val His
        340                 345                 350

Trp Gln Glu Pro Arg Ala Pro Leu Gln Gly Thr Leu Leu Gly Tyr Arg
    355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
            405                 410                 415
```

```
Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
            435                 440                 445

Pro Trp Trp Tyr Val Leu Leu Gly Ala Val Ala Ala Ala Cys Val
        450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
            530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Arg Gly Asn Arg Leu
            755                 760                 765

Lys Gln Pro Ala Asp Cys Leu Asp Gly Leu Tyr Ala Leu Met Ser Arg
770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
```

```
                835                 840                 845
Lys Asp Ser Cys Ser Cys Leu Thr Ala Ala Glu Val His Pro Ala Gly
            850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
            885                 890
```

<210> SEQ ID NO 3
<211> LENGTH: 1321
<212> TYPE: DNA
<213> ORGANISM: Homo sapiens

<400> SEQUENCE: 3

```
atggcgtggc ggtgcccag gatgggcagg gtcccgctgg cctggtgctt ggcgctgtgc      60
ggctgggcgt gcatggcccc caggggcacg caggctgaag aaagtccctt cgtgggcaac     120
ccagggaata tcacaggtgc ccggggactc acgggcaccc ttcggtgtca gctccaggtt     180
cagggagagc cccccgaggt acattggctt cgggatggac agatcctgga gctcgcggac    240
agcacccaga cccaggtgcc cctgggtgag atgaacagg atgactggat agtggtcagc     300
cagctcagaa tcacctccct gcagctttcc gacacgggac agtaccagtg tttggtgttt    360
ctgggacatc agaccttcgt gtcccagcct ggctatgttg ggctggaggg cttgccttac    420
ttcctggagg agcccgaaga caggactgtg gccgccaaca ccccccttcaa cctgagctgc   480
caagctcagg accccagca gcccgtggac ctactctggc tccaggatgc tgtcccctg      540
gccacggctc caggtcacgg ccccagcgc agcctgcatg ttccagggct gaacaagaca    600
tcctctttct cctgcgaagc ccataacgcc aagggggtca ccacatcccg cacagccacc   660
atcacagtgc tcccccagca gccccgtaac ctccacctgg tctcccgcca acccacggag    720
ctggaggtgg cttggactcc aggcctgagc ggcatctacc ccctgaccca ctgcaccctg   780
caggctgtgc tgtcagacga tgggatgggc atccaggcgg gagaaccaga ccccccagag   840
gagcccctca cctcgcaagc atccgtgccc cccatcagc ttcggctagg cagcctccat     900
cctcacaccc cttatcacat ccgcgtggca tgcaccagca gccagggccc ctcatcctgg    960
acccactggc ttcctgtgga gacgccggag ggagtgcccc tgggccccc tgagaacatt    1020
agtgctacgc ggaatgggag ccaggccttc gtgcattggc aagagcccg ggcgcccctg    1080
cagggtaccc tgttagggta ccggctggcg tatcaaggcc aggacacccc agaggtgcta   1140
atggacatag gctaaggca agaggtgacc ctggagctgc aggggacgg tctgtgtcc      1200
aatctgacag tgtgtgtggc agcctacact gctgctgggg atggaccctg agcctccca    1260
gtaccctgg aggcctggcg cccagggcaa gcacagccag tccaccagct ggtgaaggaa   1320
c                                                                   1321
```

<210> SEQ ID NO 4
<211> LENGTH: 440
<212> TYPE: PRT
<213> ORGANISM: Homo sapiens

<400> SEQUENCE: 4

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30
```

```
Glu Glu Ser Pro Phe Val Gly Asn Pro Gly Asn Ile Thr Gly Ala Arg
         35                  40                  45

Gly Leu Thr Gly Thr Leu Arg Cys Gln Leu Gln Val Gln Gly Glu Pro
 50                  55                  60

Pro Glu Val His Trp Leu Arg Asp Gly Gln Ile Leu Glu Leu Ala Asp
65                   70                  75                  80

Ser Thr Gln Thr Gln Val Pro Leu Gly Glu Asp Gln Asp Asp Asp Trp
             85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
            210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu
    435                 440
```

```
<210> SEQ ID NO 5
<211> LENGTH: 2057
<212> TYPE: DNA
<213> ORGANISM: Homo sapiens

<400> SEQUENCE: 5
atattgtgct tccaccactg ccaataacaa aataactagc aaccatgaag tgggtggaat      60
caattttttt aatttttccta ctaaattta ctgaatccag aacactgcat agaaatgaat     120
atggaatagc ttccatattg gattcttacc aatgtactgc agagataagt ttagctgacc    180
tggctaccat attttttgcc cagtttgttc aagaagccac ttacaaggaa gtaagcaaaa    240
tggtgaaaga tgcattgact gcaattgaga acccactgg agatgaacag tcttcagggt     300
gtttagaaaa ccagctacct gcctttctgg aagaactttg ccatgagaaa gaaattttgg    360
agaagtacgg acattcagac tgctgcagcc aaagtgaaga gggaagacat aactgttttc    420
ttgcacacaa aaagcccact ccagcatcga tcccactttt ccaagttcca gaacctgtca    480
caagctgtga agcatatgaa gaagacaggg agacattcat gaacaaattc atttatgaga    540
tagcaagaag gcatcccttc ctgtatgcac ctacaattct tctttgggct gctcgctatg    600
acaaaataat tccatcttgc tgcaaagctg aaaatgcagt tgaatgcttc caaacaaagg    660
cagcaacagt tacaaaagaa ttaagagaaa gcagcttgtt aaatcaacat gcatgtgcag    720
taatgaaaaa ttttgggacc cgaactttcc aagccataac tgttactaaa ctgagtcaga    780
agtttaccaa agttaatttt actgaaatcc agaaactagt cctggatgtg gcccatgtac    840
atgagcactg ttgcagagga gatgtgctgg attgtctgca ggatggggaa aaaatcatgt    900
cctacatatg ttctcaacaa gacactctgt caaacaaaat aacagaatgc tgcaaactga    960
ccacgctgga acgtggtcaa tgtataattc atgcagaaaa tgatgaaaaa cctgaaggtc   1020
tatctccaaa tctaaacagg ttttttaggag atagagattt taaccaattt tcttcagggg   1080
aaaaaaatat cttcttggca agttttgttc atgaatattc aagaagacat cctcagcttg    1140
ctgtctcagt aattctaaga gttgctaaag gataccagga gttattggag aagtgtttcc    1200
agactgaaaa ccctcttgaa tgccaagata aggagaaga agaattacag aaatacatcc    1260
aggagagcca agcattggca aagcgaagct gcggcctctt ccagaaacta ggagaatatt   1320
acttacaaaa tgcgtttctc gttgcttaca caaagaaagc ccccccagctg acctcgtcgg    1380 agctgatggc catcaccaga aaaatggcag ccacagcagc cacttgttgc caactcagtg    1440 aggacaaaact attggcctgt ggcgagggag cggctgacat tattatcgga cacttatgta    1500
tcagacatga aatgactcca gtaaaccctg gtgttggcca gtgctgcact tcttcatatg    1560
ccaacaggag gccatgcttc agcagcttgg tggtggatga acatatgtc cctcctgcat    1620 tctctgatga caagttcatt ttccataagg atctgtgcca agctcagggt gtagcgctgc    1680
aaacgatgaa gcaagagttt ctcattaacc ttgtgaagca aaagccacaa ataacagagg    1740
aacaacttga ggctgtcatt gcagatttct caggcctgtt ggagaaatgc tgccaaggcc    1800
aggaacagga agtctgcttt gctgaagagg gacaaaaact gatttcaaaa actcgtgctg    1860
ctttgggagt ttaaaattact tcaggggaag agaagacaaa acgagtcttt cattcggtgt    1920
gaacttttct ctttaatttt aactgattta acactttttg tgaattaatg aaatgataaa    1980
gacttttatg tgagatttcc ttatcacaga aataaaatat ctccaaatgt ttccttttca    2040
aaaaaaaaaa aaaaaaa                                                    2057

<210> SEQ ID NO 6
```

<211> LENGTH: 609
<212> TYPE: PRT
<213> ORGANISM: Homo sapiens

<400> SEQUENCE: 6

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
370                 375                 380

Phe Gln Thr Glu Asn Pro Leu Glu Cys Gln Asp Lys Gly Glu Glu Glu
```

```
                385                 390                 395                 400
Leu Gln Lys Tyr Ile Gln Glu Ser Gln Ala Leu Ala Lys Arg Ser Cys
                    405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
        435                 440                 445
Ala Ile Thr Arg Lys Met Ala Ala Thr Ala Thr Cys Cys Gln Leu
    450                 455                 460
Ser Glu Asp Lys Leu Leu Ala Cys Gly Glu Gly Ala Ala Asp Ile Ile
465                 470                 475                 480
Ile Gly His Leu Cys Ile Arg His Glu Met Thr Pro Val Asn Pro Gly
                485                 490                 495
Val Gly Gln Cys Cys Thr Ser Ser Tyr Ala Asn Arg Arg Pro Cys Phe
            500                 505                 510
Ser Ser Leu Val Val Asp Glu Thr Tyr Val Pro Pro Ala Phe Ser Asp
        515                 520                 525
Asp Lys Phe Ile Phe His Lys Asp Leu Cys Gln Ala Gln Gly Val Ala
    530                 535                 540
Leu Gln Thr Met Lys Gln Glu Phe Leu Ile Asn Leu Val Lys Gln Lys
545                 550                 555                 560
Pro Gln Ile Thr Glu Glu Gln Leu Glu Ala Val Ile Ala Asp Phe Ser
                565                 570                 575
Gly Leu Leu Glu Lys Cys Cys Gln Gly Gln Glu Gln Glu Val Cys Phe
            580                 585                 590
Ala Glu Glu Gly Gln Lys Leu Ile Ser Lys Thr Arg Ala Ala Leu Gly
        595                 600                 605
Val

<210> SEQ ID NO 7
<211> LENGTH: 1520
<212> TYPE: DNA
<213> ORGANISM: Homo sapiens

<400> SEQUENCE: 7
ccacgcgtcc gcggacgcgt gggcggcacg gtttcgtggg gacccaggct tgcaaagtga      60
cggtcatttt ctctttcttt ctccctcttg agtccttctg agatgatggc tctgggcgca     120
gcgggagcta cccgggtctt tgtcgcgatg gtagcggcgg ctctcggcgg ccaccctctg     180
ctgggagtga gcgccacctt gaactcggtt ctcaattcca acgctatcaa gaacctgccc     240
ccaccgctgg gcggcgctgc ggggcaccca ggctctgcag tcagcgccgc gcgggaatc     300 ctgtacccgg gcgggaataa gtaccagacc attgacaact accagccgta cccgtgcgca     360
gaggacgagg agtgcggcac tgatgagtac tgcgctagtc ccacccgcgg aggggacgca     420
ggcgtgcaaa tctgtctcgc ctgcaggaag cgccgaaaac gctgcatgcg tcacgctatg     480
tgctgccccg ggaattactg caaaaatgga atatgtgtgt cttctgatca aaatcatttc     540
cgaggagaaa ttgaggaaac catcactgaa agctttggta atgatcatag caccttggat     600
gggtattcca gaagaaccac cttgtcttca aaaatgtatc acaccaaagg acaagaaggt     660
tctgtttgtc tccggtcatc agactgtgcc tcaggattgt gttgtgctag acacttctgg     720
tccaagatct gtaaacctgt cctgaaagaa ggtcaagtgt gtaccaagca taggagaaaa     780
ggctctcatg gactagaaat attccagcgt tgttactgtg gagaaggtct gtcttgccgg     840
```

```
atacagaaag atcaccatca agccagtaat tcttctaggc ttcacacttg tcagagacac    900
taaaccagct atccaaatgc agtgaactcc ttttatataa tagatgctat gaaaaccttt    960
tatgaccttc atcaactcaa tcctaaggat atacaagttc tgtggtttca gttaagcatt   1020
ccaataacac cttccaaaaa cctggagtgt aagagctttg tttctttatg aactcccct    1080 gtgattgcag taaattactg tattgtaaat tctcagtgtg gcacttacct gtaaatgcaa   1140
tgaaactttt aattattttt ctaaaggtgc tgcactgcct attttcctc ttgttatgta    1200 aattttgta cacattgatt gttatcttga ctgacaaata ttctatattg aactgaagta    1260
aatcatttca gcttatagtt cttaaaagca taaccctta ccccatttaa ttctagagtc    1320
tagaacgcaa ggatctcttg gaatgacaaa tgataggtac ctaaaatgta acatgaaaat   1380
actagcttat tttctgaaat gtactatctt aatgcttaaa ttatatttcc ctttaggctg   1440
tgatagtttt tgaaataaaa tttaacattt aatatcatga aatgttataa gtagacataa   1500
aaaaaaaaaa aaaaaaaaa                                                1520
```

<210> SEQ ID NO 8
<211> LENGTH: 266
<212> TYPE: PRT
<213> ORGANISM: Homo sapiens

<400> SEQUENCE: 8

```
Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255
```

```
Ser Ser Arg Leu His Thr Cys Gln Arg His
            260                 265

<210> SEQ ID NO 9
<211> LENGTH: 111
<212> TYPE: PRT
<213> ORGANISM: Artificial sequence
<220> FEATURE:
<223> OTHER INFORMATION: Synthetic peptide

<400> SEQUENCE: 9

Thr Gln Ala Glu Glu Ser Pro Phe Val Gly Asn Pro Gly Asn Ile Thr
1               5                   10                  15

Gly Ala Arg Gly Leu Thr Gly Thr Leu Arg Cys Gln Leu Gln Val Gln
            20                  25                  30

Gly Glu Pro Pro Glu Val His Trp Leu Arg Asp Gly Gln Ile Leu Glu
        35                  40                  45

Leu Ala Asp Ser Thr Gln Thr Gln Val Pro Leu Gly Glu Asp Glu Gln
    50                  55                  60

Asp Asp Trp Ile Val Val Ser Gln Leu Arg Ile Thr Ser Leu Gln Leu
65                  70                  75                  80

Ser Asp Thr Gly Gln Tyr Gln Cys Leu Val Phe Leu Gly His Gln Thr
                85                  90                  95

Phe Val Ser Gln Pro Gly Tyr Val Gly Leu Glu Gly Leu Pro Tyr
                100                 105                 110
```